US012571798B2

(12) United States Patent
Kerlikowske et al.

(10) Patent No.: US 12,571,798 B2
(45) Date of Patent: Mar. 10, 2026

(54) CANCER BIOMARKERS AND METHODS OF USE THEREOF

(75) Inventors: Karla Kerlikowske, San Anselmo, CA (US); Thea D. Tlsty, San Francisco, CA (US); Mona L. Gauthier, Toronto (CA); Hal K. Berman, San Francisco, CA (US); Troy Bremer, Irvine, CA (US); Annette M. Molinaro, New Haven, CT (US)

(73) Assignees: The Regents Of The University Of California, Oakland, CA (US); Yale University, New Haven, CT (US); Prelude Corporation, Laguna Hills, CA (US)

( * ) Notice: Subject to any disclaimer, the term of this patent is extended or adjusted under 35 U.S.C. 154(b) by 366 days.

(21) Appl. No.: 13/094,729

(22) Filed: Apr. 26, 2011

(65) Prior Publication Data

US 2012/0003639 A1    Jan. 5, 2012

Related U.S. Application Data

(60) Provisional application No. 61/328,565, filed on Apr. 27, 2010.

(51) Int. Cl.

| | |
|---|---|
| *C12Q 1/68* | (2018.01) |
| *C12P 19/34* | (2006.01) |
| *C12Q 1/6883* | (2018.01) |
| *C12Q 1/6886* | (2018.01) |
| *G01N 33/574* | (2006.01) |

(52) U.S. Cl.
CPC ..... *G01N 33/57415* (2013.01); *C12Q 1/6883* (2013.01); *C12Q 1/6886* (2013.01); *C12Q 2600/158* (2013.01)

(58) Field of Classification Search
CPC ............... C12Q 1/6883; C12Q 1/6886; C12Q 2600/158
See application file for complete search history.

(56) References Cited

U.S. PATENT DOCUMENTS

| | | | |
|---|---|---|---|
| 4,318,846 A | 3/1982 | Khanna et al. |
| 4,415,732 A | 11/1983 | Caruthers et al. |
| 4,458,066 A | 7/1984 | Caruthers et al. |
| 4,591,570 A | 5/1986 | Chang |
| 4,605,735 A | 8/1986 | Miyoshi et al. |
| 4,683,195 A | 7/1987 | Mullis et al. |
| 4,683,202 A | 7/1987 | Mullis |
| 4,757,141 A | 7/1988 | Fung et al. |
| 4,889,818 A | 12/1989 | Gelfand et al. |
| 4,947,210 A | 8/1990 | Nagata et al. |
| 5,091,652 A | 2/1992 | Mathies et al. |
| 5,143,854 A | 9/1992 | Pirrung et al. |
| 5,171,695 A | 12/1992 | Ekins |
| 5,185,439 A | 2/1993 | Arnold, Jr. et al. |
| 5,223,409 A | 6/1993 | Ladner et al. |

| | | | |
|---|---|---|---|
| 5,242,828 A | 9/1993 | Bergstrom et al. |
| 5,283,174 A | 2/1994 | Arnold et al. |
| 5,288,644 A | 2/1994 | Beavis et al. |
| 5,292,658 A | 3/1994 | Cormier et al. |
| 5,313,264 A | 5/1994 | Ivarsson et al. |
| 5,322,770 A | 6/1994 | Gelfand |
| 5,324,633 A | 6/1994 | Fodor et al. |
| 5,399,491 A | 3/1995 | Kacian et al. |
| 5,403,484 A | 4/1995 | Ladner et al. |
| 5,409,818 A | 4/1995 | Davey et al. |
| 5,418,155 A | 5/1995 | Cormier et al. |
| 5,432,049 A | 7/1995 | Fischer et al. |
| 5,445,934 A | 8/1995 | Fodor et al. |
| 5,470,710 A | 11/1995 | Weiss et al. |
| 5,486,452 A | 1/1996 | Gordon et al. |
| 5,492,806 A | 2/1996 | Drmanac et al. |
| 5,498,538 A | 3/1996 | Kay et al. |
| 5,503,980 A | 4/1996 | Cantor |
| 5,510,270 A | 4/1996 | Fodor et al. |
| 5,516,637 A | 5/1996 | Huang et al. |
| 5,525,464 A | 6/1996 | Drmanac et al. |
| 5,532,128 A | 7/1996 | Eggers et al. |
| 5,538,848 A | 7/1996 | Livak et al. |
| 5,545,531 A | 8/1996 | Rava et al. |
| 5,547,732 A | 8/1996 | Edwards et al. |
| 5,547,839 A | 8/1996 | Dower et al. |
| 5,554,517 A | 9/1996 | Davey et al. |
| 5,556,752 A | 9/1996 | Lockhart et al. |
| 5,571,698 A | 11/1996 | Ladner et al. |
| 5,578,832 A | 11/1996 | Trulson et al. |
| 5,580,732 A | 12/1996 | Grossman et al. |
| 5,585,481 A | 12/1996 | Arnold, Jr. et al. |

(Continued)

FOREIGN PATENT DOCUMENTS

| | | |
|---|---|---|
| AU | 2007273055 | 1/2008 |
| AU | 2011/248632 | 12/2012 |

(Continued)

OTHER PUBLICATIONS

Hoshikawa et al (Physical Genomics 2003 vol. 12 pp. 209-219).*
Whitehead (Genome Biology 2005 vol. 6 Issue 2 Article R13).*
Chan, Eric. Integrating Transcriptomics and Proteomics. G&P magazine 2006 vol. 6 No. 3 pp. 20-26.*
Nofech-Mozes (Clinical Medicine: Oncology 2008:2 7-18).*
Provenzano (European Journal of Cancer 39 (2003) 622-630).*
Patani (Breast Cancer Res Treat (2008) 111:1-10).*
Steinman (Annals of Clinical and Laboratory Science vol. 37 No. 2 2007 pp. 127-134) (Year: 2007).*
Burstein (The New England Journal of Medicine vol. 350 No. 14 pp. 1430-1441 2004) (Year: 2004).*
Salido (Breast Cancer Research 2005 vol. 7 R267-R273) (Year: 2005).*

(Continued)

*Primary Examiner* — Stephen T Kapushoc

(74) *Attorney, Agent, or Firm* — KNOBBE, MARTENS, OLSON & BEAR, LLP

(57) ABSTRACT

Embodiments are provided for characterizing a biological sample. In some embodiments, one can estimate the risk that a subject with ductal carcinoma in situ will have a subsequent DCIS event and/or invasive cancers.

18 Claims, 51 Drawing Sheets

Specification includes a Sequence Listing.

(56) References Cited

U.S. PATENT DOCUMENTS

| | | | |
|---|---|---|---|
| 5,593,839 | A | 1/1997 | Hubbell et al. |
| 5,599,695 | A | 2/1997 | Pease et al. |
| 5,625,033 | A | 4/1997 | Kay et al. |
| 5,631,734 | A | 5/1997 | Stern et al. |
| 5,648,211 | A | 7/1997 | Fraiser et al. |
| 5,658,727 | A | 8/1997 | Barbas et al. |
| 5,661,028 | A | 8/1997 | Foote |
| 5,667,988 | A | 9/1997 | Barbas et al. |
| 5,683,888 | A | 11/1997 | Campbell |
| 5,723,591 | A | 3/1998 | Livak et al. |
| 5,736,330 | A | 4/1998 | Fulton |
| 5,741,668 | A | 4/1998 | Ward et al. |
| 5,744,312 | A | 4/1998 | Mamone et al. |
| 5,760,951 | A | 6/1998 | Dixon et al. |
| 5,777,079 | A | 7/1998 | Tsien et al. |
| 5,786,146 | A | 7/1998 | Herman et al. |
| 5,800,992 | A | 9/1998 | Fodor et al. |
| 5,804,387 | A | 9/1998 | Cormack et al. |
| 5,807,522 | A | 9/1998 | Brown et al. |
| 5,849,481 | A | 12/1998 | Urdea et al. |
| 5,851,829 | A | 12/1998 | Marasco et al. |
| 5,874,304 | A | 2/1999 | Zolotukhin et al. |
| 5,876,930 | A | 3/1999 | Livak et al. |
| 5,876,995 | A | 3/1999 | Bryan |
| 5,904,915 | A | 5/1999 | Fujibayashi et al. |
| 5,925,558 | A | 7/1999 | Tsien et al. |
| 5,948,899 | A | 9/1999 | Arnold et al. |
| 5,965,371 | A | 10/1999 | Marasco et al. |
| 5,981,180 | A | 11/1999 | Chandler et al. |
| 6,004,745 | A | 12/1999 | Arnold et al. |
| 6,007,996 | A | 12/1999 | McNamara et al. |
| 6,057,107 | A | 5/2000 | Fulton |
| 6,063,603 | A | 5/2000 | Davey et al. |
| 6,171,797 | B1 | 1/2001 | Perbost |
| 6,180,351 | B1 | 1/2001 | Cattell |
| 6,197,599 | B1 | 3/2001 | Chin et al. |
| 6,225,047 | B1 | 5/2001 | Hutchens et al. |
| 6,232,072 | B1 | 5/2001 | Fisher |
| 6,242,266 | B1 | 6/2001 | Schleifer et al. |
| 6,320,196 | B1 | 11/2001 | Dorsel et al. |
| 6,323,043 | B1 | 11/2001 | Caren et al. |
| 6,329,209 | B1 | 12/2001 | Wagner et al. |
| 6,331,393 | B1 | 12/2001 | Laird et al. |
| 6,355,934 | B1 | 3/2002 | Osgood et al. |
| 6,579,684 | B2 | 6/2003 | Price et al. |
| 6,610,484 | B1 | 8/2003 | Hung |
| 6,797,393 | B2 | 9/2004 | Qiao et al. |
| 6,919,211 | B1 | 7/2005 | Fodor et al. |
| 7,011,949 | B2 | 3/2006 | Amorese et al. |
| 7,081,340 | B2 | 7/2006 | Baker et al. |
| 7,112,404 | B2 | 9/2006 | Laird et al. |
| 7,186,512 | B2 | 3/2007 | Martienssen et al. |
| 7,446,185 | B2 | 11/2008 | Nelson |
| 7,452,727 | B2 | 11/2008 | Henning et al. |
| 11,543,411 | B2 | 1/2023 | Bremer et al. |
| 11,821,900 | B2 | 11/2023 | Bremer et al. |
| 12,332,245 | B2 | 6/2025 | Tlsty et al. |
| 2002/0197676 | A1 | 12/2002 | Lukyanov et al. |
| 2003/0225528 | A1* | 12/2003 | Baker et al. .................... 702/19 |
| 2003/0225529 | A1 | 12/2003 | Ecker et al. |
| 2005/0032085 | A1 | 2/2005 | Labas et al. |
| 2006/0063190 | A1* | 3/2006 | Fischer ................ C12Q 1/6886 435/6.14 |
| 2006/0129331 | A1 | 6/2006 | Akilesh et al. |
| 2006/0275844 | A1 | 12/2006 | Linke et al. |
| 2007/0009915 | A1 | 1/2007 | Wang |
| 2007/0077582 | A1 | 4/2007 | Slepnev |
| 2007/0105133 | A1 | 5/2007 | Clarke et al. |
| 2010/0003189 | A1* | 1/2010 | Tlsty et al. |
| 2010/0068717 | A1 | 3/2010 | Badve et al. |
| 2010/0158894 | A1 | 6/2010 | Umemura |
| 2011/0183333 | A1 | 7/2011 | Martin et al. |
| 2012/0003639 | A1 | 1/2012 | Kerlikowske et al. |
| 2013/0317083 | A1 | 11/2013 | Rigoutsos |
| 2017/0184601 | A1 | 6/2017 | Tlsty et al. |
| 2017/0350895 | A1 | 12/2017 | Bremer et al. |
| 2022/0187301 | A1 | 6/2022 | Bremer |
| 2022/0260569 | A1 | 8/2022 | Bremer |
| 2023/0136619 | A1 | 5/2023 | Bremer et al. |
| 2023/0204591 | A1 | 6/2023 | Tlsty et al. |

FOREIGN PATENT DOCUMENTS

| | | |
|---|---|---|
| AU | 2013205536 A1 | 5/2013 |
| AU | 2013205531 | 11/2016 |
| CA | 2657576 | 1/2008 |
| DK | 2939026 T3 | 9/2017 |
| EP | 0244210 | 11/1989 |
| EP | 0204157 | 10/1990 |
| EP | 0245071 | 1/1992 |
| EP | 0329822 | 6/1994 |
| EP | 0373203 | 8/1994 |
| EP | 0721 016 | 7/1996 |
| EP | 0728520 | 5/2001 |
| EP | 0785280 | 4/2003 |
| EP | 0799897 | 6/2006 |
| EP | 2041574 | 4/2009 |
| EP | 2442108 | 4/2012 |
| EP | 2442109 | 4/2012 |
| EP | 2450710 | 5/2012 |
| EP | 2564200 A1 | 3/2013 |
| EP | 3227687 | 10/2017 |
| EP | 2564200 B1 | 1/2019 |
| EP | 3508854 | 7/2019 |
| WO | WO 1991/02814 | 3/1991 |
| WO | WO 1992/15673 | 9/1992 |
| WO | WO 1995/00669 | 1/1995 |
| WO | WO 1995/07463 | 3/1995 |
| WO | WO 1995/21265 | 8/1995 |
| WO | WO 1995/22058 | 8/1995 |
| WO | WO 1995/35505 | 12/1995 |
| WO | WO 1996/31622 | 10/1996 |
| WO | WO 1997/02357 | 1/1997 |
| WO | WO 1997/10365 | 3/1997 |
| WO | WO 1997/27317 | 7/1997 |
| WO | WO 1997/29212 | 8/1997 |
| WO | WO 1998/14605 | 4/1998 |
| WO | WO 1998/26277 | 6/1998 |
| WO | WO 1999/39210 | 8/1999 |
| WO | WO 1999/49019 | 9/1999 |
| WO | WO 1999/51773 | 10/1999 |
| WO | WO 2000/04382 | 1/2000 |
| WO | WO 2000/04389 | 1/2000 |
| WO | WO 2000/04390 | 1/2000 |
| WO | WO 2000/54046 | 9/2000 |
| WO | WO 2000/56934 | 9/2000 |
| WO | WO 2001/14425 | 3/2001 |
| WO | WO 2001/40803 | 6/2001 |
| WO | WO 2002/019767 | 3/2002 |
| WO | WO 2000/63701 | 6/2002 |
| WO | WO 2005/038051 | 4/2005 |
| WO | WO 2005-083429 A2 | 9/2005 |
| WO | WO 2008/008284 * | 1/2008 |
| WO | WO 2008-008284 A2 | 1/2008 |
| WO | WO 2011/139721 | 11/2011 |
| WO | WO 2016/090323 | 6/2016 |
| WO | WO 2020/056338 | 3/2020 |

OTHER PUBLICATIONS

Mohsin (Modern Pathology 2004 vol. 17 pp. 1545-1554) (Year: 2004).*

Wiechmann and Kuerer, The Molecular Journey From Ductal Carcinoma in Situ to Invasive Breast Cancer. American Cancer Society,2008;112;2130-2142. (Year: 2008).*

Darling et al. Atypical Ductal Hyperplasia and Ductal Carcinoma in Situ as Revealed by Large-Core Needle Breast Biopsy. American Journal of Roentgenology;2000;175: 1341-1346. (Year: 2000).*

Mylonas et al. Expression of Her2/neu, Steroid Receptors (ER and PR), Ki67 and p53 in Invasive Mammary Ductal Carcinoma Associated with Ductal Carcinoma in Situ (DCIS) Versus Invasive Breast Cancer Alone. Anticancer Research; 2005;25:1719-1724. (Year: 2005).*

(56)     References Cited

OTHER PUBLICATIONS

Burstein et al. Ductal Carcinoma in Situ of the Breast. The new england journal of medicine. 2004;350:1430-1441. (Year: 2004).*

Marsh et al. Loss of heterozygosity at chromosome 9p in ductal carcinoma in situ and invasive carcinoma of the breast. British Journal of Cancer; 1998;77;9:1460-1468. (Year: 1998).*

Boland et al. COX-2 expression is associated with an aggressive phenotype inductal carcinoma in situ. British Journal of Cancer; 2004;90:423-429. (Year: 2004).*

Ruiz et al. Tissue microarrays for comparing molecular features with proliferation activity in breast cancer. Int. J. Cancer;2006; 118: 2190-2194. (Year: 2006).*

Wiechmann and Kuerer, The Molecular Journey From Ductal Carcinoma in Situ to Invasive Breast Cancer. American Cancer Society,2008;112;2130-2142. (Year: 2008) (Year: 2008).*

Darling et al. Atypical Ductal Hyperplasia and Ductal Carcinoma in Situ as Revealed by Large-Core Needle Breast Biopsy. American Journal of Roentgenology;2000;175: 1341-1346. (Year: 2000) (Year: 2000).*

Mylonas et al. Expression of Her2/neu, Steroid Receptors (ER and PR), Ki67 and p53 in Invasive Mammary Ductal Carcinoma Associated with Ductal Carcinoma in Situ (DCIS) Versus Invasive Breast Cancer Alone. Anticancer Research; 2005;25:1719-1724. (Year: 2005) (Year: 2005).*

Burstein et al. Ductal Carcinoma in Situ of the Breast. The new england journal of medicine. 2004;350: 1430-1441. (Year: 2004) (Year: 2004).*

Marsh et al. Loss of heterozygosity at chromosome 9p in ductal carcinoma in situ and invasive carcinoma of the breast. British Journal of Cancer; 1998;77;9: 1460-1468. (Year: 1998) (Year: 1998).*

Boland et al. COX-2 expression is associated with an aggressive phenotype inductal carcinoma in situ. British Journal of Cancer; 2004;90:423-429. (Year: 2004) (Year: 2004).*

Ruiz et al. Tissue microarrays for comparing molecular features with proliferation activity in breast cancer. Int. J. Cancer;2006; 118: 2190-2194. (Year: 2006) (Year: 2006).*

Dunne et al. Effect of Margin Status on Local Recurrence After Breast Conservation and Radiation Therapy for Ductal Carcinoma in Situ. Journal of Clinical Oncology; 2009; 27;10: 1615-1620. (Year: 2009).*

Burstein. The New England Journal of Medicine 350; 14; 2004; pp. 1430-1441. (Year: 2004).*

Darling et al. American Journal of Roentgenology; 2000;175: 1341-1346. (Year: 2000).*

Mylonas et al. Anticancer Research;2005;25:1719-1724. (Year: 2005).*

Patani et al. Current management of DCIS: a review. Breast Cancer Res Treat; 2008; 111:1-10. (Year: 2008).*

Wood, The Role of Clinical Trials in Changing Therapy for Ductal Carcinoma in Situ. Annals of Surgical Oncology, 2004;11(1):24S-27S. (Year: 2004).*

Boughey et al. Current Treatment and Clinical Trial Developments for Ductal Carcinoma in Situ of the Breast. Boughey et al. The Oncologist; 2007;12:1276-1287. (Year: 2007).*

Marsh. British Journal of Cancer; 1998; vol. 77 No. 9; pp. 1460-146. (Year: 1998).*

Dunne et al. J Clin Oncol; 2009;27:1615-1620. (Year: 2009).*

Burstein. The New England Journal of Medicine 350; 2004; 14; pp. 1430-1441. (Year: 2004).*

Wiechmann and Kuerer. Cancer; 2008; 15; 112(10):2130-2142. (Year: 2008).*

Yang et al. Pathology International; 2003; 53: 422-428. (Year: 2003).*

Boughey et al. The Oncologist; 2007;12:1276-1287. (Year: 2007).*

Boland. British Journal of Cancer ; 2004; vol. 90; pp. 423-429. (Year: 2004).*

Marsh. British Journal of Cancer; 1998; vol. 77 No. 9; pp. 1460-1468. (Year: 1998).*

Katrine L Henriksen, et al. "Semi-quantitative scoring of potentially predictive markers for endocrine treatment of breast cancer: a comparison between whole sections and tissue microarrays" J Clin Pathol 2007;60:397-404 (Year: 2007).*

Guoan Chen, et al. "Discordant Protein and mRNA Expression in Lung Adenocarcinomas" Molecular & Cellular Proteomics, vol. 1; No. 4; 2002; pp. 304-313. (Year: 2002).*

Lloyd Mack et al. "Relationship of a New Histological Categorization of Ductal Carcinoma In Situ of the Breast With Size and the Immunohistochemical Expression of p53, c-erb B2, bcl-2, and ki-67" Human Pathology, (Aug. 1997) vol. 28, No. 8. (Year: 1997).*

Chirag Shah, et al. "The Clinical Utility of DCISionRT on Radiation Therapy Decision Making in Patients with Ductal Carcinoma in Situ Following Breast-Conserving Surgery" Ann Surg Oncol (2021) 28:5974-5984 (Year: 2021).*

Edward B. Fish, et al. "Assessment of Treatment for Patients With Primary Ductal Carcinoma in Situ in the Breast" Annals of Surgical Oncology, 5(8):724-.73 (Year: 1998).*

Arbiser, JL. "Molecular regulation of angiogenesis and tumorigenesis by signal transduction pathways: evidence of predictable and reproducible patterns of synergy in diverse neoplasms", *Seminars in Cancer Biology.* 14 pp. 81-91 (2004).

Chow et al., "Study of COX-2, Ki67, and p53 expression to predict effectiveness of 5-flurouracil, epirubicin and cyclophosphamide with celecoxib treatment in breast cancer patients", *Biomedicine and Pharmacotherapy*, vol. 59, pp. S298-S301 (Oct. 1, 2005).

Davies et al., "Correlation between Cyclooxygenase-2 Expression and Angiogenesis in Human Breast Cancer", *Clinical Cancer Research*, vol. 9, No. 7, pp. 2651-2656 (Jul. 2003).

Ernster et al., "Detection of DCIS in women undergoing screening Mammography", *J. Natl Cancer Inst*, vol. 94 No. 20, pp. 1546-1954 (2002).

European Office Action dated Aug. 5, 2009 in corresponding European Patent Application No. 07810252.2.

European Office Action dated May 31, 2010 in corresponding European Patent Application No. 07810252.2.

European Office Action dated Dec. 8, 2010 in corresponding European Patent Application No. 07810252.2.

European Office Action dated Jul. 18, 2011 in corresponding European Patent Application No. 07810252.2.

Faratian et al., "Membranous and cytoplasmic staining of Ki67 is associated with HER2 and ER status in invasive breast carcinoma." *Histopathology* 54 pp. 254-257 (Jan. 2009).

File History, U.S. Appl. No. 12/373,047, filed May 13, 2009.

Gauthier et al., "Abrogated Response to Cellular Stress Identifies DCIS Associated with Subsequent Tumor Events and Defines Basal-like Breast Tumors", *Cancer Cell* 12 pp. 479-491 (Nov. 2007).

Gauthier et al., "p38 Regulates Cyclooxygenase-2 in Human Mammary Epithelial Cells and is Activated in Premalignant Tissue", *Cancer Research*, vol. 65, No. 5, pp. 1792-1799 (Mar. 1, 2005).

International Search Report dated Sep. 19, 2008 in International Application No. PCT-US07/15584.

International Search Report dated Sep. 14, 2011 in corresponding International Application No. PCT/US2011/034005.

Iorio et al., "MicroRNA Gene Expression Deregulation in Human Breast Cancer", *Cancer Research*, vol. 65 No. 16, pp. 7065-7070 (2005).

Kenny et al., "Quantification of Cellular Proliferation in Tumor and Normal Tissues of Patients with Breast Cancer by [${}^{18}$F]Fluorothymidine-Positron Emission Tomography Imaging: Evaluation of Analytical Methods", *Cancer Research*, vol. 65 No. 21, pp. 10104-10112 (2005).

Kepple et al., "The receptor expression pattern in ductal carcinoma in situ predicts recurrence", *The American Journal of Surgery*, 192 pp. 68-71 (2006).

Kerlikowske et al., "Biomarker Expression and Risk of Subsequent Tumors after Initial Ductal Carcinoma in situ Diagnosis", *J Natl Cancer Inst*, vol. 102 No. 9, pp. 627-637 (May 5, 2010).

Kerlikowske et al., "Characteristics associated with recurrence among women with ductal carcinoma in situ treated by lumpectomy", *J. Natl Cancer Inst*, vol. 95 No. 22, pp. 1692-1702 (2003).

(56)                    References Cited

OTHER PUBLICATIONS

Mylonas et al., "Expression of Her2/neu, Steroid Receptors (ER and PR), Ki67 and p53 in Invasive Mammary Ductal Carcinoma Associated with Ductal Carcinoma in Situ (DCIS) Versus Invasive Breast Cancer Alone", *Anticancer Research* 25 pp. 1719-1723 (May 2005).
Office Action dated Jun. 23, 2011 in U.S. Appl. No. 12/373,047.
Perrone et al., "COX-2 expression in DCIS: correlation with VEGF, HER-2/neu, prognostic molecular markers and clinicopathological features." *Histopathology* 46 pp. 561-568 (May 2005).
Plon, "Screening and Clinical Implications for BRCA1 and BRCA2 Mutation Carriers", *Journal of Mammary Gland Biology and Neoplasia*, vol. 3 No. 4, pp. 377-387 (1998).
Schorr et al., "Are the Pure in Situ Breast Ductal Carcinomas and Those Associated With Invasive Carcinoma the Same?" *Applied Immunohistochemistry and Molecular Morphology* vol. 18 No. 1 pp. 51-54 (Jan. 2010).
Tlsty et al., "Genetic and Epigenetic Changes in Mammary Epithelial Cells May Mimic Early Events in Carcinogenesis", *Journal of Mammary Gland Biology and Neoplasia*, vol. 9, No. 3, pp. 263-274 (Jul. 2004).
Tuomisto et al., "Analysis of gene and protein expression during monocyte-macrophage differentiation and cholesterol loading—cDNA and protein array study", *Atherosclerosis*, vol. 180, pp. 283-291 (2005).
Van der Groep et al., "Molecular profile of ductal carcinoma in situ of the breast in BRCA1 and BRCA2 germline mutation carriers", *Journal of Clinical Pathology* vol. 62 pp. 926-930 (Oct. 2009).
Dwek et al. Proteome and glycosylation mapping identifies post-translational modifications associated with aggressive breast cancer. Proteomics 2001, 1, 756-762.
Ushijama et al. Genes involved in breast cancers. Nippon Rinsho, Mar. 2006, 64(3): 432-436.
Annual Meeting of Japanese Society of National Medical Service, 2005, 59th, 357-763.
Office Action, dispatch date Jan. 8, 2013, received in Japanese Patent Appl. No. 2009-520751, and translation.
Office Action dated Dec. 12, 2012 received in European Patent Appl. No. 07810252.2-2401.
Partial European Search Report received in European Patent Application No. EP 11 18 8923, filed Jul. 3, 2007.
European Publication received in European Patent Application No. EP 11 18 8923, filed Jul. 3, 2007.
European Publication received in European Patent Application No. EP 11 18 8925, filed Jul. 3, 2007.
European Publication received in European Patent Application No. EP 11 18 8926, filed Jul. 3, 2007.
Office Action received for European Patent Application 11188923.4 dated Feb. 18, 2013.
Office Action received for European Patent Application 11188925.9 dated Mar. 4, 2013.
Office Action received for European Patent Application 11188926.7 dated Mar. 4, 2013.
Di Vinci et al., "p16$^{INK4a}$ Promoter Methylation and Protein Expression in Breast Fibroadenoma and Carcinoma," Int. J. Cancer, 2005, pp. 414-421, vol. 114.
European Search Report received dated Jun. 27, 2012 received in European Patent Application No. 11188923.4, filed on Jul. 3, 2007.
Kenny et al., "Quantification of Cellular Proliferation in Tumor and Normal Tissues of Patients with Breast Cancer by [$^{18}$F]Fluorothymidine-Positron Emission Tomography Imaging: Evaluation of Analytical Methods," Cancer Res. Nov. 1, 2005, vol. 65(21).
Ruiz et al., "Tissue Microarrays for Comparing Molecular Features with Proliferation Activity in Breast Cancer," Int. J. Cancer, 2006, pp. 2190-2194, vol. 118.
Stoll, "Premalignant Breast Lesions: Role for Biological Markers in Predicting Progression to Cancer," European Journal of Cancer, 1999, pp. 693-697, vol. 35(5).
Office Action dated Jul. 25, 2012, received in Australian Patent Application No. 2007273055, filed on Jul. 3, 2007.

Final Office Action dated Apr. 10, 2012, received in U.S. Appl. No. 12/373,047, filed May 13, 2009.
European Search Report received in European Patent Application No. EP 11 18 8925, filed Jul. 3, 2007.
European Search Report received in European Patent Application No. EP 11 18 8926, filed Jul. 3, 2007.
Office Action dated Feb. 9, 2012 received in European Patent Application No. 07 810 252.
Office Action dated Sep. 19, 2013 in Australian Application No. 2011248632.
Office Action dated Oct. 17, 2013 in European Application No. 07810252.2.
Office Action dated Sep. 20, 2013 in European Application No. 11188923.4.
Office Action dated Sep. 26, 2013 in European Application No. 11188925.9.
Office Action dated Sep. 26, 2013 in European Application No. 11188926.7.
Office Action dated Nov. 20, 2013 in Canadian Application No. 2657576.
Office Action dated Mar. 25, 2014 in Australian Application No. 2007273055.
Response to Canadian Office Action (dated Nov. 20, 2013) filed May 20, 2014 in corresponding Canadian Application No. 2657576.
Response to Japanese Office Action (dated Jan. 8, 2013) filed Jul. 5, 2013 in corresponding Japanese Application No. 2009-520751 with English translation.
Office Action dated Apr. 8, 2014 in Japanese Application No. 2009-520751 with English Translation.
Communication pursuant to Rules 161(1) and 162 EPC dated Dec. 7, 2012 in European Application No. 11721599.6.
Office Action dated May 29, 2015 in U.S. Appl. No. 12/373,047.
Office Action dated Sep. 24, 2014 in U.S. Appl. No. 12/373,047.
Office Action dated Jun. 16, 2015 in European Patent Application No. 07810252.2.
Office Action dated May 18, 2015 in European Patent Application No. 11188923.4.
Office Action dated May 18, 2015 in European Patent Application No. 11188925.9.
Office Action dated May 18, 2015 in European Patent Application No. 11188926.7.
Office Action dated Nov. 10, 2014 in Australian Patent Application No. 2013205531.
Office Action dated Nov. 10, 2014 in Australian Patent Application No. 2013205536.
Office Action dated Aug. 11, 2014, received in European Application No. 07810252.2.
Office Action dated Jul. 15, 2014, received in European Application No. 11188923.4.
Office Action dated Jul. 15, 2014, received in European Application No. 11188925.9.
Office Action dated Jul. 15, 2014, received in European Application No. 11188926.7.
Office Action dated Mar. 25, 2014, received in Australian Application No. 2007273055.
Office Action dated Mar. 10, 2014, received in Japanese Appl. No. 2009-520751 (with English translation).
Office Action dated Oct. 24, 2014, received in Japanese Appl. No. 2009-520751 (with English translation).
Office Action dated Nov. 20, 2013, received in Canadian Appl. No. 2,657,576.
Hoshikawa et al. Hypoxia induces different genes in the lungs of rats compared with mice. Physiol. Genomics 12: 209-219, 2003.
Chan, Eric. Integrating Transcriptomics and Proteomics. Drug Discovery and Development, Apr. 1, 2006, 6(3) 20-26.
Whitehead et al. Variation in tissue-specific gene expression among natural populations. Genome Biology 2005, 6:R13, in 14 pages.
Expression Probeset Details for HG-U133A:201930_S_AT (This document was printed from the world wide web at www.affymetrix.com/analysis/netaffx/fullrecord.affx?pk=HG-U133A:210930_S_AT on Sep. 11, 2013. This document lists a copyright date of 2013. The original publication date is unknown.).

(56)            References Cited

OTHER PUBLICATIONS

Office Action dated Apr. 15, 2016 in European Application No. 11721599.6.
Office Action dated Jun. 3, 2016 in U.S. Appl. No. 12/373,047.
Office Action dated May 12, 2016 in European Application No. 11188923.4.
Office Action dated Dec. 15, 2014 in Canadian Application No. 2657576.
U.S. Appl. No. 15/284,349, filed Oct. 3, 2013, The Regents of the University of California.
Office Action dated Dec. 19, 2016 in Canadian Application No. 2,657,576.
Witkiewicz et al., "Associate of RB/p16-Pathway Perturbations with DCIS Recurrence", The American Journal of Psychology, vol. 179, No. 3, Sep. 2011.
Office Action Dated Mar. 6, 2017 in European Application No: 11721599.6.
Office Action Dated Apr. 21, 2017 in Canadian Application 2,797,585.
Office Action Dated Jun. 12, 2017 in European Application No: 11188923.4.
Office Action Dated Jun. 21, 2017 in Canadian Application 2,657,576.
Albergaria, et al. Expression of FOXA1 and GATA-3 in Breast Cancer: The Prognostic Significance in Hormone Receptor-Negative Tumors, Breast Cancer Research, vol. 11 No. 3, pp. 1-15 (2009).
Badve et al., FOXA 1 Expression in Breast Cancer Correlation with Luminal Subtype A and 34 Survival, Clin Cancer Res, vol. 13, pp. 4415-4421, Aug. 1, 2007.
Bartova, M, et al., COX-2, p16 and Ki67 Expression in DCIS, Microinvasive and Early Invasive Breast Carcinoma with Extensive Intraductal Component, Bratislava Medical Journal, vol. 115, No., pp. 445-45, (2014).
Behling, K et al., Increased SIAH Expression Predicts Ductal Carcinoma in situ (DCIS) Progression to Invasive Carcinoma, Breast Cancer Research and Treatment, vol. 129, No. 3, pp. 717-724, (2010).
Chan et al., The expression of the ubiquitin ligase SIAH2 (seven in absentia homolog 2) is mediatedthrough gene copy number in breast cancer and is associated with a basal-like phenotype and p53 expression, Breast Cancer Res, vol. 13, R19, Feb. 9, 2011.
Crawford et al., "Histologically normal human mammary epithelia with silenced p16(INK4a) overexpress COX-2, promoting a pre-malignant program," *Cancer Cell* 2004;5(3):263-73.
Extended European Search Report dated Aug. 5, 2009, received in European Patent Appl. No. 07810252.2.
Gorringe, K, et al. Ductal Carcinoma in Situ Biology, Biomarkers and Diagnosis, Frontiers in Oncology, vol. 7, Article, 248, pp. 1-14, (2017).
Hammond et al., American Society of Clinical Oncology/College of American Pathologists Guideline Recommendations for Immunohistochemical Testing of Estrogen and Progesterone Receptors in Breast Cancer (Unabridged Version), Arch Pathol Lab Med, vol. 134, e48, Jul. 1, 2010.
Horimoto et al., Low FOXA 1 expression predicts good response to neo-adjuvant chemotherapy resulting in good outcomes for luminal HER2-negative breast cancer cases, British Journal of Cancer, vol. 112, pp. 345-351, Epub Nov. 25, 2014.
International Search Report & Written Opinion, mailed Feb. 16, 2016, in International Application PCT/US2015/064115.
Lee et al., Context-Specific Regulation of NF-KB Target Gene Expression by EZH2 in Breast Cancers, Mol Cell, vol. 43, pp. 798-810, Sep. 2, 2011.
Muggerud, A., et al, Molecular Diversity in Ductal Carcinoma in situ (DCIS) and Early Invasive Breast Cancer, Molecular Oncology, vol. 4, No. 4, pp. 357-368, (2010).
Office Action Dated Dec. 1, 2017 in Canadian Application 2,797,585.
Office Action Dated Jul. 27, 2017 in U.S. Appl. No. 15/284,349.
Office Action dated Oct. 23, 2017 in U.S. Appl. No. 15/529,966.
Office Action Dated Feb. 12, 2018 in U.S. Appl. No. 15/284,349.
Office Action dated Mar. 16, 2018 in U.S. Appl. No. 15/529,966.

Partial European Search Report Dated May 23, 2018 in European Patent Application No. EP 15865163.8.
Yu, K. et al. Gene Expression Patterns of Tumor progression in Different Breast Cancer Molecular Subtypes from an Asian-Chinese Population, Proc. Amer. Association Cancer Res., vol. 25, (2004).
Zhou, W, Aspects of Progression in Breast Carcinoma, From Ductal Carcinoma in Situ to Invasive Cancer, Acta Universitatis Asupaliensis Uppsala, Separtmentt of Surgical Sciences, Akademiska sjukhuset, SE-751 85, Uppsala, Sweden,, (2012).
Affymetrix Solutions for Cancer Analysis Data Sheet, Dated 2005.
Bouvier-Labit, C., et al. P16 and P19 Mrna Expression in Neuroglial Tumours: Correlation with KI67 Proliferation Index, Neuropathology and Applied Neurobiology, vol. 25, pp. 408-416, (1999).
Dedeoglu, B. Analysis of Differentially Expressed Genes in Breast Cancer: BRCAI-Induced Gene Expression Profiles and Meta-Analysis Gene Signature, Thesis (2009). : http://www.thesis.bilkent.edu.tr/0003813.pdf [retrieved on Aug. 29, 2018] This item lists a date of "Published Jan. 2009." However, as the listed item refers to a web page, it may have been available, in some form, at an earlier point in time.
Extended European Search Report Dated Sep. 21, 2018 in European Patent Application No. 15865163.8.
Office Action Dated May 31, 2018 in Canadian Patent Application No. 2,657,576.
Office Action Dated Nov. 29, 2018 in European Patent Application No. 11188923.4.
Office Action Dated Jan. 3, 2019 in U.S. Appl. No. 15/284,349.
Office Action Dated Feb. 23, 2018 in European Patent Application No. 11188923.4.
European Search Reported Dated Mar. 13, 2019 in European Patent Application No. 1820939.5.
Long-Term Results Show that Radiation Therapy After Lumpectomy to Remove DCIS Reduces Recurrence Risk, Published Oct. 4, 2013 <https://www.breastcancer.org/research-news/20131004> Applicants note that the webpage was printed on Mar. 12, 2018, and has a publication date of 2011, however, the webpage may have been available, in some form, prior to this date.
Older Women Diagnosed with DCIS or Early-Stage Disease Have Excellent Prognosis, Published Mar. 16, 2011 < https://www.breastcancer.org/research-news/20110316> Applicants note that the webpage was printed on Mar. 12, 2018, and has a publication date of 2011, however, the webpage may have been available, in some form, prior to this date.
Office Action Dated Mar. 18, 2019 in U.S. Appl. No. 15/529,966.
Supplementary European Search Report Dated Sep. 21, 2018 in European Patent Application Np: 15865163.8.
Wolf et al., FOXA1: Growth Inhibitor and a Favorable Prognostic Factor in Human Breast Cancer, Int. J. Cancer, vol. 120, pp. 1013-1022, (2006).
File History, U.S. Appl. No. 15/529,966, filed May 25, 2017.
Final Office Action dated Dec. 21, 2020 in U.S. Appl. No. 15/284,349.
Response to Canadian Office Action dated (Jun. 30, 2020), filed Oct. 30, 2020 received in Canadian Appl. No. 2,657,576
Response to European Office Action (Dec. 21, 2020) Response filed Jan. 18, 2021 in European Patent Application No.EP15865163.8.
Dunne et al., Effect of Margin Status on Local Recurrence After Breast Conservation and Radiation Therapy for Ductal Carcinoma in Situ, Journal of Clinical Oncology, vol. 27, No. 10, 2009.
Office Action Response filed on Dec. 10, 2020 in Canadian Patent Application No. 2797585 in 46 pages.
Office Action dated Dec. 21, 2020 received in European Patent Application No. EP15865163.8 in 3 pages.
Office Action dated Jan. 29, 2021 received in European Patent Application No. 20190672.4 in 9 pages.
Office Action Response and declaration filed on Feb. 3, 2021 in U.S. Appl. No. 15/529,966 in 23 pages.
Office Action Response filed on May 20, 2021 in U.S. Appl. No. 15/284,349 in 17 pages.
Notice of Allowance in U.S. Appl. No. 15/529,966, dated Jun. 1, 2021.

(56) References Cited

OTHER PUBLICATIONS

Belvisi, M. et al., "Induction of cyclo-oxygenase-2 by cytokines in human cultured airway smooth muscle cells: novel inflammatory role of this cell type," British Journal of Pharmacology, 1997, vol. 120, pp. 910-916.
Canadian Office Action dated May 1, 2020, in Canadian Application 2,797,585.
European Office Action dated Dec. 7, 2012, European Application No. 11721599.6.
International Search Report and Written Opinion, mailed Dec. 5, 2019, for International Application No. PCT/US2019/051128.
Sendur, M.A.N., et al., "Cadiotoxicity of novel HER2-targeted therapies," Current Medical Research and Opinion, 2013, vol. 29, No. 8, pp. 1015-1024.
Response to Office Action (dated Jun. 23, 2011) filed Sep. 23, 2011 in U.S. Appl. No. 12/373,047.
Response to US Office Action (dated Apr. 10, 2012) filed Jul. 9, 2012 in related U.S. Appl. No. 12/373,047.
Response to U.S. Office Action filed Jun. 28, 2019 in U.S. Appl. No. 15/529,966.
Response to U.S. Office Action filed Oct. 17, 2019 in U.S. Appl. No. 15/529,966.
Response to Australian Office Action (dated Jul. 25, 2012) filed Mar. 14, 2014 in corresponding Australian Application No. 2007273055.
Response to Australian Office Action (dated Mar. 25, 2014) filed Apr. 9, 2014 in corresponding Australian Application No. 2007273055.
Response to European Office Action (dated Aug. 5, 2009) filed May 17, 2010 in corresponding European Application No. 07810252.2.
Response to European Office Action (dated May 31, 2010) filed Nov. 25, 2010 in corresponding European Application No. 07810252.2.
Response to European Office Action (dated Dec. 8, 2010) filed Jun. 14, 2011 in corresponding European Application No. 07810252.2.
Response to European Office Action (dated Sep. 20, 2013) filed Jun. 30, 2014 in corresponding European Application No. 11188923.4.
Response to European Office Action (dated Sep. 26, 2013) filed Jul. 2, 2014 in corresponding European Application No. 11188925.9.
Response to European Office Action (dated Sep. 26, 2013) filed Jul. 2, 2014 in corresponding European Application No. 11188926.7.
Response to European Office Action Response filed Apr. 23, 2019 in European Patent Application No.EP15865163.8.
Response to European Communication pursuant to Rules 161(1) and 162 EPC (dated Dec. 7, 2012) filed Jun. 5, 2013 in corresponding European Application No. 11721599.6.
Response to Canadian Office Action dated (Nov. 20, 2013), filed May 20, 2014 received in Canadian Appl. No. 2,657,576.
Response to Canadian Office Action dated (Dec. 15, 2014), filed Jun. 10, 2015 received in Canadian Appl. No. 2,657,576.
Response to Canadian Office Action dated (Dec. 19, 2016), filed Feb. 24, 2017 received in Canadian Appl. No. 2,657,576.
Response to Canadian Office Action dated (Jun. 21, 2017), filed Dec. 19, 2017 received in Canadian Appl. No. 2,657,576.
Response to Canadian Office Action Dated (May 31, 2018), filed Nov. 27, 2019 in Canadian Patent Application Np. 2,657,576.
Response to Canadian Office Action dated (Apr. 21, 2017), filed Oct. 20, 2017 Canadian Application No. 2,797,585.
Response to Canadian Office Action Dated (Dec. 1, 2017), filed Jun. 1, 2018 in Canadian Application 2,797,585.
Response to Canadian Office Action Dated (Jun. 7, 2019), filed Dec. 9, 2019 in Canadian Application 2,797,585.
Response to U.S Office Action Dated (Jul. 28, 2017), filed Oct. 30, 2017 in U.S. Appl. No. 15/284,349.
Response to U.S Office Action Dated (Feb. 12, 2018), filed Jun. 11, 2018 in U.S. Appl. No. 15/284,349.
Response to U.S Office Action Dated (Jan. 3, 2019), filed Jul. 1, 2019 in U.S. Appl. No. 15/284,349.
Response to U.S Office Action Dated (Sep. 16, 2019), filed Dec. 13, 2019 in U.S. Appl. No. 15/284,349.
Response to U.S Office Action Dated (Jun. 24, 2020), filed Sep. 24, 2020 in U.S. Appl. No. 15/284,349.

Office Action dated Sep. 16, 2019 in European Application No. 11188923.4.
Office Action dated Jun. 7, 2019 in Canadian Application No. 2797585.
Office Action Response filed Jun. 28, 2019 in U.S. Appl. No. 15/529,966.
Office Action dated Jul. 17, 2019 in U.S. Appl. No. 15/529,966.
Office Action Dated Apr. 19, 2018 in European Patent Application No. 11721599.6.
Office Action Response filed Apr. 23, 2019 in European Patent Application No.EP15865163.8.
Office Action dated Sep. 30, 2014 in European Application No. 11721599.6.
Office Action Dated Sep. 16, 2019 in U.S. Appl. No. 15/284,349.
Office Action Response filed Oct. 17, 2019 in U.S. Appl. No. 15/529,966.
Office Action dated Nov. 25, 2019 in European Application No. 15 865 163.8.
European Search Reported Dated Mar. 19, 2019 in European Patent Application No. 18209239.5.
File History, U.S. Appl. No. 15/248,349, filed Oct. 3, 2016.
Office Action dated Jul. 28, 2017 in U.S. Appl. No. 15/248,349.
Cheng et al (Journal of the National Cancer Institute, 1997, 89: 1356-1360).
Prelude Press Release Dated Aug. 2, 2018 entitled Journal of Clinical Cancer Res arch Publication Demonstrates that DCISionRT® Provides Prognostic and Predictive Power for Assessing a Patient's DCIS Risk.
Zhou et al., "Tumor Markers Predicting Recurrence Type after a Primary Ductal Carcinoma in Situ", Cancer Research, vol. 71, No. 24, P4-10-01, Dec. 1, 2012, XP055643824.
Zhou et al., "A Comparison of Tumor Biology in Primary Ductal Carcinoma in Situ Recurring as Invasive Carcinoma versus a New in Situ", International Journal of Breast Cancer, vol. 2013, Jan. 1, 2013, pp. 1-8, XP055643823.
U.S. Office Action Dated Jun. 22, 2020 in U.S. Appl. No. 15/529,966.
U.S. Office Action Dated Mar. 2, 2020 in U.S. Appl. No. 15/529,966.
European Office Action Dated Jun. 11, 2021 in European Patent Application No. 18209239.5.
Office Action Response filed on Feb. 22, 2018 in U.S. Appl. No. 15/529,966 in 11 pages.
Office Action Response filed on Aug. 16, 2018 in U.S. Appl. No. 15/529,966 in 15 pages.
Office Action Response filed on May 29, 2020 in U.S. Appl. No. 15/529,966 in 15 pages.
Office Action Response filed on Feb. 3, 2021 in U.S. Appl. No. 15/529,966 in 19 pages.
Response to European Office Action filed May 28, 2020 in European Patent Application No. EP15865163.8.
U.S. Office Action dated Jun. 24, 2020, in U.S. Appl. No. 15/284,349.
Response to Office Action (dated Nov. 10, 2014) Filed Jul. 19, 2016, in Australian Patent Application No. 2013205531.
Canadian Office Action dated Dec. 9, 2015, received in Canadian Appl. No. 2,657,576.
Response to Canadian Office Action dated (Dec. 9, 2015), filed Jun. 9, 2016 received in Canadian Appl. No. 2,657,576.
Canadian Office Action dated Jun. 30, 2020, received in Canadian Appl. No. 2,657,576.
Canadian Office Action dated Jun. 14, 2021, received in Canadian Appl. No. 2,657,576.
Response to Australian Office Action dated Sep. 19, 2013 filed on Jun. 3, 2015 in Australian Application No. 2011248632.
Canadian Office Action dated Dec. 1, 2017, Canadian Application No. 2,797,585.
Response to Canadian Office Action dated Dec. 1, 2017, Filed Jun. 12, 2018, Canadian Application No. 2,797,585.
Canadian Office Action dated Jun. 7, 2019, Canadian Application No. 2,797,585.
Response to Canadian Office Action dated Jun. 7, 2019, Filed Dec. 9, 2019 Canadian Application No. 2,797,585.
Canadian Office Action dated May 1, 2020, Canadian Application No. 2,797,585.

(56) References Cited

OTHER PUBLICATIONS

Response to European Office Action dated Sep. 30, 2014, Filed Aug. 16, 2016 European Application No. 11721599.6.
Response to European Office Action dated Mar. 6, 2017, Filed Jul. 4, 2017 European Application No. 11721599.6.
Response to European Office Action dated Apr. 19, 2018, Filed Jun. 18, 2018 European Application No. 11721599.6.
Canadian Office Action dated Apr. 7, 2021 Canadian Application No. 2,797,585.
U.S. Office Action dated Sep. 23, 2021 in U.S. Appl. No. 15/284,349.
Joyce et al., Effect of Overexpressing the Transcription Factor E2F2 on Cell Cycle Progression in Rabbit Corneal Endothelial Cells, Investigative Ophthalmology & Visual Science, May 2004, vol. 45, No. 5.
Response to Canadian Office Action dated Jun. 14, 2021, filed Nov. 8, 2021 in Canadian Appl. No. 2,657,576.
Response to Canadian Office Action dated Apr. 7, 2021, Filed Oct. 7, 2021, Canadian Application No. 2,797,585.
Response to Office Action dated Jan. 29, 2021 filed on Dec. 10, 2021 in European Patent Application No. 20190672.4 in 5 pages.
Office Action Dated Dec. 7, 2021 in U.S. Appl. No. 15/529,966.
Response to European Search Reported Dated Mar. 19, 2019 filed on Jan. 9, 2020 in European Patent Application No. 18209239.5.
Response to Office Action Dated Jun. 11, 2021 filed Dec. 7, 2021 in European Patent Application No. 18209239.5.
Response to U.S. Office Action dated Sep. 23, 2021 filed Dec. 17, 2021 in U.S. Appl. No. 15/284,349.
Final Office Action Dated Mar. 1, 2022 in U.S. Appl. No. 15/529,966.
Lari, S. A., et al., Biological Markers in DCIS and Risk of Breast Recurrence: A Systematic Review, Journal of Cancer, vol. 2, pp. 232-261,2011.
Fisher, B., eta 1., Prevention of invasive breast cancer in women with ductal carcinoma in situ: An update of the National Surgical Adjuvant Breast and Bowel Project experience, Seminars in Oncology, vol. 28, Issue 4, pp. 400-418, 2001.
Cuzick, I. S., et al., Effect of tamoxifen and radiotherapy in women with locally excised ductal carcinoma in situ: long-term results from the UK/ANZ DCIS trial, The Lancet Oncology, vol. 12, Issue 1, pp. 21-29, 2011.
Allred, D. C., et al., Adjuvant tamoxifen reduces subsequent breast cancer in women with estrogen receptor-positive ductal carcinoma in situ: a study based on NSABP protocol B-24, Journal of clinical oncology : official journal of the American Society of Clinical Oncology, vol. 30, No. 12, pp. 1268-1273, 2012.
Vicini, 2021, American Society of Radiation Oncology Annual Meeting.
Office Action dated Apr. 13, 2022 received in European Patent Application No. 20190672.4 in 8 pages.
Final Office Action dated Mar. 11, 2022 in U.S. Appl. No. 15/284,349.
U.S. Appl. No. 17/664,006, filed May 18, 2022, Tlsty.
U.S. Appl. No. 17/652,466, filed Feb. 24, 2022, Bremer.
Breastcancer.org, "New Guidelines Say Lumpectomy Margins Can Be Small as Long as Tumor Has No Ink on it". 2 pages; (Mar. 12, 2018) available at https://www.breastcancer.org/research-news/20140402. This reference is a webpage and the date apparent on the webpage is listed herewith. However, the webpage may have been available, in some form, prior to this date.
Chivukula et al., "Ductal Carcinoma in Situ: One Size Does Not Fit All". Women's Health. Sep. 2010:669-672.
Declaration By Troy Bremer in U.S. Appl. No. 15/529,966, dated Feb. 2, 2021.
Marsh K. et al., "Frequent Alterations Of Cell Cycle Regulators in Early-Stage Breast Lesions As Detected By Immunohistochemistry". Br J Cancer, 1998; vol. 77, No. 9, pp. 1460-1468.
Picarsic et al., Predictors of invasive breast cancer or DCIS recurrence in estrogen receptor positive (ER+) and estrogen receptor negative (ER−) ductal carcinoma in situ (DCIS) patients with and without associated invasive carcinoma (IC) (Journal Of Clinical Oncology, 2009, 27, No. 15_Suppl; Abstract E11523).

Picarsic et al., Role of Transcription Factors [FOXA1, GATA-3] in Predicting Outcomes in Recurrent Ductal Carcinoma-in-Situ (DCIS) or Invasive Carcinoma (IC) in DCIS Patients on Core Needle Biopsies of Breast. Cancer Res (2009) 69 (24_Supplement): 2115.
Siewertsz van Reesema L. et al., "SIAH and EGFR; Two RAS Pathway Biomarkers are Highly Prognostic in Locally Advanced and Metastatic Breast Cancer". EBioMedicine. Sep. 1, 2016;11: 183-198.
Solin, L. J et al., "A Multigene Expression Assay to Predict Local Recurrence Risk for Ductal Carcinoma in Situ of the Breast". J Nat Cancer Inst., May 15, 2013; 105(10): 701-710.
Wärnberg et al., "Abstract GS5-08: A Validation of DCIS Biiological Risk Profile in a Randomised Study for Radiation Therapy with 20 Year Follow-up (SweDCIS)". Cancer Res. Feb. 15, 2018; Abstract.
Response to U.S. Office Action Dated Sep. 24, 2014, filed Mar. 23, 2015 in U.S. Appl. No. 12/373,047.
Response to U.S. Office Action Dated May 29, 2015, filed Nov. 20, 2015 in U.S. Appl. No. 12/373,047.
Response to U.S. Office Action Dated Mar. 11, 2022, filed Aug. 5, 2022 in U.S. Appl. No. 15/284,349.
U.S. Office Action dated Jan. 12, 2023 in U.S. Appl. No. 17/664,006.
Response to U.S. Office Action Dated Dec. 7, 2021, filed Feb. 9, 2022 in U.S. Appl. No. 15/529,966.
Response to U.S. Office Action Dated Mar. 1, 2022 filed Aug. 25, 2022 in U.S. Appl. No. 15/529,966.
U.S. Notice of Allowance dated Nov. 2, 2022 in U.S. Appl. No. 15/529,966.
U.S. Office Action dated Jun. 14, 2022 in U.S. Appl. No. 17/652,471.
Response to Restriction Requirement Dated Jun. 14, 2022, filed Aug. 10, 2022 in U.S. Appl. No. 17/652,471.
U.S. Office Action dated Aug. 30, 2022 in U.S. Appl. No. 17/652,471.
Canadian Office Action dated May 2, 2022 in CA Application No. 2657576.
Response to Canadian Office Action dated May 2, 2022, filed Sep. 2, 2022 and suppl. Response filed Sep. 14, 2022 in CA Application No. 2657576.
Response to European Office Action Dated Jul. 18, 2011, filed Jan. 26, 2012 in EP Application No. 07810252.2.
Response to European Office Action Dated Aug. 11, 2014, filed May 20, 2015 in EP Application No. 07810252.2.
Response to European Search Report Dated Jun. 27, 2012, filed Jan. 24, 2013 in EP Application No. 11188923.4.
Response to European Office Action Dated Feb. 18, 2013, filed Aug. 26, 2013 in EP Application No. 11188923.4.
Response to European Office Action Dated Jul. 15, 2014, filed Apr. 29, 2015 in EP Application No. 11188923.4.
Response to European Office Action Dated May 18, 2015, filed Sep. 18, 2015 in EP Application No. 11188923.4.
Response to European Office Action Dated May 12, 2016, filed Nov. 22, 2016 in EP Application No. 11188923.4.
Response to European Office Action Dated Jun. 12, 2017, filed Oct. 17, 2017 in EP Application No. 11188923.4.
Response to European Office Action Dated Feb. 23, 2018, filed Sep. 4, 2018 in EP Application No. 11188923.4.
Response to European Office Action Dated Nov. 29, 2018, filed Apr. 9, 2019 in EP Application No. 11188923.4.
Response to European Office Action Dated Sep. 16, 2019, filed Jan. 21, 2020 in EP Application No. 11188923.4.
Response to Extended Search Report Dated Mar. 20, 2012, filed Feb. 7, 2013 in EP Application No. 11188925.9.
Response to European Office Action Dated Mar. 4, 2013, filed Sep. 13, 2013 in EP Application No. 11188925.9.
Response to Extended Search Report Dated Mar. 20, 2012, filed Feb. 7, 2013 in EP Application No. 11188926.7.
Response to European Office Action Dated Mar. 4, 2013, filed Sep. 13, 2013 in European Application No. 11188926.7.
Response to European Office Action Dated Sep. 26, 2013, filed Jul. 2, 2014 in EP Application No. 11188926.7.
Partial European Search Report dated Jun. 30, 2022 in EP Application No. EP 19859855.9.
Response to Japanese Office Action Dated Apr. 8, 2014, filed Jul. 8, 2014 in JP Application No. 2009-520751.
File History, U.S. Appl. No. 17/275,406, filed Mar. 11, 2021.

(56) References Cited

OTHER PUBLICATIONS

File History, U.S. Appl. No. 17/652,471, filed Feb. 24, 2021.
Tsikitis et al., "Biology of Ductal Carcinoma in Situ Classification Based on Biologic Potential," Am J Clin Oncol. 2006; 29: 305-310.
U.S. Office Action dated Nov. 9, 2022 in U.S. Appl. No. 15/284,349.
Office Action dated Nov. 2, 2022 received in European Patent Application No. EP15865163.8 in 7 pages.
Extended European Search Report dated Oct. 20, 2022, received in European Patent Appl. No. 19859855.9.
Response to U.S. Office Action Dated Nov. 9, 2022, filed Mar. 2, 2023 in U.S. Appl. No. 15/284,349.
U.S. Office Action dated May 9, 2023 in U.S. Appl. No. 15/284,349.
Response to U.S. Office Action Dated May 9, 2023, filed Aug. 9, 2023 in U.S. Appl. No. 15/284,349.
Response to U.S. Office Action Dated Jan. 12, 2023, filed Mar. 23, 2023 in U.S. Appl. No. 17/664,006.
U.S. Office Action dated Apr. 4, 2023 in U.S. Appl. No. 17/664,006.
Response to U.S. Office Action Dated Apr. 4, 2023, filed Jun. 15, 2023 in U.S. Appl. No. 17/664,006.
Response to U.S. Office Action Dated Aug. 30, 2022, filed Feb. 24, 2023 in U.S. Appl. No. 17/652,471.
U.S. Office Action dated Mar. 9, 2023 in U.S. Appl. No. 17/652,471.
Response to U.S. Office Action Dated Mar. 9, 2023, filed Jun. 14, 2023 in U.S. Appl. No. 17/652,471.
U.S. Notice of Allowance dated Sep. 7, 2023 in U.S. Appl. No. 17/652,471.
Response to European Office Action dated Apr. 13, 2022, filed Jan. 18, 2023 in EP Application No. 20190672.4.
Response to European Office Action Dated Nov. 2, 2022, filed Mar. 10, 2023 in EP Application No.EP15865163.8.
EP Communication pursuant to Rules (70(2) and 70a(2) EPC, dated Nov. 8, 2022 in European Patent Appl. No. 19859855.9.
Response to EP Communication (70(2) and 70a(2) EPC, dated Nov. 8, 2022, filed May 12, 2023 in European Patent Appl. No. 19859855.9.
Japanese Office Action dated Aug. 17, 2023 in JP Application No. 2021-539476.
U.S. Office Action dated Dec. 20, 2023 in U.S. Appl. No. 15/284,349.
Response to U.S. Office Action Dated Dec. 20, 2023, filed Jun. 18, 2024 in U.S. Appl. No. 15/284,349.
U.S. Notice of Allowance dated Sep. 14, 2023 in U.S. Appl. No. 17/664,006.
U.S. Office Action dated Apr. 8, 2024 in U.S. Appl. No. 17/664,006.
Response to U.S. Office Action Dated Apr. 8, 2024, filed Jul. 3, 2024 in U.S. Appl. No. 17/664,006.
U.S. Office Action dated Nov. 8, 2023 in U.S. Appl. No. 17/652,466.
Response to U.S. Office Action Dated Nov. 8, 2023 filed Mar. 28, 2024 in U.S. Appl. No. 17/652,466.
U.S. Office Action dated May 9, 2024 in U.S. Appl. No. 17/652,466.
U.S. Notice of Allowance dated Oct. 18, 2023 in U.S. Appl. No. 17/652,471.
U.S. Office Action dated Feb. 16, 2024 in U.S. Appl. No. 17/275,406.
Response to U.S. Office Action Dated Feb. 16, 2024, filed Apr. 15, 2024 in U.S. Appl. No. 17/275,406.
Response to Japanese Office Action Dated Aug. 17, 2023, filed Feb. 20, 2024 in JP Application No. 2021-539476.
Shono et al., "Cyclooxygenase-2 Expression in Human Gliomas: Prognostic Significance and Molecular Correlations". Cancer Res. Jun. 1, 2001;61(11): 4375-4381.

U.S. Office Action dated Oct. 21, 2024 in U.S. Appl. No. 15/284,349.
U.S. Notice of Allowance dated Jan. 2, 2025, in U.S. Appl. No. 17/652,466.
European Office Action dated Nov. 27, 2024 in EP Application No. 18209239.5.
U.S. Office Action dated Apr. 1, 2025 in U.S. Appl. No. 17/275,406.
U.S. Notice of Allowance dated Apr. 22, 2025, received in U.S. Appl. No. 17/652,466.
Declaration By Troy Bremer in U.S. Appl. No. 13/094,729, dated Jun. 18, 2024.
Goldberg et al., "Systemic Effects of Radiotherapy in Ductal Carcinoma In Situ." JAMA Network Open. Aug. 3, 2018;1(4):e181102.
Knauer et al., The Inducible E3 Ubiquitin Ligases SIAH1 and SIAH2 perform critical roles in breast and prostate cancers. Cytokine Growth Factor Rev. Aug. 1, 2015;26(4):405-413.
Ono et al., Prognostic Significance of Progesterone Receptor Expression in Estrogen-ReceptorPositive, HER2-negative, Node-negative Invasive Breast Cancer with a Low Ki-67 Labeling Index. Clin Breast Cancer. Feb. 1, 2017;17(1):41-47.
Response to U.S. Office Action Dated Oct. 21, 2024, filed Jan. 17, 2025 in U.S. Appl. No. 15/284,349.
Response/Appeal Brief to U.S. Office Action Dated Oct. 21, 2024, filed Mar. 17, 2025 in U.S. Appl. No. 15/284,349.
U.S. Notice of Allowance dated Sep. 30, 2024, received in U.S. Appl. No. 17/664,006.
U.S. Notice of Allowance dated Jan. 28, 2025, received in U.S. Appl. No. 17/664,006.
U.S. Notice of Allowance dated May 16, 2025, received in U.S. Appl. No. 17/664,006.
Response to U.S. Office Action Dated May 9, 2024 filed Oct. 8, 2024 in U.S. Appl. No. 17/652,466.
Australian Examination Report dated Jan. 15, 2025 in AU Application No. 2019339508.
Japanese Final Office Action dated Jun. 4, 2024 in JP Application No. 2021-539476.
Response/Appeal to Japanese Office Action Dated Jun. 4, 2024, filed Oct. 3, 2024 in JP Application No. 2021-539476.
Response to Office Action Dated Nov. 27, 2024, filed Mar. 26, 2025, in EP Application No. 18209239.5.
European Office Action dated May 7, 2025 in EP Application No. 18209239.5.
U.S. PTAB—Examiner's Answer dated May 23, 2025 in U.S. Appl. No. 15/284,349.
U.S. Notice of Allowance dated Jun. 26, 2025 in U.S. Appl. No. 17/652,466.
U.S. Notice of Allowance dated Aug. 1, 2025 in U.S. Appl. No. 17/652,466.
Interview Summary dated Jun. 5, 2025 in U.S. Appl. No. 17/275,406.
Response to Office Action Dated Apr. 1, 2025, filed Jul. 1, 2025, in U.S. Appl. No. 17/275,406.
U.S. Office Action dated Sep. 24, 2025 received in U.S. Appl. No. 17/275,406.
Response to Australian Examination Report dated Jan. 15, 2025, filed Jun. 26, 2025, in AU Application No. 2019339508.
Australian Examination Report dated Jul. 11, 2025 in AU Application No. 2019339508.
Canadian Office Action dated Oct. 14, 2025 in CA 3112792.

* cited by examiner

Cells in CD73$^+$CD90$^-$ population exhibit p16$^{INK4a-}$
promoter hypermethylation

| NAME | fold | absolute value |
|---|---|---|
| AA399473::tissue factor pathway inhibitor 2 | 25.1045372 | 25.1045372 |
| AA936757::heparin-binding growth factor binding protein | 21.44376905 | 21.44376905 |
| AA447835::small proline-rich protein 1B (cornifin) | 16.60194318 | 16.60194318 |
| AA456394::four and a half LIM domains 1 | 14.21973815 | 14.21973815 |
| "AA598974::cell division cycle 2, G1 to S and G2 to M" | 11.26586192 | 11.26586192 |
| R40057 Prominin (mouse)-like 1 | -11.08709008 | 11.08709008 |
| "AA775616::secreted phosphoprotein 1 (osteopontin, bone sialoprotein I, early T-lymphocyte activation 1)" | -10.04318206 | 10.04318206 |
| "T49159::plasminogen activator inhibitor, type II (arginine-serpin)" | 8.858119257 | 8.858119257 |
| H50095::KIAA0698 gene product (Hephaestin) | -8.516280514 | 8.516280514 |
| H50095::KIAA0698 gene product | -8.516280514 | 8.516280514 |
| "AA454743::Protease, serine, 9 (neurosin)" | -8.432625426 | 8.432625426 |
| AA401035::mitogen-activated protein kinase 4 | -6.841962776 | 6.841962776 |
| "AA031513::matrix metalloproteinase 7 (matrilysin, uterine)" | -6.804722548 | 6.804722548 |
| AA461065::mercaptopyruvate sulfurtransferase | 6.634633035 | 6.634633035 |
| AA187351::ribonucleotide reductase M2 polypeptide | 6.494071798 | 6.494071798 |
| W93717::KIAA0008 gene product (cell cycle regulated homologue of dlg1) | 6.249098219 | 6.249098219 |
| AA598794::connective tissue growth factor | -6.038140704 | 6.038140704 |
| H72122::ectodermal-neural cortex (with BTB-like domain) | -5.9679533 | 5.9679533 |
| "AA458969::diacylglycerol kinase, zeta (104kD)" | -5.495154899 | 5.495154899 |
| R80217::prostaglandin-endoperoxide synthase 2 (prostaglandin G/H synthase and cyclooxygenase) | 5.144260808 | 5.144260808 |
| "AA936768::interleukin 1, alpha" | 5.045721885 | 5.045721885 |
| "AA877166::myosin regulatory light chain 2, smooth muscle isoform" | -4.872192804 | 4.872192804 |
| N22272::UDP glycosyltransferase 8 (UDP- | -4.845603928 | 4.845603928 |

FIG. 14 (cont.)

| NAME | fold | absolute value |
|---|---|---|
| galactose ceramide galactosyltransferase) | | |
| "N92901::fatty acid binding protein 4, adipocyte" | 4.810206255 | 4.810206255 |
| T80924::alpha-1-antichymotrypsin | -4.764822463 | 4.764822463 |
| "AA862465::alpha-2-glycoprotein 1, zinc" | -4.647980295 | 4.647980295 |
| AA460685::apoptosis inhibitor 4 (survivin) | 4.552530703 | 4.552530703 |
| "AA700832::retinol-binding protein 1, cellular" | -4.535504506 | 4.535504506 |
| "AA775091::delta sleep inducing peptide, immunoreactor" | 4.269652426 | 4.269652426 |
| AA682423::monoamine oxidase B | -4.201035336 | 4.201035336 |
| AA449336::Homo sapiens protein regulator of cytokinesis 1 (PRC1) mRNA | 4.198455177 | 4.198455177 |
| "AA504943::crystallin, alpha B" | -4.132210222 | 4.132210222 |
| "H99676::collagen, type VI, alpha 1" | -4.05317844 | 4.05317844 |
| AA155913::matrix Gla protein | -3.902101541 | 3.902101541 |
| AA873060::leukemia-associated phosphoprotein p18 (stathmin) | 3.899798373 | 3.899798373 |
| AA478542::A kinase (PRKA) anchor protein (gravin) 12 | -3.897631892 | 3.897631892 |
| AA228130::PC4 and SFRS1 interacting protein 1 | 3.832234873 | 3.832234873 |
| W47179::cathepsin B | -3.811231038 | 3.811231038 |
| AA630734::seryl-tRNA synthetase | 3.743009977 | 3.743009977 |
| N66132::H.sapiens mRNA for rTS beta protein | 3.7394194 | 3.7394194 |
| "R76553::Homo sapiens a disintegrin-like and metalloprotease (reprolysin type) with thrombospondin type 1 motif, 1 (ADAMTS1), mRNA" | -3.709675654 | 3.709675654 |
| "AA663995::minichromosome maintenance deficient (mis5, S. pombe) 6" | 3.666333409 | 3.666333409 |
| AA706968::ZW10 interactor | 3.625717217 | 3.625717217 |
| "T77595::hexabrachion (tenascin C, cytotactin)" | -3.5875639 | 3.5875639 |
| "AA701455::centromere protein F (350/400kD, mitosin)" | 3.56459009 | 3.56459009 |
| AA456975::apolipoprotein D | -3.514345204 | 3.514345204 |
| R25377::DEK gene | 3.445705985 | 3.445705985 |
| "R93124::aldo-keto reductase family 1, member C1 (dihydrodiol dehydrogenase 1; 20-alpha (3-alpha)-hydroxysteroid dehydrogenase)" | 3.428526848 | 3.428526848 |
| AA877815::KIAA0353 protein | -3.419786107 | 3.419786107 |

FIG. 14 (cont.)

| NAME | fold | absolute value |
|---|---|---|
| AA894927::asparagine synthetase | 3.418607599 | 3.418607599 |
| AA464691::DKFZP564I1922 protein | -3.386188595 | 3.386188595 |
| AA453783::Homo sapiens mRNA; cDNA DKFZp564B1264 (from clone DKFZp564B1264) | 3.351931997 | 3.351931997 |
| N70776::frizzled (Drosophila) homolog 1 | -3.324394529 | 3.324394529 |
| R60343::5' nucleotidase (CD73) | 3.301872358 | 3.301872358 |
| H17696::myelin basic protein | -3.292975972 | 3.292975972 |
| "AA045326::protein tyrosine phosphatase, receptor type, J" | -3.262815628 | 3.262815628 |
| H45711::Kruppel-like factor 4 (gut) | 3.233755054 | 3.233755054 |
| H56655::desmin | -3.225395716 | 3.225395716 |
| H56655::desmin | -3.225395716 | 3.225395716 |
| AA071486::serine/threonine kinase 12 (aurora b) | 3.222269301 | 3.222269301 |
| AA434342::proline arginine-rich end leucine-rich repeat protein | 3.191334035 | 3.191334035 |
| N69049::frizzled (Drosophila) homolog 7 | -3.182534525 | 3.182534525 |
| AA677706::lactotransferrin | -3.085611058 | 3.085611058 |
| AA825491::interferon regulatory factor 4 | 3.054019023 | 3.054019023 |
| "AA481745::Homo sapiens clone 23763 unknown mRNA, partial cds" | -2.981367604 | 2.981367604 |
| AA598653::osteoblast specific factor 2 (fasciclin I-like) | -2.964948654 | 2.964948654 |
| AA598653::osteoblast specific factor 2 (fasciclin I-like) | -2.964948654 | 2.964948654 |
| AA446027::early growth response 2 (Krox-20 (Drosophila) homolog) | -2.963765696 | 2.963765696 |
| AA424560::Homo sapiens mRNA full length insert cDNA clone EUROIMAGE 248114 | -2.961183797 | 2.961183797 |
| AA406449::damage-specific DNA binding protein 2 (48kD) | 2.953451608 | 2.953451608 |
| AA430504::ubiquitin carrier protein E2-C | 2.937032834 | 2.937032834 |
| AA450265::proliferating cell nuclear antigen | 2.927663883 | 2.927663883 |
| "AA936799::matrix metalloproteinase 2 (gelatinase A, 72kD gelatinase, 72kD type IV collagenase)" | -2.889141496 | 2.889141496 |
| "N53172::Human orphan G protein-coupled receptor (RDC1) mRNA, partial cds" | -2.854775432 | 2.854775432 |
| "AA136707::procollagen-lysine, 2-oxoglutarate 5-dioxygenase (lysine | -2.847604647 | 2.847604647 |

FIG. 14 (cont.)

| NAME | fold | absolute value |
|---|---|---|
| hydroxylase) 2" | | |
| AA487488::claudin 7 | -2.84276597 | 2.84276597 |
| "AA488324::budding uninhibited by benzimidazoles 1 (yeast homolog), beta" | 2.839079872 | 2.839079872 |
| AA069372::forkhead box D1 | 2.811814744 | 2.811814744 |
| AA682321::NIMA (never in mitosis gene a)-related kinase 2 | 2.769233968 | 2.769233968 |
| R62612::fibronectin 1 | -2.73243452 | 2.73243452 |
| "AA284260::keratin, hair, acidic, 4" | 2.73095183 | 2.73095183 |
| "AA633747::collagen, type VI, alpha 2" | -2.725106606 | 2.725106606 |
| H86812::heparan sulfate (glucosamine) 3-O-sulfotransferase 1 | 2.693989899 | 2.693989899 |
| "H64346::syndecan 2 (heparan sulfate proteoglycan 1, cell surface-associated, fibroglycan)" | -2.620685626 | 2.620685626 |
| N64374::KIAA0537 gene product | -2.603583125 | 2.603583125 |
| AA452095::chromosome-associated polypeptide C | 2.597279354 | 2.597279354 |
| "AA284668::plasminogen activator, urokinase" | 2.590492527 | 2.590492527 |
| "AA700904::CDC45 (cell division cycle 45, S.cerevisiae, homolog)-like" | 2.568998924 | 2.568998924 |
| AA114250::KIAA0512 gene product | -2.560317371 | 2.560317371 |
| AA858026::protein C inhibitor (plasminogen activator inhibitor III) | -2.55868225 | 2.55868225 |
| "AA459401::protease, serine-like, 1" | -2.554026376 | 2.554026376 |
| R32025::Homo sapiens mRNA full length insert cDNA clone EUROIMAGE 248114 | -2.546989913 | 2.546989913 |
| W86653::FK506-binding protein 5 | 2.533953197 | 2.533953197 |
| R26960::peripheral myelin protein 22 | -2.518041355 | 2.518041355 |
| "N45138::transforming growth factor, beta 2" | -2.51222351 | 2.51222351 |
| H19439::Down syndrome candidate region 1-like 1 | -2.511269 | 2.511269 |
| "AA775415::SMT3 (suppressor of mif two 3, yeast) homolog 2" | 2.507695209 | 2.507695209 |
| "AA451684::CD1D antigen, d polypeptide" | 2.492166748 | 2.492166748 |
| "H38804::BUB3 (budding uninhibited by benzimidazoles 3, yeast) homolog" | 2.465751636 | 2.465751636 |
| AA683041::neuronal pentraxin II | -2.464588284 | 2.464588284 |
| "AA448157::cytochrome P450, subfamily I (dioxin-inducible), polypeptide 1 (glaucoma 3, primary infantile)" | -2.454709669 | 2.454709669 |

FIG. 14 (cont.)

| NAME | fold | absolute value |
|---|---|---|
| H15662::KIAA0291 protein (unknown gene) | -2.453909951 | 2.453909951 |
| T97925::Homo sapiens clone 24921 mRNA sequence | -2.446537625 | 2.446537625 |
| W86876::KIAA0320 protein (Talin 2) | -2.4404992 | 2.4404992 |
| "AA450189::enolase 2, (gamma, neuronal)" | -2.423743905 | 2.423743905 |
| "H75632::basic helix-loop-helix domain containing, class B, 2" | -2.420770171 | 2.420770171 |
| AA633549::ribonucleotide reductase M1 polypeptide | 2.415913901 | 2.415913901 |
| AA496283::Thy-1 cell surface antigen | -2.406606635 | 2.406606635 |
| "AA451904::epididymis-specific, whey-acidic protein type, four-disulfide core" | -2.40390552 | 2.40390552 |
| N49403::KIAA0779 protein (unknown gene) | -2.402313608 | 2.402313608 |
| AA448755::cell division cycle 25B | 2.401628573 | 2.401628573 |
| AA625995::zinc finger protein 9 (a cellular retroviral nucleic acid binding protein) | 2.395489468 | 2.395489468 |
| "H90431::adrenergic, beta-2-, receptor, surface" | 2.389455711 | 2.389455711 |
| W68396::SNF-1 related kinase | 2.38689572 | 2.38689572 |
| W58092::tropomyosin 1 (alpha) | -2.36317485 | 2.36317485 |
| AA099568::uridine phosphorylase | 2.362734406 | 2.362734406 |
| H54752::replication factor C (activator 1) 4 (37kD) | 2.362483555 | 2.362483555 |
| T72877::interleukin 1 receptor antagonist | 2.35434789 | 2.35434789 |
| AA454668::prostaglandin-endoperoxide synthase 1 (prostaglandin G/H synthase and cyclooxygenase) | 2.353591061 | 2.353591061 |
| AA504625::kinesin-like 1 | 2.347033686 | 2.347033686 |
| H21041::activating transcription factor 3 | 2.344604735 | 2.344604735 |
| "AA099153::tissue inhibitor of metalloproteinase 3 (Sorsby fundus dystrophy, pseudoinflammatory)" | -2.34309237 | 2.34309237 |
| "T70109::succinate dehydrogenase complex, subunit A, flavoprotein (Fp)" | 2.326465691 | 2.326465691 |
| N73611::transcription factor Dp-1 | 2.320180588 | 2.320180588 |
| "R43605::KIAA0293 protein (Homeobox protein Cux-2, Cut-like 2, CUTL2)" | -2.31587695 | 2.31587695 |
| "R83277::origin recognition complex, subunit 1 (yeast homolog)-like" | 2.300497316 | 2.300497316 |
| AA430032::pituitary tumor-transforming 1 | 2.298871048 | 2.298871048 |
| "R52796::interleukin 13 receptor, alpha 2" | 2.29456853 | 2.29456853 |

FIG. 14 (cont.)

| NAME | fold | absolute value |
|---|---|---|
| "T49530::Homo sapiens lipase, endothelial (LIPG) mRNA" | -2.292266614 | 2.292266614 |
| "AA430540::collagen, type IV, alpha 2" | -2.284580694 | 2.284580694 |
| "T60048::actin, gamma 2, smooth muscle, enteric" | -2.283519459 | 2.283519459 |
| R24543::guanine nucleotide regulatory protein (oncogene) | 2.283367229 | 2.283367229 |
| H21943::thymopoietin | 2.277802635 | 2.277802635 |
| "R55303::nerve growth factor receptor (TNFR superfamily, member 16)" | -2.257950649 | 2.257950649 |
| AA486653::CD81 antigen (target of antiproliferative antibody 1) | 2.25023157 | 2.25023157 |
| AA157018::stromal interaction molecule 1 | -2.244449253 | 2.244449253 |
| "AA486275::protease inhibitor 2 (anti-elastase), monocyte/neutrophil" | 2.244321338 | 2.244321338 |
| AA279188::a disintegrin and metalloprotease domain 8 | 2.243999876 | 2.243999876 |
| AA598517::keratin 8 | -2.231186932 | 2.231186932 |
| "AA029299::potassium large conductance calcium-activated channel, subfamily M, beta member 1" | -2.23019652 | 2.23019652 |
| "AA155695::transcobalamin I (vitamin B12 binding protein, R binder family)" | -2.228716978 | 2.228716978 |
| AA010065::CDC28 protein kinase 2 | 2.227440864 | 2.227440864 |
| "AA634006::actin, alpha 2, smooth muscle, aorta" | -2.223991274 | 2.223991274 |
| "H99816::procollagen-lysine, 2-oxoglutarate 5-dioxygenase (lysine hydroxylase) 2" | -2.220866263 | 2.220866263 |
| "W72679::highly expressed in cancer, rich in leucine heptad repeats" | 2.216495458 | 2.216495458 |
| AA478724::insulin-like growth factor binding protein 6 | 2.210194178 | 2.210194178 |
| W58342::putative gene product | -2.20856153 | 2.20856153 |
| H15445::H.sapiens mRNA for SEX gene | -2.207907192 | 2.207907192 |
| R10382::protein C inhibitor (plasminogen activator inhibitor III) | -2.201079581 | 2.201079581 |
| "T69926::myosin, heavy polypeptide 9, non-muscle" | -2.19458309 | 2.19458309 |
| W72207::cystatin A (stefin A) | 2.194373639 | 2.194373639 |
| AA256502::proprotein convertase subtilisin/kexin type 5 | -2.192297707 | 2.192297707 |
| AA486082::serum/glucocorticoid regulated kinase | -2.190102026 | 2.190102026 |

FIG. 14 (cont.)

| NAME | fold | absolute value |
|---|---|---|
| AA459292::CDC28 protein kinase 1 | 2.184734765 | 2.184734765 |
| H14810::Homo sapiens mRNA; cDNA DKFZp434G012 (from clone DKFZp434G012) | -2.184162721 | 2.184162721 |
| R02346::small nuclear ribonucleoprotein 70kD polypeptide (RNP antigen) | -2.183170823 | 2.183170823 |
| AA455786::minichromosome maintenance deficient (S. cerevisiae) 3 | 2.177381743 | 2.177381743 |
| AA496796::chondrocyte-derived ezrin-like protein | -2.172279362 | 2.172279362 |
| T55446::high density lipoprotein binding protein (vigilin) | -2.162011595 | 2.162011595 |
| "W94714::6-phosphofructo-2-kinase/fructose-2,6-biphosphatase 3" | -2.159099985 | 2.159099985 |
| N50079::Opa-interacting protein 2 | 2.144050953 | 2.144050953 |
| "AA457738::Human 12S RNA induced by poly(rI), poly(rC) and Newcastle disease virus" | 2.13349192 | 2.13349192 |
| H53658::DKFZP564M2423 protein | 2.128483049 | 2.128483049 |
| AA485371::bone marrow stromal cell antigen 2 | -2.12600365 | 2.12600365 |
| W91879::Homo sapiens vav 3 oncogene (VAV3) mRNA | -2.12594386 | 2.12594386 |
| AA476543::similar to rat HREV107 | -2.123668929 | 2.123668929 |
| H29592::KIAA0377 gene product (histidine acid phosphatase) | 2.122666643 | 2.122666643 |
| AA663986::fibrillarin | 2.119545692 | 2.119545692 |
| "AA865469::Tubulin, alpha, brain-specific" | -2.117094751 | 2.117094751 |
| "T49146::ATP synthase, subunit b-like" | -2.115189237 | 2.115189237 |
| "H57180::phospholipase C, gamma 2 (phosphatidylinositol-specific)" | -2.114150608 | 2.114150608 |
| "AA427732::solute carrier family 12 (potassium/chloride transporters), member 7" | -2.110424989 | 2.110424989 |
| AA425602::zona pellucida glycoprotein 3A (sperm receptor) | -2.108977702 | 2.108977702 |
| AA401137::lipocalin 2 (oncogene 24p3) | -2.108086866 | 2.108086866 |
| R19158::serine/threonine kinase 15 (aurora a) | 2.107888005 | 2.107888005 |
| "N53380::protein kinase C, mu" | -2.10158732 | 2.10158732 |
| "H82081::rab3 GTPase-activating protein, non-catalytic subunit (150kD)" | -2.101115333 | 2.101115333 |
| AA012867::ADP-ribosylation factor 6 | 2.09991978 | 2.09991978 |

FIG. 14 (cont.)

| NAME | fold | absolute value |
|---|---|---|
| AA629262::polo (Drosophia)-like kinase | 2.095503346 | 2.095503346 |
| "AA480995::methylene tetrahydrofolate dehydrogenase (NAD+ dependent), methenyltetrahydrofolate cyclohydrolase" | 2.094144257 | 2.094144257 |
| N23406::MCF.2 cell line derived transforming sequence | 2.092396607 | 2.092396607 |
| N35907::KIAA0830 protein | -2.086631581 | 2.086631581 |
| "AA487797::ribonuclease, RNase A family, 1 (pancreatic)" | -2.086434909 | 2.086434909 |
| "protein tyrosine phosphatase, non-receptor type 7 isoform 2" | -2.082463705 | 2.082463705 |
| AA169814::sorting nexin 2 | 2.080004707 | 2.080004707 |
| "W68220::KIAA0101 gene product (casein kinase 1, gamma 1)" | 2.079536635 | 2.079536635 |
| T59658::Homo sapiens mRNA; cDNA DKFZp586P1622 (from clone DKFZp586P1622) | 2.079465389 | 2.079465389 |
| AA454098::kinesin-like 5 (mitotic kinesin-like protein 1) | 2.079461548 | 2.079461548 |
| AA452627::endothelin receptor type A | 2.07633863 | 2.07633863 |
| AA010158::glutamyl-prolyl-tRNA synthetase | 2.07342368 | 2.07342368 |
| AA504266::stromal antigen 2 | -2.066711339 | 2.066711339 |
| "H59203::CDC6 (cell division cycle 6, S. cerevisiae) homolog" | 2.055668511 | 2.055668511 |
| "AA676804::CCAAT/enhancer binding protein (C/EBP), gamma" | 2.049280881 | 2.049280881 |
| AA431408::DKFZP566D193 protein | 2.042963559 | 2.042963559 |
| "AA482251::phosphatidylinositol-4-phosphate 5-kinase, type I, gamma" | -2.041992847 | 2.041992847 |
| W74602::TEA domain family member 4 | 2.039490562 | 2.039490562 |
| "T69359::mannose-binding lectin (protein C) 2, soluble (opsonic defect)" | 2.03809328 | 2.03809328 |
| R33755::glutathione S-transferase pi | 2.028376501 | 2.028376501 |
| AA211446::Homo sapiens mRNA full length insert cDNA clone EUROIMAGE 180147 | -2.02679478 | 2.02679478 |
| AA464601::tetraspan 5 | 2.021238206 | 2.021238206 |
| N70773::development and differentiation enhancing factor 2 | 2.017450098 | 2.017450098 |
| "H20547::potassium inwardly-rectifying channel, subfamily J, member 6" | -2.014104484 | 2.014104484 |
| AA436406::N-myristoyltransferase 1 | -2.013115219 | 2.013115219 |
| "AA043334::small nuclear RNA activating | 2.009674037 | 2.009674037 |

FIG. 14 (cont.)

| NAME | fold | absolute value |
|---|---|---|
| complex, polypeptide 3, 50kD" | | |
| H99415::A kinase (PRKA) anchor protein 2 | -2.002624963 | 2.002624963 |
| "W49619::cadherin 2, N-cadherin (neuronal)" | -1.995322534 | 1.995322534 |
| "W49619::cadherin 2, N-cadherin (neuronal)" | -1.995322534 | 1.995322534 |
| AA416628::Homo sapiens mRNA; cDNA DKFZp564C2063 (from clone DKFZp564C2063) | -1.982452761 | 1.982452761 |
| AA018372::glutamate dehydrogenase 1 | 1.977179619 | 1.977179619 |
| R66310::peptidylglycine alpha-amidating monooxygenase | -1.970973902 | 1.970973902 |
| AA456008::transmembrane protein | -1.969522436 | 1.969522436 |
| AA630449::epididymal secretory protein (19.5kD) | -1.962778749 | 1.962778749 |
| AA159311::KIAA1090 (Wolf-Hirschhorn syndrome candidate 1) | -1.961900222 | 1.961900222 |
| H45376::nel (chicken)-like 2 | -1.953255857 | 1.953255857 |
| R38539::fibroblast growth factor 2 (basic) | -1.947635639 | 1.947635639 |
| "AA011057::lectin, galactoside-binding, soluble, 7 (galectin 7)" | -1.943164707 | 1.943164707 |
| N74662::DKFZP564B147 protein | 1.939624332 | 1.939624332 |
| "AA128561::collagen, type XVII, alpha 1" | 1.934590933 | 1.934590933 |
| AA192268::KIAA0892 protein | 1.931364415 | 1.931364415 |
| "AA521232::ras-related C3 botulinum toxin substrate 2 (rho family, small GTP binding protein Rac2)" | 1.929301347 | 1.929301347 |
| AA703652::slit (Drosophila) homolog 3 | -1.92415973 | 1.92415973 |
| "R66139::small inducible cytokine subfamily D (Cys-X3-Cys), member 1 (fractalkine, neurotactin)" | -1.922713842 | 1.922713842 |
| "AA868929::troponin T1, skeletal, slow" | 1.921673212 | 1.921673212 |
| "H29897::phospholipase C, beta 4" | -1.919274065 | 1.919274065 |
| T49652::arachidonate 5-lipoxygenase-activating protein | -1.917007338 | 1.917007338 |
| "AA916325::aldo-keto reductase family 1, member C3 (3-alpha hydroxysteroid dehydrogenase, type II)" | 1.914338217 | 1.914338217 |
| AA490210::tropomyosin 1 (alpha) | -1.912242355 | 1.912242355 |
| "W55872::nuclear factor of kappa light polypeptide gene enhancer in B-cells inhibitor, alpha" | 1.904327253 | 1.904327253 |
| "AA426025::Homer, neuronal immediate | -1.894217323 | 1.894217323 |

FIG. 14 (cont.)

| NAME | fold | absolute value |
|---|---|---|
| early gene, 2" | | |
| "R06438::myosin, light polypeptide kinase" | -1.890475337 | 1.890475337 |
| AA464540::ribosome binding protein 1 (dog 180kD homolog) | -1.885955163 | 1.885955163 |
| AA024832::Homo sapiens mRNA; cDNA DKFZp586I0324 (from clone DKFZp586I0324) | -1.876500492 | 1.876500492 |
| AA488341::cathepsin Z | -1.871330147 | 1.871330147 |
| R01139::ribosomal protein L10a | 1.869509089 | 1.869509089 |
| N22552::forkhead box C1 | -1.867762593 | 1.867762593 |
| T57556::histidine triad nucleotide-binding protein | 1.865648407 | 1.865648407 |
| AA293860::mitogen-activated protein kinase kinase kinase 4 | -1.862818445 | 1.862818445 |
| "AA129736::non-metastatic cells 5, protein expressed in (nucleoside-diphosphate kinase)" | -1.862716369 | 1.862716369 |
| N78902::leptin receptor | 1.862421207 | 1.862421207 |
| "AA456131::carbonic anhydrase VB, mitochondrial" | -1.857206911 | 1.857206911 |
| AA460270::midline 1 (Opitz/BBB syndrome) | -1.8567218 | 1.8567218 |
| AA101875::chondroitin sulfate proteoglycan 2 (versican) | -1.85637627 | 1.85637627 |
| AA004823::death associated transcription factor 1 | -1.846052726 | 1.846052726 |
| "AA461456::collagen, type V, alpha 2" | -1.843117455 | 1.843117455 |
| "R09069::glucan (1,4-alpha-), branching enzyme 1 (glycogen branching enzyme, Andersen disease, glycogen storage disease type IV)" | -1.838745632 | 1.838745632 |
| "H22136::guanylate cyclase 1, soluble, alpha 3" | -1.83462588 | 1.83462588 |
| H97597::glioma pathogenesis-related protein | -1.834069588 | 1.834069588 |
| R38117::peflin | 1.831104076 | 1.831104076 |
| "AA148736::syndecan 4 (amphiglycan, ryudocan)" | -1.830459617 | 1.830459617 |
| AA857163::amphiregulin (schwannoma-derived growth factor) | 1.830409053 | 1.830409053 |
| W49781::leupaxin | -1.830232215 | 1.830232215 |
| AA417881::bleomycin hydrolase | 1.828637476 | 1.828637476 |
| "AA455940::KIAA0473 (DnaJ (Hsp40) | -1.827130139 | 1.827130139 |

FIG. 14 (cont.)

| NAME | fold | absolute value |
|---|---|---|
| homolog, subfamily C, member 6)" | | |
| AA452556::translocating chain-associating membrane protein | -1.826217382 | 1.826217382 |
| "W72033::ras homolog gene family, member 1" | -1.8165783 | 1.8165783 |
| "AA405569::fibroblast activation protein, alpha" | -1.813897645 | 1.813897645 |
| AA115876::protease inhibitor 12 (neuroserpin) | -1.812967111 | 1.812967111 |
| AA521346::serine threonine protein kinase | -1.807083774 | 1.807083774 |
| AA521346::serine threonine protein kinase | -1.807083774 | 1.807083774 |
| "H70099::mannosyl (alpha-1,6-)-glycoprotein beta-1,2-N-acetylglucosaminyltransferase" | -1.806767875 | 1.806767875 |
| AA430512::protease inhibitor 9 (ovalbumin type) | 1.80511413 | 1.80511413 |
| N72259::cornichon-like | 1.799000155 | 1.799000155 |
| AA424629::latent transforming growth factor beta binding protein 2 | -1.79888994 | 1.79888994 |
| "T70198::adaptor-related protein complex 2, mu 1 subunit" | -1.796760465 | 1.796760465 |
| N20798::v-kit Hardy-Zuckerman 4 feline sarcoma viral oncogene homolog | -1.793765791 | 1.793765791 |
| R83000::basic transcription factor 3 | 1.793052693 | 1.793052693 |
| "AA278240::DNA segment, numerous copies, expressed probes (GS1 gene)" | -1.791686812 | 1.791686812 |
| T72171::thyroxin-binding globulin | -1.791481075 | 1.791481075 |
| "AA262080::solute carrier family 12 (sodium/potassium/chloride transporters), member 2" | -1.79001533 | 1.79001533 |
| AA284568::calponin 2 | -1.789404816 | 1.789404816 |
| AA496359::immediate early protein | 1.782262434 | 1.782262434 |
| "H19246::Human clone 23575 mRNA, partial cds" | -1.780160228 | 1.780160228 |
| N78895::KIAA0429 gene product | 1.777754156 | 1.777754156 |
| "H61449::carboxypeptidase N, polypeptide 2, 83kD" | 1.775661534 | 1.775661534 |
| AA458578::KIAA0439 (NEDD4L) | -1.774870149 | 1.774870149 |
| AA455935::Homo sapiens mRNA; cDNA DKFZp564H1916 (from clone DKFZp564H1916) | -1.77406873 | 1.77406873 |
| "R79082::protein tyrosine phosphatase, receptor type, K" | -1.769900054 | 1.769900054 |
| AA043501::v-maf musculoaponeurotic | -1.769495004 | 1.769495004 |

FIG. 14 (cont.)

| NAME | fold | absolute value |
|---|---|---|
| fibrosarcoma (avian) oncogene homolog | | |
| "R59579::prostaglandin D2 synthase (21kD, brain)" | -1.768359484 | 1.768359484 |
| "AA129135::solute carrier family 29 (nucleoside transporters), member 1" | -1.767360435 | 1.767360435 |
| AA405804::lysyl oxidase-like 1 | -1.761855997 | 1.761855997 |
| AA465355::U3 snoRNP-associated 55-kDa protein | 1.761593274 | 1.761593274 |
| "AA865878::actin related protein 2/3 complex, subunit 4 (20 kD)" | -1.760623555 | 1.760623555 |
| AA454215::Homo sapiens clone 23631 mRNA sequence | -1.756250944 | 1.756250944 |
| AA455591::EphB3 | -1.755881896 | 1.755881896 |
| AA172400::retinoic acid induced 3 | -1.755523531 | 1.755523531 |
| AA235332::Ras suppressor protein 1 | -1.752923057 | 1.752923057 |
| "AA019482::creatine kinase, mitochondrial 1 (ubiquitous)" | 1.749064804 | 1.749064804 |
| R26224::membrane-anchored glycoprotein (metastasis and invasion) | -1.742689614 | 1.742689614 |
| "AA454080::inhibitor of DNA binding 4, dominant negative helix-loop-helix protein" | -1.741951911 | 1.741951911 |
| AA102053::tyrosyl-tRNA synthetase | 1.740725446 | 1.740725446 |
| AA496541::KIAA0317 gene product | -1.740526232 | 1.740526232 |
| H26182::neuronal PAS domain protein 2 | -1.738499631 | 1.738499631 |
| T53298::insulin-like growth factor binding protein 7 | -1.736479706 | 1.736479706 |
| AA278402::actin binding protein; macrophin (microfilament and actin filament cross-linker protein) | -1.730557891 | 1.730557891 |
| "AA017526::collagen, type IX, alpha 3" | -1.725062621 | 1.725062621 |
| AA262504::eyes absent (Drosophila) homolog 3 | 1.724477676 | 1.724477676 |
| H00817::lysophospholipase I | 1.724301851 | 1.724301851 |
| AA427561::heparan sulfate proteoglycan 2 (perlecan) | -1.722998438 | 1.722998438 |
| AA055523::calmodulin-like 3 | -1.71815583 | 1.71815583 |
| AA071473::matrilin 2 | -1.71758378 | 1.71758378 |
| AA625890::myosin VI | -1.71645818 | 1.71645818 |
| "AA598487::phosphoribosylglycinamide formyltransferase, phosphoribosylglycinamide synthetase, phosphoribosylaminoimidazole synthetase" | 1.712079868 | 1.712079868 |
| W65461::dual specificity phosphatase 5 | 1.709460116 | 1.709460116 |

FIG. 14 (cont.)

| NAME | fold | absolute value |
|---|---|---|
| AA130870::microtubule-associated protein 4 | -1.708404772 | 1.708404772 |
| AA149527::KIAA0947 protein | -1.70738839 | 1.70738839 |
| "H65395::proteasome (prosome, macropain) activator subunit 2 (PA28 beta)" | 1.702879771 | 1.702879771 |
| W90128::X-box binding protein 1 | 1.701305235 | 1.701305235 |
| W68169::platelet-derived growth factor beta polypeptide (simian sarcoma viral (v-sis) oncogene homolog) | -1.699720045 | 1.699720045 |
| H96235::v-ets avian erythroblastosis virus E26 oncogene homolog 2 | 1.698626929 | 1.698626929 |
| R38619::fucose-1-phosphate guanylyltransferase | -1.697542671 | 1.697542671 |
| H51554::superkiller viralicidic activity 2 (S. cerevisiae homolog)-like | -1.694599351 | 1.694599351 |
| AA496984::KIAA1071 protein (angiomotin) | -1.694402549 | 1.694402549 |
| N51499::A kinase (PRKA) anchor protein 2 | -1.692171779 | 1.692171779 |
| N54123::KIAA0349 protein | -1.689199914 | 1.689199914 |
| R14822::RAN binding protein 1 | 1.689084163 | 1.689084163 |
| H51066::Homo sapiens mRNA for leptin receptor gene-related protein | -1.688194996 | 1.688194996 |
| R10973::tumor susceptibility gene 101 | -1.685851894 | 1.685851894 |
| AA464630::thrombospondin 1 | -1.680830935 | 1.680830935 |
| AA457330::calpain-like protease | -1.676730701 | 1.676730701 |
| R43334::KIAA0410 (Nucleoporin like 1) | -1.674641473 | 1.674641473 |
| "R66447::v-myc avian myelocytomatosis viral related oncogene, neuroblastoma derived" | -1.67320822 | 1.67320822 |
| "AA070226::selenoprotein P, plasma, 1" | -1.673037255 | 1.673037255 |
| H13300::insulin-like growth factor 1 receptor | -1.670870172 | 1.670870172 |
| AA489569::keratin 7 | -1.670236137 | 1.670236137 |
| W95636::glypican 4 | -1.669209299 | 1.669209299 |
| R83837::v-yes-1 Yamaguchi sarcoma viral related oncogene homolog | 1.66837629 | 1.66837629 |
| "AA447600::Homo sapiens clone 628 unknown mRNA, complete sequence" | 1.66783433 | 1.66783433 |
| "AA460731::collagen, type I, alpha 1" | -1.667595918 | 1.667595918 |
| H73590::immunoglobulin mu | 1.667503303 | 1.667503303 |
| "AA772816::Human acidic 82 kDa protein mRNA, complete cds" | 1.66549315 | 1.66549315 |

FIG. 14 (cont.)

| NAME | fold | absolute value |
|---|---|---|
| "AA001449::pleiotrophin (heparin binding growth factor 8, neurite growth-promoting factor 1)" | -1.66495619 | 1.66495619 |
| H73724::cyclin-dependent kinase 6 | -1.664382722 | 1.664382722 |
| AA496691::dystroglycan 1 (dystrophin-associated glycoprotein 1) | -1.664179985 | 1.664179985 |
| "AA076063::Homo sapiens mRNA for caldesmon, 3' UTR" | -1.66408493 | 1.66408493 |
| AA293653::phosphoprotein enriched in astrocytes 15 | -1.663540838 | 1.663540838 |
| "AA432271::protein kinase, AMP-activated, beta 1 non-catalytic subunit" | -1.662274271 | 1.662274271 |
| T52325::DKFZP586B2022 protein | -1.662204365 | 1.662204365 |
| R26707::Human Chromosome 16 BAC clone CIT987SK-A-363E6 | 1.66093671 | 1.66093671 |
| AA459588::H.sapiens seb4D mRNA | -1.660518704 | 1.660518704 |
| "AA443982::protein phosphatase 1, catalytic subunit, alpha isoform" | 1.65857939 | 1.65857939 |
| W77812::cisplatin resistance associated | 1.65681729 | 1.65681729 |
| N79761::DNA-dependent protein kinase catalytic subunit-interacting protein 2 | -1.655595342 | 1.655595342 |
| W80739::Homo sapiens clone 24590 mRNA sequence | -1.655490727 | 1.655490727 |
| N51740::KIAA0879 protein | -1.655092575 | 1.655092575 |
| W69106::chromobox homolog 3 (Drosophila HP1 gamma) | 1.654964431 | 1.654964431 |
| AA430382::nucleoside phosphorylase | 1.654869156 | 1.654869156 |
| AA159194::FAT tumor suppressor (Drosophila) homolog | -1.654638058 | 1.654638058 |
| AA459390::Homo sapiens mRNA; cDNA DKFZp586O2223 (from clone DKFZp586O2223) | -1.651595485 | 1.651595485 |
| AA434159::chromosome 19 open reading frame 3 | -1.650843389 | 1.650843389 |
| AA872704::ribosomal protein S25 | 1.649528226 | 1.649528226 |
| AA167375::KIAA0530 protein | 1.646649919 | 1.646649919 |
| AA456616::ribosomal protein S5 | 1.645372813 | 1.645372813 |
| AA488618::transcription factor CP2 | 1.645239368 | 1.645239368 |
| AA775447::alpha-2-macroglobulin | -1.643579834 | 1.643579834 |
| "AA678280::adaptor-related protein complex 3, beta 1 subunit" | 1.641655187 | 1.641655187 |
| H88599::predicted osteoblast protein | -1.639757216 | 1.639757216 |
| T56013::3-hydroxy-3-methylglutaryl-Coenzyme A synthase 1 (soluble) | -1.637856741 | 1.637856741 |

FIG. 14 (cont.)

| NAME | fold | absolute value |
|---|---|---|
| AA857035::biliverdin reductase B (flavin reductase (NADPH)) | 1.637722601 | 1.637722601 |
| N46419::Homo sapiens mRNA for synaptogyrin 3 | -1.635967979 | 1.635967979 |
| N59532::aminomethyltransferase (glycine cleavage system protein T) | -1.635151256 | 1.635151256 |
| "H16813::protein phosphatase, EF hand calcium-binding domain 1" | 1.634199427 | 1.634199427 |
| AA489602::heat shock protein 75 | 1.633235318 | 1.633235318 |
| AA291412::KIAA0077 protein | -1.632389996 | 1.632389996 |
| N64862::FYN-binding protein (FYB-120/130) | 1.632057516 | 1.632057516 |
| AA130235::KIAA0567 protein | 1.630180461 | 1.630180461 |
| "AA608515::Homo sapiens NADH dehydrogenase (ubiquinone) 1 alpha subcomplex, 5 (13kD, B13) (NDUFA5) mRNA" | 1.629360871 | 1.629360871 |
| AA136054::ATP citrate lyase | -1.627584586 | 1.627584586 |
| AA702548::Homo sapiens clone 24988 mRNA sequence | 1.626216641 | 1.626216641 |
| "T71284::complement component 1, q subcomponent, beta polypeptide" | -1.622771191 | 1.622771191 |
| "H50345::succinate dehydrogenase complex, subunit A, flavoprotein (Fp)" | 1.622421311 | 1.622421311 |
| "AA405190::Homo sapiens signal sequence receptor, gamma (translocon-associated protein gamma) (SSR3), mRNA" | -1.621467924 | 1.621467924 |
| "AA405190::Homo sapiens signal sequence receptor, gamma (translocon-associated protein gamma) (SSR3), mRNA" | -1.621467924 | 1.621467924 |
| N50247::myotubularin related protein 6 | 1.620565098 | 1.620565098 |
| "AA669674::eukaryotic translation initiation factor 3, subunit 6 (48kD)" | 1.619333572 | 1.619333572 |
| "W45165::capping protein (actin filament) muscle Z-line, beta" | -1.618113612 | 1.618113612 |
| AA455896::glypican 1 | -1.617076741 | 1.617076741 |
| AA489752::cyclin G2 | 1.614468287 | 1.614468287 |
| AA018569::KIAA0073 protein | 1.614324525 | 1.614324525 |
| "AA485426::interferon (alpha, beta and omega) receptor 2" | -1.614263941 | 1.614263941 |
| H56109::clone 686 protein | -1.613082972 | 1.613082972 |
| "AA701933::CUG triplet repeat,RNA-binding protein 2" | -1.61295904 | 1.61295904 |

FIG. 14 (cont.)

| NAME | fold | absolute value |
|---|---|---|
| AA777192::polymerase (RNA) II (DNA directed) polypeptide I (14.5kD) | 1.612023379 | 1.612023379 |
| AA669603::membrane protein of cholinergic synaptic vesicles | -1.61193276 | 1.61193276 |
| AA599072::Homo sapiens clone 24422 mRNA sequence | -1.610200981 | 1.610200981 |
| AA702185::aryl hydrocarbon receptor nuclear translocator | -1.609959826 | 1.609959826 |
| N24824::v-kit Hardy-Zuckerman 4 feline sarcoma viral oncogene homolog | -1.608542982 | 1.608542982 |
| "T84633::interferon, alpha-inducible protein (clone IFI-6-16)" | 1.608043797 | 1.608043797 |
| N24113::dual specificity phosphatase 3 (vaccinia virus phosphatase VH1-related) | -1.60698528 | 1.60698528 |
| AA598670::ubiquitin-activating enzyme E1 (A1S9T and BN75 temperature sensitivity complementing) | -1.605446973 | 1.605446973 |
| R60995::coagulation factor C (Limulus polyphemus) homology (cochlin) | 1.60536823 | 1.60536823 |
| "T73556::fatty-acid-Coenzyme A ligase, long-chain 1" | -1.602286078 | 1.602286078 |
| N90109::nucleolin | 1.601119446 | 1.601119446 |
| R19306::nuclear factor I/X (CCAAT-binding transcription factor) | -1.600528721 | 1.600528721 |
| AA608548::SET translocation (myeloid leukemia-associated) | 1.59920726 | 1.59920726 |
| "AA121387::Homo sapiens mRNA for KIAA0560 protein, complete cds" | 1.598638358 | 1.598638358 |
| "AA443510::polymerase (DNA directed), delta 2, regulatory subunit (50kD)" | 1.596301871 | 1.596301871 |
| "AA677167::Homo sapiens mRNA for KIAA0481 protein, complete cds" | -1.59488141 | 1.59488141 |
| H53024::calumenin | -1.593284462 | 1.593284462 |
| AA405769::phosphoenolpyruvate carboxykinase 1 (soluble) | -1.593274881 | 1.593274881 |
| "R91503::ATP-binding cassette, sub-family C (CFTR/MRP), member 2" | 1.591931725 | 1.591931725 |
| AA127116::heterogeneous nuclear ribonucleoprotein A1 | 1.591154581 | 1.591154581 |
| "AA669042::actinin, alpha 1" | -1.590721798 | 1.590721798 |
| W02265::translational inhibitor protein p14.5 | 1.590452022 | 1.590452022 |
| "W02204::solute carrier family 24 (sodium/potassium/calcium exchanger), member 1" | -1.589666867 | 1.589666867 |

FIG. 14 (cont.)

| NAME | fold | absolute value |
|---|---|---|
| AA047443::LIM domain-containing preferred translocation partner in lipoma | -1.589582191 | 1.589582191 |
| "R26046::Homo sapiens clone 23711 unknown mRNA, partial cds" | 1.588478859 | 1.588478859 |
| H01820::KIAA0981 protein | -1.587697544 | 1.587697544 |
| "AA485226::vitamin D (1,25-dihydroxyvitamin D3) receptor" | 1.58596982 | 1.58596982 |
| "AA158035::pyridoxal (pyridoxine, vitamin B6) kinase" | 1.582681016 | 1.582681016 |
| T60109::GTP-binding protein homologous to Saccharomyces cerevisiae SEC4 | -1.582664055 | 1.582664055 |
| "R73003::solute carrier family 16 (monocarboxylic acid transporters), member 4" | -1.581034398 | 1.581034398 |
| W74533::latrophilin | -1.580716387 | 1.580716387 |
| AA053035::Homo sapiens mRNA; cDNA DKFZp586M1418 (from clone DKFZp586M1418) | 1.580365479 | 1.580365479 |
| H41165::ribosomal protein S19 | 1.580337076 | 1.580337076 |
| "AA598815::proteasome (prosome, macropain) subunit, alpha type, 5" | 1.579194098 | 1.579194098 |
| R44822::phosphoribosyl pyrophosphate synthetase-associated protein 1 | -1.579163692 | 1.579163692 |
| "AA417816::protein kinase C, nu" | 1.577960477 | 1.577960477 |
| AA452981::fibulin 2 | -1.576429031 | 1.576429031 |
| AA706987::UDP-N-acetyl-alpha-D-galactosamine:polypeptide N-acetylgalactosaminyltransferase 1 (GalNAc-T1) | 1.576058985 | 1.576058985 |
| AA463924::DNA segment on chromosome X (unique) 522 expressed sequence | -1.575620627 | 1.575620627 |
| AA101299::antiquitin 1 | -1.575529635 | 1.575529635 |
| "W07798::collagen, type XVIII, alpha 1" | -1.57530752 | 1.57530752 |
| H99883::KIAA0828 protein | -1.575289547 | 1.575289547 |
| R71440::collagen-binding protein 2 (colligen 2) | -1.57524205 | 1.57524205 |
| "H65030::phospholipase A2, group VII (platelet-activating factor acetylhydrolase, plasma)" | -1.573523254 | 1.573523254 |
| AA043412::peptidylprolyl isomerase C (cyclophilin C) | -1.573185026 | 1.573185026 |
| AA609783::Homo sapiens mRNA; cDNA DKFZp586A0618 (from clone DKFZp586A0618) | -1.572743449 | 1.572743449 |
| AA031398::src homology three (SH3) and | 1.5712933 | 1.5712933 |

FIG. 14 (cont.)

| NAME | fold | absolute value |
|---|---|---|
| cysteine rich domain | | |
| AA677257::thiopurine S-methyltransferase | 1.570840483 | 1.570840483 |
| H71857::ribosomal protein S23 | -1.570734858 | 1.570734858 |
| "AA425437::immunoglobulin superfamily, member 3" | -1.570636887 | 1.570636887 |
| "W67174::Human beta-1D integrin mRNA, cytoplasmic domain, partial cds" | 1.569071248 | 1.569071248 |
| AA454970::KIAA0204 gene product | 1.568644063 | 1.568644063 |
| AA486728::vinculin | -1.568097757 | 1.568097757 |
| R42763::KIAA0319 gene product | -1.564622344 | 1.564622344 |
| AA431773::Homo sapiens clone 23716 mRNA sequence | -1.562149145 | 1.562149145 |
| "AA621201::solute carrier family 30 (zinc transporter), member 3" | -1.561012145 | 1.561012145 |
| "AA669758::nucleophosmin (nucleolar phosphoprotein B23, numatrin)" | 1.559888337 | 1.559888337 |
| N39229::Human Chromosome 16 BAC clone CIT987SK-A-211C6 | 1.559829194 | 1.559829194 |
| T63971::KIAA0758 protein | -1.559543814 | 1.559543814 |
| "AA598513::protein tyrosine phosphatase, receptor type, F" | -1.558491016 | 1.558491016 |
| "AA776294::Rab geranylgeranyltransferase, alpha subunit" | 1.558057399 | 1.558057399 |
| H54023::leukocyte immunoglobulin-like receptor 2 | -1.557682941 | 1.557682941 |
| AA046650::putative nuclear protein | -1.557316657 | 1.557316657 |
| AA629909::glycyl-tRNA synthetase | 1.557200102 | 1.557200102 |
| "AA490213::transducer of ERBB2, 1" | 1.557162683 | 1.557162683 |
| AA460599::Jun activation domain binding protein | 1.556547909 | 1.556547909 |
| R00595::ribosomal protein L7a | -1.556213335 | 1.556213335 |
| "AA455369::solute carrier family 9 (sodium/hydrogen exchanger), isoform 1 (antiporter, Na+/H+, amiloride sensitive)" | -1.556062009 | 1.556062009 |
| AA732931::syntaxin 4A (placental) | 1.55283088 | 1.55283088 |
| T72336::partner of Ral-binding protein 1 | -1.552445937 | 1.552445937 |
| "H24329::guanylate cyclase 1, soluble, alpha 3" | -1.551165227 | 1.551165227 |
| H10964::peroxisomal biogenesis factor 12 | -1.551107653 | 1.551107653 |
| "AA495846::ras homolog gene family, member B" | -1.550788081 | 1.550788081 |
| "AA018676::protein kinase, AMP-activated, gamma 1 non-catalytic subunit" | 1.550102129 | 1.550102129 |
| R08891::KIAA0676 (GTPase-activating | -1.549787074 | 1.549787074 |

FIG. 14 (cont.)

| NAME | fold | absolute value |
|---|---|---|
| protein GYP2) | | |
| "AA291972::Homo sapiens herpesvirus entry mediator B (poliovirus receptor-related 2) (HVEB), mRNA" | -1.548754346 | 1.548754346 |
| "AA644129::Fanconi anemia, complementation group A" | 1.547495295 | 1.547495295 |
| R70685::jagged1 (Alagille syndrome) | -1.547288914 | 1.547288914 |
| AA430050::KIAA0729 protein | -1.546767815 | 1.546767815 |
| AA442040::Clathrin assembly lymphoid-myeloid leukemia gene | -1.544781235 | 1.544781235 |
| AA190339::dual specificity phosphatase 3 (vaccinia virus phosphatase VH1-related) | -1.543309482 | 1.543309482 |
| AA427891::activated p21cdc42Hs kinase | -1.542956007 | 1.542956007 |
| AA488087::FK506-binding protein 9 (63 kD) | -1.542776909 | 1.542776909 |
| "N30428::nuclear receptor subfamily 3, group C, member 1" | 1.542641398 | 1.542641398 |
| H73727::ribosomal protein S14 | 1.542484352 | 1.542484352 |
| AA633993::cell division cycle 10 (homologous to CDC10 of S. cerevisiae) | 1.54159252 | 1.54159252 |
| N63623::KIAA0471 (RAB GTPase activating protein 1-like) | -1.541259727 | 1.541259727 |
| AA291556::Homo sapiens ras inhibitor (RIN1) mRNA | 1.541198509 | 1.541198509 |
| W58032::frizzled-related protein | -1.540448103 | 1.540448103 |
| AA148230::Tat-interacting protein (30kD) | -1.540213069 | 1.540213069 |
| N29585::KIAA0934 protein | -1.539942583 | 1.539942583 |
| N92519::E2F transcription factor 3 | -1.537359962 | 1.537359962 |
| AA402207::eyes absent (Drosophila) homolog 2 | -1.536366609 | 1.536366609 |
| AA190789::KIAA0746 protein | -1.535761944 | 1.535761944 |
| AA496804::sperm specific antigen 2 | -1.535121028 | 1.535121028 |
| "AA775445::platelet-activating factor acetylhydrolase, isoform Ib, alpha subunit (45kD)" | -1.534418265 | 1.534418265 |
| AA478273::APEX nuclease (multifunctional DNA repair enzyme) | 1.533464674 | 1.533464674 |
| AA490617::vaccinia related kinase 2 | 1.531022678 | 1.531022678 |
| "AA630016::chaperonin containing TCP1, subunit 8 (theta)" | -1.530728652 | 1.530728652 |
| AA458965::natural killer cell transcript 4 | -1.530057192 | 1.530057192 |
| N73761::dihydropyrimidinase | -1.529746375 | 1.529746375 |
| T67066::Homo sapiens clone 24590 mRNA sequence | -1.52969689 | 1.52969689 |

FIG. 14 (cont.)

| NAME | fold | absolute value |
|---|---|---|
| AA458622::BH-protocadherin (brain-heart) | -1.529690169 | 1.529690169 |
| T64469::p8 protein (candidate of metastasis 1) | -1.5288471 | 1.5288471 |
| AA046679::Homo sapiens clone TUA8 Cri-du-chat region mRNA | -1.528652626 | 1.528652626 |
| AA428139::KIAA0936 protein | -1.527437597 | 1.527437597 |
| AA443177::signal recognition particle 72kD | 1.527310506 | 1.527310506 |
| H23021::retinoblastoma-binding protein 8 | -1.52549385 | 1.52549385 |
| AA487589::methionine aminopeptidase; eIF-2-associated p67 | 1.525055432 | 1.525055432 |
| R70518::tumor necrosis factor alpha-inducible cellular protein containing leucine zipper domains; Huntingtin interacting protein L | -1.524434172 | 1.524434172 |
| "AA481026::SWI/SNF related, matrix associated, actin dependent regulator of chromatin, subfamily a, member 2" | 1.524196811 | 1.524196811 |
| R41691::Homo sapiens clone IMAGE 30714 | 1.523348098 | 1.523348098 |
| W95595::corneodesmosin | -1.523238781 | 1.523238781 |
| AA504442::KIAA0029 protein | -1.522313752 | 1.522313752 |
| N26645::Homo sapiens clone 24723 mRNA sequence | -1.521265502 | 1.521265502 |
| H06296::ELL gene (11-19 lysine-rich leukemia gene) | -1.520910382 | 1.520910382 |
| R38201::opioid-binding protein/cell adhesion molecule-like | 1.520308092 | 1.520308092 |
| "AA670429::secretory granule, neuroendocrine protein 1 (7B2 protein)" | -1.517795225 | 1.517795225 |
| N47111::5-hydroxytryptamine (serotonin) receptor 2C | -1.51754042 | 1.51754042 |
| AA486435::chondrocyte-derived ezrin-like protein | -1.515243691 | 1.515243691 |
| AA464612::Homo sapiens mRNA; cDNA DKFZp564H0223 (from clone DKFZp564H0223) | 1.514615397 | 1.514615397 |
| N48000::Homo sapiens mRNA; cDNA DKFZp586L141 (from clone DKFZp586L141) | -1.514598185 | 1.514598185 |
| "AA135813::thymosin, beta 4, X chromosome" | -1.513601015 | 1.513601015 |
| AA478078::KIAA0134 gene product | 1.512984846 | 1.512984846 |
| AA425450::glycoprotein (transmembrane) | -1.512853995 | 1.512853995 |

FIG. 14 (cont.)

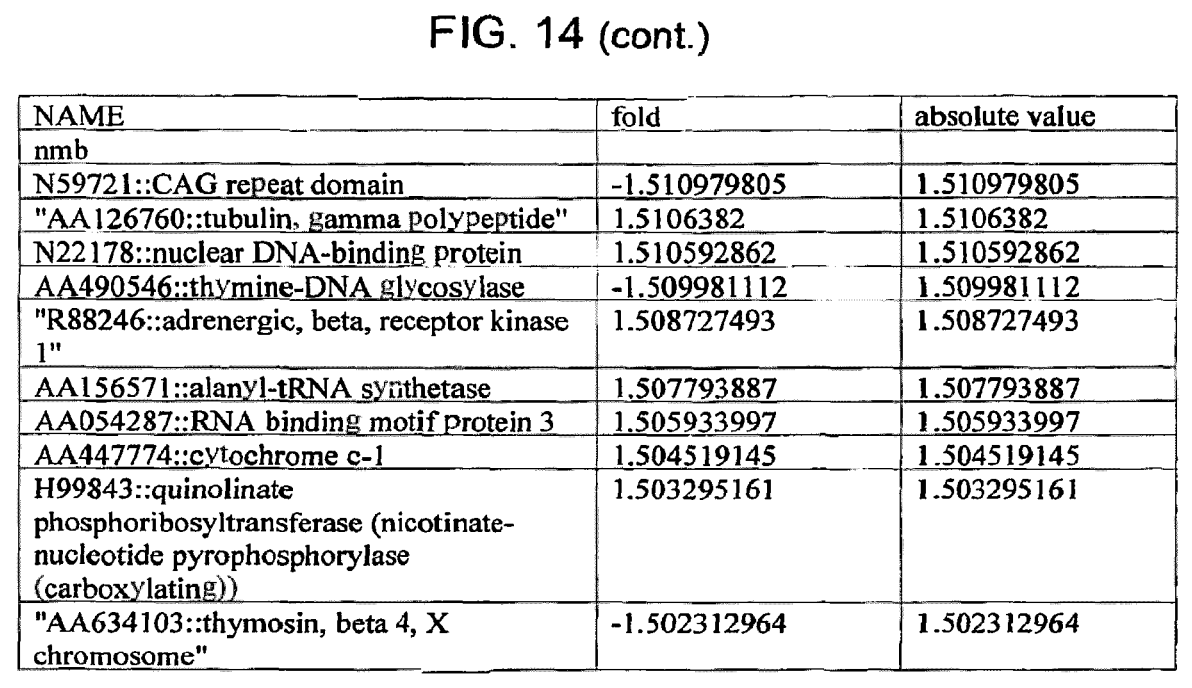

| NAME | fold | absolute value |
|---|---|---|
| nmb | | |
| N59721::CAG repeat domain | -1.510979805 | 1.510979805 |
| "AA126760::tubulin, gamma polypeptide" | 1.5106382 | 1.5106382 |
| N22178::nuclear DNA-binding protein | 1.510592862 | 1.510592862 |
| AA490546::thymine-DNA glycosylase | -1.509981112 | 1.509981112 |
| "R88246::adrenergic, beta, receptor kinase 1" | 1.508727493 | 1.508727493 |
| AA156571::alanyl-tRNA synthetase | 1.507793887 | 1.507793887 |
| AA054287::RNA binding motif protein 3 | 1.505933997 | 1.505933997 |
| AA447774::cytochrome c-1 | 1.504519145 | 1.504519145 |
| H99843::quinolinate phosphoribosyltransferase (nicotinate-nucleotide pyrophosphorylase (carboxylating)) | 1.503295161 | 1.503295161 |
| "AA634103::thymosin, beta 4, X chromosome" | -1.502312964 | 1.502312964 |

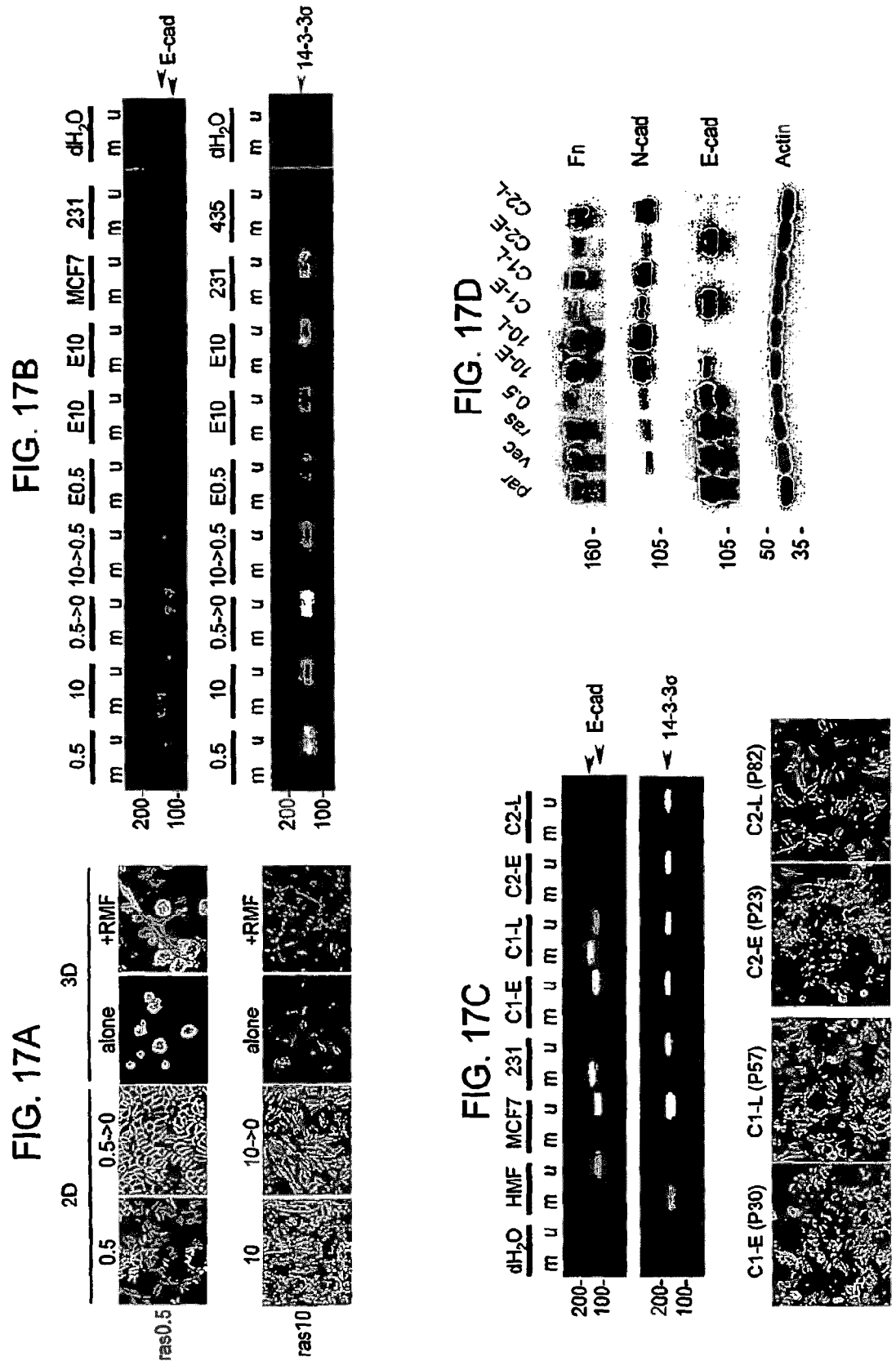

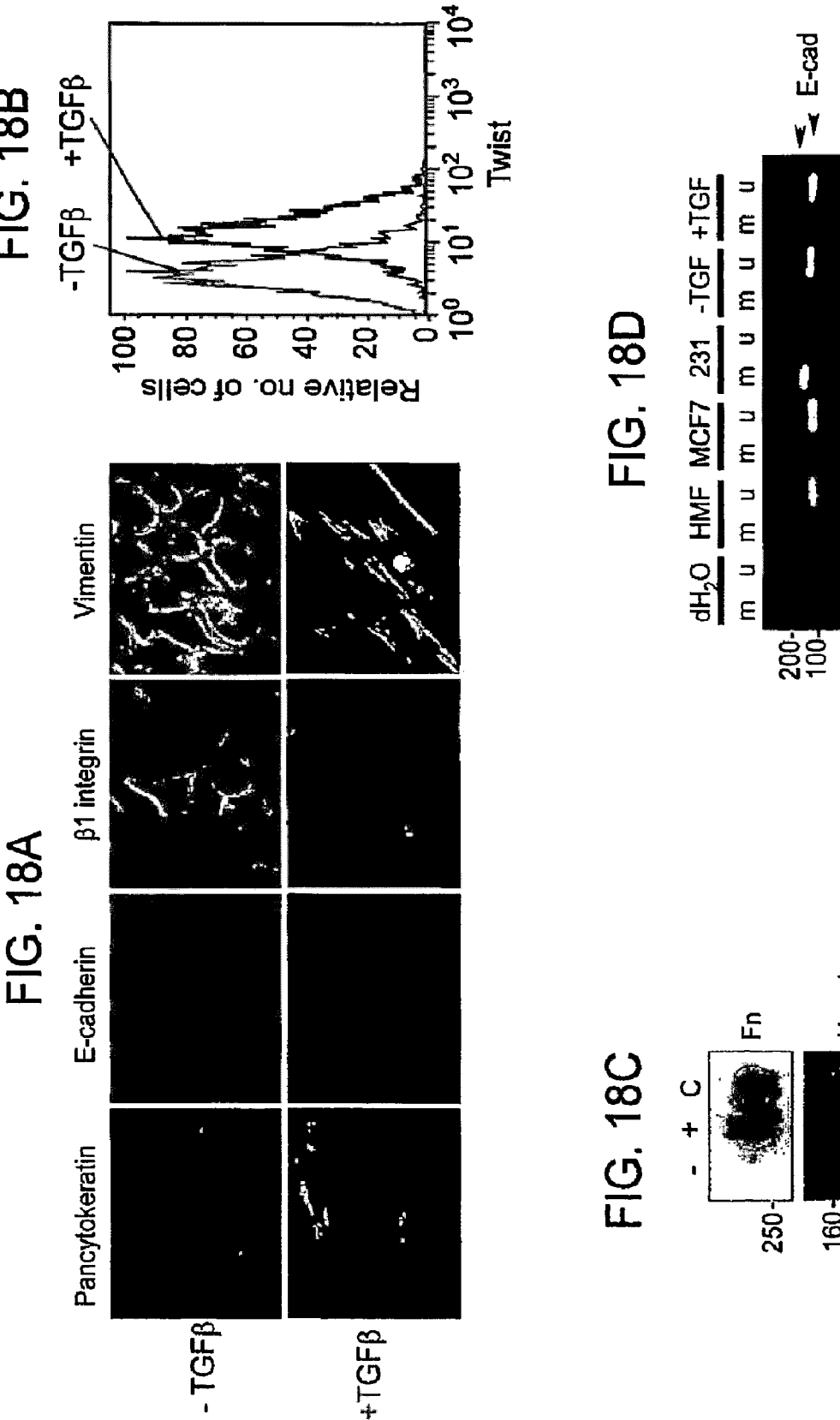

COX-2 RNA Level Arbitrary Units

Ψ*ANOVA, p=0.002

SB203580 μM      0    0.02   0.04      0    0.02   0.04      0    0.02   0.04 parent                    pWP                       TRF2

COX-2 phospho-p38

Actin

SB203580 μM      0    0.02   0.04      0    0.02   0.04      0    0.02   0.04 parent                    pWP                       TRF2

0 hrs          4 hrs          8 hrs parent pWP

TRF2

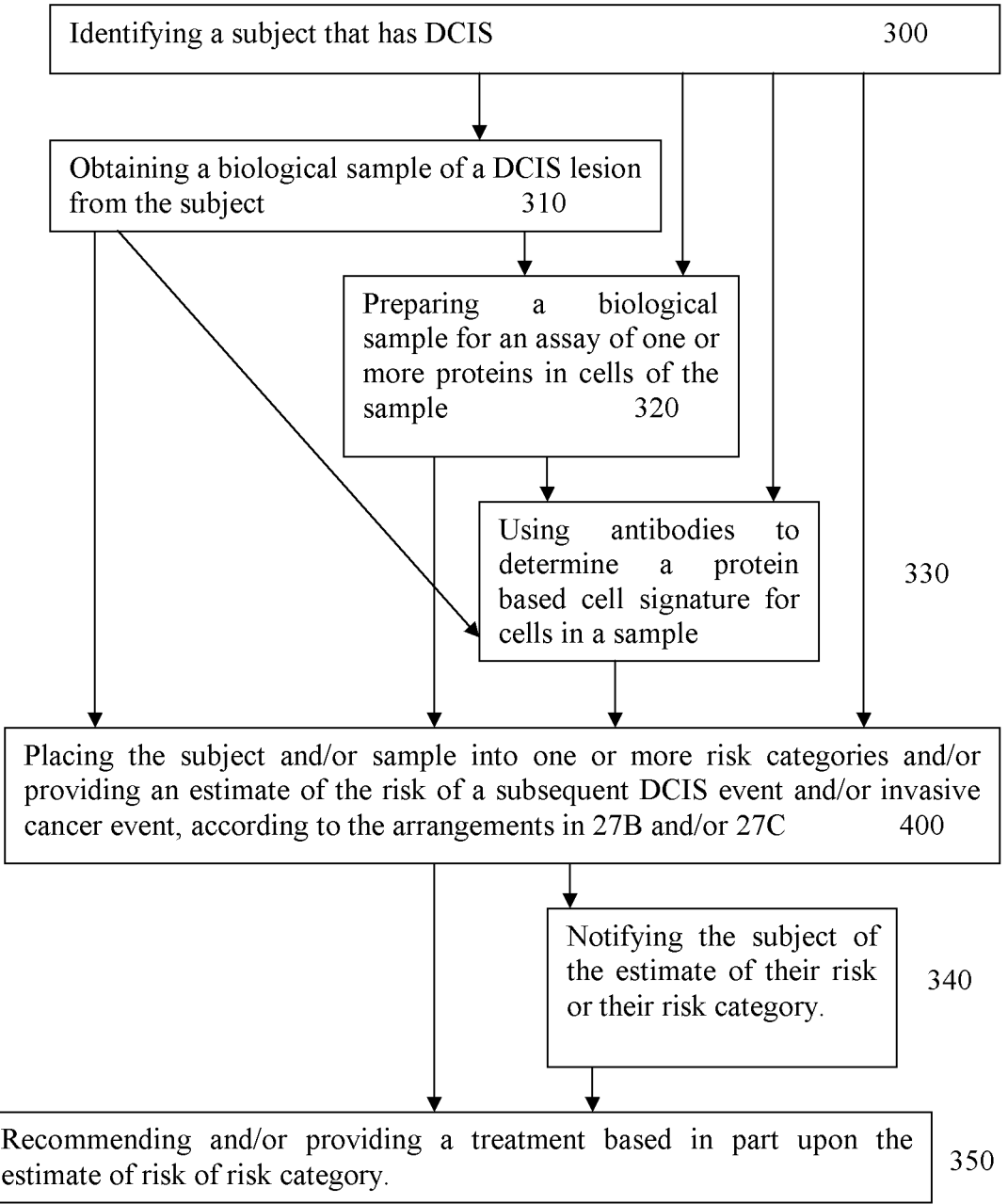

Identifying a subject that has DCIS                                    300

Obtaining a biological sample of a DCIS lesion from the subject                                    310

Preparing a biological sample for an assay of one or more proteins in cells of the sample          320

Using antibodies to determine a protein based cell signature for cells in a sample

330

Placing the subject and/or sample into one or more risk categories and/or providing an estimate of the risk of a subsequent DCIS event and/or invasive cancer event, according to the arrangements in 27B and/or 27C          400

Notifying the subject of the estimate of their risk or their risk category.          340

Recommending and/or providing a treatment based in part upon the estimate of risk of risk category.          350

FIG. 27A

CANCER BIOMARKERS AND METHODS OF USE THEREOF

RELATED APPLICATIONS

This application claims priority to U.S. provisional application No. 61/328,565, filed Apr. 27, 2010, which is incorporated by reference in its entirety.

STATEMENT REGARDING FEDERALLY SPONSORED R&D

The invention was made with government support under CA058207, CA097214, and CA122024 awarded by the NIH/National Cancer Institute. The government has certain rights in the invention.

SEQUENCE LISTING

The present application is being filed along with a Sequence Listing in electronic format. The Sequence Listing is provided as a file entitled, UC102_002A_SeqList.TXT created Apr. 25, 2011, which is 13,637 bytes in size. The information in the electronic format of the Sequence Listing is incorporated herein by reference in its entirety.

BACKGROUND

Field of the Invention

The present invention relates generally to biomarkers for cancer.

Description of the Art

Cancer, like many diseases, is not the result of a single, well-defined cause, but rather can be viewed as several diseases, each caused by different aberrations in informational pathways, that ultimately result in apparently similar pathologic phenotypes. Identification of polynucleotides that correspond to genes that are differentially expressed in cancerous, pre-cancerous, or low metastatic potential cells relative to normal cells of the same tissue type, provides the basis for diagnostic tools, facilitates drug discovery by providing for targets for candidate agents, and further serves to identify therapeutic targets for cancer therapies that are more tailored for the type of cancer to be treated.

SUMMARY OF THE INVENTION

Some embodiments provided herein provide detection methods for detecting a pre-cancerous epithelial cell signature. Some embodiments provide reagents for use in the detection methods. In some embodiments, a subject detection method is useful in various imaging, diagnostic, prognostic, and patient monitoring methods, which are also provided.

In some embodiments, a method of characterizing a sample is provided. The method can comprise providing a tissue sample from a DCIS lesion from a subject, scoring Ki67 from the tissue sample, and scoring at least one of the following: COX-2, p16, ER, PR, and ERBB2 from the tissue sample.

In some embodiments, a method of categorizing a risk that a subject that has Ductal Carcinoma in situ (DCIS) will have a subsequent DCIS event is provided. The method can comprise analyzing a cell signature of a DCIS lesion from a subject for a group of biomarkers, wherein the biomarkers comprise: at least one of the following: Ki67, ERBB2, PR, and ER and at least one of the following: COX-2 and p16. The method can also comprise placing the subject into a risk category for DCIS recurrence (and/or subsequent DCIS) based on the analysis of the cell signature.

In some embodiments, a method for categorizing a risk that a subject that has Ductal Carcinoma in situ (DCIS) will have a subsequent invasive cancer and/or DCIS event is provided. The method can comprise analyzing a cell signature from a subject for a group of biomarkers, wherein the biomarkers comprise at least three of the following: COX-2, Ki67, p16, erb-B2, and ER, and placing the subject into a risk category for a subsequent invasive cancer and/or DCIS event based upon the analysis of the cell signature for the group of biomarkers.

In some embodiments, an assay kit for detecting a risk that a subject having DCIS will experience at least one of the following: a subsequent DCIS event, invasive breast cancer, no subsequent cancer event, or some combination thereof is provided. The kit can comprise reagents for determining a mammary epithelial cell signature, wherein the signature comprises a collection of measurements of at least three characteristics of the mammary epithelial cell, and the at least three characteristics selected from one or more of the following: presence and/or level of a protein; and presence and/or level of a mRNA; presence and/or level of a post-translationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism. In some embodiments, the reagents determine at least the three of the following: COX-2, Ki67, p16, ERBB2, ER, and some combination thereof.

In some embodiments, a method for estimating risk that a subject initially diagnosed with a Ductal Carcinoma in situ (DCIS) lesion will subsequently develop invasive cancer is provided. The method can comprise obtaining a tissue sample from the initial DCIS lesion, scoring expression of Ki67, COX-2 and p16 in the tissue sample, and estimating the risk based upon the scoring of Ki67, COX-2 and p16.

In some embodiments, a method of characterizing a sample is provided. The method can comprise providing a tissue sample from a DCIS lesion from a subject, scoring Ki67 from the tissue sample, and scoring at least three of the following: COX-2, p16, ER, PR, and ERBB2 from the tissue sample.

In some embodiments, a method for categorizing a risk that a subject that has Ductal Carcinoma in situ (DCIS) will have a subsequent invasive cancer and/or DCIS event is provided. The method can comprise analyzing a cell signature from a subject for a group of biomarkers, wherein the biomarkers comprise at least four of the following: COX-2, Ki67, p16, erb-B2, and ER, and placing the subject into a risk category for a subsequent invasive cancer and/or DCIS event based upon the analysis of the cell signature for the group of biomarkers.

In some embodiments, an assay kit for detecting a risk that a subject having DCIS will experience at least one of the following: a subsequent DCIS event, invasive breast cancer, no subsequent cancer event, or some combination thereof, is provided. The kit can comprise reagents for determining a mammary epithelial cell signature, wherein the signature comprises a collection of measurements of at least four characteristics of the mammary epithelial cell, said at least four characteristics selected from one or more of the following: presence and/or level of a protein; and presence and/or level of a mRNA, presence and/or level of a post-translationally modified polypeptide, presence of a chromatin modification; presence and/or level of a sequence of DNA, presence and/or level of a microRNA, integrity of a nucleic acid; methylation status of a nucleic acid, secretion and/or release of a factor, and alteration in a metabolism. In some embodiments, the reagents determine at least the four of the following: COX-2, Ki67, p16, ERBB2, ER, and some combination thereof.

In some embodiments, a method is provided of categorizing a risk that a subject that has Ductal Carcinoma in situ (DCIS) will have a subsequent DCIS event, said method comprising analyzing a cell signature of a DCIS lesion from a subject for a group of biomarkers, wherein the biomarkers comprise: at least one of the following: Ki67, ERBB2, ER, and PR and at least one of the following: COX-2 and p16; and placing the subject into a specific risk category for DCIS recurrence based on the analysis of the cell signature.

In some embodiments, placing the subject into a specific risk category comprises placing the subject into one of at least three risk categories, wherein the at least three risk categories comprise a first risk category of DCIS recurrence, a second risk category of DCIS recurrence, and a third risk category of DCIS recurrence, wherein the risk of DCIS recurrence for the first category is lower than the risk of DCIS recurrence for the second category, and wherein the risk of DCIS recurrence for the second category is lower than the risk of DCIS recurrence for the third category. In some embodiments, the first risk category indicates a lowest risk of recurrence, wherein the third risk category indicates a highest risk of recurrence, and wherein the second risk category is divided into at least two subgroups, a first subgroup having a low risk of recurrence and a second subgroup having an intermediate risk of recurrence that is intermediate to the low risk of recurrence and the highest risk of recurrence. In some embodiments, if the tumor is ER positive, ERBB2 negative, and Ki67 negative, the subject falls within the first risk category. In some embodiments, if the tumor is PR positive, ERBB2 negative, and Ki67 negative, the subject falls within the first risk category. In some embodiments, if the DCIS lesion has a margin of 1 mm or greater that is disease free, the subject falls within the first risk category. In some embodiments, if the Van Nuys Prognostic Index is low (scores 3-4), the subject falls within the first risk category. In some embodiments, if the tumor is a) ER negative, ERBB2 positive, and Ki67 positive, or b) p16 positive, Ki67 positive, and COX-2 negative, the subject falls within the third risk category. In some embodiments, if the tumor has a margin of 1 mm or greater that is disease free, the subject falls within the third risk category. In some embodiments, if the Van Nuys Prognostic Index is high (scores 8-9), the subject falls within the third risk category.

In some embodiments, if the tumor is either a) ER negative and ERBB2 negative, b) p16 positive and Ki67 positive, c) COX-2 negative and Ki67 positive, d) COX-2 positive or Ki67 positive, or e) ERBB2 positive and ER positive the subject falls within the first subgroup of the second risk category. In some embodiments, if the tumor is ERBB2 positive and PR positive the subject falls within the first subgroup of the second risk category. In some embodiments, if the tumor is ERBB2 positive and (ER positive or PR positive) the subject falls within the first subgroup of the second risk category. In some embodiments, if the tumor has a margin of 1 mm or greater that is disease free, the subject falls within the first subgroup of the second risk category. In some embodiments, if the tumor is a) ER negative and Ki67 positive or b) ER negative and ERBB2 positive, the subject falls within the second subgroup of the second risk category. In some embodiments, if the tumor is a) ER negative and PR negative and Ki67 positive or b) ER negative and PR negative and ERBB2 positive, the subject falls within the second subgroup of the second risk category. In some embodiments, if the tumor has positive or uncertain margins, the subject falls within the second subgroup of the second risk category.

In some embodiments, the five year risk of DCIS for the first risk category is 2.7% (with a 95% CI of 2.4-3.2). In some embodiments, the eight year risk of DCIS for the first risk category is 3.9% (with a 95% CI of 3.3-4.8). In some embodiments, the five year risk of DCIS for the first subgroup of the second risk category is 7.8% (with a 95% CI of 6.8-8.7). In some embodiments, the eight year risk of DCIS for the first subgroup of the second risk category is 10.2% (with a 95% CI of 8.1-12.7). In some embodiments, the five year risk of DCIS for the second subgroup of the second category is 12% (with a 95% CI of 11.4-12.6). In some embodiments, the eight year risk of DCIS for the second subgroup of the second risk category is 14.4% (with a 95% CI of 13.6-15.2). In some embodiments, the five year risk of DCIS for the third risk category is 19.2% (with a 95% CI of 15.3-23.9). In some embodiments, the eight year risk of DCIS for the third risk category is 23.6% (with a 95% CI of 18.1-34). In some embodiments, a method also includes the step of recommending an appropriate treatment option for the DCIS lesion that the subject currently has in order to reduce the risk of a subsequent DCIS or subsequent invasive cancer event. In some embodiments, a method also includes the step of performing an appropriate treatment option for the DCIS lesion that the subject currently has in order to reduce the risk of a subsequent DCIS or subsequent invasive cancer event. In some embodiments, the placement of the subject into a risk category does not include the use of analysis of the grade of the DCIS lesion. In some embodiments, the placement of the subject into a risk category employs a single clinical and/or histopathological characteristic, and the single clinical and/or histopathological characteristic is tumor margin. In some embodiments, the placement of the subject into a risk category does not include one or more of the following: the use of analysis of the grade of the DCIS, family history, age at diagnosis, menopausal status, tumor size, tumor necrosis, multifocality, and any combination thereof. In some embodiments, a lumpectomy is performed on a subject placed in the third risk category to remove the DCIS. In some embodiments, a mastectomy is performed on a subject placed in the first risk category, if the subject is also at high risk of developing invasive cancer.

In some embodiments, a method is provided for categorizing a risk that a subject that has Ductal Carcinoma in situ (DCIS) will have a subsequent tumor event is provided. The method comprises analyzing a cell signature from a subject for a group of biomarkers, wherein the biomarkers comprise at least the following: COX-2, Ki67, p16, erb-B2, and ER; and placing the subject into a risk category for a subsequent tumor event based upon the analysis of the cell signature for the group of biomarkers. In some embodiments, the subsequent tumor event comprises either an invasive cancer or a DCIS lesion, and wherein the subject is placed into either a) a specific risk category for an invasive cancer or b) a specific risk category for a DCIS lesion. In some embodiments, placing the subject into a specific risk category for either invasive cancer or a subsequent DCIS event comprises placing the subject into either: a) one of at least four risk categories for invasive cancer, wherein the at least four risk categories comprise: a first risk category of invasive cancer, a second risk category of invasive cancer, a third risk category of invasive cancer, and a fourth risk category of invasive cancer, wherein if the tumor is Ki67 negative, COX-2 negative, and p16 negative, then the subject falls within the first category, wherein if the tumor is a) Ki67 negative and b) any of: COX-2 positive, p16 positive, or COX-2 and p 16 positive, then the subject falls within the second category, wherein if the tumor is Ki67 positive and either a) COX-2 positive, b) p16 positive, or c) COX-2 negative and p16 negative, then the subject falls within the third category, wherein, if the tumor is p16 positive, Ki67 positive, and COX-2 positive, then the subject falls within the fourth category; wherein the risk of invasive cancer for the first category is lower than the risk of invasive cancer for the second category, wherein the risk of invasive cancer for the second category is lower than the risk of invasive cancer for the third category, and wherein the risk of invasive cancer of the third category is lower than the risk of invasive cancer in the fourth category; or b) one of at least four risk categories for DCIS recurrence, wherein the at least four risk categories comprise: a first risk category of DCIS recurrence, a second risk category of DCIS recurrence, a third risk category of DCIS recurrence, and a fourth risk category of DCIS recurrence, wherein the risk of DCIS recurrence for the first category is lower than the risk of DCIS recurrence for the second category, wherein the risk of DCIS recurrence for the second category is lower than the risk of DCIS recurrence for the third category, and wherein the risk of DCIS recurrence of the third category is lower than the risk of DCIS recurrence in the fourth category, and wherein if the subject is ER positive, ERBB2 negative and Ki67 negative, then the subject falls within the first category, wherein if the subject is a) ER negative and ERBB2 negative, b) p16 and Ki67 positive, c) COX-2 negative and Ki67 positive, d) COX-2 positive and Ki67 positive, or e) ERBB2 positive and ER positive, then the subject falls within the second category, wherein if the subject is a) ER negative and Ki67 positive or b) ER negative and ERBB2 positive, then the subject falls within the third category, and wherein if the subject is a) ER negative, ERBB2 positive, and Ki67 positive, or b) p16 positive, Ki67 positive and COX-2 negative, then the subject falls within the fourth category. In some embodiments, a method also includes the step of recommending a removal procedure for the DCIS that the subject has based upon the categorization of risk, wherein if the subject is in the fourth category of risk for DCIS, the recommendation is appropriate for reducing the chance of DCIS recurrence, wherein if the subject is in the fourth category of risk for invasive cancer, the recommendation is appropriate for reducing the chance of invasive cancer. In some embodiments, the removal procedure for reducing the chance of invasive cancer comprises a mastectomy. In some embodiments, the removal procedure for reducing the chance of DCIS recurrence comprises a lumpectomy. In some embodiments, the biomarkers are selected from the following: COX-2, Ki67, p16, and some combination thereof. In some embodiments, the biomarkers include p16. In some embodiments, the five year risk of invasive cancer for the first risk category is 2.1% (with a 95% CI of 1.9 to 2.6). In some embodiments, the eight year risk of invasive cancer for the first risk category is 4.1% (with a 95% CI of 3.4 to 5.0). In some embodiments, the five year risk of invasive cancer for the second risk category is 4.4% (with a 95% CI of 4.0 to 5.0). In some embodiments, the eight year risk of invasive cancer for the second risk category is 6.9% (with a 95% CI of 6.1 to 8.0). In some embodiments, the five year risk of invasive cancer for the third risk category is 7.7% (with a 95% CI of 7.0 to 8.5). In some embodiments, the eight year risk of invasive cancer for the third risk category is 11.5% (with a 95% CI of 10.3 to 12.8). In some embodiments, the five year risk of invasive cancer for the fourth risk category is 14.1% (with a 95% CI of 13.1 to 15.3). In some embodiments, the eight year risk of invasive cancer for the fourth risk category is 19.6% (with a 95% CI of 18.0 to 21.3).

In some embodiments, a method is for categorizing a risk that a subject that has Ductal Carcinoma in situ (DCIS) will have a subsequent tumor event is provided. The method comprises analyzing a cell signature from a subject for a group of biomarkers, wherein the biomarkers comprise at least the following: COX-2, Ki67, p16, erb-B2, and PR; and placing the subject into a risk category for a subsequent tumor event based upon the analysis of the cell signature for the group of biomarkers.

In some embodiments, an assay kit for detecting a risk that a subject having DCIS will experience at least one of the following: a) a subsequent DCIS event, b) invasive breast cancer, c) no subsequent cancer event, or some combination thereof, said kit comprising reagents for determining a mammary epithelial cell (or stroma cell, and/or nonepithelial cell) signature, wherein the signature comprises a collection of measurements of at least five characteristics of the mammary epithelial cell, (stroma cell, and/or nonepithelial cell), said at least five characteristics selected from one or more of the following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism, and wherein said reagents determine at least the following: COX-2, Ki67, p16, ERBB2, and ER. In some embodiments, said reagents determine at least two or more of the following: COX-2, Ki67, p16, ERBB2, and PR. In some embodiments, said reagents determine at least the following: COX-2, Ki67, p16. In some embodiments, an assay kit includes a table that provides risk categories for specific cell signatures.

In some embodiments, an assay kit for detecting a risk that a subject having DCIS will experience a subsequent invasive breast cancer, said kit comprising a lookup table for risk assessment based on palpation and cell signature, and the reagents for determining a mammary epithelial cell (or stroma cell, and/or nonepithelial cell) signature, wherein the signature comprises a collection of measurements of at least three characteristics of the mammary epithelial cell, (stroma cell, and/or nonepithelial cell), said at least three characteristics selected from one or more of the following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism, and wherein said reagents determine at least the following: COX-2, Ki67, and p16.

In some embodiments, an assay kit for detecting a risk that a subject having DCIS will experience at least one of the following: a) a subsequent DCIS event, b) invasive breast cancer, c) no subsequent cancer event, or some combination thereof, said kit comprising reagents for determining a mammary epithelial cell (or stroma cell, and/or nonepithelial cell) signature, wherein the signature comprises a collection of measurements of at least five characteristics of the mammary epithelial cell, (stroma cell, and/or nonepithelial cell), said at least five characteristics selected from one or more of the following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism, and wherein said reagents determine at least the following: COX-2, Ki67, p16, ERBB2, and PR.

In some embodiments, a method of making a medical report related to the risk of breast cancer tumor recurrence in a subject, comprising: providing a biological sample from said subject; determining a mammary epithelial cell signature for said biological sample, wherein the signature comprises a collection of measurements of at least two characteristics of the mammary epithelial cell, said at least two characteristics selected from one or more of following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism; comparing the mammary epithelial cell signature of said biological sample with a mammary epithelial cell signature of a control sample; determining the risk of breast cancer recurrence; and generating a report related to the risk of breast cancer recurrence.

In some embodiments, a method of determining a treatment approach for a subject, said method comprising: providing a biological sample; testing the biological sample for one or more markers to provide a cell signature for the biological sample; analyzing the biological profile to determine a risk that a subject from which the sample was taken will experience one of the following: invasive cancer, recurrent DCIS, or no subsequence related event; selecting a treatment approach that is commensurate with the level of risk for the relevant experience; and performing said treatment on said subject.

8

FIGS. 8A-D depict concordance between p16 or COX-2 mRNA and protein expression in tumors.

Figure 9:
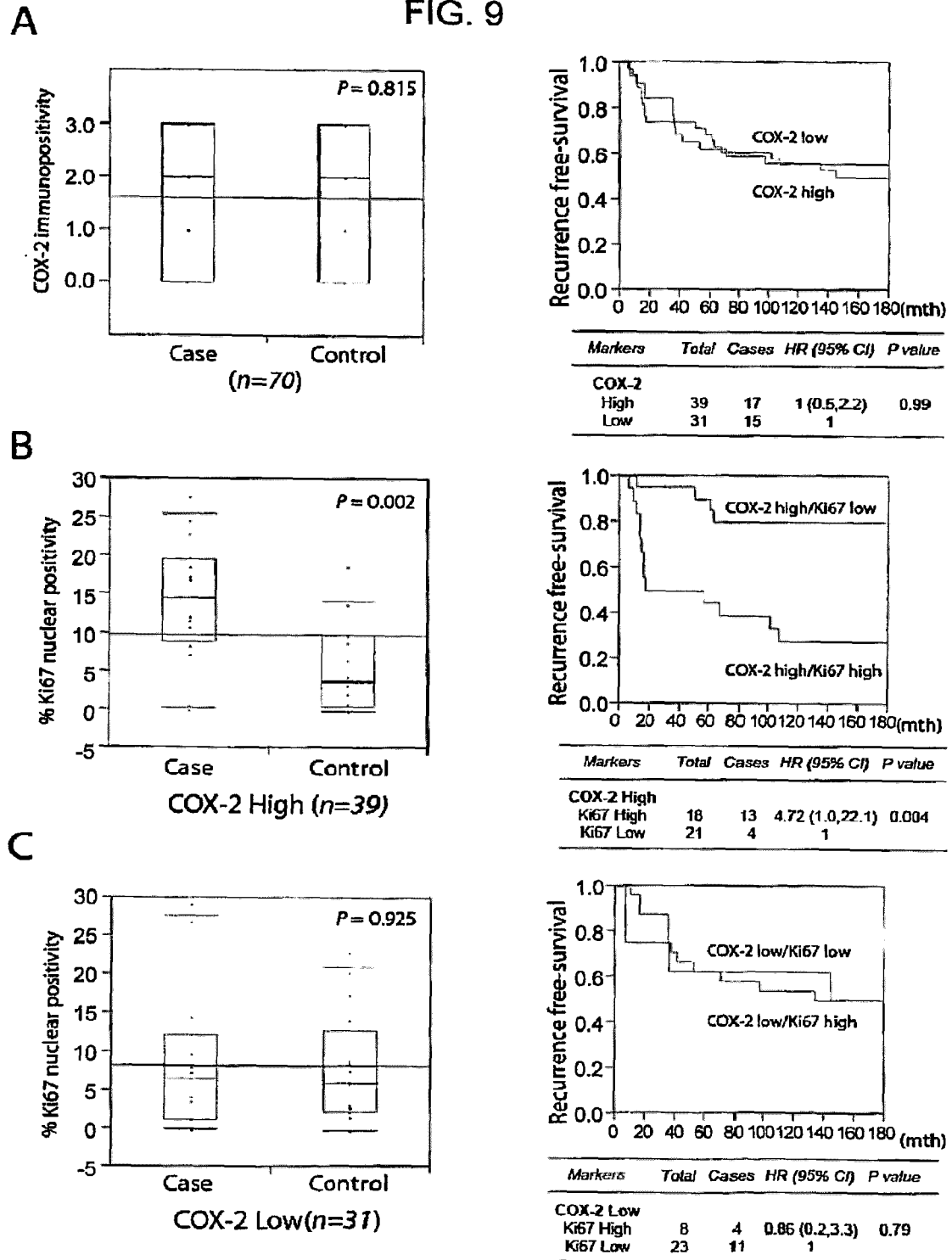

FIGS. 9A-C depict the correlation between COX-2 overexpression, coupled with proliferation, with increased risk of subsequent tumor events among women with DCIS.

Figure 10:
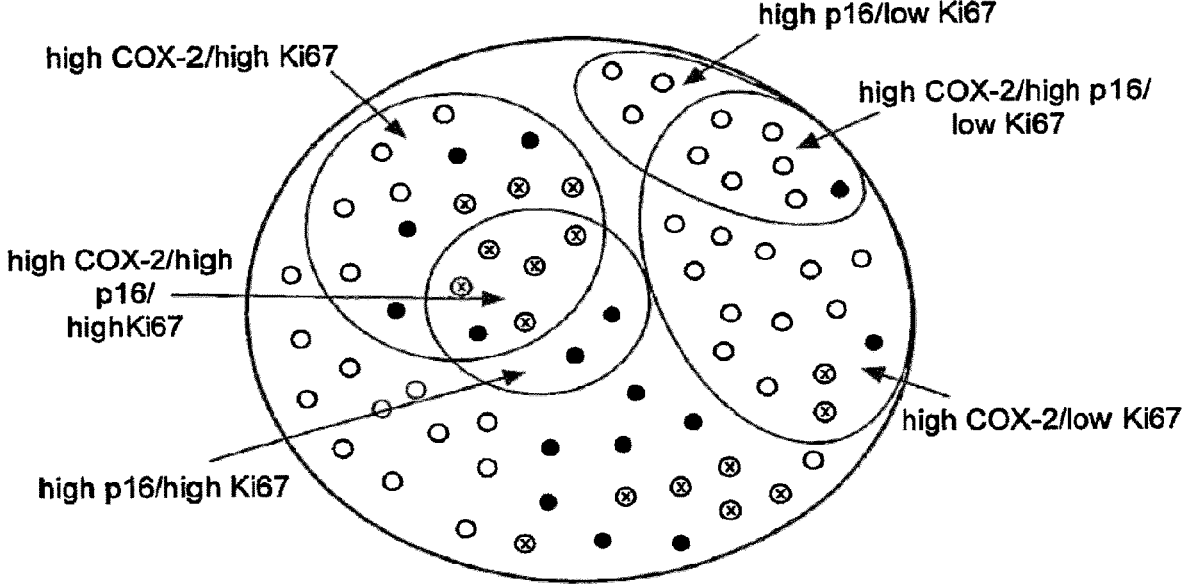

FIG. 10 is a diagram representing DCIS lesions expressing combinations of p16, COX-2 and Ki67.

Figure 11:
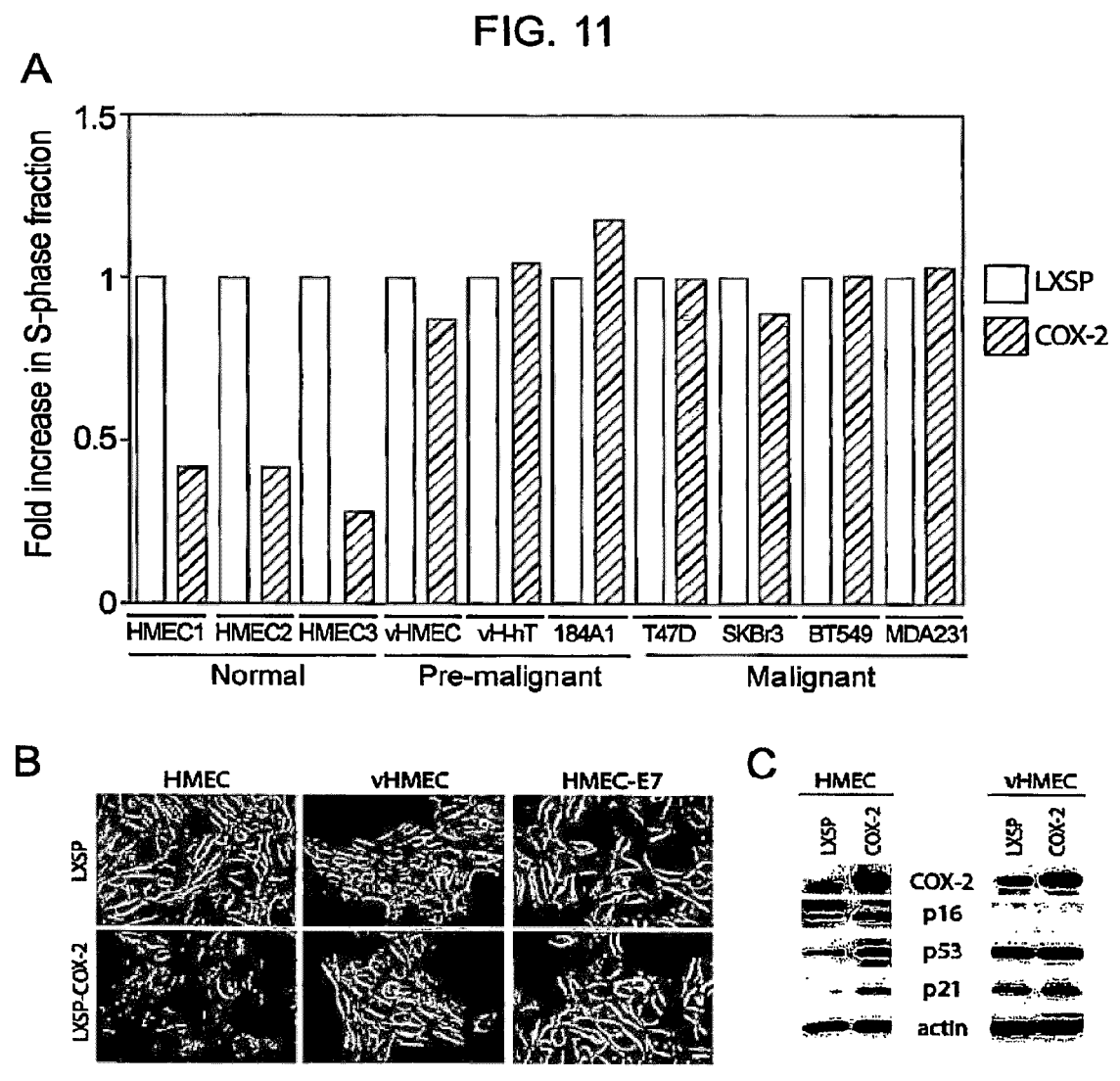

FIGS. 11A-C depict the relationship between overexpression of COX-2, in the absence or presence of proliferation, and p16/Rb dysfunction.

FIGS. 12A-E depict differential regulation of COX-2 by deregulation of distinct members of the p16/cyclin D1/Rb pathway.

Figure 13:
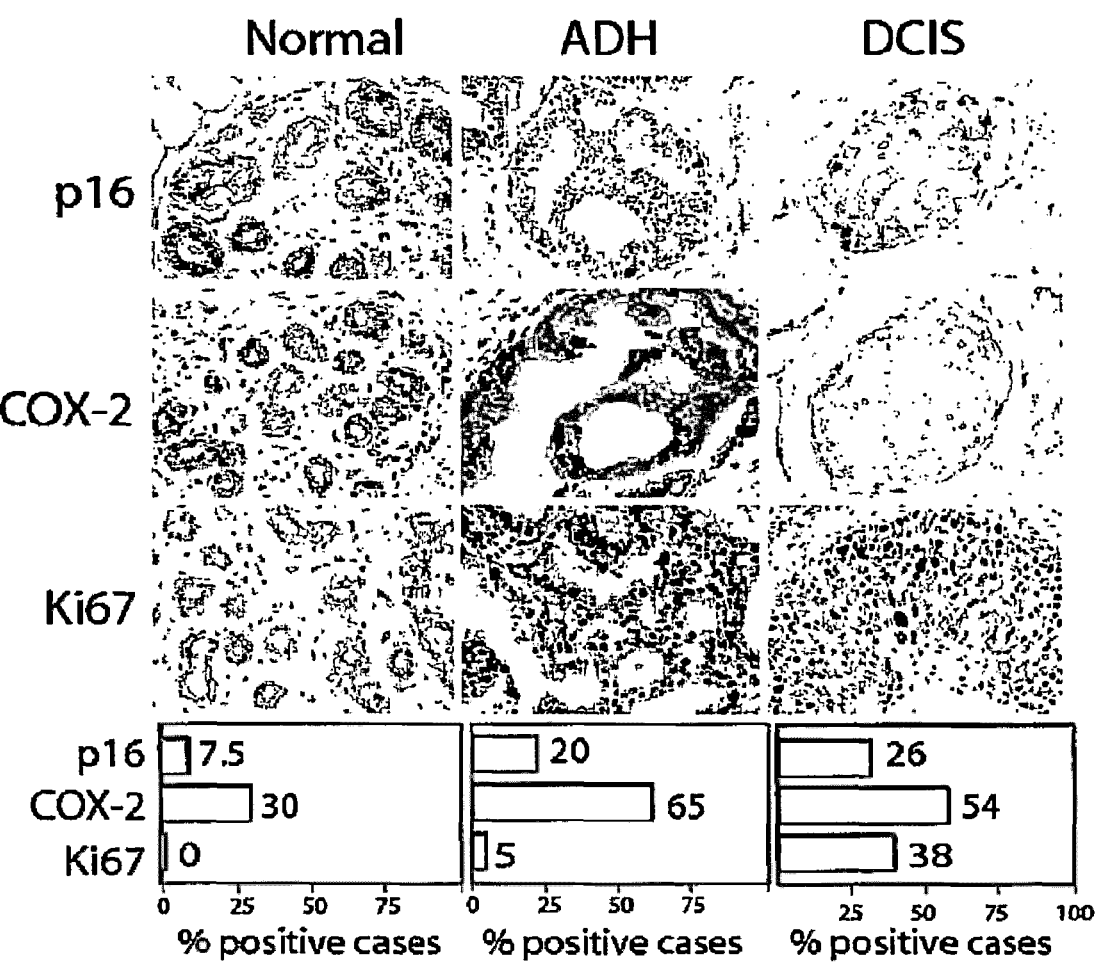

FIG. 13 depicts identification by p16 and COX-2 overexpression of a subset of epithelial cells in normal breast tissue and atypical ductal hyperplasias, for use in risk stratification.

FIG. 14 depicts mRNAs that are over-expressed or under-expressed in vHMEC, compared to normal HMEC.

Figure 15:
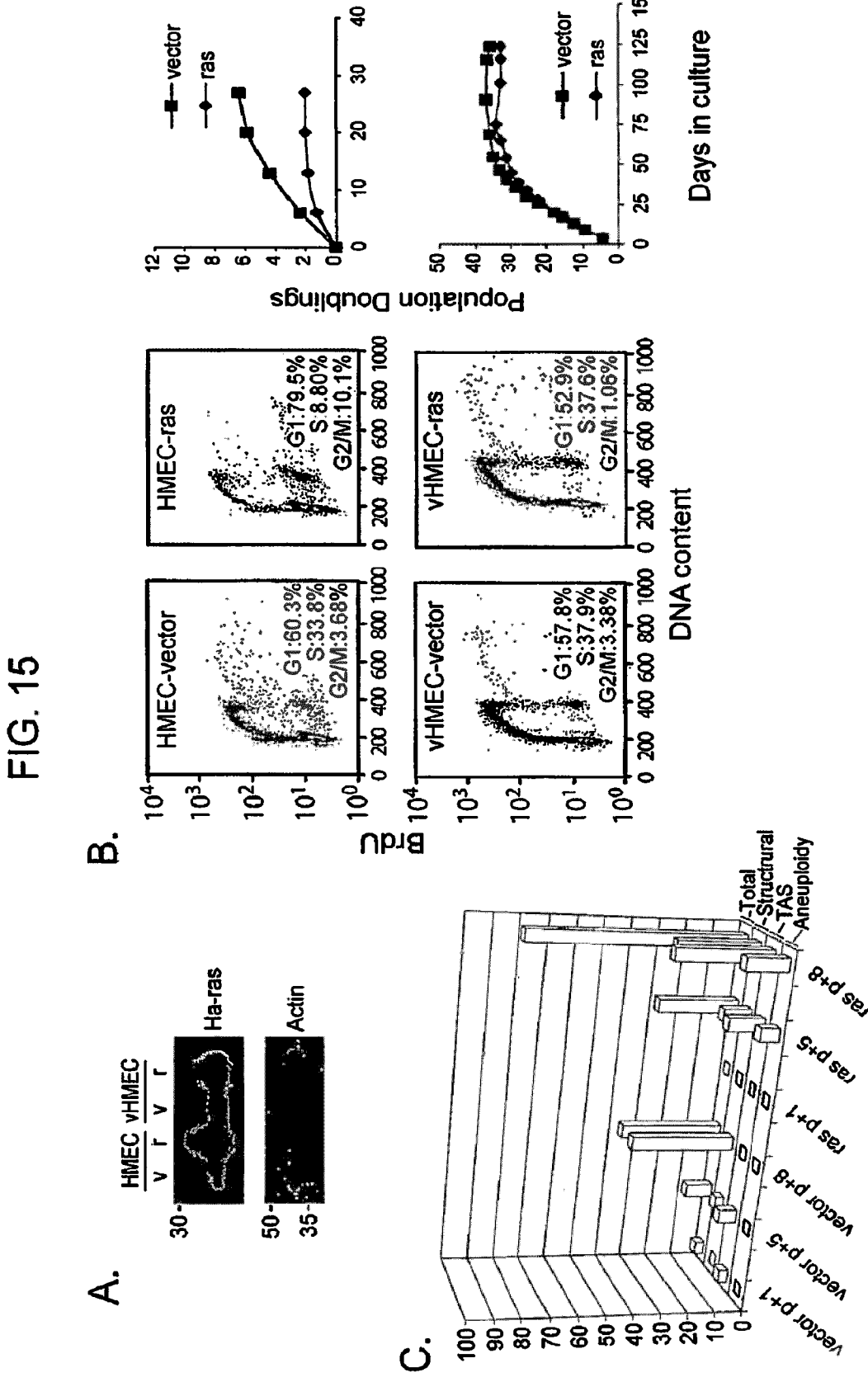

FIGS. 15A-C depict immunoblot analysis (FIG. 15A), cell cycle analysis (FIG. 15B), and chromosome analysis (FIG. 15C) of vHMEC comprising a control expression vector or a Ha-rasV12 expression vector.

Figure 16A:
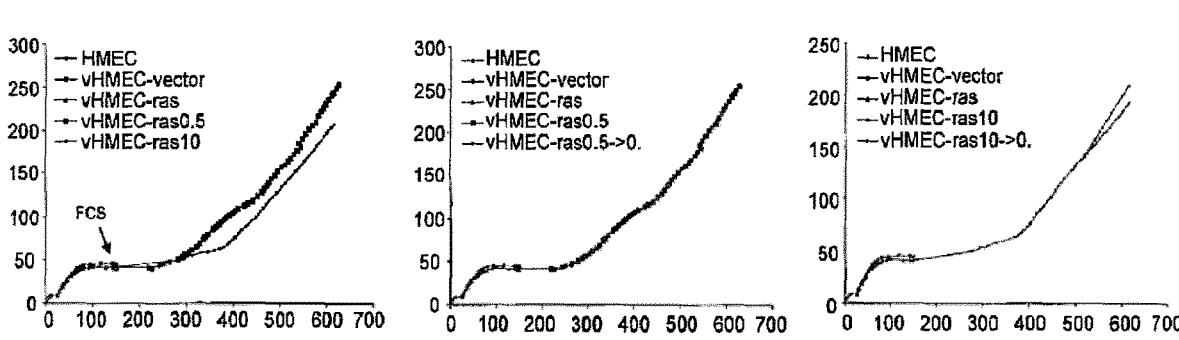
Figure 16B:
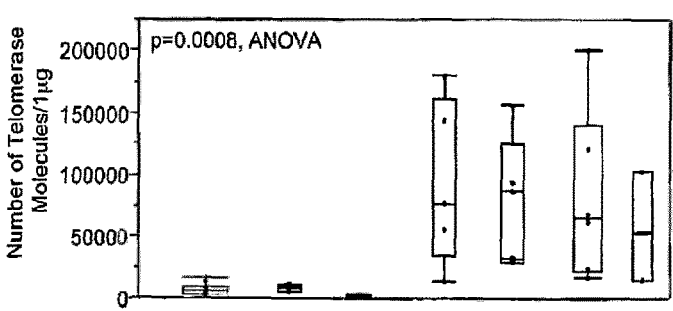

FIGS. 16A and 16B depict the effect of serum-induced extracellular signaling and intracellular ras activation on immortalization of vHMEC (FIG. 16A) and vHMEC telomerase activity (FIG. 16B).

FIGS. 17A-D depict the effect of extracellular signaling and intracellular ras activation on cellular morphology and methylation in HMEC.

FIGS. 18A-D depict the effect of TGFβ on EMT in vHMEC-ras0.5 cells.

Figure 19:
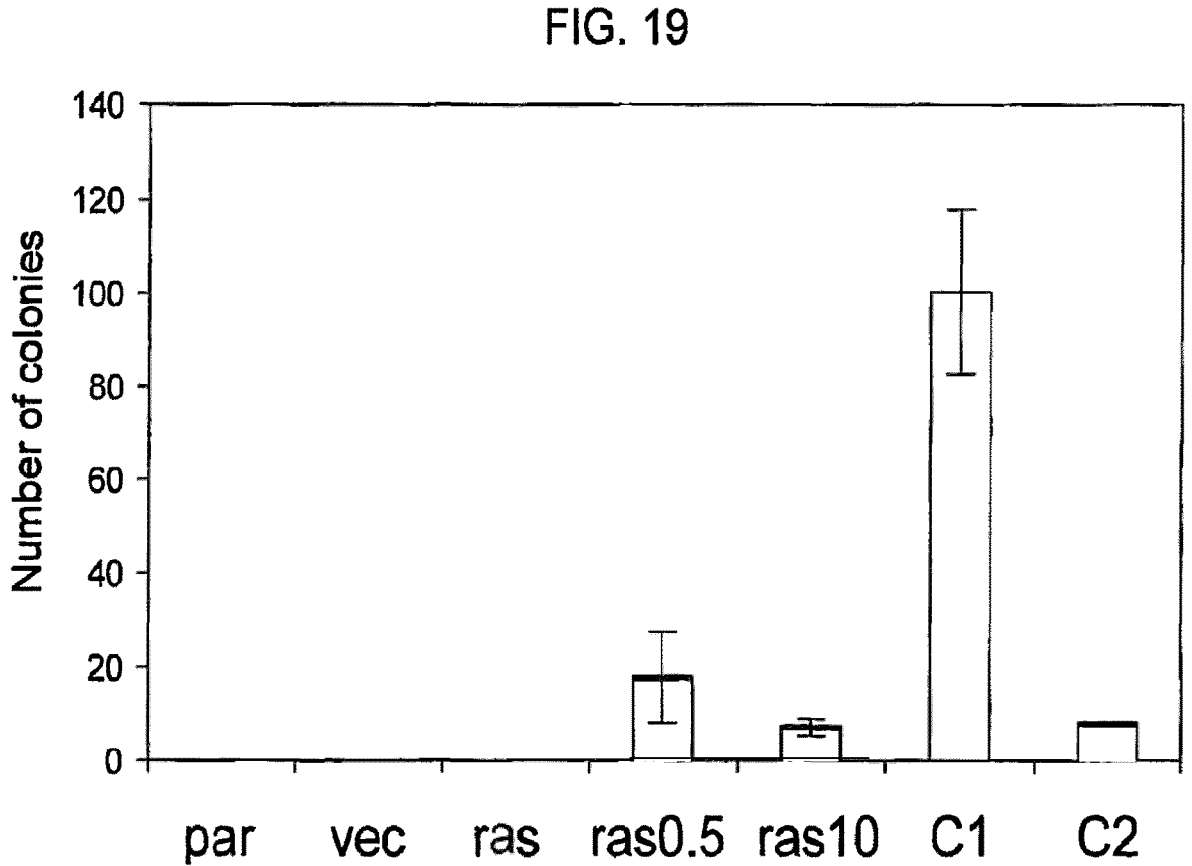

FIG. 19 depicts anchorage independent growth of vHMEC immortalized with Ha-ras.

Figure 20:
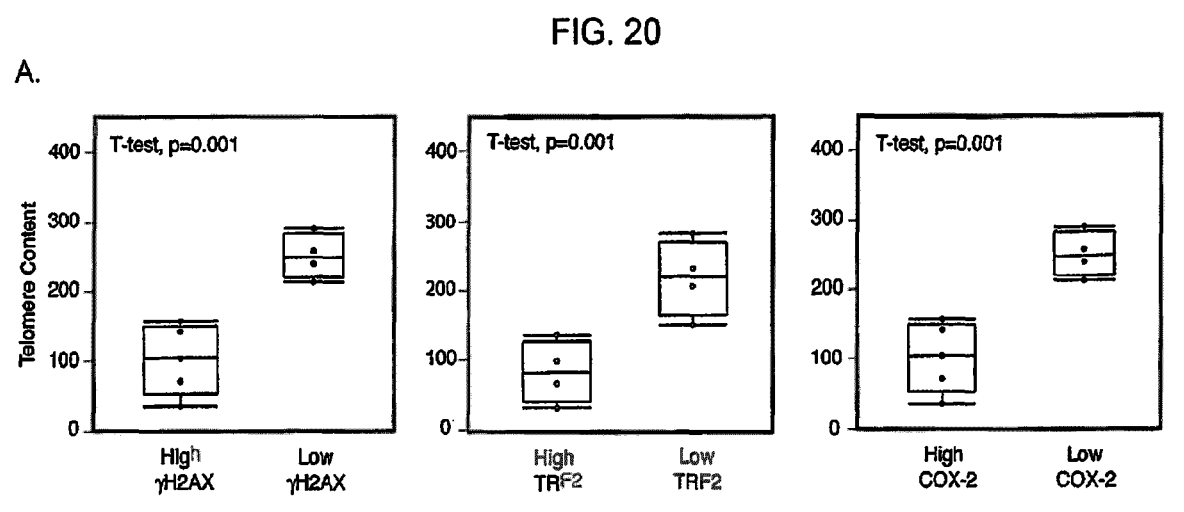

FIG. 20 depicts association of telomere Content with COX-2 expression.

Figure 21:
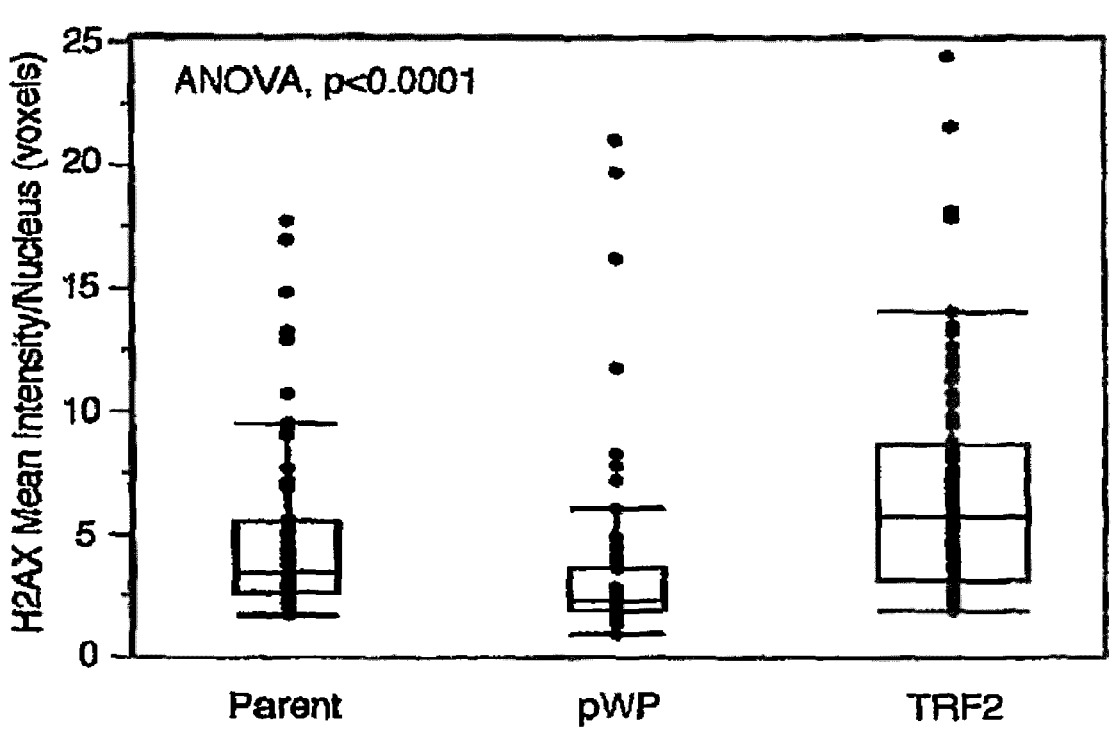

FIG. 21 depicts up-regulation of γH2AX in vHMEC expressing TRF2.

Figure 22A:
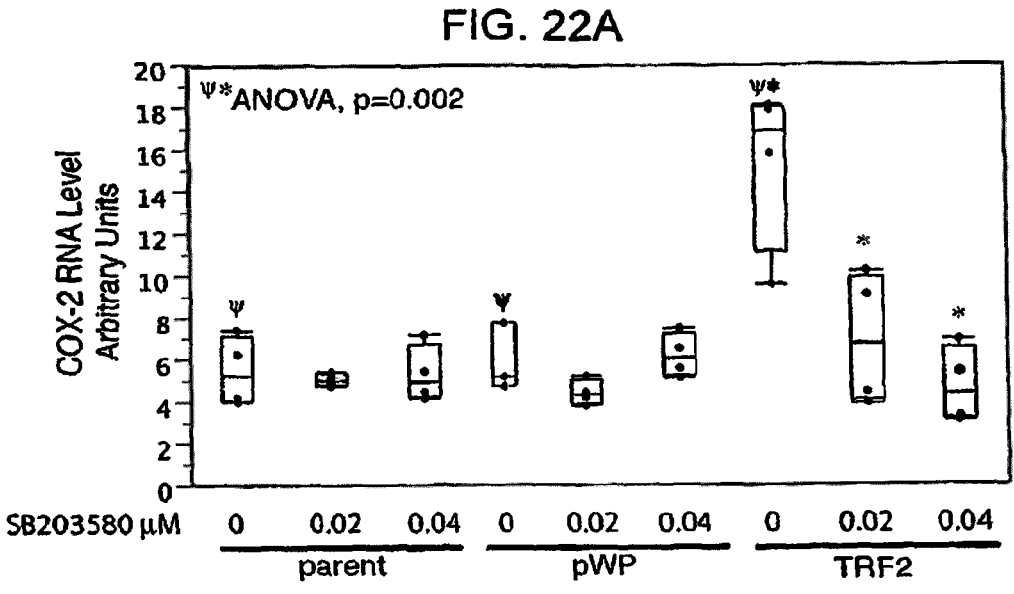
Figure 22B:
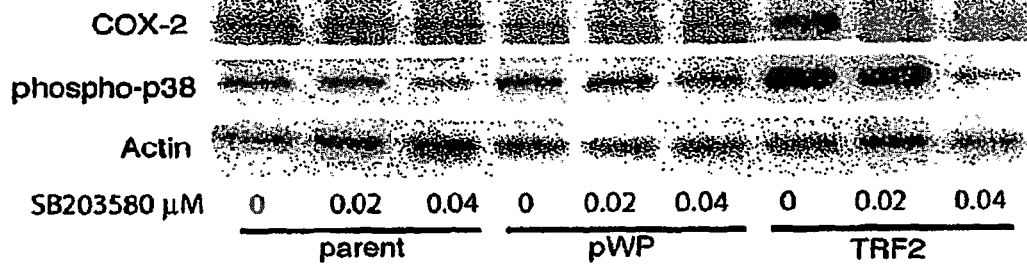
Figure 22C:
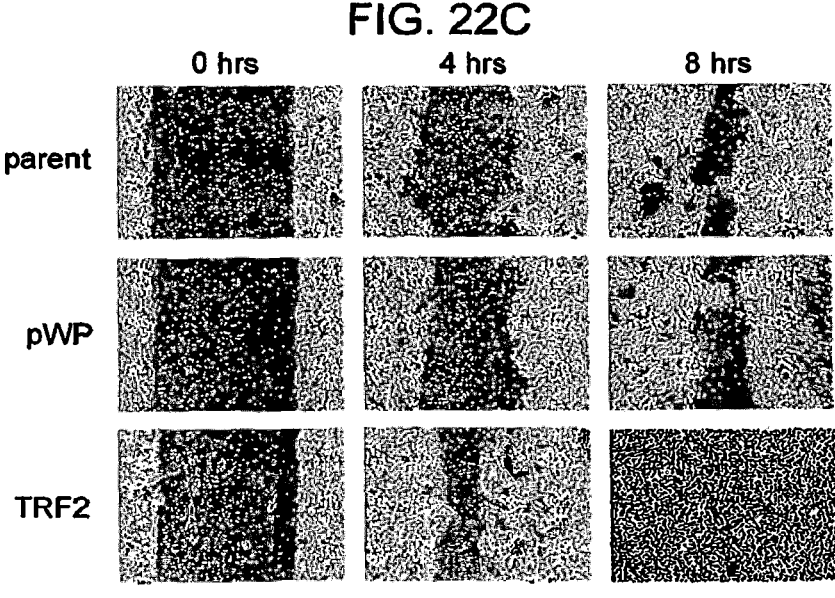

FIGS. 22A-C depict the effect of over-expressing TRF2 on COX-2 in vHMEC.

FIGS. 23A-D depict up-regulation of Activin A in vHMEC and the effect of up-regulation of Activin A on COX-2.

Figure 24A:
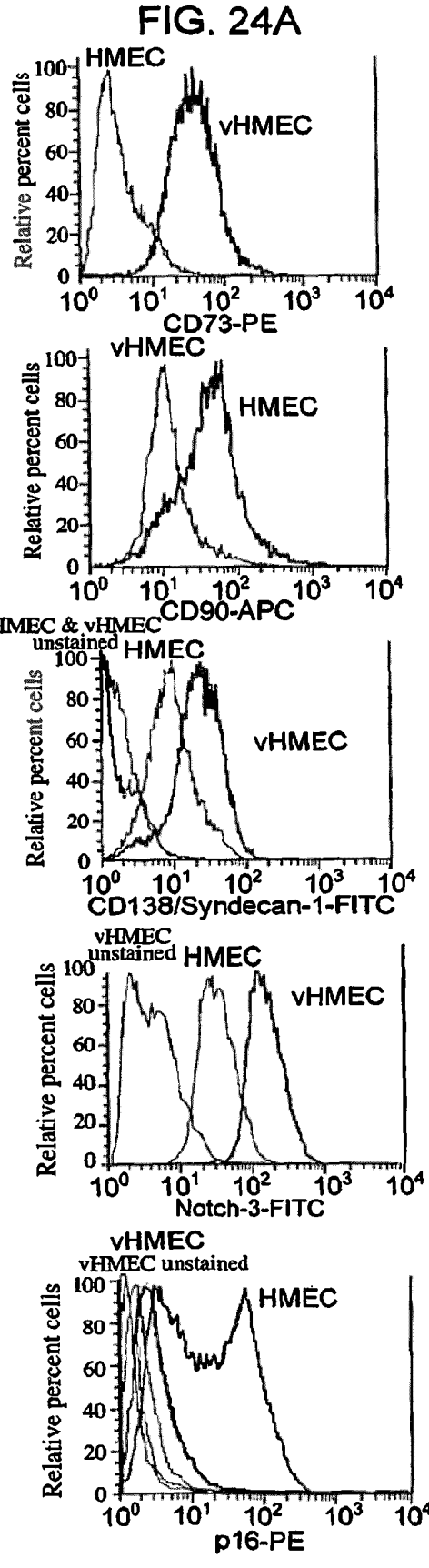
Figure 24B:
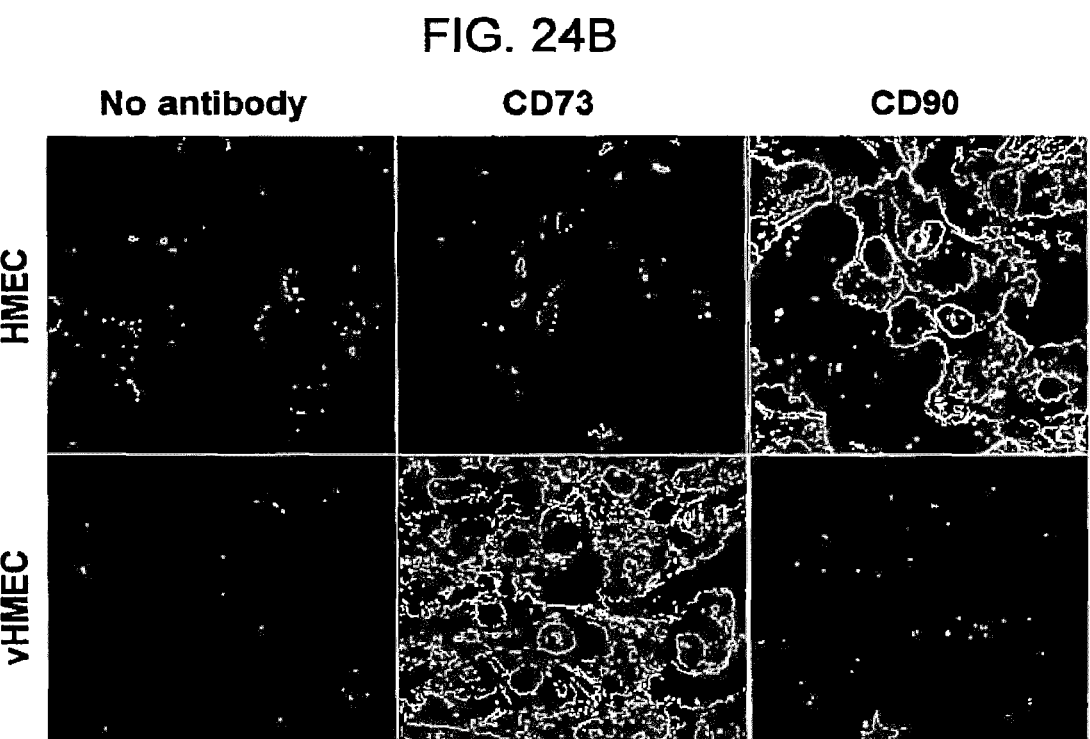
Figure 24C:
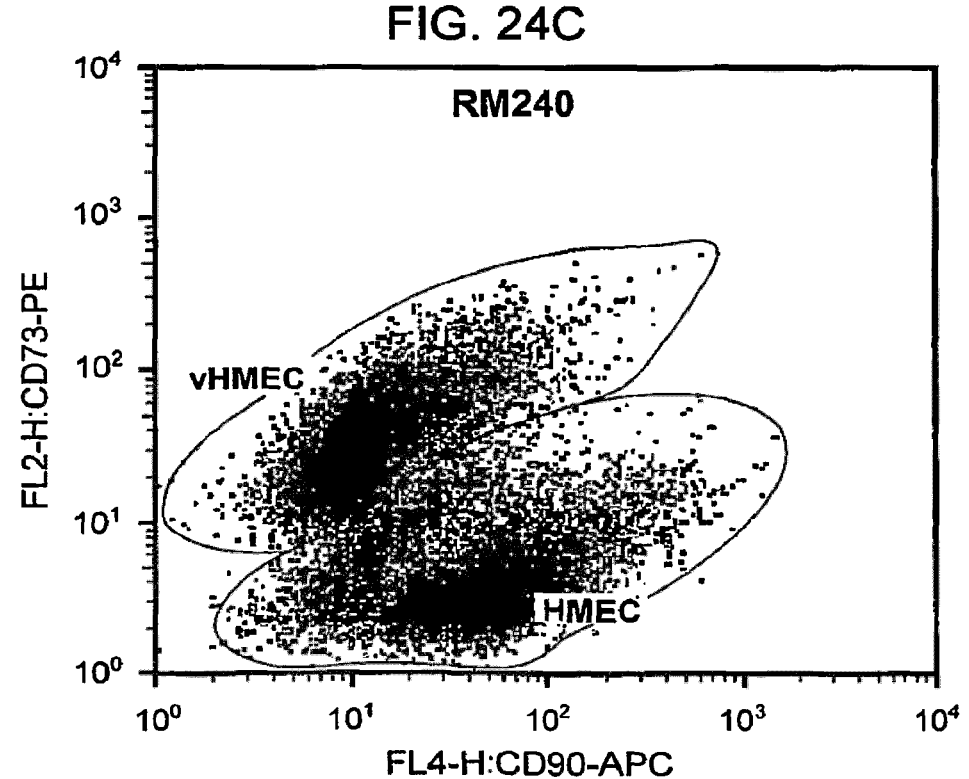

FIGS. 24A-C depict marker analysis of vHMEC and HMEC.

Figure 25:
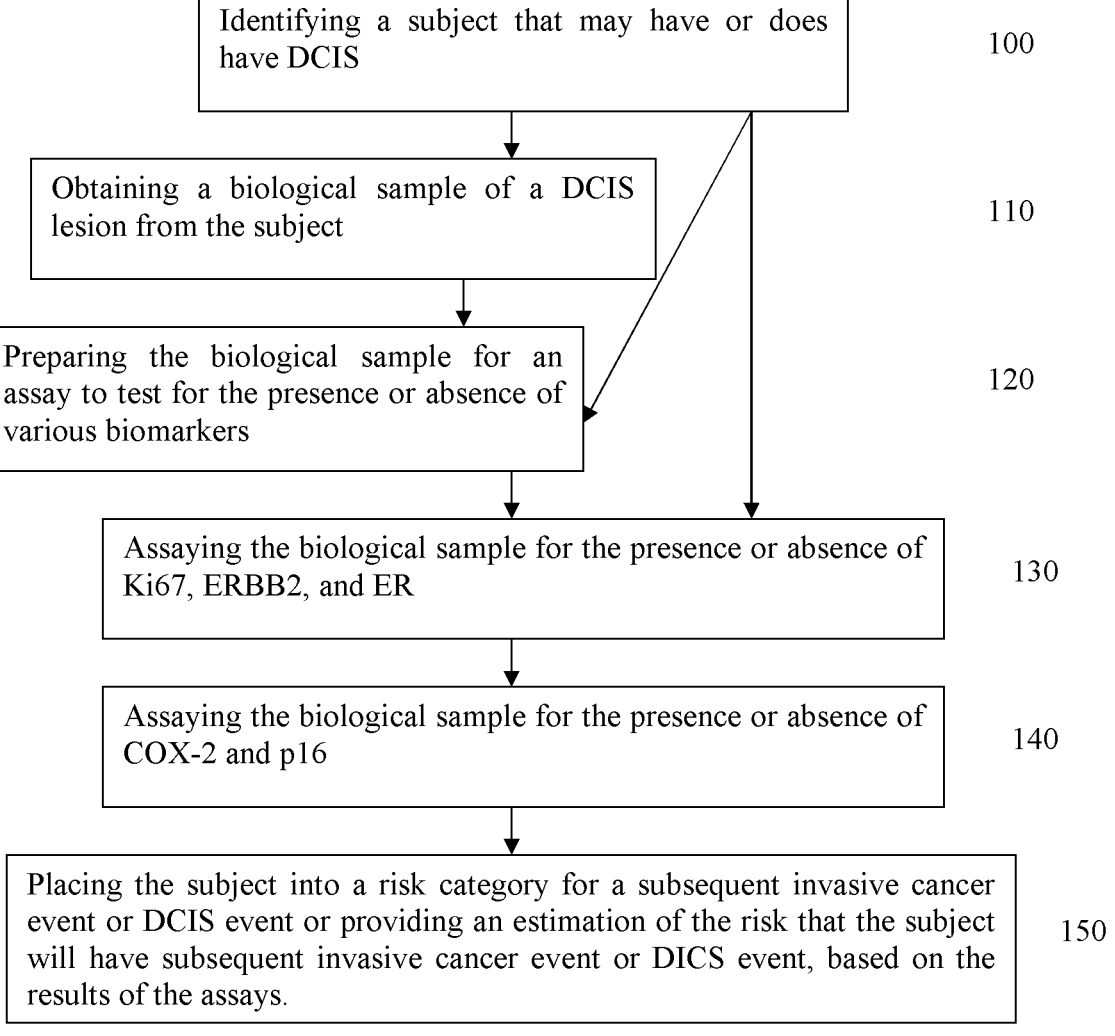

FIG. 25 is a flow chart depicting various embodiments for placing a subject into various risk categories for a subsequent DCIS event.

Figure 26:
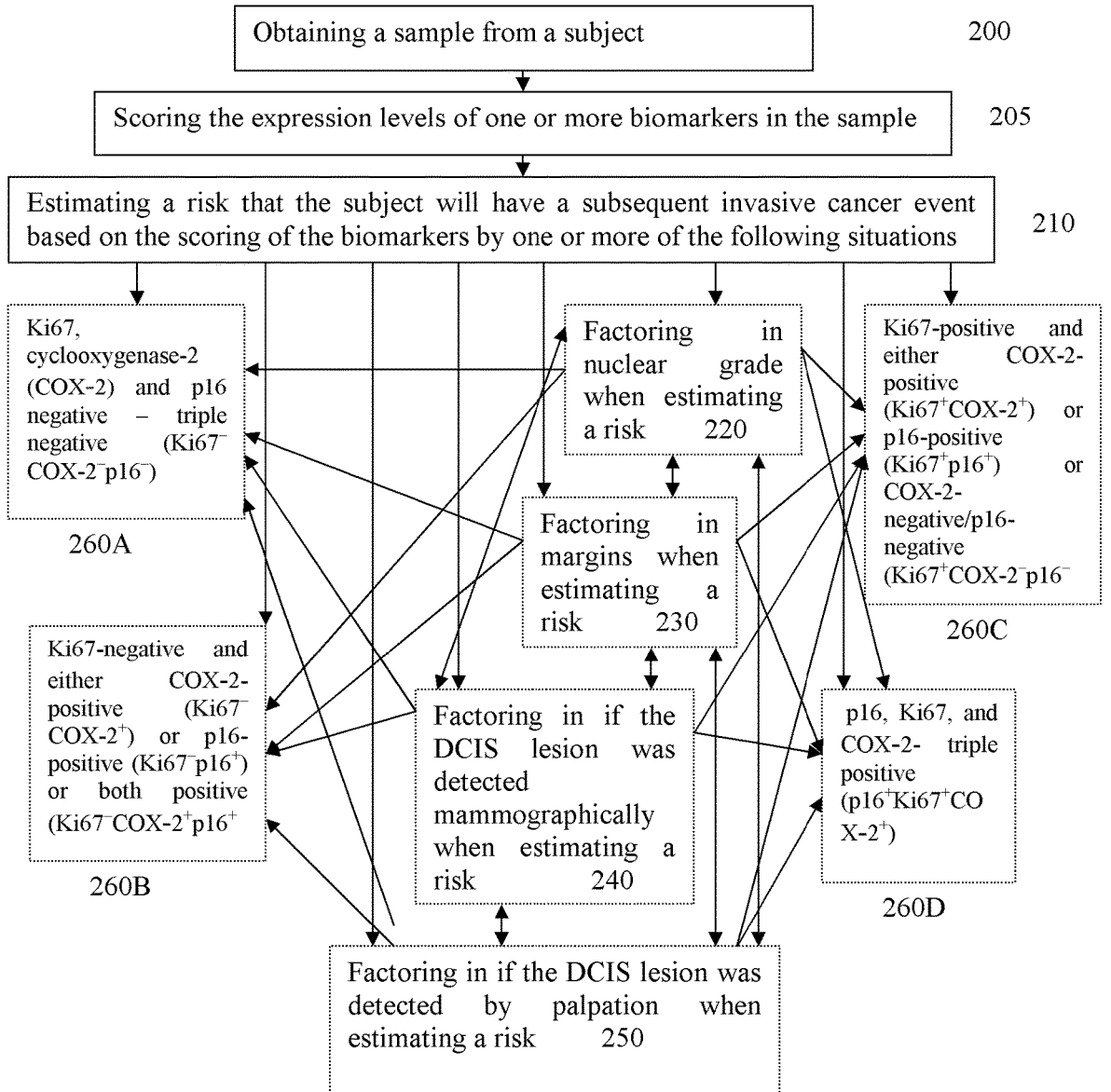

FIG. 26 is a flow chart depicting various embodiments for estimating a subject's risk of an invasive cancer.

Figure 27B:
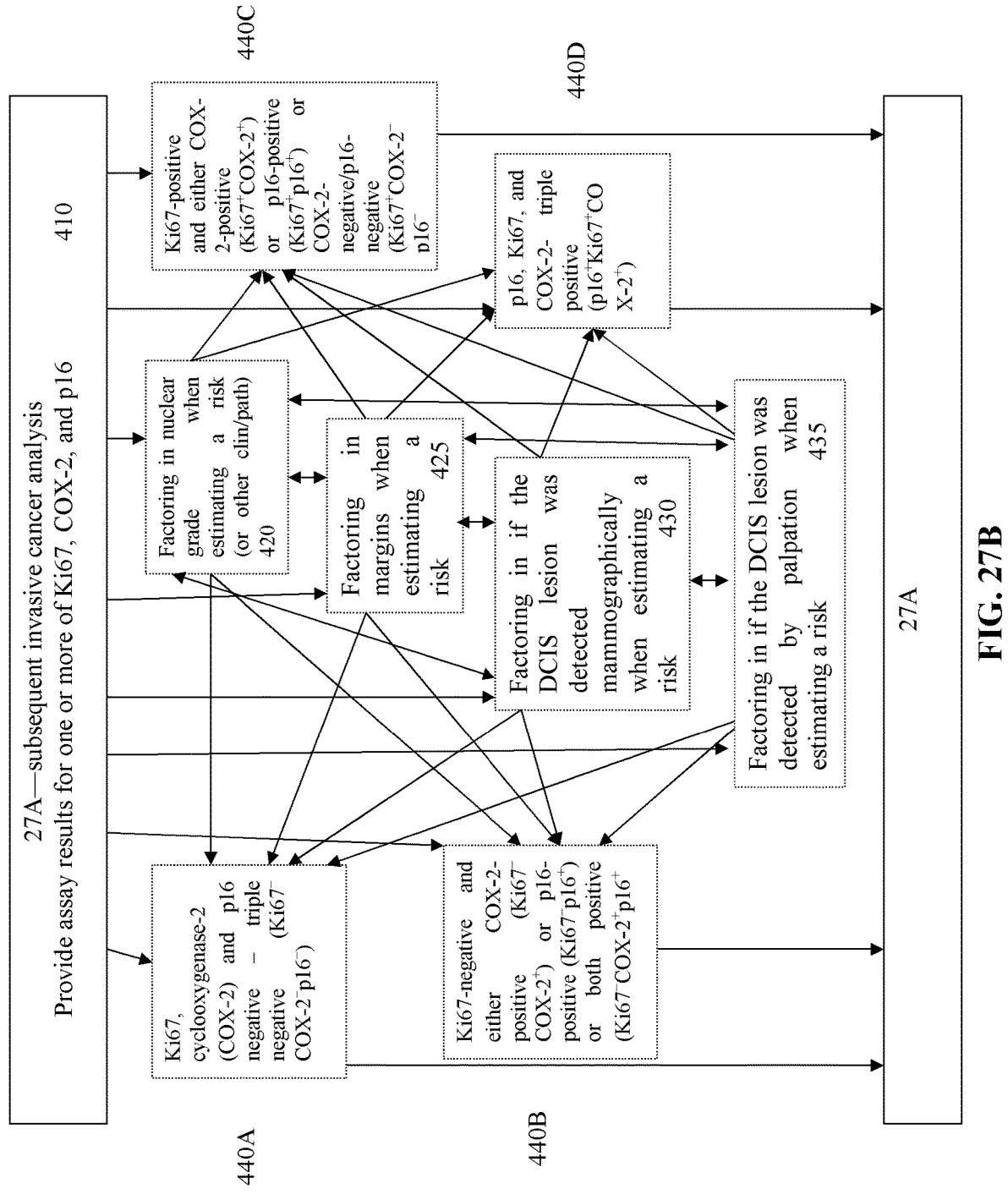
Figure 27C:
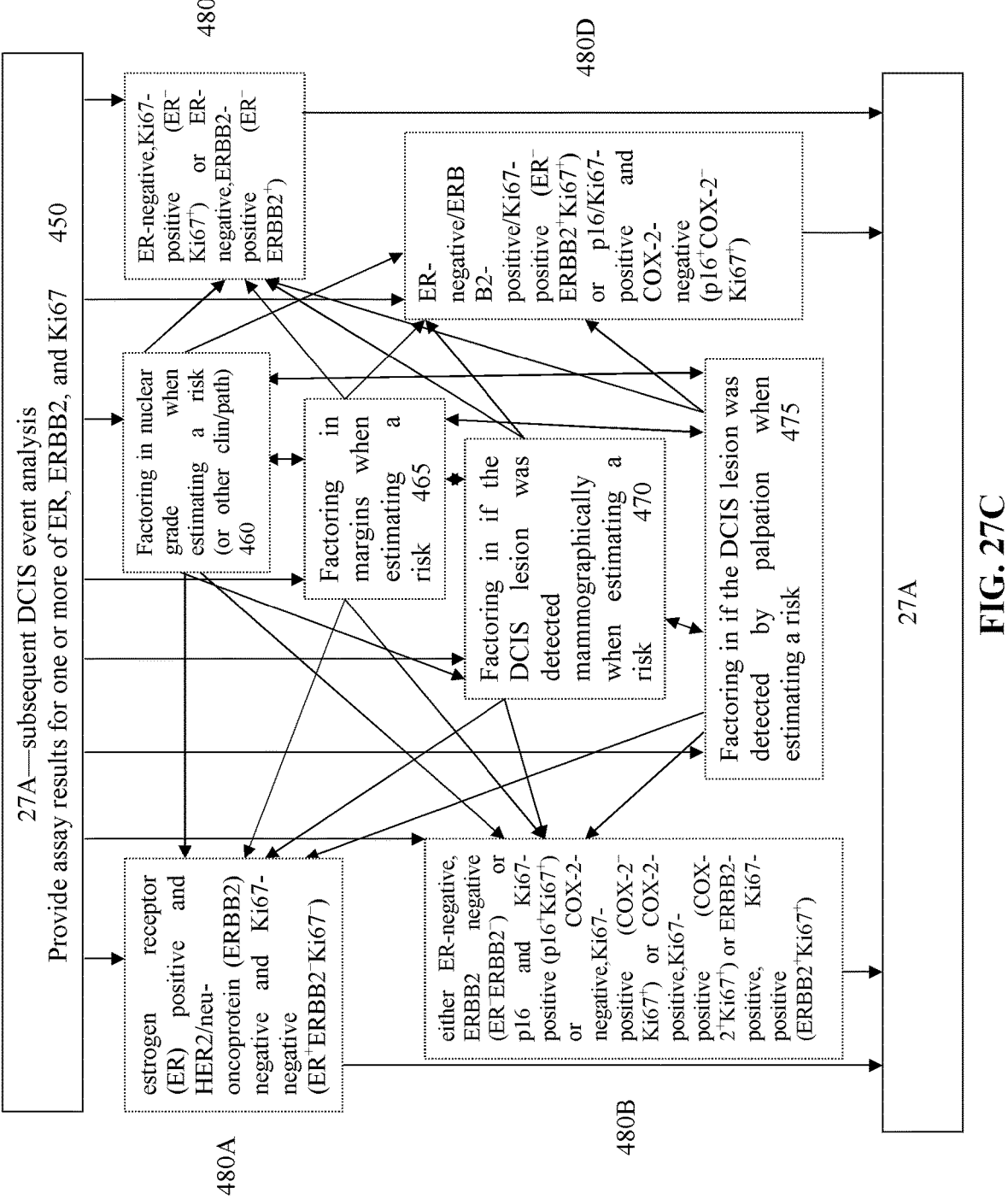

FIGS. 27A-27C are flow charts depicting various embodiments for estimating and/or categorizing a subject's risk for a subsequent invasive cancer or subsequent DCIS event.

Figure 28:
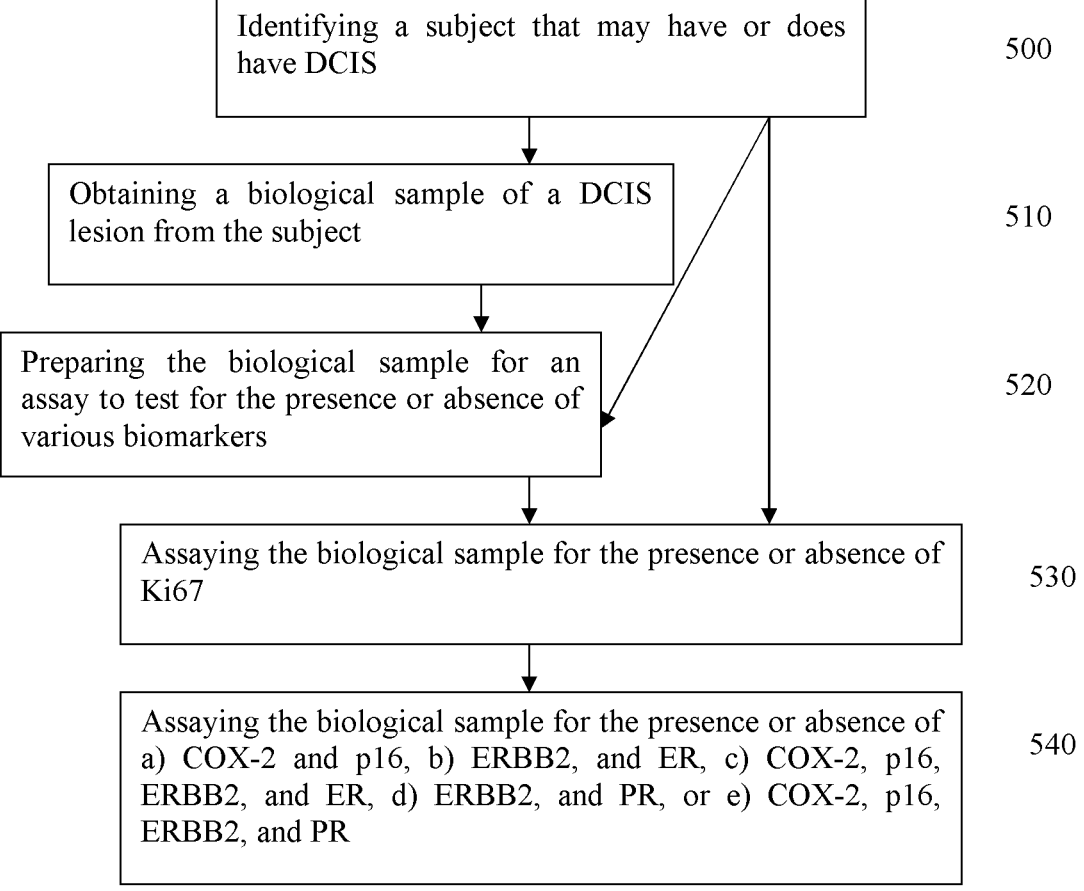

FIG. 28 depicts a flow chart depicting some embodiments for characterizing a biological sample.

DEFINITIONS

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the general description and the following detailed description are exemplary and explanatory only and are not restrictive of the invention. The term "and/or" denotes that the provided possibilities can be used together or be used in the alternative. Thus, the term "and/or" denotes that both options exist for that set of possibilities.

A "gene product" is a biopolymeric product that is expressed or produced by a gene, such as a peptide or protein. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e., cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "polynucleotide" refers to polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences (see, e.g., Niwa et al. (1999) Cell 99(7):691-702). The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. Peyrottes et al. (1996) *Nucl. Acids Res.* 24:1841-1848; Chaturvedi et al. (1996) *Nucl. Acids Res.* 24:2318-2323. A polynucleotide may comprise modified nucleotides, such as methylated nucleotides and nucleotide analogs, uracyl, other sugars, and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids (Pooga et al Curr Cancer Drug Targets. (2001) 1:231-9).

The term "capture agent" refers to an agent that binds a target molecule through an interaction that is sufficient to permit the agent to bind and concentrate the target molecule from a homogeneous mixture of different molecules. The binding interaction is typically mediated by an affinity region of the capture agent. Typical capture agents include any moiety that can specifically bind to a target molecule. In certain embodiments, a polypeptide, e.g., an antibody protein, may be employed. Capture agents usually "specifically bind" a target molecule. Accordingly, the term "capture agent" refers to a molecule or a multi-molecular complex which can specifically bind a target molecule, e.g., a phosphorylated polypeptide, with a dissociation constant ($K_D$) of less than about $10^{-6}$ M (e.g., less than about $10^{-7}$ M, less than about $10^{-8}$ M, less than about $10^{-9}$ M, less than about $10^{-10}$ M, less than about $10^{-11}$ M, less than about $10^{-12}$ M, to up to about $10^{-16}$ M) without significantly binding to other molecules.

The term "specific binding" refers to the ability of a capture agent to preferentially bind to a particular target molecule that is present in a homogeneous mixture of different target molecule. In certain embodiments, a specific binding interaction will discriminate between desirable and undesirable target molecules in a sample, typically more than about 10 to 100-fold or more (e.g., more than about 1000- or 10,000-fold).

The term "capture agent/target complex" is a complex that results from the specific binding of a capture agent with a target, i.e., a "binding partner pair". A capture agent and an target for the capture agent will usually specifically bind to each other under "conditions suitable for specific binding", where such conditions are those conditions (in terms of salt concentration, pH, detergent, protein concentration, temperature, etc.) which allow for binding to occur between capture agents and targets to bind in solution. Such conditions, particularly with respect to proteins and antibodies, include those described in Harlow and Lane (Antibodies: A Laboratory Manual Cold Spring Harbor Laboratory, Cold Spring Harbor, N.Y. (1989)) and Ausubel, et al (Short Protocols in Molecular Biology, 5th ed., Wiley & Sons, 2002).

As used herein, "binding partners" and equivalents thereof refer to pairs of molecules that can be found in a capture agent/target complex, i.e., exhibit specific binding with each other.

The phrase "surface-bound capture agent" refers to a capture agent that is immobilized on a surface of a substrate. In certain embodiments, the capture agent employed herein may be present on a surface of the same support, e.g., in the form of an array.

The term "pre-determined" refers to an element whose identity is known prior to its use. An element may be known by name, sequence, molecular weight, its function, or any other attribute or identifier. In some embodiments, the term "polypeptide of interest", i.e., a known polypeptide that is of interest, is used synonymously with the term "pre-determined polypeptide".

The term "antibody protein" is used herein to refer to a capture agent that has at least an epitope binding domain of an antibody. These terms are well understood by those in the field, and refer to a protein containing one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions. Types of antibodies, including antibody isotypes, monoclonal antibodies and antigen-binding fragments thereof (e.g., Fab, Fv, scFv, and Fd fragments, chimeric antibodies, humanized antibodies, single-chain antibodies, etc) are known and need not be described in any further detail.

A polynucleotide "derived from" or "specific for" a designated sequence, such as a target sequence of a target nucleic acid, refers to a polynucleotide sequence which comprises a contiguous sequence of approximately at least about 6 nucleotides, at least about 8 nucleotides, at least about 10-12 nucleotides, or at least about 15-20 nucleotides corresponding to, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived or specific for. Polynucleotides that are derived from" or "specific for" a designated sequence include polynucleotides that are in a sense or an antisense orientation relative to the original polynucleotide.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wisconsin, USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, California, USA. Of particular interest are alignment programs that permit gaps in the sequence. The Smith Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms.

Hybridization conditions and post-hybridization washes are useful to obtain the desired determine stringency conditions of the hybridization. One set of illustrative post hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions and post-hybridization wash conditions are hybridization conditions and post-hybridization wash conditions that are at least as stringent as the above representative conditions.

In certain embodiments, the stringency of the wash conditions that set forth the conditions which determine whether a nucleic acid is specifically hybridized to a probe. Wash conditions used to identify nucleic acids may include, e.g.: a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. Stringent conditions for washing can also be, e.g., 0.2×SSC/0.1% SDS at 42° C. In instances wherein the nucleic acid molecules are deoxyoligonucleotides ("oligos"), stringent conditions can include washing in 6×SSC/0.05% sodium pyrophosphate at 37° C. (for 14-base oligos), 48° C. (for 17-base oligos), 55° C. (for 20-base oligos), and 60° C. (for 23-base oligos). See Sambrook, Ausubel, or Tijssen (cited below) for detailed descriptions of equivalent hybridization and wash conditions and for reagents and buffers, e.g., SSC buffers and equivalent reagents and conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A "DNA-dependent DNA polymerase" is an enzyme that synthesizes a complementary DNA copy from a DNA template. Examples include DNA polymerase I from *E. coli* and bacteriophage T7 DNA polymerase. All known DNA-dependent DNA polymerases require a complementary primer to initiate synthesis. Under suitable conditions, a DNA dependent DNA polymerase may synthesize a complementary DNA copy from an RNA template.

A "DNA-dependent RNA polymerase" or a "transcriptase" is an enzyme that synthesizes multiple RNA copies from a double-stranded or partially-double stranded DNA molecule having a (usually double-stranded) promoter sequence. The RNA molecules ("transcripts") are synthesized in the 5' to 3' direction beginning at a specific position just downstream of the promoter. Examples of transcriptases are the DNA-dependent RNA polymerase from *E. coli* and bacteriophages T7, T3, and SP6.

An "RNA-dependent DNA polymerase" or "reverse transcriptase" is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

"RNAse H" is an enzyme that degrades the RNA portion of an RNA:DNA duplex. These enzymes may be endonucleases or exonucleases. Most reverse transcriptase enzymes normally contain an RNAse H activity in addition to their polymerase activity. However, other sources of the RNAse H are available without an associated polymerase activity. RNA degradation mediated by an RNAse H may result in separation of RNA from a RNA:DNA complex, or the RNAse H may cut the RNA at various locations such that portions of the RNA melt off or permit enzymes to unwind portions of the RNA.

As used herein, the term "target nucleic acid region" or "target nucleic acid" or "target molecules" refers to a nucleic acid molecule with a "target sequence" to be detected (e.g., in a method involving nucleic acid hybridization and/or amplification). The target nucleic acid may be either single-stranded or double-stranded and may or may not include other sequences besides the target sequence (e.g., the target nucleic acid may or may not include nucleic acid sequences upstream or 5' flanking sequence, may or may not include downstream or 3' flanking sequence, and in some embodiments may not include either upstream (5') or downstream (3') nucleic acid sequence relative to the target sequence. Where detection is by amplification, these other sequences in addition to the target sequence may or may not be amplified with the target sequence.

The term "target sequence" or "target nucleic acid sequence" refers to the particular nucleotide sequence of the target nucleic acid to be detected (e.g., through amplification). The target sequence may include a probe-hybridizing region contained within the target molecule with which a probe will form a stable hybrid under desired conditions. The "target sequence" may also include the complexing sequences to which the oligonucleotide primers complex and be extended using the target sequence as a template. Where the target nucleic acid is originally single-stranded, the term "target sequence" also refers to the sequence complementary to the "target sequence" as present in the target nucleic acid. If the "target nucleic acid" is originally double-stranded, the term "target sequence" refers to both the plus (+) and minus (−) strands. Moreover, where sequences of a "target sequence" are provided herein, it is understood that the sequence may be either DNA or RNA. Thus where a DNA sequence is provided, the RNA sequence is also contemplated and is readily provided by substituting "T" of the DNA sequence with "U" to provide the RNA sequence.

The term "primer" or "oligonucleotide primer" as used herein, refers to an oligonucleotide which acts to initiate synthesis of a complementary nucleic acid strand when placed under conditions in which synthesis of a primer extension product is induced, e.g., in the presence of nucleotides and a polymerization-inducing agent such as a DNA or RNA polymerase and at suitable temperature, pH, metal ion concentration, and salt concentration. Primers are generally of a length compatible with its use in synthesis of primer extension products, and are in many embodiments in the range of between 8 nucleotides and 100 nucleotides (nt) in length, such as 10 nt to 75 nt, 15 nt to 60 nt, 15 nt to 40 nt, 18 nt to 30 nt, 20 nt to 40 nt, 21 nt to 50 nt, 22 nt to 45 nt, 25 nt to 40 nt, and so on, e.g., in the range of between 18 nt and 40 nt, between 20 nt and 35 nt, between 21 and 30 nt in length, inclusive, and any length between the stated ranges. Primers can be in the range of between 10-50 nucleotides long, such as 15-45, 18-40, 20-30, 21-25 nt and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Primers are in many embodiments single-stranded for maximum efficiency in amplification, but may alternatively be double-stranded. If double-stranded, the primer is in many embodiments first treated to separate its strands before being used to prepare extension products. This denaturation step is typically effected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein, the term "probe" or "oligonucleotide probe", used interchangeable herein, refers to a structure comprised of a polynucleotide, as defined above, which contains a nucleic acid sequence complementary to a nucleic acid sequence present in the target nucleic acid analyte (e.g., a nucleic acid amplification product). The polynucleotide regions of probes may be composed of DNA, and/or RNA, and/or synthetic nucleotide analogs. Probes are generally of a length compatible with its use in specific detection of all or a portion of a target sequence of a target nucleic acid, and are in many embodiments in the range of between 8 nt and 100 nt in length, such as 8 to 75 nt, 10 to 74 nt, 12 to 72 nt, 15 to 60 nt, 15 to 40 nt, 18 to 30 nt, 20 to 40 nt, 21 to 50 nt, 22 to 45 nt, 25 to 40 nt in length, and so on, e.g., in the range of between 18-40 nt, 20-35 nt, or 21-30 nt in length, and any length between the stated ranges. In some embodiments, a probe is in the range of between 10-50 nucleotides long, such as 15-45, 18-40, 20-30, 21-28, 22-25 and so on, and any length between the stated ranges. In some embodiments, the primers are not more than about 10, 12, 15, 20, 21, 22, 23, 24, 25, 26, 27, 28, 29, 30, 35, 40, 45, 50, 55, 60, 65, or 70 nucleotides in length.

Probes contemplated herein include probes that include a detectable label. For example, when an "oligonucleotide probe" is to be used in a 5' nuclease assay, such as the TAQMAN™ assay, the probe includes at least one fluorescer and at least one quencher which is digested by the 5' endonuclease activity of a polymerase used in the reaction in order to detect any amplified target oligonucleotide sequences. In this context, the oligonucleotide probe will have a sufficient number of phosphodiester linkages adjacent to its 5' end so that the 5' to 3' nuclease activity employed can efficiently degrade the bound probe to separate the fluorescers and quenchers. When an oligonucleotide probe is used in the TMA technique, it will be suitably labeled, as described below.

Probes and primers contemplated herein include those useful in various amplification and/or detection systems, including those in which primers and probes are provided as bi-functional molecules. Exemplary amplification and/or detection systems include Sunrise™ primer-based systems, Molecular Beacons, the Taqman™ system, an Amplifluor™ hairpin primer-based system, a Scorpions technology (e.g., bi-functional molecules containing a PCR primer element covalently linked to a probe element), and a Light Upon Extension or LUX™-based system. Further exemplary detection systems include those based on a melt-curve analysis, and using intercalating dyes such as the fluorescent dye SYBR Green.

As used herein, the terms "label" and "detectable label" refer to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, strepavidin or haptens), intercalating dyes and the like. The term "fluorescer" refers to a substance or a portion thereof which is capable of exhibiting fluorescence in the detectable range.

The terms "hybridize" and "hybridization" refer to the formation of complexes between nucleotide sequences which are sufficiently complementary to form complexes via Watson-Crick base pairing. Where a primer "hybridizes" with target (template), such complexes (or hybrids) are sufficiently stable to serve the priming function required by, e.g., the DNA polymerase to initiate DNA synthesis.

The term "stringent conditions" refers to conditions under which a primer will hybridize preferentially to, or specifically bind to, its complementary binding partner, and to a lesser extent to, or not at all to, other sequences. Put another way, the term "stringent hybridization conditions" as used herein refers to conditions that are compatible to produce duplexes on an array surface between complementary binding members, e.g., between probes and complementary targets in a sample, e.g., duplexes of nucleic acid probes, such as DNA probes, and their corresponding nucleic acid targets that are present in the sample, e.g., their corresponding mRNA analytes present in the sample.

An "array," includes any one, two-dimensional or substantially two dimensional (as well as a three-dimensional) arrangement of addressable regions bearing a particular chemical moiety or moieties (e.g., polynucleotide or oligonucleotide sequences (nucleic acids), polypeptides (e.g., proteins such antibodies) associated with that region. In the broadest sense, arrays are arrays of polymeric binding agents, where the polymeric binding agents may be any of: polypeptides, proteins (e.g., antibodies), nucleic acids, synthetic mimetics of such polymeric binding agents, etc. In some embodiments of interest, the arrays are arrays of nucleic acids, including oligonucleotides, polynucleotides, cDNAs, mRNAs, synthetic mimetics thereof, and the like. Where the arrays are arrays of nucleic acids, the nucleic acids may be covalently attached to the arrays at any point along the nucleic acid chain, but are generally attached at one of their termini (e.g. the 3' or 5' terminus). In other embodiments, the arrays are arrays of polypeptides, e.g., proteins or fragments thereof, antibodies, and the like.

Any given substrate may carry one, two, four or more or more arrays disposed on a front surface of the substrate. Depending upon the use, any or all of the arrays may be the same or different from one another and each may contain multiple spots or features. An array can contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 μm to 1.0 cm. In other embodiments each feature may have a width in the range of 1.0 μm to 1.0 mm, from 5.0 μm to 500 μm, or from 10 μm to 200 μm. Non-round features may have area ranges equivalent to that of circular features with the foregoing width (diameter) ranges. At least some, or all, of the features are of different compositions (for example, when any repeats of each feature composition are excluded the remaining features may account for at least 5%, 10%, or 20% of the total number of features). Interfeature areas will typically (but not essentially) be present which do not carry any polynucleotide (or other polymer or chemical moiety of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

Each array may cover an area of less than 100 cm$^2$, or even less than 50 cm$^2$, 10 cm$^2$ or 1 cm$^2$. In many embodiments, the substrate carrying the one or more arrays will be shaped generally as a rectangular solid (although other shapes are possible), having a length of more than 4 mm and less than 1 m, than 4 mm and less than 600 mm, or less than 400 mm; a width of more than 4 mm and less than 1 m, less than 500 mm, or less than 400 mm; and a thickness of more than 0.01 mm and less than 5.0 mm, more than 0.1 mm and less than 2 mm, or more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Arrays can be fabricated using drop deposition from pulse jets of either polynucleotide precursor units (such as monomers) in the case of in situ fabrication, or the previously obtained polynucleotide. Such methods are described in detail in, for example, U.S. Pat. Nos. 6,242,266, 6,232,072, 6,180,351, 6,171,797, 6,323,043, and the references cited therein. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods.

An array is "addressable" when it has multiple regions of different moieties (e.g., different polynucleotide sequences) such that a region (i.e., a "feature" or "spot" of the array) at a particular predetermined location (i.e., an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probe" may be the one which is to be evaluated by the other (thus, either one could be an unknown mixture of polynucleotides to be evaluated by binding with the other). A "scan region" refers to a contiguous (e.g., rectangular) area in which the array spots or features of interest, as defined above, are found. The scan region is that portion of the total area illuminated from which the resulting fluorescence is detected and recorded. For the purposes of this invention, the scan region includes the entire area of the slide scanned in each pass of the lens, between the first feature of interest, and the last feature of interest, even if there exist intervening areas which lack features of interest. An "array layout" refers to one or more characteristics of the features, such as feature positioning on the substrate, one or more feature dimensions, and an indication of a moiety at a given location. "Hybridizing" and "binding", with respect to polynucleotides, are used interchangeably.

A "scanner" is device for evaluating arrays. In scanners, an optical light source, particularly a laser light source, generates a light which is focused on the array and sequentially illuminates surface regions of known location (for example, a point or line) on an array substrate. The resulting signals from the surface regions are collected either employing the same lens used to focus the light onto the array or using a separate lens positioned to one side of the lens used to focus the onto the array. The collected signals may be then transmitted through appropriate spectral filters, to an optical detector. A recording device, such as a computer memory, records the detected signals and builds up a scan file of intensities as a function of position, or time as it relates to the position. In the case of spot illumination, such intensities, as a function of position, are typically referred to in the art as "pixels". Biopolymer arrays are often scanned and/or scan results are often represented at 5 or 10 micron pixel resolution. To achieve the precision required for such activity, components such as the lasers must be set and maintained with particular alignment. Scanners may be bi-directional, or unidirectional, as is known in the art.

The scanner typically used for the evaluation of arrays includes a scanning fluorimeter. A number of different types of such devices are commercially available from different sources, such as such as Perkin-Elmer, Agilent, or Axon Instruments, etc., and examples of suitable scanners are described in U.S. Pat. Nos. 5,091,652; 5,760,951, 6,320,196 and 6,355,934.

The term "assessing" includes any form of measurement, and includes determining if an element is present or not. The terms "determining," "measuring," "evaluating," "assessing," and "assaying" are used interchangeably and includes quantitative and qualitative determinations. Assessing may be relative or absolute. "Assessing the presence" of includes determining the amount of something present, and/or determining whether it is present or absent. As used herein, the terms "determining," "measuring," and "assessing," and "assaying" are used interchangeably and include both quantitative and qualitative determinations.

The term "binds specifically," in the context of a specific binding reagent, e.g., in the context of antibody binding, refers to high avidity and/or high affinity binding of an antibody to a specific polypeptide i.e., epitope of a polypeptide, e.g., a CD73 polypeptide, a CD138 polypeptide, an ERBB2 polypeptide, an ER polypeptide, a p16 polypeptide, a Ki67 polypeptide, a notch receptor-3 polypeptide, a CD90 polypeptide, a BMI-1 polypeptide, or a COX-2 polypeptide. For example, antibody binding to an epitope on a specific target gene product or fragment thereof is stronger than binding of the same antibody to any other epitope, particularly those which may be present in molecules in association with, or in the same sample, as the specific polypeptide of interest, e.g., binds more strongly to a specific target polypeptide than to any other epitopes so that by adjusting binding conditions the antibody binds almost exclusively to the specific target epitope and not to any other epitope, or to any other polypeptide which does not comprise the epitope. Antibodies that bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a target polypeptide, e.g. by use of appropriate controls. In general, specific antibodies bind to a given polypeptide with a binding affinity of $10^{-7}$ M or more, e.g., $10^{-8}$ M or more (e.g., $10^{-9}$ M, $10^{-10}$ M, $10^{-11}$ M, etc.). In general, an antibody with a binding affinity of $10^{-6}$ M or less is not useful in that it will not bind an antigen at a detectable level using conventional methodology currently used.

A composition (e.g. a polynucleotide, polypeptide, antibody, or host cell) that is "isolated" or "in substantially isolated form" refers to a composition that is in an environment different from that in which the composition naturally occurs. For example, a polynucleotide that is in substantially isolated form is outside of the host cell in which the polynucleotide naturally occurs, and could be a purified fragment of DNA, could be part of a heterologous vector, or could be contained within a host cell that is not a host cell from which the polynucleotide naturally occurs. The term "isolated" does not refer to a genomic or cDNA library, whole cell total protein or mRNA preparation, genomic DNA preparation, or an isolated human chromosome. A composition which is in substantially isolated form is usually substantially purified.

As used herein, the term "substantially purified" refers to a compound (e.g., a polynucleotide, a polypeptide or an antibody, etc.) that is removed from its natural environment and is at least 60% free, 75% free, at least 90%, at least 95%, at least 98%, or at least 99% free from other components with which it is naturally associated. Thus, for example, a composition containing A is "substantially free of" B when at least 85% by weight of the total A+B in the composition is A. For example, A comprises at least about 90% by weight of the total of A+B in the composition, or at least about 95% or even 99% by weight. In the case of polynucleotides, "A" and "B" may be two different genes positioned on different chromosomes or adjacently on the same chromosome, or two isolated cDNA species, for example.

If one composition is "bound" to another composition, the compositions do not have to be in direct contact with each other. In other words, bonding may be direct or indirect, and, as such, if two compositions (e.g., a substrate and a polypeptide) are bound to each other, there may be at least one other composition (e.g., another layer) between to those compositions. Binding between any two compositions described herein may be covalent or non covalent. The terms "bound" and "linked" are used interchangeably herein.

As used herein, "subject," "host," "patient," and "individual" are used interchangeably to refer to a mammal, e.g., a human, a non-human primate, ungulates, canines, felines, equines, and the like.

"Diagnosis" as used herein generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and use of therametrics (e.g., monitoring a subject's condition to provide information as to the effect or efficacy of therapy).

As used herein, the term "a polypeptide associated with cancer" refers to a polypeptide encoded by a polynucleotide that is differentially expressed in a cancer cell.

The term "biological sample" encompasses a variety of sample types obtained from an organism and can be used in an imaging, a diagnostic, a prognostic, or a monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids, and tissue samples.

The terms "treatment," "treating," "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

The terms "cancer," "neoplasm," and "tumor" are used interchangeably herein to refer to cells which exhibit relatively autonomous growth, so that they exhibit an aberrant growth phenotype characterized by a significant loss of control of cell proliferation. In general, cells of interest for detection or treatment in the present application include precursors, precancerous (e.g., benign), malignant, pre-metastatic, metastatic, and non-metastatic cells. Detection of pre-cancerous cells is of particular interest.

"Cancerous phenotype" generally refers to any of a variety of biological phenomena that are characteristic of a cancerous cell, which phenomena can vary with the type of cancer. The cancerous phenotype is generally identified by abnormalities in, for example, cell growth or proliferation (e.g., uncontrolled growth or proliferation), regulation of the cell cycle, cell mobility, cell-cell interaction, or metastasis, etc.

The term "assessing" includes any form of measurement, and includes determining if an element is present or not. The terms "determining", "measuring", "evaluating", "assessing" and "assaying" are used interchangeably and include quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. A permanent genetic change is generally achieved by introduction of the DNA into the genome of the cell. Suitable methods of genetic modification include viral infection, transfection, conjugation, protoplast fusion, electroporation, particle gun technology, calcium phosphate precipitation, direct microinjection, and the like. A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, or a cell from a multicellular organism (e.g., a primary cell, a cell line) cultured as a unicellular entity, which eukaryotic cell can be, or has been, used as a recipient for a nucleic acid (e.g., an exogenous nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

The term "DCIS lesion" denotes a breast lesion that is contained within the milk ducts of the breast. DCIS lesions contain some cells with malignant features but not all such lesions behave as cancer, for example, they will not spread outside the ducts and invade surrounding breast tissue, nor will they be life threatening. DCIS has been described as a non-obligate precursor of breast cancer and as non-invasive cancer The term "risk category" denotes a grouping of risks relative to other defined groups or individuals within another group. Thus, a "risk category" system could be set up as a) high risk and low risk; b) low, medium, and high, c) lowest, low, and high; or d) lowest, low, medium, high, highest, etc. In some embodiments, the risk categories can be set up in terms of percentage of the population as a whole and the risk that someone with the specific profile had the recurrence.

The term "subgroup" denotes that a group or category can be separated into two or more parts.

The terms "first risk category", "second risk category", "third risk category" and "fourth risk category" denote options for categorizing risk, where risk categorization is done by binning people into groupings relative to people in other groupings. In some embodiments, people are grouped into categories depending upon cell profiles from DCIS lesions.

The terms "high risk," "intermediate risk," "lower risk," "lowest risk," etc., denote a relative risk assessment between various groups of people, profiles, samples, etc. The divisions of the groups need not be equal or consistent with one another (although in some embodiments they are). Thus, in a lowest, low, high, highest categorization system, "lowest" could be, but need not be defined as the 20% of the population that has the lowest risk. In some embodiments, the groupings are set so as to provide a subject or doctor a useful indicator or how to proceed with future treatments. As such, if those with a 10% or more chance of having an invasive cancer would normally pursue an aggressive treatment, then that percentage can be characterized as "high risk". In some embodiments, the terms are used consistently with the number of groupings or categories of risk that are employed to describe a population. Thus, if only three categories are required to describe a population, the terms high risk, medium risk, and low risk, can be employed and will have meaning relative to each other.

"The term "estimating risk" denotes providing a prediction that a particular event will occur. In some embodiments, the estimation is provided for a specific time frame (for example, 5 and/or 8 years).

The term "margin" denotes the tissue surrounding the DCIS lesion that has been excised from the subject. The margins can range from 10 mm or more that have no disease to positive, meaning the entire excised lesion has disease.

The term "subsequent DCIS event" denotes that a subject that has experienced (or currently is experiencing) a DCIS event will have another DCIS event. In some embodiments, a first DCIS event was diagnosed. In some embodiments, the initial DCIS event involves a DCIS lesion that is tested for various biomarkers. The "subsequent DCIS event" is subsequent to the initial DCIS event. In some embodiments, a subsequent DCIS event or invasive cancer will occur within a specified time frame in order to be considered "subsequent". In some embodiments, for the event to be "subsequent" it will occur within 20 years from the DCIS event and/or lesion removal, for example 19, 18, 17, 16, 15, 14, 13, 12, 11, 10, 9, 8, 7, 6, 5, 4, 3, 2, or 1 year from the initial occurrence, discovery, or DCIS lesion removal event.

The term "invasive cancer" denotes breast cancer and can include invasive ductal carcinoma. In some embodiments, invasive cancer comprises, consists, or consists essentially of breast cancer.

The phrase "clinical and/or histopathological characteristic" includes, in some embodiments, a nuclear grade of the DCIS, family history, age at diagnosis, menopausal status, race/ethnicity, oral contraceptives, postmenopausal hormone therapy, body mass index, tumor size, necrosis type, quantity of necrosis, cell polarity, Architectural growth pattern, calcification, and any combination thereof.

The term "grade of DCIS lesion" denotes a pathology associated with a DCIS lesion, generally determined by microscopic analysis. Various grading systems are known to one of skill in the art. DCIS lesions can be graded by nuclear features. For example, DCIS lesions can be graded into two or more categories of risk. For instance, a DCIS lesion can be categorized as low grade, intermediate grade or high grade, based on nuclear features. Alternatively, DCIS lesions can be grouped into a "high grade" and a "not high grade" grouping, with the low and intermediate grading combined. Such grading can be based on nuclear size, variations in size and shape of the nuclei, chromatin structure, nucleoli appearance and prevalence, and mitotic activity. The "grade of DCIS lesion" also can refer to the predominant architecture of the DCIS lesion, including papillary, micropapillary type, cribriform type, and solid type. Bassett L W, Jackson V, Jahanshahi R, Fu Y S, Gold R H: Diagnosis of Diseases of the Breast. WB Saunders, Philadelphia, 1997; Lagios M D, Margolin F, Westdahl P R, Rose M R: Mammographically detected duct carcinoma in situ: frequency of local recurrence following tylectomy and prognostic effect of nuclear grade on local recurrence. Cancer 1989; 63:618-24; Silverstein M J, Lagios M D, Craig P, et al: A prognostic index for ductal carcinoma in situ of the breast. Cancer 1996; 77:2267-74; Silverstein M J, Poller D N, Waisman J R, et al: Prognostic classification of breast ductal carcinoma-in-situ. Lancet 1995; 345:1154-5; Tavassoli F A: Pathology of the Breast. Elsevier, New York, 1992.

When one or more clinical and/or histopathological characteristic are "not" "used," "employed," "factored," "considered," etc. in determining a risk, what is meant is that the results from an analysis of such clinical and/or histopathological characteristic are not weighed in providing an estimate of risk or placement into a risk category. In some embodiments, the clinical and/or histopathological characteristic can still be taken and observed; however, the results do not meaningfully alter the risk assessment provided by the biomarker(s) and other noted factors.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an epithelial cell" includes a plurality of such cells and reference to "the biomarker" includes reference to one or more biomarkers and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF FURTHER EMBODIMENTS

Some embodiments of the present invention provide inter alia reagents and methods for detecting a pre-cancerous or cancerous epithelial cell. It has been found that certain signatures associated with mammary epithelial cells identify pre-cancerous cells, and indicate a level of risk that a malignant tumor will develop. Mammary epithelial cell signatures include, for example, the presence and/or levels and/or posttranslation modification of a protein or collection of proteins; the presence and/or level of a nucleic acid; and the integrity or methylation status or other parameter of a nucleic acid.

A variant mammary epithelial cell (vMEC) appears morphological normal, e.g., a vMEC is morphologically indistinguishable from a normal mammary epithelial cell. However, a vMEC has a "signature" that indicates its potential for developing into a cancerous cell, e.g., a vMEC is a pre-malignant cell. Thus, e.g., a vMEC signature distinguishes it from an MEC (e.g., a control, normal MEC that is not pre-malignant) by one or more of: 1) a lower than normal level of an mRNA, compared to the level of the mRNA in a MEC; 2) a higher than normal level of an mRNA, compared to the level of the mRNA in a MEC; 3) a lower than normal level of a protein, compared to the level of the protein in a MEC; 4) a higher than normal level of a protein, compared to the level of the protein in an MEC; 5) a higher level of a post translationally modified protein, compared to the level of the post-translationally modified protein in an MEC; 6) an increased level of genomic DNA abnormalities, compared to the level found in an MEC; and 7) an increased level of methylation of a particular promoter(s), compared to the level of methylation of the promoter(s) in an MEC.

For example, an mRNA or a protein that is differentially expressed in a vMEC, compared to a control, normal MEC, is present in the vMEC at a level from about 1.5-fold to 100-fold higher or lower than the level of the mRNA or protein in a control, normal MEC, e.g., an mRNA or a protein that is differentially expressed in a vMEC is present in the vMEC at a level of from about 1.5-fold to about 2-fold, from about 2-fold to about 2.5-fold, from about 2.5-fold to about 5-fold, from about 5-fold to about 10-fold, from about 10-fold to about 15-fold, from about 15-fold to about 20-fold, from about 20-fold to about 25-fold, from about 25-fold to about 50-fold, from about 50-fold to about 75-fold, or from about 75-fold to about 100-fold, or more, higher or lower than the level of the mRNA or protein in a control, normal MEC. In some embodiments, a control, normal MEC is a primary MEC isolated from an individual, where the control, normal MEC is a $CD73^-$ MEC, e.g., is substantially negative for CD73.

As discussed herein, expression of protein or mRNA can be scored as positive or negative. A control sample can be used to calibrate the expression level of a biomarker. Expression of a particular biomarker in a DCIS sample, for example, can be compared to the expression of the biomarker in a cell line or tissue sample having a known expression. For example, for the measurement of ER, PR, ERBB2, Ki67, COX-2, p53 and p16, the following control cell lines and tissues can be used: ER, breast tumor case and cell line MCF-7; PR, breast tumor case and cell line T47D; Ki67, breast tumor case; p53, colon tumor case and cell line T47D; ERBB2, breast tumor case and cell line SKBR3; COX-2, a DCIS case; and p16, normal breast tissue and colon tumor.

Methods for detecting a pre-cancerous or cancerous epithelial cell find use in various clinical settings, e.g., imaging methods, diagnostic methods, prognostic methods, and monitoring methods. Reagents suitable for use in a subject method include, for example: 1) reagents that detect the presence and/or level of a selected protein or collection of proteins; 2) reagents that detect posttranslational modifications of gene expression-controlling proteins; 3) reagents that detect the level of a selected DNA; 4) reagents that detect the integrity of a selected DNA; 5) reagents that detect methylation status of a selected DNA; 6) reagents that detect the presence and/or a level of a selected mRNA or collection of mRNA; 7) reagents that detect the presence and/or level of a selected microRNA; 8) reagents for proteomics analyses; and 9) reagents for biological assays.

Reagents

As noted above, the present invention provides reagents for detecting a mammary epithelial cell signature that provides for identification of risk that a mammary epithelial cell will become malignant. Some of these reagents are described in more detail below. Some embodiments also provide reagents for assessing for a patient with DCIS, the risk of a subsequent DCIS event, and/or a subsequent invasive cancer. Exemplary reagents are described in more detail below as well.

Reagents for Detecting a Mammary Epithelial Cell Signature

Some embodiments of the present invention provide inter alia reagents for detecting a mammary epithelial cell (MEC) signature, e.g., an MEC signature that is indicative of a pre-cancerous MEC. An "MEC signature" includes, but is not limited to: 1) the presence and/or level of a selected protein or collection of proteins; 2) the presence or absence of a posttranslational modification of a selected protein or collection of proteins; 3) the presence of a chromatin modification; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

Suitable reagents include, but are not limited to, 1) reagents that detect the presence and/or level of a selected protein or collection of proteins; 2) reagents that detect posttranslational modifications of gene expression-controlling proteins; 3) reagents that detect the level of a selected DNA; 4) reagents that detect the integrity of a selected DNA; 5) reagents that detect methylation status of a selected DNA; 6) reagents that detect the presence and/or a level of a selected mRNA or collection of mRNA; 7) reagents that detect the presence and/or level of a selected microRNA; 8) reagents for proteomics analyses; and 9) reagents for use in biological assays.

Specific Binding Agents

Specific binding agents (also referred to as "capture agents") are provided, which are useful in a subject detection method, where specific binding agents include specific binding agents that detect the presence and/or level of a protein in an MEC, specific binding agents that detect the presence and/or levels of a selected posttranslationally modified protein, and the like. "Specific binding agents" include, e.g., antibodies, antigen-binding fragments of an antibody; an epitope-binding fragment of an antibody; or other protein that bind specifically to an epitope on a target polypeptide. The discussion below refers to antibody reagents. However, any specific binding agent is suitable for use. Hence, where the disclosure refers to "antibody reagents," other specific binding agents are also contemplated.

Antibody reagents are provided, which are useful in a subject detection method. In some embodiments, an antibody reagent detects the presence and/or levels of a selected protein or collection of proteins in an MEC. In other embodiments, an antibody reagent detects the presence and/or levels of a selected posttranslationally modified protein, e.g., a protein that controls gene expression.

A subject antibody reagent can be in substantially isolated form, e.g., in an environment other than its naturally-occurring environment. In some embodiments, a subject antibody reagent is a synthetic antibody reagent, or a recombinant antibody reagent. In some embodiments, the antibody reagents are immobilized on an insoluble support. In some embodiments, a panel of antibodies is provided, where a panel of antibodies is two or more different antibodies, each specific for a different polypeptide that comprises an MEC signature. The antibody reagents bind specifically to a selected target polypeptide or collection of selected target polypeptides.

Suitable antibody reagents include antibodies of any isotype; single-chain Fv; Fab; Fab; Fv; $F(ab')_2$; artificial antibodies; and the like. Suitable antibodies also include "artificial" antibodies, e.g., antibodies and antibody fragments produced and selected in vitro. In some embodiments, such antibodies are displayed on the surface of a bacteriophage or other viral particle. In many embodiments, such artificial antibodies are present as fusion proteins with a viral or bacteriophage structural protein, including, but not limited to, M13 gene III protein. Methods of producing such artificial antibodies are well known in the art. See, e.g., U.S. Pat. Nos. 5,516,637; 5,223,409; 5,658,727; 5,667,988; 5,498,538; 5,403,484; 5,571,698; and 5,625,033. In some embodiments, the antibodies are monoclonal antibodies. In some embodiments, an antibody reagent is directly or indirectly detectably labeled.

Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. Other suitable detectable labels include fluorescent dyes, e.g., Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, $DiOC_7$ (3), $DiIC_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

In some embodiments, an antibody reagent comprises, covalently linked to the antibody reagent, a protein that provides for a detectable signal. Suitable proteins include, but are not limited to, fluorescent proteins and enzymes (e.g., β-galactosidase, luciferase, horse radish peroxidase, alkaline phosphatase, etc.). Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., Science 263(5148): 802-805 (Feb. 11, 1994); an enhanced GFP (EGFP), Clontech—Genbank Accession Number U55762); a blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418,155, 5,683,888, 5,741,668, 5,777,079, 5,804,387, 5,874,304, 5,876,995, and 5,925,558; a GFP from species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like.

Indirect labels include second antibodies specific for an antibody reagent, wherein the second antibody is labeled as described above; and members of specific binding pairs, e.g., biotin-avidin, and the like.

In some embodiments, the antibodies are immobilized on an insoluble support, e.g., in an antibody diagnostic device, in an antibody array, etc. Antibodies can be immobilized directly or indirectly (e.g., via a linker molecule) to an insoluble support for use in a diagnostic assay to detect a target polypeptide in a biological sample. An antibody reagent can be immobilized by covalent or non-covalent attachment to an insoluble support. Insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (MA), and the like); sheets, e.g., nylon, nitrocellulose, and the like; and chips, e.g., $SiO_2$ chips such as those used in microarrays. Accordingly, the invention further provides assay devices comprising one or more antibody reagents attached to a solid support.

The present invention further provides inter alia an array of antibodies, e.g., monoclonal antibodies, attached to an insoluble support in an array. In some embodiments, a subject antibody array provides for detection of a target polypeptide that is indicative of a pre cancerous epithelial cell.

Suitable antibodies are obtained by immunizing a host animal with peptides comprising all or a portion of a target protein. Suitable host animals include mouse, rat sheep, goat, hamster, rabbit, etc. The host animal will generally be from a different species than the immunogen where the immunogen is from a naturally occurring source, e.g., a human sample, where representative host animals include, but are not limited to, e.g., rabbits, goats, mice, etc.

Methods for producing and using antibody arrays are known in the art; and any known method can be used. See, e.g., U.S. Pat. No. 6,797,393.

In one embodiment, the antibody reagents are arranged in the form of an array. An array can be created by spotting captures agents onto a substrate (e.g., glass, nitrocellulose, etc.) and attaching those capture agents to the substrate. The antibody reagents can be bound to the substrate by either covalent bonds or by non-specific interactions, such as hydrophobic interactions. Techniques for constructing arrays and methods of using these arrays are described in, for example, Schena et al. (1996) *Proc Natl Acad Sci USA.* 93(20):10614-9; Schena et al. (1995) *Science* 270(5235): 467-70; Shalon et al. (1996) *Genome Res.* 6(7):639-45, U.S. Pat. No. 5,807,522, EP 799 897; WO 97/29212; WO 97/27317; EP 785 280; WO 97/02357; U.S. Pat. Nos. 5,593,839; 5,578,832; EP 728 520; U.S. Pat. No. 5,599,695; EP 721 016; U.S. Pat. No. 5,556,752; WO 95/22058; and U.S. Pat. No. 5,631,734. The antibody reagents utilized in the arrays can be of varying types and can include, for example, antibodies, including antibody fragments, aptamers, avimers, or peptidomimetics.

Common physical substrates for making protein arrays include glass or silicon slides, magnetic particles or other micro beads, functionalized with aldehyde or other chemical groups to help immobilize proteins. The substrate can also be coated with PLL (polylysine), nitrocellulose, PVDF membranes or modified with specific chemical reagents to adsorb capture agents. The desirable properties of an ideal surface include: chemical stability before, during, and after the coupling procedure, suitability for a wide range of capture agents (e.g., hydrophilic and hydrophobic, low MW and high MW), minimal non-specific binding, low or no intrinsic background in detection, presentation of the capture agents in a fully-functional orientation, production of spots with predictable and regular morphology (shape, signal uniformity).

The variables in the immobilization of proteins include: type of capture agent (e.g., antibody reagent), nature of surface (including any pretreatment prior to use), and the immobilization method. Both adsorption and covalent attachment have been used for protein arrays. Orientation of the capture agent is very important in presenting it to the ligand or the surface in a functional state. Although covalent attachment using a variety of chemically activated surfaces (e.g., aldehyde, amino, epoxy) as well as attachment by specific biomolecular interactions (e.g., biotin-streptavidin) provide a stable linkage and good reproducibility, chemical derivatization of the surface may alter the biological activity of the capture agent and/or may result in multi-site attachment.

In some embodiments, antibody arrays are made with a non-contact deposition printer. The printer uses thermal ink jet heads that can print many solutions simultaneously to produce hundreds of spots of 50-60 µm in diameter with a spacing of 150 µm between spots. The droplet volume ranges between 35 pL to 1.5 mL. The heating element is made out of TaAl or other suitable materials, and is capable of achieving temperatures that can vaporize a sufficient volume of printing buffer to produce a bubble that will push out a precise volume of the antibody solution on the substrate. Selection of printing buffer is important, in that the buffer accomplishes the following: increases printing efficiency (measure of the number of spots that are printed to the total number of spots that are attempted), reduces sample spreading, promotes uniform delivery, stabilizes the capture agents that are being printed, reduces sample drying, and increases the visibility of the printed spots. In addition to the printing buffer, other variables that affect printing include: size of the drops, the method of washing and drying the print head, and the speed at which the dispensing head moves. Various modifications may be within these conditions.

Antibody Reagents that Detect the Presence and/or Level of a Selected Protein or Collection of Proteins In some embodiments, a subject antibody (or panel of antibodies) detects the presence and/or level of a selected protein (or collection of proteins) produced by an MEC. Detection of the presence and/or level of a selected protein or collection of proteins produced by an MEC allows prediction of the likelihood that the MEC is pre-cancerous, e.g., will progress to form a tumor. For example, in some embodiments, a subject antibody or antibody array detects the presence and/or level of a selected target polypeptide, or collection of target polypeptides, that constitute a vMEC signature, e.g., the polypeptide(s) are present in a vMEC at a higher or lower than normal level, compared to a control, normal MEC (e.g., compared to a CD73⁻ MEC).

Suitable antibodies include antibodies that bind specifically to a target polypeptide identified in FIG. 14. Suitable antibodies include antibodies that bind specifically to a target polypeptide selected from: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR, TRF2, activin, and MEK1/2. These proteins are discussed in greater detail below.

CD73 (also referred to as 5'-ribonucleotide phosphohydrolase) is a membrane-bound enzyme that catalyzes the conversion of AMP to bioactive adenosine at neutral pH; and also has functions independent of its enzyme activity. CD73 is expressed on various cells include endothelial cells, pericytes, follicular dendritic cells, and subsets of T cells. Amino acid sequences of human CD73 are known, and are presented in, e.g., GenBank Accession Nos. AAH65937, NP_002517, and AI40168.

CD90, also known as Thy-1, is a 25-37 kD, glycosylphosphatidylinositol anchored, cell surface glycoprotein found on many cell types. Amino acid sequences of human CD90 are known, and are presented in, e.g., GenBank Accession Nos. PO4216, AAG13904, AAH65559, and NP_006279. See also, Seki et al. (1985) *Proc. Natl. Acad. Sci. U.S.A.* 82:6657-6661.

CD138, also known as syndecan-1, is a transmembrane heparan sulfate proteoglycans. Amino acid sequences of human CD138 are known, and are presented in, e.g., GenBank Accession Nos. AAH08765, P18827, and NP_002988.

ER, also known as estrogen receptor 1, is an approximately 53-67 kD protein found on many cell types. Amino acid sequences of human ER are known and are presented in, e.g., GenBank Accession Nos. NP_000116.2, NP_001116212.1, NP_001116213.1, and NP_001116214.1.

PR, also known as progesterone receptor, has two variant approximately 94 kD and 120 kD proteins found on many cell types. Amino acid sequences of human PR are known and are presented in, e.g., GenBank Accession Nos. NP_000917.3.

Notch3 (or "notch-3 receptor") is a membrane-spanning protein that comprises multiple tandem repeats of a calcium-binding, epidermal growth factor (EGF)-like domain. Amino acid sequences of human notch3 are known and are presented in, e.g., GenBank Accession Nos. AAB91371, AAC15789, AAC14346, and NP_000426.

COX-2 ("cyclooxygenase-2") is an enzyme that converts arachidonic acid to prostaglandin $H_2$. Amino acid sequences of human COX-2 are known, and are presented in, e.g., GenBank Accession Nos. AAA58433 and NP_000954.

Ki67 (also referred to as "Ki67 antigen") is a nuclear antigen expressed in proliferating cells but not in quiescent cells, and thus is used as a "proliferation marker" to measure proliferation of cells. Multiple isoforms of Ki67 have been identified. Ki67 includes multiple repeats of an approximately 22 amino acid motif, referred to as the "Ki67" motif. Schluter et al. (1993) *J. Cell Biol.* 123:513-522. Amino acid sequences of a 3256-amino acid isoform of human Ki-67 are known, and are presented in, e.g., GenBank Accession Nos. CAA46519, CAI16902, CAH73169, and EAW49178. Amino acid sequences of a 2896-amino acid isoform of human Ki-67 are known, and are presented in, e.g., GenBank Accession Nos. CAA46520, CAI16903, CAH73170, and EAW49179. Amino acid sequences of a 2801-amino acid isoform of human Ki-67 are known, and are presented in, e.g., GenBank Accession No. EAW49177.

p16 (also known as INK4a, MTS1, CDK4I, and cyclin dependent kinase inhibitor 2A) is a cyclin dependent kinase inhibitor. p16, a member of the INK4 family, binds to and inhibits cyclin-dependent kinase-4 (CDK4). Amino acid sequences of human p16 are known, and are presented in, e.g., GenBank Accession Nos. P42771 (156 amino acid form); NP_000068 (156 amino acid form); NP_478102 (173 amino acid form); and NP_478104 (116 amino acid form).

IGF2 (also known as somatomedin A) is a single chain polypeptide that shares amino acid sequence identity of about 47% with insulin. Amino acid sequences of 180 amino acid human IGF2 are known, and are presented in, e.g, GenBank Accession No. ABD93451, and GenBank Accession No. ABM83647.

YKL-40 is a secreted glycoprotein of the chitinase family. YKL-40 is a major secretory protein of human chondrocytes and synoviocytes. Hakala et al. J. Biol. Chem. 268 (34), 25803-25810 (1993). Amino acid sequences of human YKL-40 are known, and are presented in, e.g., GenBank Accession No. AAA16074; and U.S. Pat. No. 6,579,684.

Epidermal growth factor receptor (EGF-R) is also referred to as ErbB-1 or HER1. EGF-R is the cell-surface receptor for members of the epidermal growth factor family (EGF-family) of extracellular protein ligands. EGFR (epidermal growth factor receptor) exists on the cell surface and is activated by binding of its specific ligands, including epidermal growth factor and transforming growth factor $\alpha$ (TGF$\alpha$). Amino acid sequences of human EGF-R are known, and are presented in, e.g., GenBank Accession Nos. AAG35786 (p110); and AAG35787 (p60).

ERBB2, also known as the HER2/neu-oncoprotein ("erbB-2," "ERBB-2," etc.). Amino acid sequences of ERBB2 are known, and are presented in, e.g., GenBank Accession No. NP_004439.2 and NP_001005862.1, and U.S. Pat. No. 7,446,185.

c-jun is the cellular counterpart of the transforming protein of the chicken retrovirus ASV17. Via a leucine zipper, c-Jun forms homodimers and heterodimers with Fos and other jun-related proteins which, together, comprise the AP-1 transcription factor that binds TPA response elements (TREs). c-Jun therefore mediates transcriptional regulation in response to a variety of stimulants. Amino acid sequences of human c-jun are known, and are presented in, e.g., GenBank Accession Nos. AAH68522 and NP_002219.

Proliferating cell nuclear antigen (PCNA) (also referred to as cyclin, or DNA polymerase delta auxiliary protein) is involved in DNA replication and repair. Amino acid sequences of human PCNA are known, and are presented in, e.g., GenBank Accession Nos. AAH00491 and NP_872590.

Cyclin B1 plays a role in cell cycle control. M-phase promoting factor or maturation promoting factor (MPF), the key regulator of the $G_2 \rightarrow M$ transition during the cell cycle, is regulated by phosphorylation of both of its component proteins: the serine/threonine protein kinase cdc2 and a B-type cyclin. Amino acid sequences of human cyclin B1 are known, and are presented in, e.g., GenBank Accession Nos. NP_114172, EAW51306, and AAP88038.

C-kit, also known as CD 117, is a cytokine receptor expressed on the surface of hematopoietic stem cells as well as other cell types. C-kit is the receptor for the cytokine stem cell factor (SCF), also known as "steel factor" or "c-kit ligand." Amino acid sequences of human c-kit are known, and are presented in, e.g., GenBank Accession Nos. AAH71593 and AAC50968.

Signal Transducer and Activator of Transcription-3 (STAT3) is a member of a family of STATs. STATS are transcription factors that are phosphorylated by JAK kinases in response to cytokine activation of a cell surface receptor tyrosine kinases. Bromberg et al. (1999) *Cell* 98:295-303;

and Ihle (2001) *Curr. Opin. Cell Biol.* 13:211-217. Amino acid sequences of human STAT3 are known, and are presented in, e.g., GenBank Accession Nos. NP_644805, NP_003141, NP_998827, and CAA10032.

The cyclin D1 proto-oncogene is an important regulator of G1 to S-phase transition and an important cofactor for several transcription factors in numerous cell types. Amino acid sequences of human cyclin D1 are known, and are presented in, e.g., GenBank Accession Nos. NP_444284, AAH23620, AAH25302, AAH01501, and AAH14078.

Phosphatidylinositol 3-kinases (PI3K) generate lipids that control a wide variety of intracellular signalling pathways. Mammals have eight distinct catalytic subunits and seven regulatory subunits. Catalytic subunit isoforms include p110α, p110β, p110δ, and p110γ. Amino acid sequences of human PI3K catalytic subunits are known, and are presented in, e.g., GenBank Accession Nos. NP_005017, O00329, and CAI15702 (p110δ); NP_006209, AAI13604, and P42336 (p110α); NP_002640, P48736, and AAH35683 (p110γ); and NP_006210, AAI14433, and P42338 (p11013). See also, Kang et al. (2006) *Proc. Natl. Acad. Sci. USA* 103:1289; and Vanhaesebroeck et al. (2005) *TRENDS Biochem. Sci.* 30:194.

Mitogen-activated protein (MAP) kinases (MAPK) are serine/threonine specific protein kinases that respond to extracellular stimuli (e.g., mitogens) and regulate various cellular activities, such as gene expression, mitosis, differentiation, and cell survival/apoptosis. MAPK include MAPK1 (ERK2, MAPK1), MAPK3 (ERK1), MAPK6 (ERK3), MAPK7 (ERK7), MAPK8 (JNK1), MAPK9 (JNK2), MAPK10 (JNK3), MAPK11 (p38bMAPK), MAPK12 (p38gMAPK), MAPK13, and MAPK14 (p38 MAPK). Amino acid sequences of human MAPK are known, and are presented in, e.g., GenBank Accession Nos. NP_002736, NP_620407, and AAH99905 (MAPK1); AAH13992, P27361, EAW79912, EAW79912, EAW77913, EAW79914, and EAW79915 (MAPK3); NP_002739, AAH35492, and EAW77434 (MAPK6); NP_620603, NP_620601, and EAW50887 (MAPK7); AAI30571, NP_620637, and NP_620635 (MAPK8); CAG38817, AAH32539, and AAY46156 (MAPK9); AAH65516, AAH51731, and P53779 (MAPK10); CAG30400, NP_002742, and AAH27933 (MAPK11); CAG30401, NP_002960, and AAH15741 (MAPK12); CAG46488, CAI9690, and CAB08438 (MAPK13); CAG38743, AAH31574, and AAH00092 (MAPK14).

Mitogen-activated protein (MAP) kinases require dual phosphorylation on threonine and tyrosine residues in order to gain enzymatic activity. This activation is carried out by a family of enzymes known as MAP kinase kinases (MAPKKs, MKKs, or MEKs). MAPKK include MAP2K1 (MEK1), MAP2K2 (MEK2), MAP2K3 (MEK3), MAP2K4 (Mkk4, JNKK1), MAP2K5 (MEK5), MAP2K6 (MKK6), MAP2K7 (JNKK2). Amino acid sequences of human MAPKKs are known, and are presented in, e.g., GenBank Accession Nos. AAI39730, NP_002746, and Q02750 (MAP2K1); NP_109587, AAH18645, and P36507 (MAP2K2).

TRF2 is a telomere-binding protein. Telomere-binding proteins TRF1 and TRF2 interact with several other telomere regulators including TIN2, PTOP, POT 1, and RAP1 to ensure proper maintenance of telomeres. TRF2 mediates t-loop formation and end protection. Liu et al. (2004) *J. Biol. Chem.* 279:51338. Amino acid sequences of human TRF2 (500 amino acids) are known, and are presented in, e.g., GenBank Accession Nos. NP_05643, Q15554, and AAB81135.

Activin A is a homodimer of the activin βA subunits. The activin βA monomer can also form a heterodimer with inhibin α, to produce the activin A antagonist, inhibin A. Amino acid sequences of human activin βA (426 amino acids) are known, and are presented in, e.g, GenBank Accession Nos. EAL24001, EAW94141, and AAH07858.

In some embodiments, the present invention provides an antibody panel, comprising two or more antibodies with specificity for two or more polypeptides that are differentially expressed in pre-cancerous epithelial cells or surrounding epithelial cells. In some embodiments, a subject antibody panel comprises antibody reagents that provide for detection of two, three, four, five, or all of CD73, CD138, notch receptor-3, CD90, BMI-1, and COX-2. In other embodiments, a subject antibody panel comprises antibody reagents that provide for detection of CD90 and CD73. In other embodiments, a subject antibody panel comprises antibody reagents that provide for detection of Ki67 and COX-2. In other embodiments, a subject antibody panel comprises antibody reagents that provide for detection of Ki67 and p16. In other embodiments, a subject antibody panel comprises antibody reagents that provide for detection of Ki67, COX-2, and p16. In other embodiments, a subject antibody panel comprises antibody reagents that provide for detection of two, three, four, five, or all of ER, PR, ERBB2, Ki67, COX-2, or p16. In some embodiments, the antibody panel comprises antibody reagents that provide for detection of the following combinations, simultaneously: ER, ERBB2, Ki67, COX-2, and p16; PR, ERBB2, Ki67, COX-2, and p16; ER, ERBB2, and Ki67; PR, ERBB2, and Ki67; and Ki67, COX-2, and p16. In some embodiments, the antibody panel is configured such that it allows for the simultaneous characterization of one or more of the following arrangements: a) Ki67, cyclooxygenase-2 (COX-2) and p16 negative-triple negative ($Ki67^{-COX-}2^-p16^-$), b) Ki67-negative and either COX-2-positive ($Ki67^-COX-2^+$) or p16-positive ($Ki67^-p16^+$) or both positive ($Ki67^-COX-2^+p16^+$); c) Ki67-positive and either COX-2-positive ($Ki67^+COX-2^+$) or p16-positive ($Ki67^+p16^+$) or COX-2-negative/p16-negative ($Ki67^+COX-2^-p16^-$); d) p16, Ki67, and COX-2-triple positive ($p16^+Ki67^+COX-2^+$); e) estrogen receptor (ER) positive and HER2/neu-oncoprotein (ERBB2) negative and Ki67-negative ($ER^+ERBB2^-Ki67^-$); f) either ER negative, ERBB2 negative ($ER^-ERBB2^-$) or p16 and Ki67-positive ($p16^+Ki67^+$) or COX-2-negative, Ki67-positive ($COX-2^-Ki67^+$) or COX-2-positive, Ki67-positive ($COX-2^+Ki67^+$) or ERBB2-positive, Ki67-positive ($ERBB2^+Ki67^+$); g) ER-negative, Ki67-positive ($ER^-Ki67^+$) or ER-negative, ERBB2-positive ($ER^-ERBB2^+$); h) ER-negative/ERBB2-positive/Ki67-positive ($ER^-ERBB2^+Ki67^+$) or p16/Ki67-positive and COX-2-negative ($p16^+COX-2^-Ki67^+$); and/or (i) progesterone receptor (PR) positive and HER2/neu-oncoprotein (ERBB2) negative and Ki67⁻ negative ($ER^+ERBB2^-Ki67^-$). As will be appreciated by those of skill in the art, such a configuration can be readily achieved by selecting appropriate detectable markers with sufficiently different detection properties such that the positive and/or negative results indicated above can be viewed simultaneously with one another, for example, by selecting markers with appropriate emission spectra so that at least 2, 3, 4, or 5 of the above markers can be detected simultaneously. In other embodiments, a subject antibody panel comprises antibody reagents that provide for detection of TRF2 and activin. In other embodiments, a subject antibody panel comprises antibody reagents that provide for detection of activin, and markers that are induced by activin.

Antibody Reagents that Detect the Presence and/or Level of Posttranslationally Modified Polypeptides In some embodiments, a subject antibody detects the presence and/or level of a posttranslationally modified polypeptide produced by an MEC. Posttranslationally modified polypeptides that are targets for a subject antibody reagent include histone deacetylase (HDAC) polypeptides. Posttranslational modifications of HDAC polypeptides include methylation and acetylation. In some embodiments, an antibody reagent specifically binds to an HDAC epitope(s) that is not modified, e.g., the antibody reagent binds specifically to an HDAC epitope that comprises only encoded amino acids. In other embodiments, an antibody reagent specifically binds to an acetylated HDAC polypeptide, e.g., the antibody reagents binds specifically to an HDAC epitope that is acetylated. In other embodiments, an antibody reagent specifically binds to a methylated HDAC polypeptide, e.g., the antibody reagents binds specifically to an HDAC epitope that is methylated.

Antibody Reagents that Detect a Chromatin Modification

In some embodiments, an antibody reagent for use in a subject detection method includes an antibody reagent that detects a modification of one or more intracellular proteins. Modification of an intracellular matrix includes, e.g., modification of chromatin, e.g., acetylation of chromatin by an HDAC (e.g., polycomb-group (PcG) protein modifications; histone modifications); etc. In some embodiments, an antibody reagent detects a chromatin epitope that is acetylated. In other embodiments, an antibody reagent detects a chromatin epitope that is deacetylated. In other embodiments, an antibody reagent detects a chromatin epitope that is methylated. In other embodiments, an antibody reagent detects a chromatin epitope that is demethylated.

Antibody Reagents that Detect Modification of an Extracellular Matrix Component

In some embodiments, an antibody reagent for use in a subject detection method includes an antibody reagent that detects a modification in an extracellular matrix (ECM) component. ECM modifications that can be detected using a subject antibody reagent include, but are not limited to, enzymatic cleavage of an ECM component into fragments; sulfation; removal of one or more sulfate groups; phosphorylation; dephosphorylation; glycosylation; deglycosylation; and the like. ECM includes, but is not limited to, collagen, fibronectin, elastin, laminin, etc.

Antibody Reagents that Detect Secretion and/or Release of a Molecule

In some embodiments, an antibody reagent for use in a subject detection method includes an antibody reagent that detects a secreted or released molecule from a cell, e.g., an MEC, a fibroblast that is cultured in vitro with a reporter epithelial cell, etc. Secreted or released molecules that can be detected using an antibody reagent include, e.g., proteins. MEC can also secrete one or more of a nucleic acid, a calcium ion, etc., and such molecules can be detected using other reagents, as described below.

Binding Reagents that Detect Methylated DNA

In some embodiments, a binding reagent for use in a subject detection method includes a binding reagent that detects methylated DNA, e.g., where the methylation status of a selected DNA provides an indication as to whether a cell, e.g., an MEC, is pre-cancerous. Binding reagents that detect methylated DNA are known in the art and include binding reagents that specifically bind a nucleotide sequence comprising a $C^{me}pG$ sequence, where $C^{me}$ is methylated cytosine. Suitable $C^{me}pG$-specific binding reagents include methylated-CpG binding domain proteins (MBD) (e.g., MECP2; MBD2; etc.); a methylated-CpG-binding domain of an MBD protein; an antibody reagent specific for a methylated-CpG; and the like. See, e.g., Yegnasubramanian et al. (2006) Nucl. Acids Res. 34:e19. Proteins containing a methyl-binding domain include, but are not limited to, MBD 1, MBD2, MBD3, MBD4, MeCP1 and MeCP2. See, for example, Bird et al. (1999) Cell 99:451-454.

Specific Binding Reagent Panels

Specific binding reagent panels are provided. As noted above, in some embodiments, a specific binding reagent is an antibody; however, specific binding reagents other than antibodies are also contemplated. Where the disclosure refers to an "antibody reagent panel," it should be understood that the disclosure applies as well to panels of other specific binding reagents. Antibody reagent panels (specific binding reagent panels) are provided, where a subject antibody reagent panel includes two or more of: 1) an antibody reagent that provides for detection of the presence and/or level of a selected protein or collection of proteins, e.g., a selected protein or collection of proteins that provide for detection of a pre-cancerous MEC; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell, e.g., from an MEC, from a fibroblast that is cultured in vitro with a reporter epithelial cell, etc; and 6) a binding reagent that provides for detection of a methylated DNA.

In some embodiments, a subject antibody reagent panel includes two or more of: 1) two or more different antibody reagents that provide for detection of the presence and/or level of two or more selected proteins, e.g., two or more selected proteins that provide for detection of a pre-cancerous MEC; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more antibodies that bind specifically to two or more of the protein markers identified in FIG. 14. In some embodiments, a subject antibody reagent panel includes two or more of: 1) two or more different antibody reagents that provide for detection of the presence and/or level of two or more of CD73, CD138, notch receptor-3, CD90, BMI-1, PR, ER, COX-2, Ki67, p16, ERBB2, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more of: 1) two or more different antibody reagents that provide for detection of the presence and/or level of two or more of CD73, CD138, notch receptor-3, CD90, BMI-1, and COX-2; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more of: 1) two or more different antibody reagents that provide for detection of the presence and/or level of COX-2, Ki67, and p16; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

In some embodiments, a subject antibody reagent panel includes two or more of: 1) two or more different antibody reagents that provide for detection of the presence and/or level of TRF2 and activin; 2) an antibody reagent that provides for detection of the presence and/or level of a posttranslationally modified polypeptide; 3) an antibody reagent that provides for detection of a chromatin modification; 4) an antibody reagent that provides for detection of modification of an ECM component; 5) an antibody reagent that provides for detection of secretion or release of a molecule from a cell; and 6) a binding reagent that provides for detection of a methylated DNA.

As noted above, in some embodiments, an antibody reagent panel comprises two or more antibody reagents immobilized onto an insoluble support. In some embodiments, a subject antibody reagent panel comprises an array of antibody reagents.

Nucleic Acid Reagents

The present invention provides nucleic acid reagents for use in a subject detection method (e.g., in a subject imaging method, a subject diagnostic method, a subject prognostic method, a subject method for determining efficacy of a treatment method, etc.). The nucleic acid reagents are in substantially isolated form, and can be synthetic or recombinant. The nucleic acid reagents include reagents that provide for one or more of: 1) detection of the level of a selected DNA; 2) detection of the integrity of a selected DNA; 3) detection of the methylation status of a selected DNA; 4) detection of the presence and/or a level of a selected mRNA or collection of mRNA; and 5) detection of the presence and/or level of a selected microRNA or collection of microRNAs.

Reagents for Detecting the Level of a Selected DNA

In some embodiments, a subject nucleic acid reagent provides for detection of the level of a selected DNA in an MEC. For example, in some embodiments, a selected DNA is amplified (e.g., present in greater than the normal copy number) in an MEC that is pre cancerous. In other embodiments, a selected DNA is deleted (entirely or in part) in an MEC that is pre-cancerous. Suitable nucleic acid reagents for detecting the level of a selected DNA in an MEC include nucleic acid reagents that function as primers for nucleic acid amplification; nucleic acid reagents that function as nucleic acid probes; and the like. In some embodiments, one or more additional, non-nucleic acid, reagent is provided in a system for use in detecting the level of a selected DNA in an MEC. Such additional reagents include, for example, a restriction endonuclease that cuts at a site adjacent to and/or within an amplified region of a selected DNA; and the like. As an example, a subject system can include a restriction endonuclease that cuts at a site adjacent to and/or within an amplified region of a selected DNA; and a nucleic acid reagent that functions as a probe and provides for determination of the relative levels of the selected DNA in a test MEC, compared to one or more control MEC. Genomic loci that are amplified in a pre-cancerous MEC include loci in chromosome 14q. Genomic loci that are deleted in a pre cancerous MEC include loci in chromosomes 3p, 4, 5, and 6q. Such amplifications and/or deletions can be detected by array profiling, by karyotyping, etc.

Reagents for Detecting the Integrity of a Selected DNA

In some embodiments, a subject nucleic acid reagent provides for detection of the integrity of a selected DNA in an MEC. For example, in some embodiments, a subject nucleic acid reagent provides for detection of one or more of: a translocation of a selected DNA, an inversion of a selected DNA, deletion of all or a portion of a selected DNA, and telomere integrity, in an MEC. Suitable nucleic acid reagents for detecting the integrity of a selected DNA in an MEC include nucleic acid reagents that function as primers for nucleic acid amplification; nucleic acid reagents that function as nucleic acid probes; and the like. In some embodiments, one or more additional, non-nucleic acid, reagent is provided in a system for use in detecting the integrity of a selected DNA in an MEC. Such additional reagents include, for example, a restriction endonuclease that cuts at a site adjacent to and/or within a selected DNA; and the like. As an example, a subject system can include a restriction endonuclease that cuts at a site adjacent to and at a site within a selected DNA; and a nucleic acid reagent that functions as a probe and provides for determination of the integrity of the selected DNA in a test MEC, compared to one or more control MEC.

Reagents that Provide for Detection of the Methylation Status of a Selected DNA

In some embodiments, a subject nucleic acid reagent provides for detection of the methylation status of a selected DNA in an MEC. Suitable nucleic acid reagents include nucleic acid reagents that function as primers for nucleic acid amplification; nucleic acid reagents that function as nucleic acid probes; and the like. Nucleic acid reagents can be used in a variety of methods to detect DNA methylation status, where suitable methods include, but are not limited to, methylation-specific polymerase chain reaction (MSP; Herman et al. (1996) *Proc. Natl. Acad. Sci. USA* 93:9821-9826); MethylLight (Eads et al. (2000) *Nucl. Acids Res.* 28:E32; and U.S. Pat. No. 6,331,393); HeavyMethyl (Cottrell et al. (2004) *Nucl. Acids Res.* 32:e10); MethylQuant (Thomassin et al. (2004) *Nucl. Acids Res.* 32:e168; and the like.

A number of methods involve treatment of DNA with a bisulfite reagent, which converts unmethylated cytosines to uracils, leaving only methylated cytosines unchanged (see, e.g., WO 05/038051). Following bisulfite treatment, individual cytosine positions can be detected by a primer extension reaction (Gonzalgo and Jones (1997) Nucleic Acids Res. 25:2529-31; and WO 95/00669) or by enzymatic digestion (Xiong and Laird (1997) Nucleic Acids Res. 25: 2535-4). Alternatively, following bisulfite treatment, a methylation-specific polymerase chain reaction (PCR) can be carried out, using primers that bind either to methylated or unmethylated DNA only and that therefore selectively amplify only DNA with a defined methylation. MethylLight is a variation of MSP, and involves use of a methylation-specific real time detection probe (MethyLight), which makes the assay both homogenous and quantitative. HeavyMethyl is also a variation on MSP. In the HeavyMethyl method, the priming is methylation specific, but non-extendable oligonucleotide blockers provide this specificity instead of the primers themselves. The blockers bind to bisulfite-treated DNA in a methylation-specific manner, and their binding sites overlap the primer binding sites. When the blocker is bound, the primer cannot bind and therefore the amplicon is not generated. When the blocker is not bound, the primer-binding site is accessible and the amplicon is generated. HeavyMethyl in combination with real-time detection with methylation-specific fluorogenic probes provides sensitive and specific detection of DNA methylation.

In some embodiments, a subject system will include, in addition to a nucleic acid reagent, one or more additional reagents, e.g., a methylation-sensitive restriction endonuclease (e.g., a restriction endonuclease that recognizes and cleaves a nucleic acid having a particular nucleotide sequence only when the sequence is unmethylated); a methylation insensitive restriction endonuclease (e.g., a restriction endonuclease that recognizes and cleaves a nucleic acid having a particular nucleotide sequence, regardless of the methylation status of the nucleotide sequence); and the like. The term "methylation-sensitive enzyme" refers to a restriction enzymes that does not cleave DNA (or cleaves DNA poorly) if one or more nucleotides in its recognition site are methylated. Suitable methylation-sensitive and methylation-insensitive restriction endonucleases that are suitable for use include, but are not limited to, MboI, DpnII, HpaII, BsmBI, Sau3A, and ClaI.

Reagents that Provide for Detection of the Level and/or Presence of an mRNA

A subject nucleic acid reagent includes a nucleic acid probe, or collection of nucleic acid probes, that provides for detection of the presence and/or level of an mRNA (or a cDNA copy of an mRNA) in an MEC. In some embodiments, a subject nucleic acid reagent is a nucleic acid primer, or a collection of nucleic acid primers, that provides for detection of the presence and/or level of an mRNA (or a cDNA copy of an mRNA) in an MEC. For example, a subject nucleic acid reagent includes a nucleic acid probe, or collection of nucleic acid probes, a nucleic acid primer, or a collection of nucleic acid primers, that provides for detection of the presence and/or level of an mRNA (or a cDNA copy of an mRNA) that is differentially expressed in a pre-cancerous MEC. For example, an mRNA (or a cDNA copy) that is differentially expressed in a pre-cancerous MEC can be expressed at a level that is at least about 25%, at least about 50%, at least about 75%, at least about 100% (or 2-fold), at least about 5-fold, at least about 10-fold, at least about 50-fold, or at least about 100-fold, or more, higher than the level of the mRNA in a normal (non-pre-cancerous) MEC. As another example, an mRNA (or a cDNA copy) that is differentially expressed in a pre-cancerous MEC can be expressed at a level that is at least about 20%, at least about 30%, at least about 40%, at least about 50%, at least about 60%, at least about 70%, at least about 80%, or at least about 90% lower than the level of the mRNA in a normal (e.g., non-pre-cancerous) MEC.

Exemplary nucleic acid probes include probes that detect, in an MEC (e.g., a vMEC, or a normal MEC), one or more of the mRNA set forth in FIG. 14. Exemplary nucleic acid probes include probes that detect, in an MEC (e.g., a vMEC, or a normal MEC), one or more of the following mRNA (or cDNA copy of an mRNA): CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject nucleic acid reagent is a collection of nucleic acid probes that provides for detection of two or more of the following mRNA (or cDNA copy of an mRNA): CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject nucleic acid reagent is a collection of nucleic acid probes that provides for detection of the presence and/or level of two, three, four, five, or all of CD73, CD138, notch receptor-3, CD90, BMI-1, and COX-2 mRNAs (or cDNA copies of same). In other embodiments, a subject nucleic acid reagent is a collection of nucleic acid probes that provides for detection of the presence and/or level of Ki67, COX-2, and p16 mRNA (or cDNA copies of same). In some embodiments, a subject nucleic acid reagent is a collection of nucleic acid probes that provides for detection of the presence and/or level of any two, 3, 4, 5 or more of ER, ERBB2, Ki67, COX-2, and p16 mRNA (or cDNA copies of same).

Nucleic acid probes that are suitable for detecting the presence and/or level of an mRNA that is differentially expressed in a pre-cancerous MEC can have a length of from about 10 nucleotides to about 100 nucleotides (nt), e.g., from about 10 nt to about 15 nt, from about 15 nt to about 20 nt, from about 20 nt to about 25 nt, from about 25 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt.

Nucleic acids comprising nucleotide sequences encoding CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2 are known in the art; and can form the basis for the design and preparation of a nucleic acid reagent, or collection of nucleic acid reagents, including probes and primers. For example, nucleotide sequences encoding human CD73 are presented in GenBank Accession Nos. BC065937, NM_002526, and AL589666; nucleotide sequences encoding human CD90 are presented in GenBank Accession Nos. AF261093, NM_006288, and BC065559; nucleotide sequences encoding human CD138 are presented in GenBank Accession Nos. NM_002997, and BC008765; nucleotide sequences encoding human notch-3 receptor are presented in GenBank Accession Nos. U97669, AC004663, AH006054, and NM000435; nucleotide sequences encoding human COX-2 are presented in GenBank Accession Nos. M90100, and NM_000963; nucleotide sequences encoding human Ki-67 are presented in GenBank Accession Nos. X65551, X65550, AL355529, and AL390236; nucleotide sequences encoding human p16 are presented in GenBank Accession Nos. NM_000077, NM_058195, and NM_058197; nucleotide sequences encoding human TRF2 are presented in GenBank Accession Nos NM_005652 and AF002999; nucleotide sequences encoding human activin βA chain are presented in GenBank Accession Nos CH236951 and BC007858; nucleotide sequences encoding human ERBB2 are presented in GenBank Accession No. NM_004448 and; nucleotide sequences encoding human ER are presented in GenBank Accession Nos. NM_000125.3, NM_001122740.1, NM_001122741.1, and NM_001122742.1.

Reagents that Provide for Detection of the Presence and/or Level of a microRNA In some embodiments, a subject nucleic acid reagent provides for detection of the presence and/or level of a microRNA that is expressed in a pre-cancerous MEC, e.g., that is differentially expressed in a pre-cancerous MEC, compared to a normal (non-precancerous MEC). MicroRNAs that can be detected using a subject nucleic acid reagent include, but are not limited to, mir 196b (HoxA9), (p14), 328, 30A-3P, 125b, 30E-3P, 680,134, 604, 128b, 128a, 331, 520F, 299-3P, 520H, 510, 365, 520G, 9, 324-3P, 351,125A, 764-5P, 302D, 520D, 652, 520C, 350, 585, 621, 542-5P, 560, 126, and 341. See, e.g., Griffiths-Jones et al. (2006) "miR-Base: microRNA sequences, targets and gene nomenclature" *Nucleic Acids Res.* 34:D140-D144; GenBank Accession No. NT 007819; Kim et al. (2004) *Proc. Natl. Acad. Sci. USA* 101:360-365; Weber (2005) *FEBS J.* 272:59-73.

For specific microRNA sequences, see, e.g.: 1) 328: Kim et al. (2004) *Proc. Natl. Acad. Sci. USA* 101:360-365; and Weber (2005) *FEBS J.* 272:59-73; 2) 196b: Yekta et al. (2004) *Science* 304:594-596; 3) 30A-3p: Kasashima et al. ((2004) *Biochem. Biophys. Res. Comm.* 322:403-410; 4) 125b: Lee et al. (2005) *J. Biol. Chem.* 280:16635-16641; 5) 30e-3p: Kasashima et al. (2004) *Biochem. Biophys. Res. Comm.* 322:403-410; and Weber (2005) *FEBS J.* 272:59-73; 6) 680: Weber (2005) *FEBS J.* 272:59-73; and Fu et al. (2005) *FEBS Lett.* 579:3849-3854; 7) 134: Altuvia et al. (2005) *Nucl. Acids Res.* 33:2697-2706; and Suh et al. (2004) *Dev Biol.* 270:488-498; 8) 604: Cummins et al. (2006) *Proc Natl Acad Sci USA.* 103:3687-3692; 9) 128b: Lim et al. (2003) *Science* 299:1540; 10) 128a: Kasashima et al. ((2004) *Biochem. Biophys. Res. Comm.* 322:403-410; 11) 331: Kim et al. (2004) *Proc. Natl. Acad. Sci. USA* 101:360-365; and Weber (2005) FEBS J. 272:59-73; 12) 520F: Bentwich et al. (2005) *Nat. Genet.* 37:766-770; 13) 299-3P: Altuvia et al. (2005) *Nucl. Acids Res.* 33:2697-2706; and Weber (2005) *FEBS J.* 272:59-73; 14) 520H: Bentwich et al. (2005) *Nat. Genet.* 37:766-770; 15) 510: Bentwich et al. (2005) *Nat. Genet.* 37:766-770; 16) 365: Bentwich et al. (2005) *Nat. Genet.* 37:766-770; 17) 520G: Bentwich et al. (2005) *Nat. Genet.* 37:766-770; 18) 324-3P: Kim et al. (2004) *Proc. Natl. Acad. Sci. USA* 101:360-365; and Weber (2005) *FEBS J.* 272:59-73; 19) 125A: Lagos-Quintana et al. (2002) *Curr Biol.* 12:735-739; 20) 302D: Suh et al. (2004) *Dev Biol.* 270:488-498; 21) 520D: Bentwich et al. (2005) *Nat. Genet.* 37:766-770; 22) 652: 22) 652: Cummins et al. (2006) *Proc Natl Acad Sci USA.* 103:3687-3692; 23) 520C: Bentwich et al. (2005) *Nat. Genet.* 37:766-770; 24) 585: Cummins et al. (2006) *Proc Natl Acad Sci USA.* 103:3687-3692; 25) 621: Cummins et al. (2006) *Proc Natl Acad Sci USA.* 103:3687-3692; 26) 542-5p: Sewer et al. (2005) BMC Bioinformatics. 6:267; 27) 560: Cummins et al. (2006) *Proc Natl Acad Sci USA.* 103:3687-3692; and 28) 126: Lagos-Quintana et al. (2002) *Curr Biol.* 12:735-739.

A suitable sequence includes a stem-loop sequence; a mature sequence; a sequence complementary to a stem-loop sequence; and a sequence complementary to a mature sequence.

MicroRNA sequences include, e.g.,

```
1) 328: stem-loop sequence:
                                       (SEQ ID NO: 1)
UGGAGUGGGGGGGCAGGAGGGGCUCAGGGAGAAAGUGCAUACAGCCCC

UGGCCCUCUCUGCCCUUCCGUCCCCUG;
```

```
-continued
mature sequence:
                                       (SEQ ID NO: 2)
CUGGCCCUCUCUGCCCUUCCGU;

nucleotide sequence complementary to mature
sequence:
                                       (SEQ ID NO: 3)
5'-ACGGAAGGGCAGAGAGGGCCAG-3';

2) 196b: stem-loop sequence:
                                       (SEQ ID NO: 4)
ACUGGUCGGUGAUUUAGGUAGUUUCCUGUUGUUGGGAUCCACCUUUCU

CUCGACAGCACGACACUGCCUUCAUUACUUCAGUUG;

mature sequence:
                                       (SEQ ID NO: 5)
UAGGUAGUUUCCUGUUGUUGG;

nucleotide sequence complementary to mature
sequence:
                                       (SEQ ID NO: 6)
5'-CCAACAACAGGAAACTACCTA-3';

3) 30A-3P: stem-loop sequence:
                                       (SEQ ID NO: 7)
GCGACUGUAAACAUCCUCGACUGGAAGCUGUGAAGCCACAGAUGGGCU

UUCAGUCGGAUGUUUGCAGCUGC;

mature sequence:
                                       (SEQ ID NO: 8)
UGUAAACAUCCUCGACUGGAAG;

nucleotide sequence complementary to mature
sequence:
                                       (SEQ ID NO: 9)
5'-CTTCCAGTCGAGGATGTTTACA-3';

4) 125b: stem-loop sequence:
                                       (SEQ ID NO: 10)
UGCGCUCCUCUCAGUCCCUGAGACCCUAACUUGUGAUGUUUACCGUUU

AAAUCCACGGGUUAGGCUCUUGGGAGCUGCGAGUCGUGCU;

mature sequence:
                                       (SEQ ID NO: 11)
UCCCUGAGACCCUAACUUGUGA;

nucleotide sequence complementary to mature
sequence:
                                       (SEQ ID NO: 12)
5'-TCACAAGTTAGGGTCTCAGGGT-3';

5) 30e-3p: stem-loop sequence:
                                       (SEQ ID NO: 13)
GGGCAGUCUUUGCUACUGUAAACAUCCUUGACUGGAAGCUGUAAGGUG

UUCAGAGGAGCUUUCAGUCGGAUGUUUACAGCGGCAGGCUGCCA;

mature sequence:
                                       (SEQ ID NO: 14)
CUUUCAGUCGGAUGUUUACAGC;

nucleotide sequence complementary to mature
sequence:
                                       (SEQ ID NO: 15)
5'-GCTGTAAACATCCGACTGAAAG-3';

6) 680: stem-loop sequence:
                                       (SEQ ID NO: 16)
CCUGCCGGGGCUAAAGUGCUGACAGUGCAGAUAGUGGUCCUCUCCGUG

CUACCGCACUGUGGGUACUUGCUGCUCCAGCAGG;

mature sequence: mature sequence:
                                       (SEQ ID NO: 17)
UAAAGUGCUGACAGUGCAGAU;
```

-continued nucleotide sequence complementary to mature
sequence:
                                        (SEQ ID NO: 18)
5'-ATCTGCACTGTCAGCACTTTA-3';

7) 134: stem-loop sequence:
                                        (SEQ ID NO: 19)
CAGGGUGUGUGACUGGUUGACCAGAGGGGCAUGCACUGUGUUCACCCU

GUGGGCCACCUAGUCACCAACCCUC;

mature sequence:
                                        (SEQ ID NO: 20)
UGUGACUGGUUGACCAGAGGG;

nucleotide sequence complementary to mature
sequence:
                                        (SEQ ID NO: 21)
5'-CCCTCTGGTCAACCAGTCACA-3';

8) 604: stem-loop sequence:
                                        (SEQ ID NO: 22)
AGAGCAUCGUGCUUGACCUUCCACGCUCUCGUGUCCACUAGCAGGCAG

GUUUUCUGACACAGGCUGCGGAAUUCAGGACAGUGCAUCAUGGAGA;

mature sequence:
                                        (SEQ ID NO: 23)
AGGCUGCGGAAUUCAGGAC;

nucleotide sequence complementary to mature
sequence:
                                        (SEQ ID NO: 24)
5'-GTCCTGAATTCCGCAGCCT-3';

9) 128b: stem-loop sequence:
                                        (SEQ ID NO: 25)
UGUGCAGUGGGAAGGGGGGCCGAUACACUGUACGAGAGUGAGUAGCAG

GUCUCACAGUGAACCGGUCUCUUUCCCUACUGUGUC;

mature sequence:
                                        (SEQ ID NO: 26)
UCACAGUGAACCGGUCUCUUUC;

nucleotide sequence complementary to mature
sequence:
                                        (SEQ ID NO: 27)
5'-GAAAGAGACCGGTTCACTGTGA-3';

10) 128a: stem-loop sequence:
                                        (SEQ ID NO: 28)
UGAGCUGUUGGAUUCGGGGCCGUAGCACUGUCUGAGAGGUUUACAUUU

CUCACAGUGAACCGGUCUCUUUUUCAGCUGCUUC;

mature sequence:
                                        (SEQ ID NO: 29)
UCACAGUGAACCGGUCUCUUUU;

nucleotide sequence complementary to mature
sequence:
                                        (SEQ ID NO: 30)
5'-AAAAGAGACCGGTTCACTGTGA-3';

11) 331: stem-loop sequence:
                                        (SEQ ID NO: 31)
GAGUUUGGUUUUGUUUGGGGUUUGUUCUAGGUAUGGUCCCAGGGAUCCC

AGAUCAAACCAGGCCCCUGGGCCUAUCCUAGAACCAACCUAAGCUC;

mature sequence:
                                        (SEQ ID NO: 32)
GCCCCUGGGCCUAUCCUAGAA;

nucleotide sequence complementary to mature
sequence:
                                        (SEQ ID NO: 33)
5'-TTCTAGGATAGGCCCAGGGGC-3';

-continued 12) 520F: stem-loop sequence:
                                        (SEQ ID NO: 34)
UCUCAGGCUGUGACCCUCUAAAGGGAAGCGCUUUCUGUGGUCAGAAAG

AAAAGCAAGUGCUUCCUUUUAGAGGGUUACCGUUUGGGA;

mature sequence:
                                        (SEQ ID NO: 35)
AAGUGCUUCCUUUUAGAGGGUU;

nucleotide sequence complementary to mature
sequence:
                                        (SEQ ID NO: 36)
5'-AACCCTCTAAAAGGAAGCACTT-3';

13) 299-3P: stem-loop sequence:
                                        (SEQ ID NO: 37)
AAGAAAUGGUUUACCGUCCCACAUACAUUUUGAAUAUGUAUGUGGGAU

GGUAAACCGCUUCUU;

mature sequence:
                                        (SEQ ID NO: 38)
UAUGUGGGAUGGUAAACCGCUU;

nucleotide sequence complementary to mature
sequence:
                                        (SEQ ID NO: 39)
5'-AAGCGGTTTACCATCCCACATA-3';

14) 520H: stem-loop sequence:
                                        (SEQ ID NO: 40
UCCCAUGCUGUGACCCUCUAGAGGAAGCACUUUCUGUUUGUUGUCUGA

GAAAAAACAAAGUGCUUCCCUUUAGAGUUACUGUUUGGGA;

mature sequence:
                                        (SEQ ID NO: 41)
ACAAAGUGCUUCCCUUUAGAGU;

nucleotide sequence complementary to mature
sequence:
                                        (SEQ ID NO: 42)
5'-ACTCTAAAGGGAAGCACTTTGA-3';

15) 510: stem-loop sequence:
                                        (SEQ ID NO: 43)
GUGGUGUCCUACUCAGGAGAGUGGCAAUCACAUGUAAUUAGGUGUGAU

UGAAACCUCUAAGAGUGGAGUAACAC;

mature sequence:
                                        (SEQ ID NO: 44)
UACUCAGGAGAGUGGCAAUCACA;

nucleotide sequence complementary to mature
sequence:
                                        (SEQ ID NO: 45)
5'-TGTGATTGCCACTCTCCTGAGTA-3';

16) 365: stem-loop sequence:
                                        (SEQ ID NO: 46)
ACCGCAGGGAAAAUGAGGGACUUUUGGGGGCAGAUGUGUUUCCAUUCC

ACUAUCAUAAUGCCCCUAAAAAAUCCUUAUUGCUCUUGCA;

mature sequence:
                                        (SEQ ID NO: 47)
UAAUGCCCCUAAAAAUCCUUAU;

nucleotide sequence complementary to mature
sequence:
                                        (SEQ ID NO: 48)
5'-ATAAGGATTTTTAGGGGCATTA-3';

17) 520G: stem-loop sequence:
                                        (SEQ ID NO: 49)
UCCCAUGCUGUGACCCUCUAGAGGAAGCACUUUCUGUUUGUUGUCUGA

GAAAAAACAAAGUGCUUCCCUUUAGAGUGUUACCGUUUGGGA;

-continued mature sequence:

(SEQ ID NO: 50)
ACAAAGUGCUUCCCUUUAGAGUGU;

nucleotide sequence complementary to mature
sequence:

(SEQ ID NO: 51)
5'-ACACTCTAAAGGGAAGCACTTTGA-3';

18) 324-3P: stem-loop sequence:

(SEQ ID NO: 52)
CUGACUAUGCCUCCCCGCAUCCCCUAGGGCAUUGGUGUAAAGCUGGAG

ACCCACUGCCCCAGGUGCUGCUGGGGGUUGUAGUC;

mature sequence:

(SEQ ID NO: 53)
CCACUGCCCCAGGUGCUGCUGG;

nucleotide sequence complementary to mature
sequence:

(SEQ ID NO: 54)
5'-CCAGCAGCACCTGGGGCAGTGG-3';

19) 125A: stem-loop sequence:

(SEQ ID NO: 55)
UGCCAGUCUCUAGGUCCCUGAGACCCUUUAACCUGUGAGGACAUCCAG

GGUCACAGGUGAGGUUCUUGGGAGCCUGGCGUCUGGCC;

mature sequence:

(SEQ ID NO: 56)
UCCCUGAGACCCUUUAACCUGUG;

nucleotide sequence complementary to mature
sequence:

(SEQ ID NO: 57)
5'-CACAGGTTAAAGGGTCTCAGGGT-3';

20) 302D: stem-loop sequence:

(SEQ ID NO: 58)
CCUCUACUUUAACAUGGAGGCACUUGCUGUGACAUGACAAAAAUAAGU

GCUUCCAUGUUUGAGUGUGG;

mature sequence:

(SEQ ID NO: 59)
UAAGUGCUUCCAUGUUUGAGUGU;

nucleotide sequence complementary to mature
sequence:

(SEQ ID NO: 60)
5'-ACACTCAAACATGGAAGCACTTA-3';

21) 520D: stem-loop sequence:

(SEQ ID NO: 61)
UCUCAAGCUGUGAGUCUACAAAGGGAAGCCCUUUCUGUUGUCUAAAAG

AAAAGAAAGUGCUUCUCUUUGGUGGGUUACGGUUUGAGA;

mature sequence:

(SEQ ID NO: 62)
UCUACAAAGGGAAGCCCUUUCUG;

nucleotide sequence complementary to mature
sequence:

(SEQ ID NO: 63)
5'-CAGAAAGGGCTTCCCTTTGTAGA-3';
22) 652: stem-loop sequence:

(SEQ ID NO: 64)
ACGAAUGGCUAUGCACUGCACAACCCUAGGAGAGGGUGCCAUUCACAU

AGACUAUAAUUGAAUGGCGCCACUAGGGUUGUGCAGUGCACAACCUAC

AC;

mature sequence:

(SEQ ID NO: 65)
AAUGGCGCCACUAGGGUUGUGCA;

-continued nucleotide sequence complementary to mature
sequence:

(SEQ ID NO: 66)
5'-TGCACAACCCTAGTGGCGCCATT-3';

23) 520C: stem-loop sequence:

(SEQ ID NO: 67)
UCUCAGGCUGUCGUCCUCUAGAGGGAAGCACUUUCUGUUGUCUGAAAG

AAAAGAAAGUGCUUCCUUUUAGAGGGUUACCGUUUGAGA;

mature sequence:

(SEQ ID NO: 68)
AAAGUGCUUCCUUUUAGAGGGUU;

nucleotide sequence complementary to mature
sequence:

(SEQ ID NO: 69)
5'-AACCCTCTAAAAGGAAGCACTTT-3';

24) 585: stem-loop sequence:

(SEQ ID NO: 70)
UGGGGUGUCUGUGCUAUGGCAGCCCUAGCACACAGAUACGCCCAGAGA

AAGCCUGAACGUUGGGCGUAUCUGUAUGCUAGGGCUGCUGUAACAA;

mature sequence:

(SEQ ID NO: 71)
UGGGCGUAUCUGUAUGCUA;

nucleotide sequence complementary to mature
sequence:

(SEQ ID NO: 72)
5'-TAGCATACAGATACGCCCA-3';

25) 621: stem-loop sequence:

(SEQ ID NO: 73)
UAGAUUGAGGAAGGGGCUGAGUGGUAGGCGGUGCUGCUGUGCUCUGAU

GAAGACCCAUGUGGCUAGCAACAGCGCUUACCUUUUGUCUCUGGGUCC;

mature sequence:

(SEQ ID NO: 74)
GGCUAGCAACAGCGCUUACCU;

nucleotide sequence complementary to mature
sequence:

(SEQ ID NO: 75)
5'-AGGTAAGCGCTGTTGCTAGCC-3';

26) 542-5p: stem-loop sequence:

(SEQ ID NO: 76)
CAGAUCUCAGACAUCUCGGGGAUCAUCAUGUCACGAGAUACCAGUGUG

CACUUGUGACAGAUUGAUAACUGAAAGGUCUGGGAGCCACUCAUCUUC

A;

mature sequence:

(SEQ ID NO: 77)
UCGGGGAUCAUCAUGUCACGAG;

nucleotide sequence complementary to mature
sequence:

(SEQ ID NO: 78)
5'-CTCGTGACATGATGATCCCCGA-3';

27) 560: stem-loop sequence:

(SEQ ID NO: 79)
UCCCCUCUGGCGGCUGCGCACGGGCCGUGUGAGCUAUUGCGGUGGGCU

GGGGCAGAUGACGCGUGCGCCGGCCGGCCGCCGAGGGGCUACCGUUC;

mature sequence:

(SEQ ID NO: 80)
GCGUGCGCCGGCCGGCCGCC;

-continued

```
nucleotide sequence complementary to mature
sequence:
                                (SEQ ID NO: 81)
5'-GGCGGCCGGCCGGCGCACGC-3';
and 28) 126: stem-loop sequence:
                                (SEQ ID NO: 82)
CGCUGGCGACGGGACAUUAUUACUUUUGGUACGCGCUGUGACACUUCA

AACUCGUACCGUGAGUAAUAAUGCGCCGUCCACGGCA;

mature sequence:
                                (SEQ ID NO: 83)
CAUUAUUACUUUUGGUACGCG;

nucleotide sequence complementary to mature
sequence:
                                (SEQ ID NO: 84)
5'-CGCGTACCAAAAGTAATAATG-3'.
```

Nucleic acids that provide for detection of the presence and/or level of a microRNA that is differentially expressed in a pre-cancerous HMEC can comprises a nucleotide sequence that is complementary to all or a portion of a target microRNA. For example, the nucleotide sequence 5'-CGCGTACCAAAAGTAATAATG-3' is complementary to the mature sequence of the 126 microRNA.

Nucleic acid reagents that provide for detection of the presence and/or level of a microRNA that is differentially expressed in a pre-cancerous HMEC can have a length of from about 10 nucleotides to about 100 nucleotides (nt), e.g., from about 10 nt to about 15 nt, from about 15 nt to about 20 nt, from about 20 nt to about 25 nt, from about 25 nt to about 30 nt, from about 30 nt to about 40 nt, from about 40 nt to about 50 nt, from about 50 nt to about 60 nt, from about 60 nt to about 70 nt, from about 70 nt to about 80 nt, from about 80 nt to about 90 nt, or from about 90 nt to about 100 nt.

In some embodiments, a subject nucleic acid reagent provides for detection of the presence and/or level of a microRNA that is differentially expressed in a pre-cancerous MEC is immobilized onto an insoluble support. In some embodiments, the reagents include two or more nucleic acid probes that provide for detection of the presence and/or level of two or more microRNAs that are differentially expressed in a pre-cancerous MEC. In some embodiments, the two or more nucleic acid probes that provide for detection of the presence and/or level of two or more microRNAs that are differentially expressed in a pre-cancerous MEC are immobilized onto an insoluble support.

Target Nucleic Acids

Target nucleic acids include nucleic acids that are abnormally expressed in a pre-cancerous epithelial cell, where the abnormal expression levels are thus associated with an increased risk of developing cancer (e.g., a carcinoma, e.g., breast cancer) and/or are associated with a pre-cancerous or cancerous state of a cell such as an epithelial cell and/or are indicative of the presence of a pre-cancerous cell in the individual. For example, abnormal expression levels of a target nucleic acid will in some cases be associated with abnormal levels of target mRNA and/or target polypeptide in an epithelial cell. Exemplary, non-limiting target nucleic acids are the nucleic acids listed in FIG. 14. Exemplary, non-limiting target nucleic acids are CD73, CD138, notch receptor-3, CD90, BMI-1, COX-2, ER, ERBB2, Ki67, p16, IGF2, YKL-40, EGF R, c-jun, PCNA, jnk, cyclin B1, c-kit, STAT3, cyclin D1, PI3K, MAPK, MAPKK, DDR, TRF2, activin, and MEK1/2. Exemplary, non-limiting target nucleic acids are CD73, CD138, notch receptor-3, CD90, BMI-1, and COX-2 nucleic acids. Exemplary combinations of nucleic acids, which in some embodiments can be tested for simultaneously, include COX-2, p16, and Ki67; Ki67, ER, and ERBB2; and COX-2, p16, Ki67, ER, and ERBB2.

In some embodiments, abnormal levels of a target mRNA that, when present in a cell, are associated with a precancerous or cancerous state of the cell, are levels that are significantly higher or lower than normal levels of the target mRNA found in a non-cancerous cell of the same cell type. In some embodiments, abnormal levels of a target mRNA that, when present in a test cell, are indicative of the presence of a cancerous cell in the individual from whom the test cell was obtained, are levels that are significantly higher or lower than normal levels of the target mRNA typically found in the test cell in an individual who does not have cancer.

An abnormally high level of a target mRNA that, when present in a cell, is associated with a precancerous or cancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the target mRNA in a non-cancerous cell of the same cell type, e.g., an epithelial cell.

For example, an abnormally high level of a target mRNA that, when present in an epithelial cell, is associated with a precancerous state of the cell, is a level that is at least about 25%, at least about 50%, at least about 100% (or 2-fold), at least about 3-fold, at least about 5-fold, at least about 10-fold, at least about 25-fold, or at least about 50-fold, or more, higher than the level of the target mRNA in a non-cancerous epithelial cell.

An abnormally low level of a target mRNA that, when present in a cell, is associated with a precancerous or cancerous state of the cell, is a level that is about 75% or less, about 60% or less, about 50% or less, about 25% or less, or about 10% or less, than the level of the target mRNA in a non-cancerous cell of the same cell type For example, an abnormally low level of a target mRNA that, when present in an epithelial cell, is associated with a precancerous state of the epithelial cell, is a level that is about 75% or less, about 60% or less, about 50% or less, about 25% or less, or about 10% or less, than the level of the target mRNA in a non-cancerous epithelial cell.

Sources of Target Nucleic Acids

Where the detection methods involve detection of a target nucleic acid, the target nucleic acids are detected in samples obtained from a tissue comprising cells. In some embodiments, the cells are obtained from a tissue suspected of comprising cancer cells.

The source of the tissue will depend, at least in part, on the type of pre cancerous epithelial cell that is being detected. For example, target nucleic acids can be obtained from lung tissue (for detection of a pre-cancerous lung epithelial cell); from pancreas; from prostate; etc.

In the context of breast cancer, the source of target nucleic acid is breast tissue. In some embodiments, the tissue is a breast biopsy. In other embodiments, the tissue is an axillary lymph node tissue. In the context of breast cancer, suitable sources of target nucleic acids include breast cells and lymph node cells, e.g., cells obtained via fine needle aspiration biopsy; cells obtained via core needle biopsy; cells obtained from lymph nodes in the vicinity of the breast (e.g., axillary lymph nodes); and the like.

In the context of breast cancer, breast cancers that can be detected using a subject method include mammary carcinoma, adenocarcinoma, ductal carcinoma in situ, lobular (small cell) carcinoma, intraductal carcinoma, medullary breast cancer, mucinous breast cancer, tubular breast cancer, papillary breast cancer, Paget's disease, inflammatory breast cancer, and hormone dependent tumors of the breast.

Nucleic Acid Probes

Some embodiments of the present invention provides inter alia detection, diagnostic, and staging methods, e.g., methods for detecting and diagnosing cancer (e.g., breast cancer and other carcinomas) in an individual; methods of identifying individuals at risk of developing cancer (e.g., breast cancer); and methods of staging cancer (e.g., breast cancer). The methods can generally involve detecting an abnormal level of a target mRNA in a biological sample obtained from the individual. The subject methods can be carried out using a method involving nucleic acid hybridization, amplification, or both.

Nucleic acid hybridization can be carried out using a nucleic acid probe that detects a level of a target mRNA that is abnormally expressed in a pre-cancerous epithelial cell. Where abnormal expression of a target nucleic acid is to be detected, nucleic acid probes suitable for use include nucleic acid probes that hybridize to and provide for detection of a target nucleic acid that is overexpressed or underexpressed in an epithelial cell, e.g., a pre-cancerous epithelial cell. The present invention provides such nucleic acid probes Suitable nucleic acid probes are in some embodiments in the range of between 10-50 nucleotides long, such as 10 to 50, 12 to 45, 15 to 40, 20 to 35, 25 to 30 nucleotides, and the like. For example, probes will in some embodiments be in the range of between 18 to 40, 19 to 35, 20 to 30, 21 to 29, 22 to 28, 23 to 27, 24-25 nucleotides long, and any length between the stated ranges. Probes of about 20 to 22 nucleotides in length are of particular interest in some embodiments.

A suitable probe may be coupled to a label for detection. There are several methods and compositions known for derivatizing oligonucleotides with reactive functionalities which permit the addition of a label. For example, several approaches are available for biotinylating probes so that radioactive, fluorescent, chemiluminescent, enzymatic, or electron dense labels can be attached via avidin. See, e.g., Broken et al., Nucl. Acids Res. (1978) 5:363-384 which discloses the use of ferritin-avidin-biotin labels; and Chollet et al. Nucl. Acids Res. (1985) 13:1529-1541 which discloses biotinylation of the 5' termini of oligonucleotides via an aminoalkylphosphoramide linker arm. Several methods are also available for synthesizing amino-derivatized oligonucleotides which are readily labeled by fluorescent or other types of compounds derivatized by amino-reactive groups, such as isothiocyanate, N-hydroxysuccinimide, or the like, see, e.g., Connolly (1987) Nucl. Acids Res. 15:3131-3139, Gibson et al. (1987) Nucl. Acids Res. 15:6455-6467 and U.S. Pat. No. 4,605,735 to Miyoshi et al. Methods are also available for synthesizing sulfhydryl-derivatized oligonucleotides which can be reacted with thiol-specific labels, see, e.g., U.S. Pat. No. 4,757,141 to Fung et al., Connolly et al. (1985) Nuc. Acids Res. 13:4485-4502 and Spoat et al. (1987) Nucl. Acids Res. 15:4837-4848. A comprehensive review of methodologies for labeling DNA fragments is provided in Matthews et al., Anal. Biochem. (1988) 169:1-25.

For example, probes may be fluorescently labeled by linking a fluorescent molecule to the non-ligating terminus of the probe. Guidance for selecting appropriate fluorescent labels can be found in Smith et al., Meth. Enzymol. (1987) 155:260-301; Karger et al., Nucl. Acids Res. (1991) 19:4955-4962; Haugland (1989) Handbook of Fluorescent Probes and Research Chemicals (Molecular Probes, Inc., Eugene, Oreg.). Exemplary fluorescent labels include fluorescein and derivatives thereof, such as disclosed in U.S. Pat. No. 4,318,846 and Lee et al., Cytometry (1989) 10:151-164, and 6-FAM, JOE, TAMRA, ROX, HEX-1, HEX-2, ZOE, TET-1 or NAN-2, and the like.

Additionally, probes can be labeled with an acridinium ester (AE). Current technologies allow the AE label to be placed at any location within the probe. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. An AE molecule can be directly attached to the probe using non-nucleotide-based linker arm chemistry that allows placement of the label at any location within the probe. See, e.g., U.S. Pat. Nos. 5,585,481 and 5,185,439.

If a solid support is used in the assay (e.g., to capture amplicons of target nucleic acid using a probe), the oligonucleotide probe may be attached to the solid support in a variety of manners. For example, the probe may be attached to the solid support by attachment of the 3' or 5' terminal nucleotide of the probe to the solid support. In some embodiments, the probe is attached to the solid support by a linker which serves to distance the probe from the solid support. The linker is in many embodiments at least 15-30 atoms in length, or at least 15-50 atoms in length. The required length of the linker will depend on the particular solid support used. For example, a six atom linker is generally sufficient when high cross-linked polystyrene is used as the solid support.

A wide variety of linkers are known in the art which may be used to attach the oligonucleotide probe to the solid support. The linker may be formed of any compound which does not significantly interfere with the hybridization of the target sequence to the probe attached to the solid support. The linker may be formed of a homopolymeric oligonucleotide which can be readily added on to the linker by automated synthesis. Alternatively, polymers such as functionalized polyethylene glycol can be used as the linker. In some embodiments, polymers such as functionalized polyethylene glycol are used because they do not significantly interfere with the hybridization of probe to the target oligonucleotide. In some embodiments, the linked is polyethylene glycol.

The linkages between the solid support, the linker and the probe are normally not cleaved during removal of base protecting groups under basic conditions at high temperature. Examples of suitable linkages include carbamate and amide linkages.

Examples of suitable types of solid supports for immobilization of the oligonucleotide probe include controlled pore glass, glass plates, polystyrene, avidin-coated polystyrene beads, cellulose, nylon, acrylamide gel and activated dextran.

In some embodiments, methods of detecting a level of a target mRNA in a cell will involve amplifying the target nucleic acid, using a pair of nucleic acid primers.

In general, primers provide for amplification of a target nucleic acid to produce a target nucleic acid amplification product (also referred to as an "amplicon"). Primers will in some embodiments be used in conjunction with a nucleic acid probe. 5' primers generally bind to a region to provide for amplification of the target nucleic, and in many embodiments bind to a 5' portion of the target sequence. 3' primers generally bind to a sequence that is complementary to a 3' portion of the nucleic acid generated by extension from the 5' primer.

Target nucleotide sequences to which 5' and 3' primers hybridize will be separated from one another by from about 10 nucleotides to about 1000 nucleotides, e.g., from about 10 nucleotides to about 20 nucleotides, from about 20 nucleotides to about 30 nucleotides, from about 30 nucleotides to about 40 nucleotides, from about 40 nucleotides to about 50 nucleotides, from about 50 nucleotides to about 60 nucleotides, from about 60 nucleotides to about 70 nucleotides, from about 70 nucleotides to about 100 nucleotides, from about 100 nucleotides to about 150 nucleotides, from about 150 nucleotides to about 200 nucleotides, from about 200 nucleotides to about 250 nucleotides, from about 250 nucleotides to about 300 nucleotides, from about 300 nucleotides to about 400 nucleotides, from about 400 nucleotides to about 500 nucleotides, or from about 500 nucleotides to about 1000 nucleotides.

The amplification product will in many embodiments have a length in a range of from about 30 nucleotides (or base pairs, bp) to about 1000 nucleotides (or base pairs), e.g., from about 30 bp to about 50 bp, from about 50 bp to about 60 bp, from about 60 bp to about 70 bp, from about 70 bp to about 80 bp, from about 80 bp to about 90 bp, from about 90 bp to about 100 bp, from about 100 bp to about 150 bp, from about 150 bp to about 200 bp, from about 200 bp to about 250 bp, from about 250 bp to about 300 bp, from about 300 bp to about 350 bp, from about 350 bp to about 400 bp, from about 400 bp to about 500 bp, from about 500 bp to about 600 bp, from about 700 bp, from about 700 bp to about 800 bp, from about 800 bp to about 900 bp, or from about 900 bp to about 1000 bp (e.g., about 1 kb).

In some embodiments, the primer sequences are in the range of between 10-75 nucleotides in length, such as 10 to 70 nucleotides, 12 to 65 nucleotides, 15 to 60 nucleotides, 20 to 55 nucleotides, 25 to 50 nucleotides, 30 to 45 nucleotides, and the like. In some embodiments, primers are in the range of between 18 to 40, 19 to 35, 20 to 30, 21 to 29, 22 to 28, 23 to 27, 24-25 nucleotides long, and any length between the stated ranges. Primers of about 20 to 22 nucleotides in length are of particular interest in some embodiments.

In some embodiments, the first and/or the second primer comprises a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA); radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Nucleic Acid Arrays

In some embodiments, nucleic acid probe that provides for detection of a target nucleic acid is present in an array.

A subject nucleic acid array comprises an array of probe nucleic acids immobilized on a solid support surface. Nucleic acid probes are generally oligonucleotides, e.g. oligonucleotides of at least about 12 nucleotides (nt), at least about 15 nt, at least about 18 nt, at least about 20 nt, at least about 25 nt, at least about 30 nt, at least about 40 nt, at least about 50 at least about, at least about 60 nt, or longer. Such an array may comprise a series of oligonucleotides, each of which can specifically hybridize to a different target nucleic acid.

A variety of different array formats are known in the art, with a wide variety of different probe structures, substrate compositions and attachment technologies. Representative array structures of interest include those described in U.S. Pat. Nos. 6,919,211, 5,143,854; 5,288,644; 5,324,633; 5,432,049; 5,470,710; 5,492,806; 5,503,980; 5,510,270; 5,525,464; 5,547,839; 5,580,732; 5,661,028; 5,800,992; the disclosures of which are herein incorporated by reference; as well as WO 95/21265; WO 96/31622; WO 97/10365; WO 97/27317; EP 373 203; and EP 785 280.

Essentially, any conceivable substrate for a subject nucleic acid may be employed. The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc. The substrate is typically flat but may take on a variety of alternative surface configurations. For example, the substrate may contain raised or depressed regions on which the synthesis takes place. The substrate and its surface in many embodiments form a rigid support on which to carry out the hybridization reactions described herein. For instance, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, polycarbonate, or combinations thereof. Other substrate materials will be readily apparent to those of skill in the art upon review of this disclosure. In an exemplary embodiment, the substrate is flat glass or single-crystal silicon with surface relief features of less than 10 $\mu$m.

According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, or the like.

Surfaces on the solid substrate will in many embodiments be composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. In many embodiments, the surface will contain reactive groups, which could be carboxyl, amino, hydroxyl, or the like. In many embodiments, the surface will be optically transparent and will have surface Si—OH functionalities, such as are found on silica surfaces.

A number of methods are available for creating microarrays of nucleic acids to be used in DNA hybridization assays. Exemplary are PCT Application Serial No. WO95/

35505, published Dec. 28, 1995; U.S. Pat. No. 5,445,934, issued Aug. 29, 1995; and Drmanac et al. (1993) *Science* 260:1649-1652. Yershov et al. (1996) *Genetics* 93:4913-4918 describe an alternative construction of an oligonucleotide array. The construction and use of oligonucleotide arrays is reviewed by Ramsay (1998) supra. Methods of using high density oligonucleotide arrays are known in the art. For example, Milosavljevic et al. (1996) Genomics 37:77-86 describe DNA sequence recognition by hybridization to short oligomers.

The systems and kits of the subject invention may include the above-described arrays. The systems and kits may further include one or more additional reagents employed in the various methods, such as primers for generating target nucleic acids, dNTPs and/or rNTPs, which may be either premixed or separate, one or more uniquely labeled dNTPs and/or rNTPs, such as biotinylated or Cy3 or Cy5 tagged dNTPs, gold or silver particles with different scattering spectra, or other post synthesis labeling reagent, such as chemically active derivatives of fluorescent dyes, enzymes, such as reverse transcriptases, DNA polymerases, RNA polymerases, and the like, various buffer mediums, e.g. hybridization and washing buffers, prefabricated probe arrays, labeled probe purification reagents and components, like spin columns, etc., signal generation and detection reagents, e.g. streptavidin-alkaline phosphatase conjugate, chemifluorescent or chemiluminescent substrate, and the like.

Internal Control Nucleic Acids

In certain embodiments, an internal control (IC) or an internal standard is added to serve as a control to show that any negative result is not due to failure of the assay. The use of the IC permits the control of the separation process, the amplification process, and the detection system, and permits the monitoring of assay performance and quantification for the sample(s). The IC can be included at any suitable point, for example, in the lysis buffer. In one embodiment, the IC comprises phage nucleic acid. Where a solid support is used in the assay, the solid support may additionally include probes specific to the internal standard (IC probe), thereby facilitating capture when using the IC probe. The IC probe can optionally be coupled with a detectable label that is different from the detectable label for the target sequence. In embodiments where the detectable label is a fluorophore, the IC can be quantified spectrophotometrically and by limit of detection studies.

In another embodiment, an IC, as described herein, is combined with RNA isolated from the sample according to standard techniques known to those of skill in the art, and described herein. The RNA is then reverse-transcribed using a reverse transcriptase to provide copy DNA. The cDNA sequences can be optionally amplified (e.g., by PCR) using labeled primers. The amplification products are separated, typically by electrophoresis, and the amount of radioactivity (proportional to the amount of amplified product) is determined. The amount of mRNA in the sample can then calculated where desired by comparison with the signal produced by the known standards.

Synthesis of Primers and Probes

Primers and probes described above are designed based on target sequences and are readily synthesized by standard techniques, e.g., solid phase synthesis via phosphoramidite chemistry, as disclosed in U.S. Pat. Nos. 4,458,066 and 4,415,732, incorporated herein by reference; Beaucage et al. (1992) Tetrahedron 48:2223-2311; and Applied Biosystems User Bulletin No. 13 (1 Apr. 1987). Other chemical synthesis methods include, for example, the phosphotriester method described by Narang et al., Meth. Enzymol. (1979) 68:90 and the phosphodiester method disclosed by Brown et al., Meth. Enzymol. (1979) 68:109. Poly(A) or poly(C), or other non-complementary nucleotide extensions may be incorporated into probes using these same methods. Hexaethylene oxide extensions may be coupled to probes by methods known in the art. Cload et al. (1991) J. Am. Chem. Soc. 113:6324-6326; U.S. Pat. No. 4,914,210 to Levenson et al.; Durand et al. (1990) Nucleic Acids Res. 18:6353-6359; and Horn et al. (1986) Tet. Lett. 27:4705-4708.

Biological Assay Reagents

Some embodiments of the present invention provide inter alia reagents for use in a subject biological assay. For example, as described in more detail below, in some embodiments, a subject method involves contacting a test fibroblast obtained from a patient with a reporter epithelial cell; and determining the effect, if any, of the fibroblast on physical or functional property of the reporter epithelial cell. Reagents and systems for carrying out such a biological assay are provided.

System components can include one or more of a reporter epithelial cell; binding reagents (e.g., antibody reagents) for detecting the presence and/or level of markers present in a reporter epithelial cell; nucleic acid reagents for detecting the presence and/or level of a nucleic acid (e.g., an mRNA, a cDNA copy of an mRNA, etc.) in a reporter epithelial cell; components for assessing mobility of a reporter epithelial cell (e.g., ability to cross a membrane); reagents (e.g., as described above) for detecting epigenetic modification of a reporter epithelial cell (e.g., histone modification; DNA hypermethylation; etc.); reagents for detecting secretion or release of molecules from a test fibroblast; reagents for detecting a phenotypic change in a reporter cell; and reagents for detecting secretion or release from a reporter epithelial cell.

Suitable reporter epithelial cells include primary epithelial cells and immortalized epithelial cells (e.g., immortalized epithelial cell lines). In some embodiments, a reporter epithelial cell is a primary mammary epithelial cell, e.g., a primary human mammary epithelial cell. Primary human mammary epithelial cells can be obtained from a suitable source such as reduction mammoplasty. Reporter epithelial cells can be cultured as described in, e.g., Band and Sager (1989) *Proc. Natl. Acad. Sci. USA* 86:1249-1253; Hammond et al. (1984) *Proc. Natl. Acad. Sci. USA* 81:5435; and Romanov et al. (2001) *Nature* 409:633.

In some embodiments, a reporter epithelial cell is genetically modified with a nucleic acid comprising a nucleotide sequence encoding a polypeptide that provides a detectable signal. Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., Science 263(5148):802-805 (Feb. 11, 1994); an enhanced GFP (EGFP), Clontech—Genbank Accession Number U55762); a blue fluorescent protein (BFP; 1. Quantum Biotechnologies, Inc. 1801 de Maisonneuve Blvd. West, 8th Floor, Montreal (Quebec) Canada H3H1J9; 2. Stauber, R. H. Biotechniques 24(3):462-471 (1998); 3. Heim, R. and Tsien, R. Y. Curr. Biol. 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418, 155, 5,683,888, 5,741,668, 5,777,079, 5,804,387, 5,874,304, 5,876,995, and 5,925,558; a GFP from species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like. Enzymes that catalyze production of a product that provides a detectable signal include, but are not limited to, luciferase, β-galacto-sidase, horse radish peroxidase, and alkaline phosphatase.

Genetically Modified vMEC

In some embodiments, a reporter epithelial cell is an isolated vMEC (e.g, a CD73⁺MEC) that has been geneti-cally modified with a nucleic acid comprising a nucleotide sequence encoding an oncogene. The present invention thus provides an isolated reporter epithelial cell, where the reporter epithelial cell is a CD73⁺MEC that has been geneti-cally modified with an exogenous nucleic acid comprising a nucleotide sequence encoding an oncogene. Suitable onco-genes include, but are not limited to, a ras family oncogene, a src family oncogene, Harvey murine sarcoma virus ras (v-Ha-ras), Kirsten murine sarcoma virus ras (v-Ki ras), fyn, myc, erbB2, src, yes, sis, and the like.

In some embodiments, the oncogene is operably linked to a heterologous promoter. Non-limiting examples of suitable eukaryotic promoters include CMV immediate early, HSV thymidine kinase, early and late SV40, LTRs from retrovi-rus, and mouse metallothionein-I. Selection of the appropri-ate vector and promoter is well within the level of ordinary skill in the art. In some embodiments, the heterologous promoter is a constitutive promoter. In other embodiments, the heterologous promoter is an inducible promoter. Suitable inducible promoters include, but are not limited to, a tetra-cycline-inducible promoter, a steroid inducible promoter (e.g., a glucocorticoid-inducible promoter), and the like. A subject genetically modified, isolated vMEC is immortal-ized, but has not undergone cancerous transformation. In some embodiments, a subject genetically modified, immor-talized vMEC is grown in medium containing 5% serum. In other embodiments, a subject genetically modified, immor-talized vMEC is grown in medium containing 10% serum.

A subject genetically modified, isolated, immortalized vMEC is useful for detecting stromal components that has the capacity to induce a cancerous transformation of a vMEC, e.g., that has carcinogenic potential. A subject genetically modified, isolated, immortalized vMEC appears morphologically normal. Upon contact with a stromal com-ponent that has the capacity to induce a cancerous transfor-mation of a vMEC, the genetically modified vMEC under-goes a change that is indicative of tumor progression. Such changes include, but are not limited to, increased motility; acquisition of mesenchymal features; increased telomerase activity; phenotypic changes associated with de novo meth-ylation, e.g., methylation of a promoter region; anchorage-independent growth; genomic instability; and capacity for in vivo survival.

In some embodiments, a subject genetically modified, immortalized vMEC is further genetically modified with a nucleic acid comprising a nucleotide sequence encoding a protein that provides for a detectable signal. Suitable pro-teins include, but are not limited to, fluorescent proteins and enzymes (e.g., β-galactosidase, luciferase, horse radish per-oxidase, alkaline phosphatase, etc.). Polypeptides that pro-vide a detectable signal include fluorescent proteins, chro-mogenic proteins, enzymes that catalyze the production of a product that is luminescent, fluorescent, or colored, etc. Suitable fluorescent proteins are as described above (e.g., including a green fluorescent protein, a red fluorescent protein, a yellow fluorescent protein, etc.).

Detection Methods

Some embodiments of the present invention provide inter alia methods of detecting a cell in a mammary tissue that is precancerous or has an increased likelihood of inducing a cancerous transformation in a neighboring mammary tissue cell. A subject detection method is useful in a variety of clinical applications, including imaging methods, diagnostic methods, prognostic methods, and monitoring methods, which are also provided.

A subject detection method generally involves detecting a mammary epithelial cell signature in a biological sample. In some embodiments, a biological sample is a sample that comprises cells, which can include living cells, dead cells, cells that have been treated for histochemical analysis, etc. In other embodiments, a biological sample is a liquid sample that may or may not include living cells, where liquid samples include bodily fluids such as nipple aspirate fluid, urine, blood, serum, plasma, and the like. In other embodi-ments, a biological sample is a liquid sample that may or may not include living cells, where the liquid sample is a lavage sample, e.g., a ductal lavage sample. In some embodiments, a biological sample has been treated prior to use in a subject detection method, e.g., by enrichment for one or more components (e.g., proteins, nucleic acids, etc.); removal of cells or cell debris; processing for histochemical analysis; and the like.

In some embodiments, a subject detection method pro-vides for detection of a pre-cancerous mammary epithelial cell. Detection of a pre-cancerous MEC involves detection of an MEC signature, e.g., a signature that is indicative of a pre-cancerous MEC. An "MEC signature" includes, but is not limited to: 1) the presence and/or level of a selected protein or collection of proteins; 2) the presence or absence of a posttranslational modification of a selected protein or collection of proteins; 3) the presence of a chromatin modi-fication; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

As an example, a subject method will in some embodi-ments involve administering a detectable labeled binding reagent, e.g., a detectably labeled antibody, to an individual; and detecting binding of the antibody reagent to a pre-cancerous mammary epithelial cell in the individual. Detect-ing binding of the antibody reagent to a pre-cancerous mammary epithelial cell in the individual can be carried out using standard methods, e.g., magnetic resonance imaging, histochemical analysis, and the like. As another example, in some embodiments a subject method will be carried out on a tissue sample obtained from an individual being tested, e.g., where the tissue sample, will be contacted with a specific binding reagent (e.g., an antibody reagent; a nucleic acid reagent, etc., as described above).

Detection of a pre-cancerous MEC is useful in a variety of clinical applications, including imaging methods, diag-nostic methods, prognostic methods, and monitoring meth-ods. For example, a subject imaging method provides for detection of a pre cancerous MEC in a female individual, e.g., an individual who presents as "normal," e.g., an indi-vidual who would normally undergo a routine examination or screening procedure that would be carried out on an individual who is not considered at high risk for breast cancer. As another example, detection of a pre-cancerous MEC is useful in a diagnostic method, e.g., alone or in conjunction with a mammogram, magnetic resonance imaging (MM), or other standard diagnostic test, to detect the presence of a pre-cancerous MEC in mammary tissue. As a further example, detection of a pre-cancerous MEC is useful in a prognostic method, e.g., following a procedure such as benign breast biopsy (BBB), to determine the need for a cancer treatment regimen such as chemotherapy. Finally, detection of a pre-cancerous MEC is useful in a monitoring method, e.g., to determine the efficacy of treatment for breast cancer, and/or to determine patient response to treatment for breast cancer.

It should be appreciated that a subject detection method can involve one, two, three, or more of the above-mentioned detection methods. In other embodiments, a subject method involves detecting two or more features of an MEC signature, e.g., a subject method can involve detecting two, three, four, five, or more of: 1) the presence and/or level of a selected protein or collection of proteins produced by an MEC; 2) the presence or absence of a posttranslational modification of a selected protein or collection of proteins in an MEC; 3) the presence of a chromatin modification in an MEC; 4) the level of a selected DNA or collection of DNA in an MEC; 5) the integrity of a selected DNA or collection of DNA in an MEC; 6) the methylation status of a selected DNA or collection of DNA in an MEC; 7) the presence and/or level of a selected mRNA or collection of mRNA in an MEC; 8) the presence and/or level of a selected microRNA or collection of microRNA in an MEC; and 9) secretion and/or release of a factor from an MEC.

Methods for Detecting a Variant Mammary Epithelial Cell

Methods for detecting a variant (e.g., pre-cancerous) mammary epithelial cell are provided. Detection of a pre-cancerous MEC involves detection of an MEC signature, e.g., a signature that is indicative of a pre-cancerous MEC. An "MEC signature" includes, but is not limited to, one or more of the following features: 1) the presence and/or level of a selected protein or collection of proteins; 2) the presence or absence of a posttranslational modification of a selected protein or collection of proteins; 3) the presence of a chromatin modification; 4) the level of a selected DNA or collection of DNA; 5) the integrity of a selected DNA or collection of DNA; 6) the methylation status of a selected DNA or collection of DNA; 7) the presence and/or level of a selected mRNA or collection of mRNA; 8) the presence and/or level of a selected microRNA or collection of microRNA; and 9) secretion and/or release of a factor from an MEC.

In some embodiments, a subject detection method involves detection of a gene product (e.g., polypeptides; nucleic acids) produced by an MEC. In one embodiment, the methods involve contacting a sample with a probe specific for the gene product of interest (e.g., marker polypeptide). "Probe" as used herein in such methods is meant to refer to a molecule that specifically binds a gene product of interest (e.g., the probe binds to the target gene product with a specificity sufficient to distinguish binding to target over non-specific binding to non-target (background) molecules). "Probes" include, but are not necessarily limited to, antibodies (e.g., antibodies, antibody fragments that retain binding to a target epitope, single chain antibodies, and the like); polynucleotides (e.g., oligonucleotide probes); and other polypeptide, peptide, or molecule (e.g., receptor ligand) that specifically binds a target gene product of interest.

Subject detection methods include one or more of: 1) detecting the presence and/or level of a selected protein or collection of proteins in an MEC; 2) detecting the presence of posttranslational modifications of gene expression-controlling proteins in an MEC; 3) detecting the level of a selected DNA or collection of selected DNA in an MEC; 4) detecting the integrity of a selected DNA in an MEC; 5) detecting the methylation status of a selected DNA in an MEC; 6) detecting the presence and/or a level of a selected mRNA or collection of mRNA in an MEC; 7) detecting the presence and/or level of a selected microRNA in an MEC; and 8) detecting secretion and/or release of a molecule (e.g., a protein, a nucleic acid, an ion, etc.) from an MEC; and 9) detecting a physical, morphological, or functional change in an MEC when contacted with a test fibroblast.

In some embodiments, the method for detecting the presence or absence of a pre-cancerous epithelial cell in a subject includes detecting a pattern of gene product expression present in a biological sample obtained from a subject; and comparing the pattern of gene product expression from the biological sample to a library of gene product expression pattern known to be indicative of the presence or absence of a pre-cancerous epithelial cell, wherein the comparing indicates the presence or absence of a pre-cancerous epithelial cell.

The probe and sample suspected of having the gene product of interest are contacted under conditions suitable for binding of the probe to the gene product. For example, contacting is generally for a time sufficient to allow binding of the probe to the gene product (e.g., from several minutes to a few hours), and at a temperature and conditions of osmolarity and the like that provide for binding of the probe to the gene product at a level that is sufficiently distinguishable from background binding of the probe (e.g., under conditions that minimize non-specific binding). Suitable conditions for probe-target gene product binding can be readily determined using controls and other techniques available and known to one of ordinary skill in the art.

As such, in some embodiments, the pattern of gene product expression will be detected and compared to the library of gene product expression patterns known to be indicative of the presence or absence of a pre-cancerous epithelial cell. In certain embodiments, the assessment of gene product expression of a single gene product will provide a preliminary result and will be followed up with the assessment of at least a second gene product expression.

The present invention also provides inter alia a method for monitoring progression of a pre-cancerous epithelial cell in a subject by detecting a first pattern of expression of gene products present in a biological fluid sample obtained from a subject at a first time point, wherein said first pattern is indicative of a pre-cancerous epithelial cell; detecting a second pattern of expression of gene products present in a biological sample obtained from a subject at a second time point; and comparing the first and second patterns of expression of gene products from the biological samples, wherein the comparing provides for monitoring of the progression of the pre-cancerous epithelial cell from the first time point to the second time point.

In certain embodiments, the method of monitoring progression of a pre cancerous epithelial cell in a subject will include detecting a pattern of expression of gene products present in a biological sample obtained from a subject at more than two time points, such as three or more. In general, the time points for detecting a pattern of expression of gene products can be separated by any amount of time that is desired. For example, the first time point and second time point can be separated by about 3 months, about 6 months, or about 1 year or more, such as about 3 or more years.

In general, it will be appreciated by one of skill in the art that the duration of time between the first time point and the second time point must be sufficient to provide for a monitoring of the progression of the pre-cancerous epithelial cell.

In certain embodiments, a subject detection method provides for monitoring the progression of a pre-cancerous epithelial cell in an individual. In some embodiments, the monitoring of the pre-cancerous epithelial cell in the subject is conducted without concomitant treatment for cancer. In such embodiments, the method of monitoring will provide information as to the status of the pre-cancerous epithelial cell, which information is used to determine whether treatment is warranted, to determine the type of treatment that should be initiated, and/or the treatment regimen. In some embodiments, monitoring is carried out once a year, every 6 months, every 4 months, every 3 months, or once per month.

The monitoring of the pre-cancerous epithelial cell in the subject can be conducted in parallel with a preventive approach (e.g., to remove precursors) and/or a treatment regimen for a cancer, e.g., a carcinoma. In such embodiments, the method of monitoring the pre cancer or cancer during treatment will provide information of whether the treatment is improving the condition, or having no effect or an adverse effect on the condition. In such embodiments, the first time point may be either just before, concurrent with, or just after the in initiation of a treatment regimen and the second time point may be a time point following a desired treatment period. For example, in such embodiments, the second time point may be about 6 month or more following initiation of treatment, including about 1 year, about 2 years, or more. For example, the detection of the pattern of expression of gene products present in a biological sample obtained from the subject may be determined about once every 6 months to monitor progression of the disease and efficacy of the treatment regimen.

In general, methods of the invention involving detection of a gene product (e.g., polypeptides or polynucleotides). The probe and sample suspected of having the gene product of interest are contacted under conditions suitable for binding of the probe to the gene product. For example, contacting is generally for a time sufficient to allow binding of the probe to the gene product (e.g., from several minutes to a few hours), and at a temperature and conditions of osmolarity and the like that provide for binding of the probe to the gene product at a level that is sufficiently distinguishable from background binding of the probe (e.g., under conditions that minimize non-specific binding). Suitable conditions for probe-target gene product binding can be readily determined using controls and other techniques available and known to one of ordinary skill in the art.

The detection methods can be provided as part of a kit. Thus, the invention further provides kits for detecting the presence/absence and/or a level of expression of a marker of the invention, and/or a polypeptide in a human biological sample. The kits of the invention for detecting a marker polypeptide generally comprise a moiety that specifically binds the polypeptide, which may be a specific antibody. The kit may optionally provide additional components that are useful in the procedure, including, but not limited to, buffers, developing reagents, labels, reacting surfaces, means for detection, control samples, standards, instructions, and interpretive information.

Detecting the Presence and/or Level of a Selected Polypeptide or Collection of Polypeptides In some embodiments, a subject detection method involves detecting the presence and/or levels of a selected polypeptide or collection of polypeptides produced by an MEC. The methods generally involve use of a probe to detect the polypeptide(s). In these embodiments, the probe is an antibody or other polypeptide, peptide, or molecule (e.g., receptor ligand) that specifically binds a target polypeptide of interest.

In some embodiments, a subject detection method involves detecting the presence and/or level of one or more of the polypeptides listed in FIG. 14. In some embodiments, a subject detection method involves detecting the presence and/or level of one or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a subject detection method involves detecting the presence and/or level of one or more of: CD73, CD138, notch receptor-3, CD90, BMI-1, and COX-2. In some embodiments, a subject detection method involves detecting the presence and/or level of CD73, CD138, notch receptor-3, CD90, BMI-1, and COX-2. In some embodiments, a subject detection method involves detecting the presence and/or level of Ki67 and p16. In some embodiments, a subject detection method involves detecting the presence and/or level of Ki67 and COX-2. In some embodiments, a subject detection method involves detecting the presence and/or level of Ki67, p16, and COX-2. In some embodiments, the method involves detecting the presence and/or level of any two or more of ER, ERBB2, Ki67, p16, and COX-2. In some embodiments, the method involves detecting the presence of PR, ERBB2, Ki67, p16, and COX-2. In some embodiments, the method involves detecting the presence of ER, PR, ERBB2, Ki67, p16, and COX-2. In some embodiments, the method involves detecting the presence of ER, ERBB2, Ki67, p16, and COX-2. In some embodiments, the method involves simultaneously detecting the presence and/or level of the combination of: COX-2, p16, and Ki67; Ki67, ER, and ERBB2; and/or COX-2, p16, Ki67, ER, and ERBB2. In some embodiments, the method involves simultaneously detecting the presence and/or level of the combination of: COX-2, p16, and Ki67; Ki67, PR, and ERBB2; and/or COX-2, p16, Ki67, PR, and ERBB2.

The selected polypeptides (also referred to herein as "biomarkers"), or collection of selected polypeptides, can be detected by any suitable method. Detection paradigms that can be employed to this end include enzymatic methods, including immunological-based methods, optical methods, electrochemical methods (voltametry and amperometry techniques), atomic force microscopy, and radio frequency methods, e.g., multipolar resonance spectroscopy. It is to be understood that the present invention is not limited to a particular detection method. However, in some embodiments detection is by, for example, fluorescent detection, spectrometric detection, chemiluminescent detection, matrix assisted laser desorption-time-of flight (MALDI-TOF) detection, high pressure liquid chromatographic detection, charge detection, mass detection, radio frequency detection, and light diffraction detection. Exemplary detection methods that are suitable for use with the subject methods are described herein.

In some embodiments, protein or polypeptide markers include protein transcripts.

In some embodiments, detection a selected polypeptide or collection of polypeptides is by use of capture reagents specific to the polypeptides. In some embodiments, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different polypeptides can be mixed in the same place, or they can be attached to solid phases in different physical or addressable locations. For example, one can load multiple columns with derivatized beads, each column able to capture a single polypeptide. Alternatively, one can pack a single column with different beads derivatized with capture reagents against a variety of polypeptides, thereby capturing all the polypeptide analytes in a single place. Accordingly, antibody-derivatized bead-based technologies, such as Multi-Analyte Profiling (xMAP™) technology of Luminex (Austin, Tex.) can be used to detect the polypeptide(s).

Luminex xMAP™ is based on polystyrene particles (microspheres) that are internally labeled with two different fluorophores. When excited by a 635-nm laser, the fluorophores emit light at different wavelengths, e.g., 658 and 712 nm. By varying the 658-nm/712-nm emission ratios, the beads are individually classified by the unique Luminex 100 IS analyzer. A third fluorophore coupled to a reporter molecule allows for quantification of the interaction that has occurred on the microsphere surface. The Luminex xMAP™ technology is described, for example, in U.S. Pat. Nos. 5,736,330, 5,981,180, and 6,057,107, all of which are specifically incorporated by reference.

In yet another embodiment, the surfaces of biochips can be derivatized with the capture reagents directed against specific polypeptides. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound thereto.

Immunoassays

Any of a variety of known immunoassay methods can be used for detection, including, but not limited to, immunoassay, using an antibody specific for the polypeptide, e.g., by enzyme-linked immunosorbent assay (ELISA), radioimmunoassay (MA), immunohistochemistry; and the like; and functional assays for the encoded polypeptide, e.g., binding activity or enzymatic activity.

In some embodiments, a subject detection method involves detecting the presence and/or level of one or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a subject detection method involves detecting the presence and/or level of one or more of: CD73, CD138, notch receptor-3, CD90, BMI-1, and COX-2. In some embodiments, a subject detection method involves detecting the presence and/or level of CD73, CD138, notch receptor-3, CD90, BMI-1, and COX-2. In some embodiments, a subject detection method involves detecting the presence and/or level of Ki67 and p16. In some embodiments, a subject detection method involves detecting the presence and/or level of Ki67 and COX-2. In some embodiments, a subject detection method involves detecting the presence and/or level of Ki67, p16, and COX-2. In some embodiments, the method involves detecting the presence and/or level of any two or more of ER, ERBB2, Ki67, p16, and COX-2. In some embodiments, the method involves detecting the presence and/or level of any two or more of PR, ERBB2, Ki67, p16, and COX-2. In some embodiments, the method involves detecting the presence and/or level of any three or more of PR, ERBB2, Ki67, p16, and COX-2. In some embodiments, the method involves detecting the presence of ER, ERBB2, Ki67, p16, and COX-2. In some embodiments, the method involves detecting the presence and/or level of PR, ERBB2, Ki67, p16, and COX-2. In some embodiments, the method involves detecting the presence and/or level of ER, PR, ERBB2, Ki67, p16, and COX-2. In some embodiments, the method involves simultaneously detecting the presence and/or level of the combination of: COX-2, p16, and Ki67; Ki67, ER, and ERBB2; and/or COX-2, p16, Ki67, ER, and ERBB2. In some embodiments, the method involves simultaneously detecting the presence and/or level of the combination of: COX-2, p16, and Ki67; Ki67, PR, and ERBB2; and/or COX-2, p16, Ki67, PR, and ERBB2. In some embodiments, the method involves simultaneously detecting the presence and/or level of the combination of: COX-2, p16, and Ki67; Ki67, ER, PR, and ERBB2; and/or COX-2, p16, Ki67, ER, PR, and ERBB2.

For example, an immunofluorescence assay can be easily performed on a biological sample obtained from a patient, e.g., a tissue biopsy. It is also possible to perform such assays in plasma.

To increase the sensitivity of the assay, the immunocomplex may be further exposed to a second antibody, which is labeled and binds to the first antibody, which is specific for the encoded polypeptide. Typically, the secondary antibody is detectably labeled, e.g., with a fluorescent marker. The cells which express the encoded polypeptide will be fluorescently labeled and easily visualized under the microscope. See, for example, Hashido et al. (1992) *Biochem. Biophys. Res. Comm.* 187:1241-1248.

As will be readily apparent to the ordinarily skilled artisan upon reading the present specification, the detection methods and other methods described herein can be varied. Such variations are within the intended scope of the invention. For example, in the above detection scheme, the probe for use in detection can be immobilized on a solid support, and the test sample (e.g., biological sample obtained from a patient) contacted with the immobilized probe. Binding of the test sample to the probe can then be detected in a variety of ways, e.g., by detecting a detectable label bound to the test sample.

Thus, generally the methods comprise: a) contacting a sample comprising an MEC with an antibody specific for one or more of: CD73, CD138, notch receptor-3, CD90, BMI-1, COX-2, ER. ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2; and b) detecting binding between the antibody and molecules of the sample. The level of antibody binding (either qualitative or quantitative) indicates that the MEC is pre-cancerous. For example, where the marker polypeptide is present at a level greater than that associated with a negative control level, the MEC is pre-cancerous, and the patient is susceptible to or at risk of developing breast cancer.

Suitable controls include a sample known not to contain the marker polypeptide; a sample contacted with an antibody not specific for the marker polypeptide; a sample having a level of polypeptide that is elevated in a cancerous epithelial cell. A variety of methods to detect specific antibody-antigen interactions are known in the art and can be used in the method, including, but not limited to, standard immunohistological methods, immunoprecipitation, an enzyme immu-
noassay, and a radioimmunoassay.

In general, the specific antibody will be detectably
labeled, either directly or indirectly. Direct labels include
radioisotopes; enzymes having detectable products (e.g.,
luciferase, β-galactosidase, and the like); fluorescent labels
(e.g., fluorescein isothiocyanate, rhodamine, phycoerythrin,
and the like); fluorescence emitting metals, e.g., $^{152}$Eu, or
others of the lanthanide series, attached to the antibody
through metal chelating groups such as EDTA; chemilumi-
nescent compounds, e.g., luminol, isoluminol, acridinium
salts, and the like; bioluminescent compounds, e.g.,
luciferin, aequorin (green fluorescent protein), and the like.
In some embodiments, an antibody reagent comprises, cova-
lently linked to the antibody reagent, a protein that provides
for a detectable signal. Suitable proteins include, but are not
limited to, fluorescent proteins and enzymes (e.g., β-galac-
tosidase, luciferase, horse radish peroxidase, alkaline phos-
phatase, etc.). For example, suitable proteins include fluo-
rescent proteins, chromogenic proteins, enzymes that
catalyze the production of a product that is luminescent,
fluorescent, or colored, etc.

Suitable fluorescent proteins include, but are not limited
to, a green fluorescent protein (GFP; Chalfie, et al., Science
263(5148):802-805 (Feb. 11, 1994); an enhanced GFP
(EGFP), e.g., Genbank Accession Number U55762); a blue
fluorescent protein; an enhanced yellow fluorescent protein;
a fluorescent protein as described in, e.g., WO 92/15673,
WO 95/07463, WO 98/14605, WO 98/26277, WO
99/49019, U.S. Pat. Nos. 5,292,658, 5,418,155, 5,683,888,
5,741,668, 5,777,079, 5,804,387, 5,874,304, 5,876,995, and
5,925,558; a GFP from species such as *Renilla reniformis,
Renilla mulleri,* or *Ptilosarcus guernyi, as described in, e.g.,*
WO 99/49019 or Peelle et al. (2001) *J. Protein Chem.*
20:507-519; any of a variety of fluorescent and colored
proteins from Anthozoan species, as described in, e.g., Matz
et al. (1999) *Nature Biotechnol.* 17:969-973, U.S. Patent
Publication No. 2002/0197676, or U.S. Patent Publication
No. 2005/0032085; and the like.

Other suitable detectable labels include fluorescent dyes,
e.g., Fluorescein, Rhodamine, Texas Red, Cy2, Cy3, Cy5,
VECTOR Red, ELF™ (Enzyme-Labeled Fluorescence),
Cy0, Cy0.5, Cy1, Cy1.5, Cy3, Cy3.5, Cy5, Cy7, Fluor X,
Calcein, Calcein-AM, CRYPTOFLUOR™, Orange (42
kDa), Tangerine (35 kDa), Gold (31 kDa), Red (42 kDa),
Crimson (40 kDa), BHMP, BHDMAP, Br-Oregon, Lucifer
Yellow, Alexa dye family, N-[6-(7-nitrobenz-2-oxa-1,3-di-
azol-4-yl)amino]caproyl] (NBD), BODIPY™, boron dipyr-
romethene difluoride, Oregon Green, MITOTRACKER™
Red, DiOC$_7$ (3), DiIC$_{18}$, Phycoerythrin, Phycobiliproteins
BPE (240 kDa) RPE (240 kDa) CPC (264 kDa) APC (104
kDa), Spectrum Blue, Spectrum Aqua, Spectrum Green,
Spectrum Gold, Spectrum Orange, Spectrum Red, NADH,
NADPH, FAD, Infra-Red (IR) Dyes, Cyclic GDP-Ribose
(cGDPR), Calcofluor White, Tyrosine and Tryptophan.

The antibody may be attached (coupled) to an insoluble
support, such as a polystyrene plate or a bead. Indirect labels
include second antibodies specific for antibodies specific for
the encoded polypeptide ("first specific antibody"), wherein
the second antibody is labeled as described above; and
members of specific binding pairs, e.g., biotin-avidin, and
the like. The biological sample may be brought into contact
with and immobilized on a solid support or carrier, such as
nitrocellulose, that is capable of immobilizing cells, cell
particles, or soluble proteins. The support may then be
washed with suitable buffers, followed by contacting with a
detectably-labeled first specific antibody. Detection methods are known in the art and will be chosen as appropriate to the
signal emitted by the detectable label. Detection is generally
accomplished in comparison to suitable controls, and to
appropriate standards.

In some embodiments, a subject detection method
involves use of an array of specific binding reagents, e.g., an
antibody reagent array. An array can be created by spotting
captures agents onto a substrate (e.g., glass, nitrocellulose,
etc.) and attaching those capture agents to the substrate. The
antibody reagents can be bound to the substrate by either
covalent bonds or by non-specific interactions, such as
hydrophobic interactions. Techniques for constructing
arrays and methods of using these arrays are described in,
for example, Schena et al. (1996) *Proc Natl Acad Sci USA.*
93(20):10614-9; Schena et al. (1995) *Science* 270(5235):
467-70; Shalon et al. (1996) *Genome Res.* 6(7):639-45, U.S.
Pat. No. 5,807,522, EP 799 897; WO 97/29212; WO
97/27317; EP 785 280; WO 97/02357; U.S. Pat. Nos.
5,593,839; 5,578,832; EP 728 520; U.S. Pat. No. 5,599,695;
EP 721 016; U.S. Pat. No. 5,556,752; WO 95/22058; and
U.S. Pat. No. 5,631,734. The antibody reagents utilized in
the arrays can be of varying types and can include, for
example, antibodies, including antibody fragments, aptam-
ers, avimers, or peptidomimetics.

Common physical substrates for making protein arrays
include glass or silicon slides, magnetic particles or other
micro beads, functionalized with aldehyde or other chemical
groups to help immobilize proteins. The substrate can also
be coated with PLL (polylysine), nitrocellulose, PVDF
membranes or modified with specific chemical reagents to
adsorb capture agents. The desirable properties of an ideal
surface include: chemical stability before, during, and after
the coupling procedure, suitability for a wide range of
capture agents (e.g., hydrophilic and hydrophobic, low MW
and high MW), minimal non-specific binding, low or no
intrinsic background in detection, presentation of the capture
agents in a fully-functional orientation, production of spots
with predictable and regular morphology (shape, signal
uniformity).

The variables in the immobilization of proteins include:
type of capture agent (e.g., antibody reagent), nature of
surface (including any pretreatment prior to use), and the
immobilization method. Both adsorption and covalent
attachment have been used for protein arrays. Orientation of
the capture agent is very important in presenting it to the
ligand or the surface in a functional state. Although covalent
attachment using a variety of chemically activated surfaces
(e.g., aldehyde, amino, epoxy) as well as attachment by
specific biomolecular interactions (e.g., biotin-streptavidin)
provide a stable linkage and good reproducibility, chemical
derivatization of the surface may alter the biological activity
of the capture agent and/or may result in multi-site attach-
ment.

In one embodiment, antibody arrays are made with a
non-contact deposition printer. The printer uses thermal ink
jet heads that can print many solutions simultaneously to
produce hundreds of spots of 50-60 μm in diameter with a
spacing of 150 μm between spots. The droplet volume
ranges between 35 pL to 1.5 mL. The heating element is
made out of TaAl or other suitable materials, and is capable
of achieving temperatures that can vaporize a sufficient
volume of printing buffer to produce a bubble that will push
out a precise volume of the antibody solution on the sub-
strate. Selection of printing buffer is important, in that the
buffer accomplishes the following: increases printing effi-
ciency (measure of the number of spots that are printed to
the total number of spots that are attempted), reduces sample spreading, promotes uniform delivery, stabilizes the capture agents that are being printed, reduces sample drying, and increases the visibility of the printed spots. In addition to the printing buffer, other variables that affect printing include: size of the drops, the method of washing and drying the print head, and the speed at which the dispensing head moves. Various modifications may be within these conditions.

Immunohistochemical Assays

In some embodiments, a subject detection method is an immunohistochemical assay. See, e.g., U.S. Pat. No. 6,007, 996 for a discussion of various immunohistochemical methods. In general, the method involves contacting a sample comprising an MEC with an antibody specific for a target polypeptide (e.g., one or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2); and detecting binding, if any, of the antibody to an epitope(s) present in the MEC.

In general, the specific antibody will be detectably labeled, either directly or indirectly. Direct labels include radioisotopes; enzymes having detectable products (e.g., luciferase, β-galactosidase, and the like); fluorescent labels (e.g., fluorescein isothiocyanate, rhodamine, phycoerythrin, and the like); fluorescence emitting metals, e.g., $^{152}$Eu, or others of the lanthanide series, attached to the antibody through metal chelating groups such as EDTA; chemiluminescent compounds, e.g., luminol, isoluminol, acridinium salts, and the like; bioluminescent compounds, e.g., luciferin, aequorin (green fluorescent protein), and the like. Other suitable detectable labels include fluorescent dyes, e.g., Fluorescein, Rhodamine, Texas Red, Cy2, Cy3, Cy5, VECTOR Red, ELF™ (Enzyme-Labeled Fluorescence), Cy0, Cy0.5, Cy1, Cy1.5, Cy3, Cy3.5, Cy5, Cy7, Fluor X, Calcein, Calcein-AM, CRYPTOFLUOR™, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-[6-(7-nitrobenz-2-oxa-1,3-diazol-4-yl)amino]caproyl] (NBD), BODIPY™, boron dipyrromethene difluoride, Oregon Green, MITOTRACKER™ Red, DiOC$_7$ (3), DiIC$_{18}$, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

In some embodiments, a sample comprising an MEC is contacted with antibody reagent(s) or other binding reagent(s) specific for one or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, a sample comprising an MEC is contacted with antibody reagent(s) or other binding reagent(s) specific for one or more of: CD73, CD138, notch receptor-3, CD90, BMI-1, and COX-2. In some embodiments, a sample comprising an MEC is contacted with antibody reagent(s) or other binding reagent(s) specific for CD73, CD138, notch receptor-3, CD90, BMI-1, and COX-2. In some embodiments, a sample comprising an MEC is contacted with antibody reagent(s) or other binding reagent(s) specific for Ki67 and p16. In some embodiments, a sample comprising an MEC is contacted with antibody reagent(s) or other binding reagent(s) specific for Ki67 and COX-2. In some embodiments, a sample comprising an MEC is contacted with antibody reagent(s) or other binding reagent(s) specific for Ki67, p16, and COX-2. In some embodiments, a sample comprising an MEC is contacted with antibody reagent(s) or other binding reagent(s) specific for any two or more of ER, ERBB2, Ki67, p16, and COX-2. In some embodiments, a sample comprising an MEC is contacted with antibody reagent(s) or other binding reagent(s) specific for any two or more of PR, ERBB2, Ki67, p16, and COX-2. In some embodiments, a sample comprising an MEC is contacted with antibody reagent(s) or other binding reagent(s) specific for any three or more of ER, PR, ERBB2, Ki67, p16, and COX-2. In one embodiment, the method involves detecting the presence of ER, ERBB2, Ki67, p16, and COX-2. In some embodiments, the method involves detecting the presence of PR, ERBB2, Ki67, p16, and COX-2. In some embodiments, the method involves detecting the presence of ER, PR, ERBB2, Ki67, p16, and COX-2.

In some embodiments, e.g., where two or more antibodies are used, each antibody being specific for a different target polypeptide, each of the two or more antibodies is detectably labeled with a different label, where the two or more different labels are distinguishable from one another. In some embodiments, the antibody for COX-2 will have a first label, the antibody for p16 will have a second label, the antibody for Ki67 will have a third label, the antibody for ER will have a fourth label, and the antibody for ERBB2 will have a fifth label, where all 5 labels can be detected and distinguished from one another simultaneously. In some embodiments, the antibody for COX-2 will have a first label, the antibody for p16 will have a second label, and the antibody for Ki67 will have a third label, where all 3 labels can be detected and distinguished from one another simultaneously. In some embodiments, the antibody for Ki67 will have a first label, the antibody for ER will have a second label, and the antibody for ERBB2 will have a third label, where all 3 labels can be detected and distinguished from one another simultaneously. In some embodiments, the antibody for Ki67 will have a first label, the antibody for PR will have a second label, and the antibody for ERBB2 will have a third label, where all three labels can be detected and distinguished from one another simultaneously. In some embodiments, the antibody for Ki67 will have a first label, the antibody for ER will have a second label, the antibody for PR will have the same second label, and the antibody for ERBB2 will have a third label, where all 3 labels can be detected and distinguished from one another simultaneously. In some embodiments, the antibody for Ki67 will have a first label, the antibody for ER will have a second label, the antibody for PR will a third label, and the antibody for ERBB2 will have a fourth label, where all four labels can be detected and distinguished from one another simultaneously.

Polypeptide Arrays

Polypeptide arrays provide a high throughput technique that can assay a large number of polypeptides in a sample. This technology can be used as a tool to test for expression of a marker polypeptide and detection of a pre-cancerous epithelial cell. In some embodiments, a subject array comprises a probe for detection of one or more of the polypeptides listed in FIG. 14. Of particular interest are arrays which comprise a probe for detection of one or more of the following polypeptides: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

A variety of methods of producing arrays, as well as variations of these methods, are known in the art and contemplated for use in the invention. For example, arrays can be created by spotting polypeptide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Samples of polypeptides can be detectably labeled (e.g., using radioactive or fluorescent labels) and then hybridized to the probes. Alternatively, the polypeptides of the test sample can be immobilized on the array, and the probes detectably labeled and then applied to the immobilized polypeptides. In most embodiments, the "probe" is detectably labeled. In other embodiments, the probe is immobilized on the array and not detectably labeled. In such embodiments, the sample is applied to the polypeptide array and bound gene products (e.g., peptides) are detected using secondary labeled probes.

Examples of such protein arrays are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

In some embodiments, the array will include a first probe for detection of COX-2, a second probe for detection for p16, a third probe for detection for Ki67, a fourth probe for detection for ER, and a fifth probe for detection for ERBB2, where all 5 probes can be monitored and distinguished from one another simultaneously. In some embodiments, the array will include a first probe for detection of COX-2, a second probe for detection for p16, a third probe for detection for Ki67, a fourth probe for detection for PR, and a fifth probe for detection for ERBB2, where all 5 probes can be monitored and distinguished from one another simultaneously. In some embodiments, the array will include a first probe for detection of COX-2, a second probe for detection for p16, a third probe for detection for Ki67, a fourth probe for detection for ER, and a fifth probe for detection for PR, and a sixth probe for detection for ERBB2, where all 6 probes can be monitored and distinguished from one another simultaneously. In some embodiments, the array will include a first probe for detection of COX-2, a second probe for detection for p16, and a third probe for detection for Ki67, where all 3 probes can be monitored and distinguished from one another simultaneously. In some embodiments, the array will include a first probe for detection for Ki67, a second probe for detection for PR, and a third probe for detection for ERBB2, where all 3 probes can be monitored and distinguished from one another simultaneously. In some embodiments, the array will include a first probe for detection for Ki67, a second probe for detection for ER, a third probe for detection for PR, and a fourth probe for detection for ERBB2, where all 4 probes can be monitored and distinguished from one another simultaneously. In some embodiments, the array will include a first probe for detection for Ki67, a second probe for detection for ER, the same second probe for detection for PR, and a third probe for detection for ERBB2, where all 3 probes can be monitored and distinguished from one another simultaneously. In some embodiments, the array will include a first probe for detection for Ki67, a second probe for detection for ER, and a third probe for detection for ERBB2, where all 3 probes can be monitored and distinguished from one another simultaneously. In some embodiments, the array will include probes for the detection of Ki67 and at least a) COX-2 and p16, b) ER and ERBB2, or c) PR and ERBB2.

Detecting Posttranslational Modification of a Factor

In some embodiments, a subject detection method involves detecting posttranslational modification of one or more factors (e.g., polypeptides), present in a MEC, that control gene expression and/or that modulate chromatin, and/or that modulate DNA methylation. In some embodiments, a subject detection method involves detecting a posttranslational modification of a Polycomb group (PcG) repressor complex (e.g., modification of a PcG protein such as EED) and/or a posttranslational modification of a histone deacetylase. Posttranslational modifications of chromatin polypeptides include methylation and acetylation. In some embodiments, a subject detection method involves use of an antibody reagent that specifically binds a chromatin polypeptide, e.g., a chromatin epitope that is susceptible to posttranslational modification or that has been posttranslationally modified. A suitable antibody reagent is contacted with a sample comprising an MEC, or with a sample comprising MEC proteins, and binding, if any, of the antibody reagent to a chromatin polypeptide in the sample is detected. For example, in some embodiments, an antibody reagent specifically binds to a chromatin epitope(s) that is not modified, e.g., the antibody reagent binds specifically to a chromatin epitope that comprises only encoded amino acids. In other embodiments, an antibody reagent specifically binds to an acetylated chromatin polypeptide, e.g., the antibody reagents binds specifically to a chromatin epitope that is acetylated. In other embodiments, an antibody reagent specifically binds to a methylated chromatin polypeptide, e.g., the antibody reagents binds specifically to a chromatin epitope that is methylated. The antibody reagent can be detectably labeled, as described above Detecting Chromatin Modifications In some embodiments, a subject detection method involves detecting chromatin modification in an MEC. In some embodiments, a subject detection method involves detection of histone acetylation. Suitable detection methods include immunohistochemical methods; and other immunological methods (e.g., immunoprecipitation; protein blot assays; etc.).

Detecting Secreted or Released Molecules

In some embodiments, a subject detection method involves detecting molecules secreted or released from an MEC. For example, in some embodiments, an MEC is obtained from an individual and is cultured in vitro; and a profile of molecules secreted or released from the cultured MEC is detected. In other embodiments, a reporter MEC is cultured in vitro in the presence of a fibroblast obtained from an individual; and a profile of molecules secreted or released from the reporter MEC is detected. Molecules secreted or released from an MEC include, but are not limited to, proteins, nucleic acids, and ions.

Proteins that are secreted or released from an MEC can be detected as described above, using any number of different assay formats, including, e.g., immunological assays, where in some embodiments, an array of antibody reagents is used to detect two or more proteins secreted or released from an MEC.

Nucleic acids that are secreted or released from an MEC can be detected as described below, using a nucleic acid probe and/or a nucleic acid primer. For example, in some embodiments, an array of nucleic acid probes is used to detect two or more nucleic acids secreted or released from an MEC.

Ions that can be detected include, e.g., calcium ions, potassium ions, sodium ions, magnesium ions, chloride ions, hydrogen ions (pH), and the like. Suitable ion-indicating agents include fluorescent calcium indicators, e.g., fura dyes (e.g., fura-2, fura-4F, fura-5F, fura-6F, fura-FF, Fura Red), fluo dyes (e.g., fluo-3, fluo-4), indo dyes (e.g., indo-1), rhodamine dyes (e.g., rhod-2, X-rhod-1), Oregon Green 488, Calcium Green, Calcium Crimson, and quin-2; membrane-permeant acetoxymethyl (AM) ester forms of any of the aforementioned fluorescent calcium indicators; membrane-impermeant salt forms of any of the aforementioned fluorescent calcium indicators; fluorescent sodium indicators, e.g., benzofuran isophthalate (SBFI), Sodium Green, CoroNa Green; fluorescent potassium indicators, e.g., PBF1, CD222; fluorescent magnesium indicators, e.g., Mag-Fluo-4, Mag-Fura-2, Mag-Fura-5, Mag-Fura-Red, Mag-indo-1, Mag-rho-2, Magnesium Green; fluorescent chloride indicators, e.g., trans-1,2-bis(4-[1'-MQ-1"-dimethyl-AQ-xylyl]-pyridinium)ethylene (Bis-DMXPQ), 7-(β-D-ribofuranosylamino) pyrido[2,1-h]-pteridin-11-ium-5-olate (LZQ), Lucigenin, and a variety of 6-methoxyquinolinium derivatives such as 6-Methoxy-N-(3-sulfopropyl)quinolinium (SPQ), N (Ethoxycarbonylmethyl)-6-methoxyquinolinium bromide (MQAE) and 6-Methoxy-N ethylquinolinium iodide (MEQ); and fluorescent pH indicators, e.g., biscarboxyethyl carboxyfluorescein (BCECF) and 2',7'-bis-(2-carboxypropyl)-5-(6-)-carboxyfluorescein (BCPCF). Other suitable methods and reagents include those described in, e.g., U.S. Patent Publication No. 2006/0148104.

Detecting the Presence and/or Level of an mRNA

In some embodiments, a subject detection method involves detecting the presence and/or level of a selected mRNA, or a collection of selected mRNA, in an MEC. In some embodiments, a cDNA copy of a selected mRNA, or cDNA copies of a collection of selected mRNA, is detected. In some embodiments, a subject detection method will involve nucleic acid hybridization with a nucleic acid probe, nucleic acid amplification with a nucleic acid primer pair, or both. Nucleic acid hybridization and nucleic acid amplification methods are known to those skilled in the art. Exemplary nucleic acid hybridization and nucleic acid amplification methods are discussed in detail below. The following provides detail of exemplary nucleic acid-based methods for detection, and examples of how such can be adapted for use in the methods of the invention.

In some embodiments, a subject method for detecting the presence and/or level of an mRNA, a collection of mRNA, in an MEC involves contacting, under stringent hybridization conditions, a subject nucleic acid probe with a target nucleic acid in a sample; and detecting the level of target mRNA in the sample. In some embodiments, where the detected level of target mRNA indicates that target mRNA is overexpressed or underexpressed in the cell, the cell is considered precancerous. In some embodiments, a cDNA copy of a target mRNA is generated. In some embodiments, the target nucleic acid (mRNA or cDNA copy) is amplified using a nucleic acid primer pair.

In some embodiments, a subject method involves detecting, in an MEC (or a nucleic acid sample obtained from an MEC), the presence and/or level of one or more mRNAs (or a cDNA copy thereof) listed in FIG. 14. In some embodiments, a subject method involves detecting, in an MEC (or a nucleic acid sample obtained from an MEC), the presence and/or level of one or more of the following mRNA (or cDNA copy thereof): CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In some embodiments, a subject method involves detecting, in an MEC (or a nucleic acid sample obtained from an MEC), the presence and/or level of two or more (e.g., two, three, four, five, or more) of the following mRNA (or cDNA copy of an mRNA): CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, the combination comprises at least one of the following: 1) ER, ERBB2, Ki67, COX-2, and p16; 2) ER, ERBB2, Ki67; and 3) Ki67, COX-2, and p16.

In some embodiments, a subject method involves detecting, in an MEC (or a nucleic acid sample obtained from an MEC), the presence and/or level of two, three, four, five, or all of CD73, CD138, notch receptor-3, CD90, BMI-1, and COX-2 mRNAs (or cDNA copies of same). In some embodiments, a subject method involves detecting, in an MEC (or a nucleic acid sample obtained from an MEC), the presence and/or level of Ki67, COX-2, and p16 mRNA (or cDNA copies of same). In some embodiments, a subject method involves detecting, in an MEC (or a nucleic acid sample obtained from an MEC), the presence and/or level of two, three, four, five, or all of CD73, CD138, notch receptor-3, CD90, BMI-1, and COX-2 mRNAs (or cDNA copies of same). In some embodiments, a subject method involves detecting, in an MEC (or a nucleic acid sample obtained from an MEC), the presence and/or level of Ki67 and COX-2 mRNA (or cDNA copies of same). In some embodiments, a subject method involves detecting, in an MEC (or a nucleic acid sample obtained from an MEC), the presence and/or level of Ki67 and p16 mRNA (or cDNA copies of same). In some embodiments, a subject method involves detecting, in an MEC (or a nucleic acid sample obtained from an MEC), the presence and/or level of any two or more of ER, ERBB2, Ki67, p16, and COX-2 (or cDNA copies of same). In some embodiments, a subject method involves detecting, in an MEC (or a nucleic acid sample obtained from an MEC), the presence and/or level of any two or more of PR, ERBB2, Ki67, p16, and COX-2 (or cDNA copies of same). In some embodiments, a subject method involves detecting, in an MEC (or a nucleic acid sample obtained from an MEC), the presence and/or level of any three or more of ER, PR, ERBB2, Ki67, p16, and COX-2 (or cDNA copies of same). In one embodiment, the method involves detecting the presence of ER, ERBB2, Ki67, p16, and COX-2 (or cDNA copies of same). In some embodiments, the method involves detecting the presence of PR, ERBB2, Ki67, p16, and COX-2 (or cDNA copies of same). In one embodiment, the method involves detecting the presence of ER, PR, ERBB2, Ki67, p16, and COX-2 (or cDNA copies of same).

A number of methods are available for analyzing nucleic acids for the presence and/or level of a specific nucleic acid in a cell, or in a sample comprising nucleic acids obtained from a cell (e.g., a cell lysate, etc.). The mRNA can be assayed directly. In some embodiments, an mRNA is detected by microarray analysis; see, e.g., U.S. Patent Publication No. 2007/0009915.

In some embodiments, an mRNA is reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2-14.33.

In some embodiments, the method involves contacting the sample under stringent hybridization conditions with a subject nucleic acid probe and detecting binding, if any, of the probe to a target nucleic acid in the sample. A variety of nucleic acid hybridization methods are well known to those skilled in the art, and any known method can be used. In many embodiments, the nucleic acid probe will be detectably labeled.

Where a subject method involves detecting a level of a target nucleic acid in a cell, the method will in some embodiments include amplification of the target nucleic acid, forming a target amplification product; and can further include a step of hybridizing the target amplification product with a nucleic acid probe.

In some embodiments, the method involves contacting a sample (e.g., under stringent hybridization conditions) with a subject nucleic acid primer pair, where the primer pair, under conditions that permit primer-initiated nucleic acid amplification, amplifies any target nucleic acid present in the sample, generating an amplification product (where amplification product is generated when target nucleic acid present in the sample).

Conditions that permit primer-initiated nucleic acid amplification and catalytic nucleic acid activity are well known to those skilled in the art, and include the presence of a DNA polymerase; deoxynucleotide triphosphates; and magnesium ions. Suitable reaction conditions are well known to those skilled in the art of nucleic acid amplification. The DNA polymerase is generally one that has high affinity for binding at the 3'-end of an oligonucleotide hybridized to a nucleic acid strand. The DNA polymerase is generally one that has little or no $5' \rightarrow 3'$ exonuclease activity so as to minimize degradation of primer, termination or primer extension polynucleotides. The DNA polymerase is generally one that has little to no proofreading activity. In many embodiments, the DNA polymerase is thermostable, e.g., is catalytically active at temperatures in excess of about 75° C. DNA polymerases that are suitable for use in a subject method include, but are not limited to, DNA polymerases discussed in U.S. Pat. Nos. 5,648,211 and 5,744,312, which include exo$^-$ Vent (New England Biolabs), exo$^-$ Deep Vent (New England Biolabs), Bst (BioRad), exo$^-$ Pfu (Stratagene), Bca (Panvera), sequencing grade Taq (Promega); thermostable DNA polymerases from *Thermoanaerobacter thermohydrosulfuricus*; and the like. In some embodiments, the reaction mixture includes an RNAse H.

Magnesium ions are typically present in the reaction mix in a concentration of from about 1 mM to about 100 mM, e.g., from about 1 mM to about 3 mM, from about 3 mM to about 5 mM, from about 5 mM to about 10 mM, from about 10 mM to about 25 mM, from about 25 mM to about 50 mM, from about 50 mM to about 75 mM, or from about 75 mM to about 100 mM.

Usually the reaction mixture will comprise four different types of dNTPs corresponding to the four naturally occurring bases are present, i.e. dATP, dTTP, dCTP and dGTP. In the subject methods, each dNTP will typically be present at a final concentration in the reaction, ranging from about 10 μM to 5000 μM, e.g., from about 10 μM to about 50 μM, from about 50 μM to about 100 μM, from about 100 μM to about 200 μM, from about 200 μM to about 500 μM, from about 500 μM to about 1000 μM, from about 1000 μM to about 2000 μM, from about 2000 μM to about 3000 μM, from about 3000 μM to about 4000 μM, or from about 4000 μM to about 5000 μM. In some embodiments, each dNTP will be present at a final concentration in the reaction of from about 20 μM to 1000 μM, from about 100 μM to about 200 μM, or from about 50 μM to about 200 μM.

The amplification reaction mixture typically includes an aqueous buffer medium that includes a source of monovalent ions, a source of divalent cations and a buffering agent. Any convenient source of monovalent ions, such as KCl, K-acetate, NH$_4$-acetate, K glutamate, NH$_4$Cl, ammonium sulfate, and the like may be employed. The divalent cation may be magnesium, manganese, zinc and the like, where the cation will typically be magnesium. Any convenient source of magnesium cation may be employed, including MgCl$_2$, Mg-acetate, and the like. Representative buffering agents or salts that may be present in the buffer include Tris, Tricine, HEPES, MOPS and the like, where the amount of buffering agent will typically range from about 5 to 150 mM, from about 10 to 100 mM, or from about 20 to 50 mM, where in certain embodiments the buffering agent will be present in an amount sufficient to provide a pH ranging from about 6.0 to 9.5, e.g., pH 7.3 at 72° C. Other agents which may be present in the buffer medium include chelating agents, such as EDTA, EGTA and the like.

Each primer nucleic acid is present in the reaction mixture at a concentration of from about 50 nM to about 900 nM, e.g., the 3' primer and the 5' primer nucleic acid are each independently present at a concentration of from about 50 nM to about 75 nM, from about 75 nM to about 100 nM, from about 100 nM to about 150 nM, from about 150 nM to about 200 nM, from about 200 nM to about 250 nM, from about 250 nM to about 300 nM, from about 300 nM to about 400 nM, from about 400 nM to about 500 nM, from about 500 nM to about 600 nM, from about 600 nM to about 700 nM, from about 700 nM to about 800 nM, or from about 800 nM to about 900 nM.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2', 4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

In one embodiment, a subject method involves amplifying nucleic acids from a sample, which amplifying step follows a reverse transcription step to provide a cDNA template for amplification. In some embodiments, the level of a target mRNA can be indicated, where overexpression or underexpression of a target mRNA indicates a cancerous or precancerous cell. In general, amplification-based methods involve reverse transcription of mRNA in a sample and amplifying the resulting cDNA from the sample using a primer and at least one other primer, as described above, and assessing the amplified nucleic acids.

As is known in the art, an amplified nucleic acid may be assessed by a number of methods, including, for example, determining the presence or absence of the nucleic acid, determining the size of the nucleic acid or determining the abundance of a nucleic acid in relation to another amplified nucleic acid. In most embodiments, an amplified nucleic acid is assessed using gel electrophoresis, nucleic acid hybridization, sequencing, and/or detection of a signal from a label bound to the amplified nucleic acid. Methods of amplifying (e.g., by polymerase chain reaction) nucleic acid, methods of performing primers extension, and methods of assessing nucleic acids are generally well known in the art (e.g., see Ausubel, et al, Short Protocols in Molecular Biology, 3rd ed., Wiley & Sons, 1995 and Sambrook, et al, Molecular Cloning: A Laboratory Manual, Third Edition, (2001) Cold Spring Harbor, N.Y.) and need not be described in any great detail.

For example, primers and probes described above may be used in polymerase chain reaction (PCR)-based techniques to detect target nucleic acid (e.g., to detect a level of target mRNA; etc.) in biological samples. PCR is a technique for amplifying a desired target nucleic acid sequence contained in a nucleic acid molecule or mixture of molecules. In PCR, a pair of primers is employed in excess to hybridize to the complementary strands of the target nucleic acid. The primers are each extended by a polymerase using the target nucleic acid as a template. The extension products become target sequences themselves after dissociation from the original target strand. New primers are then hybridized and extended by a polymerase, and the cycle is repeated to geometrically increase the number of target sequence molecules. The PCR method for amplifying target nucleic acid sequences in a sample is well known in the art and has been described in, e.g., Innis et al. (eds.) PCR Protocols (Academic Press, NY 1990); Taylor (1991) Polymerase chain reaction: basic principles and automation, in PCR: A Practical Approach, McPherson et al. (eds.) IRL Press, Oxford; Saiki et al. (1986) Nature 324:163; as well as in U.S. Pat. Nos. 4,683,195, 4,683,202 and 4,889,818, all incorporated herein by reference in their entireties.

In particular, PCR uses relatively short oligonucleotide primers which flank the target nucleotide sequence to be amplified, oriented such that their 3' ends face each other, each primer extending toward the other. The polynucleotide sample is extracted and denatured, e.g. by heat, and hybridized with first and second primers which are present in molar excess. Polymerization is catalyzed in the presence of the four deoxyribonucleotide triphosphates (dNTPs—dATP, dGTP, dCTP and dTTP) using a primer- and template-dependent polynucleotide polymerizing agent, such as any enzyme capable of producing primer extension products, for example, *E. coli* DNA polymerase I, Klenow fragment of DNA polymerase I, T4 DNA polymerase, thermostable DNA polymerases isolated from *Thermus aquaticus* (Taq), available from a variety of sources (for example, Perkin Elmer), *Thermus thermophilus* (United States Biochemicals), *Bacillus stearothermophilus* (Bio-Rad), or *Thermococcus litoralis* ("Vent" polymerase, New England Biolabs). This results in two "long products" which contain the respective primers at their 5' ends covalently linked to the newly synthesized complements of the original strands.

The reaction mixture is then returned to polymerizing conditions, e.g., by lowering the temperature, inactivating a denaturing agent, or adding more polymerase, and a second cycle is initiated. The second cycle provides the two original strands, the two long products from the first cycle, two new long products replicated from the original strands, and two "short products" replicated from the long products. The short products have the sequence of the target sequence with a primer at each end. On each additional cycle, an additional two long products are produced, and a number of short products equal to the number of long and short products remaining at the end of the previous cycle. Thus, the number of short products containing the target sequence grows exponentially with each cycle. PCR is typically carried out with a commercially available thermal cycler, e.g., Perkin Elmer.

RNAs encoding a deacylase of interest can be amplified by reverse transcribing the mRNA into cDNA, and then performing PCR (RT-PCR), as described above. Alternatively, a single enzyme may be used for both steps as described in U.S. Pat. No. 5,322,770. mRNA may also be reverse transcribed into cDNA, followed by asymmetric gap ligase chain reaction (RT-AGLCR) as described by Marshall et al. (1994) PCR Meth. App. 4:80-84.

The fluorogenic 5' nuclease assay, known as the TAQMAN™ assay (Perkin Elmer), is a powerful and versatile PCR-based detection system for nucleic acid targets. For a detailed description of the TAQMAN™ assay, reagents and conditions for use therein, see, e.g., Holland et al., Proc. Natl. Acad. Sci, U.S.A. (1991) 88:7276-7280; U.S. Pat. Nos. 5,538,848, 5,723,591, and 5,876,930, all incorporated herein by reference in their entireties. Hence, primers and probes derived from regions of a target nucleic acid as described herein can be used in TAQMAN™ analyses to detect a level of target mRNA in a biological sample. Analysis is performed in conjunction with thermal cycling by monitoring the generation of fluorescence signals. The assay system dispenses with the need for gel electrophoretic analysis, and has the capability to generate quantitative data allowing the determination of, for example, the level of target mRNA (e.g., to detect the presence of a pre-cancerous epithelial cell; etc.).

The fluorogenic 5' nuclease assay is conveniently performed using, for example, AMPLITAQ GOLD™ DNA polymerase, which has endogenous 5' nuclease activity, to digest an internal oligonucleotide probe labeled with both a fluorescent reporter dye and a quencher (see, Holland et al., Proc. Natl. Acad. Sci. USA (1991) 88:7276-7280; and Lee et al., Nucl. Acids Res. (1993) 21:3761-3766). Assay results are detected by measuring changes in fluorescence that occur during the amplification cycle as the fluorescent probe is digested, uncoupling the dye and quencher labels and causing an increase in the fluorescent signal that is proportional to the amplification of target nucleic acid.

The amplification products can be detected in solution or using solid supports. In this method, the TAQMAN™ probe is designed to hybridize to a target sequence within the desired PCR product. The 5' end of the TAQMAN™ probe contains a fluorescent reporter dye. The 3' end of the probe is blocked to prevent probe extension and contains a dye that will quench the fluorescence of the 5' fluorophore. During subsequent amplification, the 5' fluorescent label is cleaved off if a polymerase with 5' exonuclease activity is present in the reaction. Excision of the 5' fluorophore results in an increase in fluorescence which can be detected.

In particular, the oligonucleotide probe is constructed such that the probe exists in at least one single-stranded conformation when unhybridized where the quencher molecule is near enough to the reporter molecule to quench the fluorescence of the reporter molecule. The oligonucleotide probe also exists in at least one conformation when hybridized to a target polynucleotide such that the quencher molecule is not positioned close enough to the reporter molecule to quench the fluorescence of the reporter molecule. By adopting these hybridized and unhybridized conformations, the reporter molecule and quencher molecule on the probe exhibit different fluorescence signal intensities when the probe is hybridized and unhybridized. As a result, it is possible to determine whether the probe is hybridized or unhybridized based on a change in the fluorescence intensity of the reporter molecule, the quencher molecule, or a combination thereof. In addition, because the probe can be designed such that the quencher molecule quenches the reporter molecule when the probe is not hybridized, the probe can be designed such that the reporter molecule exhibits limited fluorescence unless the probe is either hybridized or digested.

Accordingly, some embodiments of the present invention provides inter alia methods for amplifying a target nucleotide sequence using a nucleic acid polymerase having 5' to 3' nuclease activity, one or more primers capable of hybridizing to the target sequence or its extension product, and an oligonucleotide probe capable of hybridizing to the target sequence 3' relative to the primer. During amplification, the polymerase digests the oligonucleotide probe when it is hybridized to the target sequence, thereby separating the reporter molecule from the quencher molecule. As the amplification is conducted, the fluorescence of the reporter molecule is monitored, with fluorescence corresponding to the occurrence of nucleic acid amplification. The reporter molecule is in some embodiments a fluorescein dye and the quencher molecule is in some embodiments a rhodamine dye.

The target nucleic acids described herein may also be used as a basis for transcription-mediated amplification (TMA) assays. TMA provides a method of identifying target nucleic acids present in very small amounts in a biological sample. Such nucleic acids may be difficult or impossible to detect using direct assay methods. In particular, TMA is an isothermal, autocatalytic nucleic acid target amplification system that can provide more than a billion RNA copies of a target sequence. The assay can be done qualitatively, to accurately detect the presence or absence of the target sequence in a biological sample. The assay can also provide a quantitative measure of the amount of target sequence over a concentration range of several orders of magnitude. TMA provides a method for autocatalytically synthesizing multiple copies of a target nucleic acid sequence without repetitive manipulation of reaction conditions such as temperature, ionic strength and pH.

Generally, TMA includes the following steps: (a) isolating nucleic acid from the biological sample of interest (e.g., breast tissue; axillary lymph node tissue; etc.); and (b) combining into a reaction mixture (i) the isolated nucleic acid, (ii) first and second oligonucleotide primers, the first primer having a complexing sequence sufficiently complementary to the 3' terminal portion of an RNA target sequence, if present (for example the (+) strand), to complex therewith, and the second primer having a complexing sequence sufficiently complementary to the 3' terminal portion of the target sequence of its complement (for example, the (−) strand) to complex therewith, wherein the first oligonucleotide further comprises a sequence 5' to the complexing sequence which includes a promoter, (iii) a reverse transcriptase or RNA and DNA dependent DNA polymerases, (iv) an enzyme activity which selectively degrades the RNA strand of an RNA-DNA complex (such as an RNAse H) and (v) an RNA polymerase which recognizes the promoter.

The components of the reaction mixture may be combined stepwise or at once. The reaction mixture is incubated under conditions whereby an oligonucleotide/target sequence is formed, including DNA priming and nucleic acid synthesizing conditions (including ribonucleotide triphosphates and deoxyribonucleotide triphosphates) for a period of time sufficient to provide multiple copies of the target sequence. The reaction advantageously takes place under conditions suitable for maintaining the stability of reaction components such as the component enzymes and without requiring modification or manipulation of reaction conditions during the course of the amplification reaction. Accordingly, the reaction may take place under conditions that are substantially isothermal and include substantially constant ionic strength and pH. The reaction conveniently does not require a denaturation step to separate the RNA-DNA complex produced by the first DNA extension reaction.

Suitable DNA polymerases include reverse transcriptases, such as avian myeloblastosis virus (AMV) reverse transcriptase (available from, e.g., Seikagaku America, Inc.) and Moloney murine leukemia virus (MMLV) reverse transcriptase (available from, e.g., Bethesda Research Laboratories).

Promoters or promoter sequences suitable for incorporation in the primers are nucleic acid sequences (either naturally occurring, produced synthetically or a product of a restriction digest) that are specifically recognized by an RNA polymerase that recognizes and binds to that sequence and initiates the process of transcription whereby RNA transcripts are produced. The sequence may optionally include nucleotide bases extending beyond the actual recognition site for the RNA polymerase which may impart added stability or susceptibility to degradation processes or increased transcription efficiency. Examples of useful promoters include those which are recognized by certain bacteriophage polymerases such as those from bacteriophage T3, T7 or SP6, or a promoter from *E. coli*. These RNA polymerases are readily available from commercial sources, such as New England Biolabs and Epicentre.

Some of the reverse transcriptases suitable for use in the methods herein have an RNAse H activity, such as AMV reverse transcriptase. In some embodiments, an exogenous RNAse H, such as *E. coli* RNAse H, is added, even when AMV reverse transcriptase is used. RNAse H is readily available from, e.g., Bethesda Research Laboratories.

The RNA transcripts produced by these methods may serve as templates to produce additional copies of the target sequence through the above-described mechanisms. The system is autocatalytic and amplification occurs autocatalytically without the need for repeatedly modifying or changing reaction conditions such as temperature, pH, ionic strength or the like.

Another method of detection involves use of target sequence-specific oligonucleotide probes, which contain a region of complementarity to the target sequence described above. The probes may be used in hybridization protection assays (HPA). In this embodiment, the probes are conveniently labeled with acridinium ester (AE), a highly chemiluminescent molecule. See, e.g., Nelson et al. (1995) "Detection of Acridinium Esters by Chemiluminescence" in Nonisotopic Probing, Blotting and Sequencing, Kricka L. J. (ed) Academic Press, San Diego, Calif.; Nelson et al. (1994) "Application of the Hybridization Protection Assay (HPA) to PCR" in The Polymerase Chain Reaction, Mullis et al. (eds.) Birkhauser, Boston, Mass.; Weeks et al., Clin. Chem. (1983) 29:1474-1479; Berry et al., Clin. Chem. (1988) 34:2087-2090. One AE molecule is directly attached to the probe using a non-nucleotide-based linker arm chemistry that allows placement of the label at any location within the probe. See, e.g., U.S. Pat. Nos. 5,585,481 and 5,185,439. Chemiluminescence is triggered by reaction with alkaline hydrogen peroxide which yields an excited N-methyl acridone that subsequently collapses to ground state with the emission of a photon. Additionally, AE causes ester hydrolysis which yields the nonchemiluminescent-methyl acridinium carboxylic acid.

When the AE molecule is covalently attached to a nucleic acid probe, hydrolysis is rapid under mildly alkaline conditions. When the AE-labeled probe is exactly complementary to the target nucleic acid, the rate of AE hydrolysis is greatly reduced. Thus, hybridized and unhybridized AE-labeled probe can be detected directly in solution, without the need for physical separation.

HPA generally includes, comprises, or consists of the following steps: (a) the AE-labeled probe is hybridized with the target nucleic acid in solution for about 15 to about 30 minutes. A mild alkaline solution is then added and AE coupled to the unhybridized probe is hydrolyzed. This reaction takes approximately 5 to 10 minutes. The remaining hybrid-associated AE is detected as a measure of the amount of target present. This step takes approximately 2 to 5 seconds. In some embodiments, the differential hydrolysis step is conducted at the same temperature as the hybridization step, typically at 50 to 70 degrees celsius. Alternatively, a second differential hydrolysis step may be conducted at room temperature. This allows elevated pHs to be used, for example in the range of 10-11, which yields larger differences in the rate of hydrolysis between hybridized and unhybridized AE-labeled probe. HPA is described in detail in, e.g., U.S. Pat. Nos. 6,004,745; 5,948,899; and 5,283,174, the disclosures of which are incorporated by reference herein in their entireties.

TMA is described in detail in, e.g., U.S. Pat. No. 5,399,491, the disclosure of which is incorporated herein by reference in its entirety. In one example of a typical assay, an isolated nucleic acid sample, suspected of containing a deacylase-encoding nucleic acid as described herein, is mixed with a buffer concentrate containing the buffer, salts, magnesium, nucleotide triphosphates, primers, dithiothreitol, and spermidine. The reaction is optionally incubated at about 100° C. for approximately two minutes to denature any secondary structure. After cooling to room temperature, reverse transcriptase, RNA polymerase, and RNAse H are added and the mixture is incubated for two to four hours at 37° C. The reaction can then be assayed by denaturing the product, adding a probe solution, incubating 20 minutes at 60° C., adding a solution to selectively hydrolyze the unhybridized probe, incubating the reaction six minutes at 60° C., and measuring the remaining chemiluminescence in a luminometer.

Oligonucleotides will in some embodiments be used in nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's. Using NASBA, large amounts of single stranded RNA are generated from either single-stranded RNA or DNA, or double-stranded DNA. When RNA is to be amplified, the ssRNA serves as a template for the synthesis of a first DNA strand by elongation of a first primer containing an RNA polymerase recognition site. This DNA strand in turn serves as the template for the synthesis of a second, complementary, DNA strand by elongation of a second primer, resulting in a double-stranded active RNA-polymerase promoter site, and the second DNA strand serves as a template for the synthesis of large amounts of the first template, the ssRNA, with the aid of a RNA polymerase. The NASBA technique is known in the art and described in, e.g., European Patent 329,822, International Patent Application No. WO 91/02814, and U.S. Pat. Nos. 6,063,603, 5,554,517 and 5,409,818, all of which are incorporated herein in their entireties.

The target nucleic acids described herein are also useful in nucleic acid hybridization and amplification techniques that utilize branched DNA molecules. In a basic nucleic acid hybridization assay, single-stranded analyte nucleic acid is hybridized to a labeled single-stranded nucleic acid probe and resulting labeled duplexes are detected. Variations of this basic scheme have been developed to facilitate separation of the duplexes to be detected from extraneous materials and/or to amplify the signal that is detected. One method for amplifying the signal uses amplification multimers that are polynucleotides with a first segment that hybridizes specifically to the analyte nucleic acid or a strand of nucleic acid bound to the analyte and iterations of a second segment that hybridizes specifically to a labeled probe. The amplification is theoretically proportional to the number of iterations of the second segment. The multimers may be either linear or branched. Two general types of branched multimers are useful in these techniques: forked and combed. Methods for making and using branched nucleic acid molecules are known in the art and described in, e.g., U.S. Pat. No. 5,849,481, incorporated herein by reference in its entirety.

As is readily apparent, design of the assays described herein is subject to a great deal of variation, and many formats are known in the art. The above descriptions are merely provided as guidance and one of skill in the art can readily modify the described protocols, using techniques well known in the art.

Detection Using Nucleic Acid Arrays

In some embodiments, a subject method of detecting a target nucleic acid involves detection of the target nucleic acid in a sample of nucleic acids that is labeled with at least a first and a second distinguishable detectable label. In some embodiments, the method includes the following steps a) contacting a nucleic acid probe for a target nucleic acid with the sample under conditions sufficient for specific binding to occur between the probe and the target nucleic acid; and b) identifying the amount of the first and second labels in the resultant target nucleic acid/probe complex, thereby determining the amount of the target nucleic acid in the sample.

For example, in some embodiments, the method involves: a) contacting a probe for a target nucleic acid with a sample of nucleic acids under conditions sufficient for duplex nucleic acids to be produced between the probe and the target nucleic acid, and b) identifying the amount of the first and second labels in the resultant duplex nucleic acid.

In an exemplary microarray assay, a microarray is hybridized with differentially labeled RNA or DNA populations derived from two different samples. For example, RNA (either total RNA or poly A⁺ RNA) is isolated from cells or tissues of interest and is reverse transcribed to yield cDNA. Labeling can be performed during reverse transcription by incorporating a labeled nucleotide in the reaction mixture. Various labels can be used; for example, the nucleotide is conjugated with the fluorescent dyes Cy3 or Cy5. For example, Cy5-dUTP and Cy3-dUTP can be used. cDNA derived from one sample (representing, for example, a particular cell type, tissue type or growth condition) is labeled with one fluor while cDNA derived from a second sample (representing, for example, a different cell type, tissue type, or growth condition) is labeled with the second fluor. Similar amounts of labeled material from the two samples are cohybridized to the microarray. In the case of a microarray assay in which the samples are labeled with Cy5 (which fluoresces red) and Cy3 (which fluoresces green), the primary data (obtained by scanning the microarray using a detector capable of quantitatively detecting fluorescence intensity) are ratios of fluorescence intensity (red/green, R/G). These ratios represent the relative concentrations of cDNA molecules that hybridized to the cDNAs represented on the microarray and thus reflect the relative expression levels of the mRNA corresponding to each cDNA/gene represented on the microarray.

In certain embodiments, the nucleic acid is extracted from a source (e.g., a cell, group of cells, tissue, culture, etc.) of interest, and includes RNA (e.g., unspliced RNA or mRNA, etc.), or DNA (e.g., genomic DNA of a nucleus or organelle, etc.). In certain embodiments, the sample is a genetic copy of the nucleic acid extracted from a source, such as cDNA, amplified DNA or RNA, or a nucleic acid that contains modified nucleotide residues (e.g., amino-allyl nucleotides). Nucleic acid compositions suitable for labeling in the subject methods are well known in the art, and their further description may be found in several publications, including Brumbaugh et al (Proc Natl Acad Sci USA 85, 5610-4, 1988), Hughes et al. (Nat Biotechnol 19, 342-7, 2001), Eberwine et al (Biotechniques. 20:584-91, 1996), Ausubel, et al, (Short Protocols in Molecular Biology, 3rd ed., Wiley & Sons, 1995) and Sambrook, et al, (Molecular Cloning: A Laboratory Manual, Third Edition, (2001) Cold Spring Harbor, N.Y.).

In some embodiments, the sample contains labeled nucleic acid, where individual nucleic acid molecules within the sample are labeled with at least two, (e.g., two, three, four, five, six, seven or eight or more) detectably distinguishable labels. At least 2, at least about 4, at least about 6, at least about 8, at least about 10, at least about 15, at least about 20, at least about 25, at least about 30, or at least about 40 or at least about 50 or more of each distinguishable detectable label may associated with a single nucleic acid molecule. In certain embodiments, however, particularly those that involve separately labeling two portions of the same sample and mixing the labeled portions together to make a labeled sample, individual nucleic acid molecules within the sample may be labeled with only one type of label.

Labels of interest include directly detectable and indirectly detectable non-radioactive labels such as fluorescent dyes. Directly detectable labels are those labels that provide a directly detectable signal without interaction with one or more additional chemical agents. Examples of directly detectable labels include fluorescent labels. Indirectly detectable labels are those labels which interact with one or more additional members to provide a detectable signal. In this latter embodiment, the label is a member of a signal producing system that includes two or more chemical agents that work together to provide the detectable signal. Examples of indirectly detectable labels include biotin or digoxigenin, which can be detected by a suitable antibody coupled to a fluorochrome or enzyme, such as alkaline phosphatase. In some embodiments, the label is a directly detectable label. Directly detectable labels of particular interest include fluorescent labels.

Suitable fluorescent labels include a fluorophore moiety. Specific fluorescent dyes of interest include: xanthene dyes, e.g. fluorescein and rhodamine dyes, such as fluorescein isothiocyanate (FITC), 6-carboxyfluorescein (commonly known by the abbreviations FAM and F), 6-carboxy-2',4', 7',4,7-hexachlorofluorescein (HEX), 6-carboxy-4',5'-dichloro-2', 7'-dimethoxyfluorescein (JOE or J), N,N,N',N'-tetramethyl-6-carboxyrhodamine (TAMRA or T), 6-carboxy-X-rhodamine (ROX or R), 5-carboxyrhodamine-6G (R6G$^5$ or G$^5$), 6-carboxyrhodamine-6G (R6G$^6$ or G$^6$), and rhodamine 110; cyanine dyes, e.g. Cy3, Cy5 and Cy7 dyes; coumarins, e.g umbelliferone; benzimide dyes, e.g.

Hoechst 33258; phenanthridine dyes, e.g. Texas Red; ethidium dyes; acridine dyes; carbazole dyes; phenoxazine dyes; porphyrin dyes; polymethine dyes, e.g. cyanine dyes such as Cy3, Cy5, etc; BODIPY dyes and quinoline dyes. Specific fluorophores of interest that are commonly used in subject applications include: Pyrene, Coumarin, Diethylaminocoumarin, FAM, Fluorescein Chlorotriazinyl, Fluorescein, R110, Eosin, JOE, R6G, Tetramethylrhodamine, TAMRA, Lissamine, ROX, Napthofluorescein, Texas Red, Napthofluorescein, Cy3, and Cy5, etc.

As mentioned above, the labels used in the subject methods are distinguishable, meaning that the labels can be independently detected and measured, even when the labels are mixed. In other words, the amounts of label present (e.g., the amount of fluorescence) for each of the labels are separately determinable, even when the labels are co located (e.g., in the same tube or in the same duplex molecule or in the same feature of an array). Suitable distinguishable fluorescent label pairs useful in the subject methods include Cy-3 and Cy-5 (Amersham Inc., Piscataway, NJ), Quasar 570 and Quasar 670 (Biosearch Technology, Novato CA), Alexafluor555 and Alexafluor647 (Molecular Probes, Eugene, OR), BODIPY V-1002 and BODIPY V1005 (Molecular Probes, Eugene, OR), POPO-3 and TOTO-3 (Molecular Probes, Eugene, OR), and POPRO3 TOPRO3 (Molecular Probes, Eugene, OR). Further suitable distinguishable detectable labels may be found in Kricka et al. (Ann Clin Biochem. 39:114-29, 2002).

In general, at least two distinguishable labels are covalently attached to nucleic acids in a sample. Means for labeling nucleic acids are generally well known in the art (e.g. Brumbaugh et al Proc Natl Acad Sci USA 85, 5610-4, 1988; Hughes et al. Nat Biotechnol 19, 342-7, 2001, Eberwine et al Biotechniques. 20:584-91, 1996, Ausubel, et al, Short Protocols in Molecular Biology, 3rd ed., Wiley & Sons, 1995 Sambrook, et al, Molecular Cloning: A Laboratory Manual, Third Edition, 2001 Cold Spring Harbor, N.Y. and DeRisi et al. Science 278:680-686, 1997; Patton W F. Electrophoresis. 2000 21:1123-44; MacBeath G. Nat. Genet. 2002 32 Suppl1:526-32; and Biotechnol Prog. 1997 13:649-58). These means usually involve either direct chemical modification of the analyte, or a labeled nucleotide that is incorporated into a nucleic acid by nucleic acid replication, e.g., using a polymerase.

Chemical modification methods for labeling a nucleic acid sample can include incorporation of a reactive nucleotide into a nucleic acid, e.g., an amine-allyl nucleotide derivative such as 5-(3-aminoallyl)-2'-deoxyuridine 5'-triphosphate, using an RNA-dependent or DNA-dependent DNA or RNA polymerase, e.g., reverse transcriptase or T7 RNA polymerase, followed by chemical conjugation of the reactive nucleotide to a label, e.g. a N-hydroxysuccinimdyl of a label such as Cy-3 or Cy5 to make a labeled nucleic acids (Brumbaugh et al Proc Natl Acad Sci USA 85, 5610-4, 1988 and Hughes et al. Nat Biotechnol 19, 342-7, 2001). Such chemical conjugation methods may be combined with RNA amplification methods (e.g. those of Eberwine et al Biotechniques. 20:584-91, 1996), to produce labeled DNA or RNA.

Suitable labels may also be incorporated into a sample by means of nucleic acid replication, where modified nucleotides such as modified deoxynucleotides, ribonucleotides, dideoxynucleotides, etc., or closely related analogues thereof, e.g. a deaza analogue thereof, in which a moiety of the nucleotide, typically the base, has been modified to be bonded to the label. Modified nucleotides are incorporated into a nucleic acid by the actions of a nucleic acid dependent DNA or RNA polymerases, and a copy of the nucleic acid in the sample is produced that contains the label. Methods of labeling nucleic acids by a variety of methods, e.g., random priming, nick translation, RNA polymerase transcription, etc., are well generally known in the art (see, e.g., Ausubel, et al, Short Protocols in Molecular Biology, 3rd ed., Wiley & Sons, 1995 Sambrook, et al, Molecular Cloning: A Laboratory Manual, Third Edition, 2001 Cold Spring Harbor, N.Y. and DeRisi et al. Science 278:680-686, 1997).

In some embodiments of the invention, a nucleic acid sample is labeled using a mixture of labels. In other words, two or more distinguishably detectable labels are mixed together, usually in a single vessel or tube, sometimes in equal proportions, in a single labeling reaction for a sample. The two or more labels may be for the same nucleotide e.g. "T" or "U", or a mixture of two, three or four nucleotides. In certain embodiments, however, if the samples are identical (e.g. they are two portions of a sample, or two nucleic acids samples made from the same source), the samples may be labeled separately and combined to make a labeled sample. As such, the subject methods do not involve labeling two different samples (e.g. samples from two different tissues, times, or conditions), each with distinguishable label, and mixing the samples together.

Once labeled, the sample is usually applied to a substrate that includes at least one probe, and incubated under conditions suitable for an analyte/probe complex, e.g. a nucleic acid duplex (i.e. a RNA/RNA, DNA/RNA, or DNA/DNA duplex) to be formed between a probe and a labeled nucleic acid in the sample, if such a labeled nucleic acid is present. In other words, the labeled nucleic acid sample is incubated with a substrate that contains at least one probe under conditions suitable for binding of the labeled nucleic acid to the probe. In certain embodiments, the substrate that includes the probe is an array of probes, where each probe is contained in a feature of the array, and where an array includes at least about 20, at least about 50, at least about 100, at least about 200, at least about 500, at least about 1,000, at least about 2,000, at least about 5,000, at least about 10,000, at least about 20,000, at least about 50,000, or up to about 100,000 or more features. Arrays used in the subject methods may have known amounts of probes present in a feature of the array. For example, if the concentration of a probe in a solution of probe to be deposited as known, and, the volume of the probe solution that is deposited in a feature is known, an amount of probe present in a feature of an array may be known.

After incubation, labeled sample that is not bound with a probe is typically washed away from the substrate, and the substrate, now including the labeled nucleic acid/probe duplexes, is scanned. The amount of each label associated with features of the array (each feature containing, e.g., a target nucleic acid/probe complex or a probe if no target nucleic acid is present) is then determined. In most embodiments, the substrate is scanned in two channels corresponding to the distinguishing features of the probes, such that the amounts of each label associated with each feature is determined independently (i.e. without interference) from other labels. In certain embodiments, scanning results in two scans, one for each channel, and usually represents a pixilated image of the substrate that reflects the amount of label associated with the features of the substrate. For example, each pixel of the image is accorded a signal level that represents the level of brightness of the label signal. As mentioned above, scanning methods are well known in the art (e.g., DeRisi et al. Science 278:680-686, 1997), and several suitable scanners are commercially available from Perkin-Elmer, Agilent, or Axon Instruments, etc., and are described in U.S. Pat. Nos. 5,091,652; 5,760,951, 6,320,196 and 6,355,934), the disclosures of which are herein incorporated by reference.

Detecting the Presence and/or Levels of a microRNA

In some embodiments, a subject method involves detecting the presence and/or levels of a microRNA synthesized by an MEC. MicroRNAs that can be detected using a subject method include, but are not limited to, mir 196b (HoxA9), (p14), 328, 30A-3P, 125b, 30E-3P, 680, 134, 604, 128b, 128a, 331, 520F, 299-3P, 520H, 510, 365, 520G, 9, 324-3P, 351, 125A, 764-5P, 302D, 520D, 652, 520C, 350, 585, 621, 542-5P, 560, 126, and 341.

MicroRNAs (miRNAs) are encoded by genes, which encode transcripts containing short double-stranded RNA hairpins. MiRNAs are transcribed as longer precursors, termed pre-miRNAs, which can be 50 to 80 nucleotides in length, and which are sometimes found in clusters and frequently found in introns. Upon transcription, miRNAs undergo nuclear cleavage by an RNase III endonuclease, producing the 60-70-nt stem-loop precursor miRNA (pre-miRNA) with a 5' phosphate and a 2-nt 3 overhang. The pre-miRNAs are cleaved by Dicer about two helical turns away from the ends of the pre-miRNA stem loop, producing double stranded RNA with strands that are approximately the same length (21 to 24 nucleotides), and possess the characteristic 5'-phosphate and 3'-hydroxyl termini. One of the strands of this short lived intermediate accumulates as the mature miRNA and is subsequently incorporated into a ribonucleoprotein complex, the miRNP. MiRNAs interact with target mRNAs at specific sites to induce cleavage of the message or inhibit translation.

Detection of microRNAs can be carried out using any of a variety of methods. One approach uses stem-loop reverse transcription (RT) followed by TaqMan PCR analysis (Chen et al. Nucleic Acids Res. 2005; 33(20), e179). This method includes reverse transcription at low temperature. Another approach is to use a composite primer for reverse transcription which includes a gene-specific portion and a tail sequence used for PCR amplification (Raymond et al. RNA. 2005 November; 11(11):1737-44). Another approach, described in U.S. Patent Publication No. 2007/0077582) is based on using a target miRNA as a primer for extension by DNA polymerase on a specific oligonucleotide template; the specific oligonucleotide sequence is longer than the target miRNA sequence and contains at its 3'-end a sequence complementary to target miRNA, and a spacer sequence adjacent to that complementary sequence, which is used in subsequent signal amplification. Also suitable for use is a microarray analysis method as described in, e.g., U.S. Patent Publication No. 2007/0009915. A quantitative RT-PCR approach that can be used in the mirVana™ method (Ambion).

DNA Detection Methods

In some embodiments, a subject detection method involves detecting the levels and/or integrity and/or methylation status and/or packaging of a selected DNA, or collection of DNA, present in an MEC.

Detecting a Level of a Selected DNA

In some embodiments, a subject detection method involves detecting the level of a selected DNA in an MEC. For example, in some embodiments, a variant MEC (e.g., an MEC that is pre-cancerous) has a deletion of all or part of one or more of chromosome 3p, chromosome 5p, chromosome 6p, chromosome 8p, chromosome 11q, chromosome 16q, and chromosome 22. In other embodiments, a variant MEC (e.g., an MEC that is pre-cancerous) has an amplification or all or a part of one or more of c-myc, her2/neu, or cyclin D1.

Detecting deletion of all or part of a DNA can be carried out using any of a number of well-established methods. In some embodiments, deletion is detected by histochemical analysis. In some embodiments, deletion is detected via metaphase karyotype analysis of the chromosomes present in an MEC. Suitable methods of detecting a DNA deletion include, but are not limited to, array comparative genomic hybridization, fluorescent in situ hybridisation (FISH), quantitative multiplex PCR, Southern blotting, multiplex amplifiable probe hybridization (MAPH), multiplex amplifiable probe hybridization (MLPA), and the like. See, e.g., White et al. (2003) *J. Med. Genetics* 40:e113; and Edgley et al. (2002) *Nucl. Acids Res.* 30:e52;

In some embodiments, detecting a DNA deletion is carried out by use of restriction endonucleases that cleave outside of a gene comprising a deletion, e.g., where one restriction endonuclease cleaves at a site 5' of the deletion and a second restriction endonuclease cleaves 3' of the deletion, such that a restriction fragment is generated that is shorter than the length of a restriction fragment generated using the same restriction endonucleases, using as a substrate the same gene without a deletion.

As another example, amplification using primer pairs spanning the deletion will result in different sized products corresponding to the deleted and undeleted (e.g., control) gene, which can be distinguished on the basis of size (e.g., by gel electrophoresis). These primer pairs can be used individually or in a nested PCR experiment. It will also be apparent to one of skill that hybridization methods (e.g., Northern hybridization) or RNAse protection assays using nucleic acid probe specific for the gene (e.g., a control, undeleted gene), or a nucleic acid probe specific for a region flanking the gene, can be used to detect and distinguish undeleted (control) genes and deleted variants.

Detecting amplification of all or part of a DNA can be carried out using any of a number of well-established methods.

Representational Oligonucleotide Microarray Analysis (ROMA) detects genomic amplifications and deletions with boundaries defined at a resolution of ~50 kb. See, e.g., Lucito et al. (2003) *Genome Res.* 13:2291-2305. A ROMA method can be used to detect amplification or deletion of all or a portion of a selected DNA. In another embodiment, a method such as comparative genomic hybridization (CGH) is used. See, e.g., U.S. Pat. No. 7,011,949. CGH is a method for detecting deletions and amplifications in one sample of genomic DNA relative to another individual sample; the method involves comparing the intensity of hybridization of microarray features to each target sample, each labeled with different fluorescent dyes In another embodiment, a method as described in U.S. Patent Publication No. 2006/0129331 is used.

In some embodiments, karyotype or other chromosomal analysis using gene specific nucleic acid probes is carried out to detect amplification (i.e., change in copy number), deletion (including total deletion, partial deletion), insertion, substitution, or changes in the chromosomal location (e.g., translocation) of a selected gene. For example, alterations to a selected gene are identified by karyotype analysis, using any of a variety of methods known in the art. One useful technique is in situ hybridization (ISH). For example, when in situ hybridization techniques are used for karyotype analysis, a detectable or detectably-labeled probe is hybridized to a chromosomal sample in situ to locate a selected gene sequence. ISH can comprise one or more of the following steps: (1) fixation of the tissue, cell or other biological structure to be analyzed; (2) prehybridization treatment of the biological structure to increase accessibility of target DNA (e.g., denaturation with heat or alkali), and to reduce nonspecific binding (e.g., by blocking the hybridization capacity of repetitive sequences, e.g., using human genomic DNA); (3) hybridization of one or more nucleic acid probes (e.g., conventional nucleic acids, PNAs, or other nucleic acid analogs) to the nucleic acid in the biological structure or tissue; (4) posthybridization washes to remove nucleic acid fragments not bound in the hybridization; and, (5) detection of the hybridized nucleic acid fragments. The reagent used in each of these steps and their conditions for use can vary, depending on the particular application. It will be appreciated that these steps can be modified in a variety of ways well known to those of skill in the art.

In one embodiment of ISH, a gene-specific probe is labeled with a fluorescent label (fluorescent in situ hybridization; "FISH"). In some embodiments, it is desirable to use dual color fluorescent in situ hybridization, in which two probes are utilized, each labeled by a different fluorescent dye. A test probe that hybridizes to the selected sequence of interest is labeled with one dye, and a control probe that hybridizes to a different region is labeled with a second dye. A nucleic acid that hybridizes to a stable portion of the chromosome of interest, such as the centromere region, can be used as the control probe. In this way, one can account for differences between efficiency of hybridization from sample to sample.

Detecting Integrity of a Selected DNA

In some embodiments, a subject detection method involves detecting the integrity of a selected DNA in an MEC, e.g., detecting one or more of: an aneuploidy; telomeric content; a translocation; an aberrant pattern; and the like. Aberrant patterns in DNA include, but are not limited to "firestorms" (e.g., multiple closely spaced amplicons); "sawtooth" patterns (e.g., characterized by many narrow segments of duplication and deletion); and the like. See, e.g., Hicks et al. (2006) *Genome Res.* 16:1465-1479.

Detecting Methylation Status of a Selected DNA

In some embodiments, a subject detection method involves detecting the methylation status of a DNA. For example, in some embodiments, a subject detection method involves detecting the methylation status of a selected promoter, e.g., a p16 promoter, e.g., a $p16^{INK4a}$ promoter.

Various methods can be used to determine the methylation status of a selected DNA. For example, indirect methods for DNA methylation pattern determinations at specific loci that have been developed rely on techniques that alter the genomic DNA in a methylation dependent manner before an amplification event. There—are two primary methods that have been utilized to achieve this methylation-dependent DNA alteration. The first is digestion by a restriction enzyme that is affected in its activity by 5-methylcytosine in a CpG sequence context. The cleavage, or lack of it, can subsequently be revealed by Southern blotting or by PCR. The other technique that has received recent widespread use—is the treatment of genomic DNA with sodium bisulfite. Sodium bisulfite treatment converts all unmethylated cytosines in the DNA to uracil by deamination, but leaves the methylated cytosine residues intact. Subsequent PCR amplification replaces the uracil residues with thymines and the 5-methylcytosine residues with cytosines. The resulting sequence difference has been detected using standard DNA sequence detection techniques, primarily PCR.

An exemplary method involves use of a bisulfite treatment-based method followed by a PCR reaction to analyze specific loci within the genome. There are two principally different ways in which the sequence difference generated by the sodium bisulfite treatment can be revealed. The first is to design PCR primers that uniquely anneal with either methylated or unmethylated converted DNA. This technique is referred to as "methylation specific PCR" or "MSP". See, e.g., U.S. Pat. No. 5,786,146. The method used by all other bisulfite-based techniques (such as bisulfite genomic sequencing, COBRA and Ms-SNuPE) is to amplify the bisulfite-converted DNA using primers that anneal at locations that lack CpG dinucleotides in the original genomic sequence. In this way, the PCR primers can amplify the sequence in between the two primers, regardless of the DNA methylation status of that sequence in the original genomic DNA. This results in a pool of different PCR products, all with the same length and differing in their sequence only at the sites of potential DNA methylation at CpGs located in between the two primers. The difference between these methods of processing the bisulfite converted sequence is that in MSP, the methylation information is derived from the occurrence or lack of occurrence of a PCR product, whereas in the other techniques a mix of products is always generated and the mixture is subsequently analyzed to yield quantitative information on the relative occurrence of the different methylation states. A method such as described in U.S. Pat. No. 7,186,512 is also suitable for use.

In some embodiments, the methods involve contacting a genomic sample of DNA with a modifying agent that modifies unmethylated cytosine (e.g., sodium bisulfite), to produce a converted nucleic acid; (b) amplifying the converted nucleic acid by means of oligonucleotide primers in the presence of one or a plurality of specific oligonucleotide probes, where the one or the plurality of the oligonucleotide primers or the specific probe(s) is/are capable of distinguishing between unmethylated and methylated nucleic acid (e.g., a CpG specific probe capable of distinguishing between unmethylated and methylated nucleic acid); and (c) detecting, in real-time during the amplification, the methylated nucleic acid based on amplification-mediated probe displacement. See, e.g., U.S. Pat. No. 7,112,404. Amplification and detection can occur simultaneously as measured by fluorescence-based real-time quantitative PCR ("RT-PCR") using specific, dual-labeled dual label TaqMan® oligonucleotide probes. The displaceable probes can be specifically designed to distinguish between methylated and unmethylated CpG sites present in the original, unmodified nucleic acid sample. Sodium bisulfite readily reacts with the 5,6-double bond of cytosine, but not with methylated cytosine, to produce a sulfonated cytosine intermediate that undergoes deamination under alkaline conditions to produce uracil. Because Taq polymerase recognizes uracil as thymine and 5-methylcytidine (m5C) as cytidine, the sequential combination of sodium bisulfite treatment and PCR amplification results in the ultimate conversion of unmethylated cytosine residues to thymine (C→U→T) and methylated cytosine residues ("mC") to cytosine (mC→mC→C). Thus, sodium bisulfite treatment of genomic DNA creates methylation-dependent sequence differences by converting unmethylated cyotsines to uracil, and upon PCR the resultant product contains cytosine only at positions where methylated cytosine occurs in the unmodified nucleic acid.

In some embodiments, the specific primers are designed to be substantially complementary to each strand of the genomic locus of interest. Typically, one primer is complementary to the negative, (−) strand of the locus (the "lower" strand of a horizontally situated double-stranded DNA molecule) and the other is complementary to the positive (+) strand ("upper" strand). In some embodiments, the primers are designed to overlap potential sites of DNA methylation (CpG nucleotides) and specifically distinguish modified unmethylated from methylated DNA. This sequence discrimination can be based upon the differential annealing temperatures of perfectly matched, versus mismatched oligonucleotides. In some embodiments, primers are typically designed to overlap from one to several CpG sequences. In other embodiments, e.g., in a quantitative embodiment, the primers do not overlap any CpG sequences.

Proteomics Analysis

In some embodiments, a subject detection method involves a proteomics analysis of an MEC. In some embodiments, an antibody reagent array is used, where the array comprises antibody reagents specific for two or more of the proteins listed in FIG. 14. In some embodiments, an antibody reagent array is used, where the array comprises antibody reagents specific for two or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2.

In other embodiments, a polypeptide array is used. Polypeptide arrays provide a high throughput technique that can assay a large number of polypeptides in a sample. This technology can be used as a tool to test for expression of a marker polypeptide and detection of a pre-cancerous epithelial cell. Of particular interest are arrays which comprise a probe for detection of one or more of the following polypeptides: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. In some embodiments, the arrays comprise probes for at least one of the following combinations: 1) ER, ERBB2, Ki67, COX-2, and p16; 2) ER, ERBB2, Ki67; and 3) Ki67, COX-2, and p16. In some embodiments, the arrays comprise probes for at least one of the following combinations: 1) PR, ERBB2, Ki67, COX-2, and p16; 2) PR, ERBB2, Ki67; and 3) Ki67, COX-2, and p16. In some embodiments, the arrays comprise probes for at least one of the following combinations: 1) ER, PR, ERBB2, Ki67, COX-2, and p16; 2) ER, PR, ERBB2, Ki67; and 3) Ki67, COX-2, and p16.

A variety of methods of producing arrays, as well as variations of these methods, are known in the art and contemplated for use in the invention. For example, arrays can be created by spotting polypeptide probes onto a substrate (e.g., glass, nitrocellulose, etc.) in a two-dimensional matrix or array having bound probes. The probes can be bound to the substrate by either covalent bonds or by non-specific interactions, such as hydrophobic interactions.

Samples of polypeptides can be detectably labeled (e.g., using radioactive or fluorescent labels) and then hybridized to the probes. Alternatively, the polypeptides of the test sample can be immobilized on the array, and the probes detectably labeled and then applied to the immobilized polypeptides. In most embodiments, the "probe" is detectably labeled. In other embodiments, the probe is immobilized on the array and not detectably labeled. In such embodiments, the sample is applied to the polypeptide array and bound gene products (e.g., peptides) are detected using secondary labeled probes.

Examples of such protein arrays are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828. Proteomics applications include those described in U.S. Pat. Nos. 4,591,570; 5,171,695; 5,436,170; 5,486,452; 5,532,128 and 6,197,599 as well as published PCT application Nos. WO 99/39210; WO 00/04832; WO 00/04389; WO 00/04390; WO 00/54046; WO 00/63701; WO 01/14425 and WO 01/40803, the disclosures of which are herein incorporated by reference.

As noted above, in some embodiments, an antibody reagent array is used to detect proteins produced by an MEC (e.g. a variant MEC), where the array comprises antibody reagents specific for two or more of: CD73, CD138, notch receptor-3, CD90, BMI-1, COX-2, ER, ERBB2, Ki67, p16, IGF2, YKL-40, EGF-R, c-jun, PCNA, jnk, cyclin B1, c-kit, STAT3, cyclin D1, PI3K, MAPK, MAPKK, DDR2, TRF2, activin, and MEK1/2. Thus, e.g., use of an array of a plurality of distinct binding agents ("protein-binding agents" or "protein-binding reagents"), wherein each binding agent includes at least an epitope binding domain of an antibody molecule, is contemplated. The arrays employed in the subject methods can have a plurality of probe spots, each made up of a distinct binding agent (i.e., a plurality of copies of distinct binding agent molecule) stably associated with the surface of a solid support.

Each probe composition of a protein-binding reagent arrays is made up of multiple copies of a binding agent, where each binding agent includes at least an epitope binding domain of antibody. By epitope binding domain is meant a region or portion of an antibody molecule that specifically binds to an antigen, more particularly a determinant or epitope of a given antigen. As such, in some embodiments, the protein-binding reagents are antibodies, including specific antigen binding fragments and mimetics thereof. Where antibodies are the binding agent, they may be derived from polyclonal compositions, such that a heterogeneous population is used, where antibodies differing by specificity are each immobilized on the substrate surface; or monoclonal compositions, in which a homogeneous population of identical antibodies that have the same specificity for the target analyte, e.g., protein, are each immobilized on the substrate surface. As such, the binding agent may be either a monoclonal or a polyclonal antibody in certain embodiments.

In yet other embodiments, the binding agent making up the subject probe compositions is an antibody binding fragment or mimetic, where these fragments and mimetics have the requisite binding affinity for the target analyte, e.g., protein. For example, antibody fragments, such as Fv, F(ab)$_2$ and Fab may be prepared by cleavage of the intact protein, e.g. by protease or chemical cleavage. Also of interest are recombinantly produced antibody fragments, such as single chain antibodies or scFvs, where such recombinantly produced antibody fragments retain the binding characteristics of the above antibodies, i.e., they include the epitope binding domain (which means the whole domain or a least a functional portion thereof) of an antibody specific for the particular analyte. Such recombinantly produced antibody fragments generally include at least the $V_H$ and $V_L$ domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art. The binding agents typically have a strong affinity for their analyte, where this affinity is at least about $10^{-6}$, usually at least about $10^{-8}$ and typically ranges from about $10^{-8}$ to about $10^{-13}$, usually from about $10^{-9}$ to about $10^{-12}$, where the affinity is the affinity as measured following immobilization of the antibody onto the surface using the binding affinity assay described in Pellequer, J. L., Van Regenmortel, M. H., J Endocrinol, 139, (3) 495-501.

The probe spots made up of the binding agents as described above and present on the array may be any convenient shape, and can be circular, elliptoid, oval or some other analogously curved shape. The total amount or mass of molecules present in each spot will be sufficient to provide for adequate binding and detection of analytes during the assay in which the array is employed. The total mass of binding agents in each spot can be at least about 10 pg, at least about 100 pg, or at least about 1 ng, where the total mass may be as high as 20 ng or higher. In some embodiments, the total mass of binding agent in each spot does not exceed about 10 ng, or does not exceed about 5 ng. Where the target protein is detectably labeled, the copy number of all of the individual binding agents in a spot will be sufficient to provide enough binding sites for tagged target molecule (e.g., protein being detected) to yield a detectable signal, and can range from about 100 fluorescence units (FU) to about 65500 FU, or from about 250 FU to about 45000 FU.

Where the probe spot has an overall circular dimension, the diameter of the spot can range from about 10 to about 5,000 μm, from about 20 to about 1,000 μm, or from about 50 to about 500 μm. The surface area of each spot can be at least about 100 μm$^2$, at least about 200 μm$^2$, or at least about 400 μm$^2$, and may be as great as about 25 mm$^2$ or greater; in some embodiments, the surface area of each spot does not exceed about 5 mm$^2$, or about 1 mm$^2$. The density of binding agents "probe" spots on the array, as well as the overall density of probe and non-probe spots (where the latter are described in greater detail below) may vary greatly. As used herein, the term spot refers to any spot on the array surface that is made up of binding agents, whether control or probe binding agents, and as such includes both probe spots and non-probe spots. The density of the probe spots on the solid surface is at least about 5/cm$^2$ and usually at least about 10/cm$^2$ and may be as high as about 100/cm$^2$, about 200/cm$^2$, about 300/cm$^2$, about 500/cm$^2$, about 1000/cm$^2$, about 5000/cm$^2$ or higher, but in many embodiments does not exceed about 1000/cm$^2$, and in these embodiments usually does not exceed about 500/cm$^2$ or about 400/cm$^2$ in many embodiments, and in certain embodiments does not exceed about 300/cm$^2$. The spots may be arranged in a spatially defined and physically addressable manner, in any convenient pattern across or over the surface of the array, such as in rows and columns so as to form a grid, in a circular pattern, and the like, where generally the pattern of spots will be present in the form of a grid across the surface of the solid support.

In the subject arrays, the spots of the pattern are stably associated with or immobilized on the surface of a solid support, where the support may be a flexible or rigid support. By "stably associated" it is meant that the binding agents of the spots maintain their position relative to the solid support under incubation (e.g., binding) and washing conditions, as described below. As such, the individual binding agent members that make up the spots can be non-covalently or covalently stably associated with the support surface based on technologies well known to those of skill in the art. Examples of non-covalent association include non-specific adsorption, binding based on electrostatic (e.g. ion, ion pair interactions), hydrophobic interactions, hydrogen bonding interactions, specific binding through a specific binding pair member covalently attached to the support surface, and the like. Examples of covalent binding include covalent bonds formed between the spot binding agents and a functional group present on the surface of the rigid support, where the functional group may be naturally occurring or present as a member of an introduced linking group. In some embodiments, the binding agents making up the spots on the array surface, are covalently bound to the support surface, e.g., through covalent linkages formed between moieties present on the binding agents, e.g., amines, and the substrate surface, etc, as may be present on a glass substrate, e.g., aminated glass. See e.g., the specific covalent attachment protocol exemplified below.

As mentioned above, the array is present on either a flexible or rigid substrate. By flexible is meant that the support is capable of being bent, folded or similarly manipulated without breakage. Examples of solid materials which are flexible solid supports with respect to the present invention include membranes, flexible plastic films, and the like. By rigid is meant that the support is solid and does not readily bend, i.e. the support is not flexible. As such, the rigid substrates of the subject arrays are sufficient to provide physical support and structure to the polymeric targets present thereon under the assay conditions in which the array is employed, particularly under high throughput handling conditions. Furthermore, when the rigid supports of the subject invention are bent, they are prone to breakage.

The solid supports upon which the subject patterns of spots are presented in the subject arrays may take a variety of configurations ranging from simple to complex, depending on the intended use of the array. Thus, the substrate could have an overall slide or plate configuration, such as a rectangular or disc configuration. In many embodiments, the substrate will have a rectangular cross-sectional shape, having a length of from about 10 mm to 200 mm, usually from about 40 to 150 mm and more usually from about 75 to 125 mm and a width of from about 10 mm to 200 mm, usually from about 20 mm to 120 mm and more usually from about 25 to 80 mm, and a thickness of from about 0.01 mm to 5.0 mm, usually from about 0.01 mm to 2 mm and more usually from about 0.01 to 1 mm. Thus, in one representative embodiment the support may have a micro-titer plate format, having dimensions of approximately 125×85 mm. In another representative embodiment, the support may be a standard microscope slide with dimensions of from about 25×75 mm.

The substrates of the protein-binding reagent arrays can be fabricated from a variety of materials. The materials from which the substrate is fabricated should ideally exhibit a low level of non-specific binding during binding events. In some embodiments, a material is used that is transparent to visible and/or UV light. For flexible substrates, materials of interest include: nylon, both modified and unmodified, nitrocellulose, polypropylene, and the like. For rigid substrates, specific materials of interest include: glass; plastics, e.g. polytetrafluoroethylene, polypropylene, polystyrene, polycarbonate, and blends thereof, and the like; metals, e.g. gold, platinum, and the like; etc. Also of interest are composite materials, such as glass or plastic coated with a membrane, e.g., nylon or nitrocellulose, etc.

The substrates of the subject arrays comprise at least one surface on which the pattern of spots is present, where the surface may be smooth or substantially planar, or have irregularities, such as depressions or elevations. The surface on which the pattern of spots is present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g. peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, polyacrylamides, and the like, where the polymers may be hetero- or homopolymeric, and may or may not have separate functional moieties attached thereto, e.g. conjugated.

In certain embodiments, e.g., where the binding agent is a whole antibody or analogous structure, an antibody universal binding layer is present on the substrate surface, e.g., covalently bound to the substrate surface, which layer acts as a linking group or tethering element between the antibody binding agent in the substrate surface and serves to tether the antibody binding agent to the substrate surface. The basic principle is to utilize proteins and ligands with affinity towards antibodies (including but not limited to Protein A, Protein G, Protein L, Protein LA) which are covalently immobilized to a glass, plastic or any other type of surfaces. After the immobilization of the universal binding layer, the antibody binding agents are deposited on the same locations and reversibly immobilized. The universal binding layer of affinity ligands thus forms a layer which protects the consequently bound antibodies from detrimental surface effects. An additional benefit is the directed mode of immobilization as compared to that of direct covalent attachment of the antibodies to activated surfaces. This results in 100% availability of the antigen binding sites on the antibodies for consequent detection of antigens. It also provides universal conditions for binding, since the formation of ligand/antibody complex is obtained under mild physiological conditions where as covalent immobilization of proteins is often performed under conditions that might be detrimental to their biological activity.

The total number of spots on the substrate will vary depending on the number of different probe spots (binding agent probe compositions) one wishes to display on the surface, as well as the number of non probe spots, e.g., control spots, orientation spots, calibrating spots and the like, as may be desired depending on the particular application in which the subject arrays are to be employed. Generally, the pattern present on the surface of the array will comprise at least about 10 distinct spots, usually at least about 20 spots, and more usually at least about 50 distinct spots, where the number of distinct spots may be as high as 10,000 or higher, but will usually not exceed about 5,000 distinct spots, and more usually will not exceed about 3,000 distinct spots and in many instances will not exceed about 2,000 distinct spots. In certain embodiments, each distinct probe spot or probe composition is presented in duplicate, i.e. so that there are two duplicate probe spots displayed on the array for a given target. The number of probe spots present in the array will typically make up a substantial proportion of the total number of spots on the array, where in many embodiments the number of probe spots is at least about 50 number %, usually at least about 80 number % and more usually at least about 90 number % of the total number of spots on the array. As such, in many embodiments the total number of spots on the array ranges from about 10 to about 20,000, usually from about 20 to about 10,000 and more usually from about 100 to 5,000.

In the arrays of the subject invention (particularly those designed for use in high throughput applications, such as high throughput analysis applications), a single pattern of probe spots may be present on the array or the array may comprise a plurality of different spot patterns, each pattern being as defined above. When a plurality of different spot patterns are present, the patterns may be identical to each other, such that the array comprises two or more identical spot patterns on its surface, or the spot patterns may be different, e.g. in arrays that have two or more different sets of probes present on their surface, e.g., an array that has a pattern of spots corresponding to first population of target analytes and a second pattern of spots corresponding to a second population of analytes. Where a plurality of spot patterns are present on the array, the number of different spot patterns is at least 2, at least 6, or at least 24 or 96, where the number of different patterns will generally not exceed about 384.

Where the array includes a plurality of spot patterns on its surface, the array can include a plurality of reaction chambers, wherein each chamber has a bottom surface having associated therewith a pattern of spots and at least one wall, usually a plurality of walls surrounding the bottom surface. See e.g. U.S. Pat. No. 5,545,531, the disclosure of which is herein incorporated by reference. Of particular interest in many embodiments are arrays in which the same pattern of spots in reproduced in 24 or 96 different reaction chambers across the surface of the array.

Within any given pattern of spots on the array, there may be a single spot that corresponds to (i.e., specifically binds to) a given analyte target or a number of different spots that correspond to the same analyte, where when a plurality of different spots are present that correspond to the same analyte, the probe compositions of each spot that corresponds to the same analyte may be identical or different. In other words, a plurality of different analytes are represented in the pattern of spots, where each analyte may correspond to a single spot or a plurality of spots, where the probe compositions among the plurality of spots corresponding to the same analyte may be the same or different. Where a plurality of spots (of the same or different composition) corresponding to the same analyte is present on the array, the number of spots in this plurality will be at least about 2 and may be as high as 10; and in some embodiments will not exceed about 5. In some embodiments, any given analyte is represented by only a single type of probe spot, which may be present only once or multiple times on the array surface, e.g. in duplicate, triplicate etc.

The number of distinct or different probe spots present on the array, and therefore the number of different analytes represented on the array, is at least about 2, usually at least about 10 and more usually at least about 20, where in many embodiments the number of different analytes represented on the array is at least about 50, or at least about 100. The number of different analytes represented on the array may be as high as 5,000 or higher, and in some embodiments will not exceed about 3,000 or about 2,500. An analyte is considered to be represented on an array if it is able to specifically bind to one or probe compositions on the array.

The arrays employed in the subject methods may be fabricated using any convenient protocol, where the protocol may vary depending on the nature of the substrate, the nature of any intervening surface layer, e.g., whether or not a universal binding layer is present, and the nature of the binding agents. Where the substrate is a glass substrate or analogous material, typically the surface of the substrate is first activated to provide for functional groups suitable for use in the covalent bonding, either directly or through a linking group, of the binding agent. For example, glass surfaces may be aminated so as to display amine functional groups via silanization, according to well known surface chemistry protocols. In many embodiments, the binding agent is then immobilized on the functionalized surface, e.g., through direct or indirect covalent bonding, e.g., by non-covalent binding to a covalently bound universal binding layer of molecules, as described above. In some embodiments a surface activation agent is used, e.g., an agent that provides a linking group capable of forming a covalent linkage between aminated moieties, such as PIDTC and DVS.

Following surface preparation, e.g., surface activation, a binding agent composition is immobilized on the substrate surface to produce a spot of the array. The binding agent composition can be an aqueous composition. In some embodiments, the concentration ranges of the deposited binding agent composition is at least about 0.1 mg/mL, or at least about 0.2 mg/mL, where the concentration may be as great as 1 mg/mL or greater. The purity of the binding agent composition typically is at least about 90%, at least about 95%, or at least about 97% pure.

The binding agent composition is deposited on the array surface using any convenient protocol. In many embodiments, the binding agent composition is applied using a pin or analogous deposition device. Also of interest are pipette devices, ink jet devices, etc., which are extensively described in the array preparation art. The particular device and protocol employed to spot the subject binding agents is not critical, so long as it results in a functional probe spot, i.e., a probe spot that specifically binds to its target analyte.

Following deposition of the binding agent compositions to produce the pattern of probe spots on the array, the surface is then contacted with a blocking agent in order to block non-specific binding sites on the array surface. Any convenient blocking agent may be employed, where representative blocking agents include, but are not limited to, nonfat milk, BSA, gelatin, preimmune serum and the like, where standard blocking protocols may be employed.

Following preparation and blocking, as described above, the array is typically stored for a period of time prior to use. The array may be stored in any convenient format, including both dry and wet formats, so long as the activity of the array, i.e., the binding ability of the probe spots on the array for their specific analytes, is not adversely affected. By not adversely affected is meant that the sensitivity of the array does not change with respect to a given analyte as compared to the array immediately following blocking by a value that exceeds about 10 fold, and usually does not change by a value that exceeds about 5 fold. In many embodiments, the period of time for which the array is stored prior to use in the subject methods, described in greater detail below, is at least about 2 days, usually at least about 6 months and more usually at least about 9 months and may be as long as about 1 year or longer, where the array is typically not stored for a period that exceeds about 6 months prior to use.

The sample that is contacted with the substrate surface may vary greatly, depending upon the nature of the assay to be performed. In general, the sample is an aqueous fluid sample. The amount of fluid sample also varies with respect to the nature of the device, the nature of the sample, etc. In many embodiments, the amount of sample that is contacted with the substrate surface ranges from about 1 µl to about 5 ml, e.g., from about 1 µl to about 5 µm, from about 5 µl to about 10 µm, from about 10 µl to about 25 µm, from about 25 µl to about 50 µl, from about 50 µl to about 100 µm, from about 100 µl to about 500 µm, from about 500 µl to about 1 ml, or from about 1 ml to about 5 ml.

The fluid sample can be a cell lysate; a cell lysate that has been processed by one or more steps, e.g., removal of cellular debris, and the like; a cell fraction; a cell culture supernatant (e.g., the medium in which a cell is cultured in vitro; the fluid surrounding a cell in vivo; and the like. In obtaining the fluid sample, the initial physiological source (e.g., tissue, collection of cells, etc.) may be subjected to a number of different processing steps, where such processing steps might include tissue homogenation, protein extraction and the like, where such processing steps are known to the those of skill in the art. Of particular interest in many embodiments is the use of cellular extracts as the sample.

In certain embodiments, the initial fluid sample derived from a particular source, e.g., a cell extract, may be subjected to a fractionation protocol that reduces the complexity of the protein composition of the sample. By reduce the complexity is meant that the total mass of all of the proteins in the sample is reduced by at least about 10 fold, by at least about 100 fold, or at least about 1000 fold.

In certain embodiments, the fractionation protocol employed is one that reduces the amount of highly abundant proteins in the sample. In this embodiment, a pool of covalently attached antibodies, e.g., one or more columns of antibodies, is employed for enrichment of antigen analytes of interest from an initial sample, e.g., whole cell extracts. After reversible adsorption of the antigens of interest on the multi-antibody column, the non adsorbed material is washed away with washing buffer and the specifically retarded antigens are eluted and collected for further labeling and incubation with the array containing binding agent spots for the antigen/analytes of interest, e.g., the same antibodies that were used for initial enrichment. In this manner, the initial sample is fractionated so as to reduce the complexity and enrich the sample for the analytes of interest.

In some embodiments, the analytes of interest (e.g., proteins) present in the sample are labeled prior to contact with the array. By labeled is meant that the analytes are modified to be joined to, either covalently bonded to or stably but non-covalently bound to, a member of a signal producing system and are thus detectable, either directly or through combined action with one or more additional members of a signal producing system. Examples of directly detectable labels include isotopic and fluorescent moieties. Isotopic moieties or labels of interest include $^{32}P$, $^{33}P$, $^{35}S$, $^{125}I$, $^{3}H$, and the like. Fluorescent moieties or labels of interest include coumarin and its derivatives, e.g. 7-amino-4-methylcoumarin, aminocoumarin, bodipy dyes, such as Bodipy FL, cascade blue, fluorescein and its derivatives, e.g. fluorescein isothiocyanate, Oregon green, rhodamine dyes, e.g. texas red, tetramethylrhodamine, eosins and erythrosins, cyanine dyes, e.g. Cy3 and Cy5, macrocyclic chelates of lanthanide ions, e.g. Quantum Dye™, fluorescent energy transfer dyes, such as thiazole orange-ethidium heterodimer, TOTAB, etc. Labels may also be members of a signal producing system that act in concert with one or more additional members of the same system to provide a detectable signal. Illustrative of such labels are members of a specific binding pair, such as ligands, e.g. biotin, fluorescein, digoxigenin, antigen, polyvalent cations, chelator groups and the like, where the members specifically bind to additional members of the signal producing system, where the additional members provide a detectable signal either directly or indirectly, e.g. antibody conjugated to a fluorescent moiety or an enzymatic moiety capable of converting a substrate to a chromogenic product, e.g. alkaline phosphatase conjugate antibody; and the like.

The analytes (e.g., proteins produced by an MEC, e.g., a variant MEC) can be labeled according to any convenient protocol, where the particular protocol employed may vary greatly with respect to the overall assay protocol being practiced and the nature of the specific label. For example, where the analytes are labeled with detectably labeled antibodies, e.g., fluorescently labeled antibodies, the labeling protocol typically comprises contacting the analyte with the labeled antibodies and incubating the sample under conditions sufficient for the labeled antibody to specifically bind to the analyte in the sample. In these embodiments, the labeled antibodies employed as labeling reagents are specific for an eptitope of the analyte that is available for binding even when the analyte is bound to a probe spot on the array surface.

The functional moiety of the functionalized labels may vary greatly, and is chosen in view of the functional moiety present on the analytes in the sample, e.g., amine groups on the proteins analytes present in the sample. In other words, the functional moiety present on the functionalized label must be one that reacts with the functional moiety present on the analyte to produce a covalent bond between the analyte and the label. Representative functional moieties that may be present on the label include: amino, sulfhydryl, sulfoxyl, aminosulfhydryl, azido, epoxide, isothiocyanate, isocyanate, anhydride, monochlorotriazine, dichlorotriazine, mono- or dihalogen substituted pyridine, mono- or disubstituted diazine, maleimide, epoxide, aziridine, sulfonyl halide, acid halide, alkyl halide, aryl halide, alkylsulfonate, N-hydroxysuccinimide ester, imido ester, hydrazine, azidonitrophenyl, azide, 3-(2-pyridyl dithio)-propionamide, glyoxal, aldehyde, iodoacetyl, cyanomethyl ester, p-nitrophenyl ester, o-nitrophenyl ester, hydroxypyridine ester, carbonyl imidazole, and the like.

In certain embodiments where the analytes are labeled prior to contact with the array, the sample preparation protocol employs a single type of buffer for both the cellular extraction and labeling steps. In other words, a single buffer composition is employed in both the extraction step, where the proteins of the cell are separated from other cellular components/structures, and in the labeling step, where the analytes present in extract are labeled with a detectable label. The single extraction/labeling buffer employed in these embodiments is one that provides for high extraction efficiency, where high extraction efficiency is meant at least about 90% or at about 95% (by weight) of the proteins are extracted with the extraction/labeling buffer, as compared to the amount of proteins extracted by SDS boiling. In addition, the buffer is a buffer that extracts proteins from all cellular compartments/locations. This single cellular extract/labeling buffer can be characterized by including detergents and other components, when present, that are free of primary amines. Representative detergents employed that may be present in the buffer include, but are not limited to: octyl- β-D-glucopyranoside (ODG), NP-40, Empigen, Pluronic, and the like. The amount of each detergent present in the extraction/labeling buffer may vary, but typically ranges from about 0.01% to about 10%, from about 0.05% to about 5%, or from about 0.1% to about 2%. In addition, the pH of the buffer is selected such that it provides for suitable conditions for both cellular extraction and labeling. As such, the pH can range from about 7 to about 12, or from about 8 to about 10.

Following sample preparation and any analyte labeling, where desired, the analyte containing fluid sample is contacted with the array of binding agents and contact is maintained under sufficient conditions and for a period of time sufficient for binding of analyte to specific binding pair members on the array surface to occur. For example, the array and analyte containing sample are incubated together for at least about 10 min., usually at least about 20 min., and more usually at least about 30 min., where the incubation time may be as long as about 480 min. or longer, and in some embodiments does not exceed about 60 min. During incubation, the array and sample are maintained at a temperature that typically ranges from about 20° C. to about 28° C., usually from about 22° C. to about 26° C. In many embodiments, the array and sample are subjected to mixing or agitation during the incubation step.

During incubation, the pH of the liquid medium is maintained at a value ranging from about 6.5 to about 8.5, or from about 7.0 to about 8.0. Also present may be one or more buffers, e.g., Tris, sodium citrate and the like; salts, e.g., NaCl, sodium sulfate, and the like; surfactants/surfactants, e.g., Pluronics, Tweens, glycerol, ethylene glycol, etc.

While the contact of the array and analyte containing fluid medium, as well as metal chelating polysaccharide, may be accomplished using any convenient protocol, in many embodiments, the initial sample is first pre-incubated with an incubation buffer that includes the metal ion chelating polysaccharide to produce a preincubated analyte containing sample, which preincubated sample is then contacted with the array for the incubation period. In these embodiments, the incubation buffer employed at least includes the metal ion chelating polysaccharide as described above. In addition, the incubation buffer typically includes a number of additional components, including buffering agents, salts, surfactants, etc.

Following incubation, non-array bound components of the analyte containing medium contacted with the array surface during incubation are separated or removed from the surface. This separation step can be accomplished using one or more washing steps, in which the array surface is contacted and separated from, including flushed with, one or more different fluid compositions.

The array surface can be subjected to a sequential washing protocol, in which the array surface is washed with a plurality of distinct washing solutions. The number of different washings employed in these embodiments varies, but typically ranges from about 3 to 10, usually from about 5 to 9 and more usually from about 6 to 8, where in certain embodiments, 7 distinct washings are employed. In these embodiments, the series of different washing mediums employed provides a modulation or change in the nature of the washing medium and components therein, e.g., in order to subject the array surface to a sequential or step-wise change or modulation of conditions, e.g., amount/type of detergent, salt concentration, buffering agent, additives, etc. In these embodiments, the different washing conditions to which the array is subjected during the sequential wash protocol are ones that provide for a decrease in background and cross-reactivity during detection, and therefore an increase in signal to noise ratio and/or selectivity, so as to provide the sensitive results discussed above. In certain embodiments, the washing conditions are ones that provide for an increase in signal to noise ratio and/or selectivity of at least about 2-fold, at least about 5-fold, or at least about 10 fold and compared to a control assay in which only a single wash step with a wash fluid that is the same as the incubation fluid is performed. In certain embodiments, the sequential wash protocol is characterized by initially employing a high salt wash, e.g., to remove electrostatically bound molecules, followed by sequential use of wash fluids of decreasing detergent composition, and/or a change of buffers, e.g., from Tris to sodium citrate.

If the analytes in the sample (e.g., proteins produced by an MEC) are not labeled prior to incubation, as described above, they are labeled at some point prior to detection. As such, the surface bound analytes can be labeled following incubation and an initial wash step, e.g., where the labels are labeled antibodies capable of binding to already surface bound analytes. Alternatively, the labels can be functionalized to covalently bind to any molecule displaying a corresponding functional group, e.g., a primary amine. In these embodiments, the sample incubated array is contacted with the labeling composition under conditions sufficient for labeling to occur. An initial signal is then obtained from the array, followed by a washing step to remove bound analytes and other components. A second signal is then obtained. This second signal is then subtracted from the initial signal to obtain a final signal that is representative or related to the amount of analyte bound to the array, which signal is employed as described below to derive the amount of analyte in the sample.

Following washing, the array surface is read or scanned for the presence of binding complexes between analytes in the assayed sample and binding agents of the probe spots of the array. In other words, analyte/binding agent complexes on the surface of the array are detected.

Any convenient protocol may be employed for detecting the binding agents on the array surface. Many different protocols for detecting the presence of surface bound binding complexes are known to those of skill in the art, where the detection method may be qualitative or quantitative depending on the particular application in which the subject method is being performed, where the particular detection protocol employed may or may not use a detectable label. Representative detection protocols that may be employed include those described in WO 00/04389 and WO 00/04382; the disclosures of which are herein incorporated by reference. Representative non-label protocols include surface plasmon resonance, total internal reflection, Brewster Angle microscopy, optical waveguide light mode spectroscopy, surface charge elements, ellipsitometry, etc., as described in U.S. Pat. No. 5,313,264, the disclosure of which is herein incorporated by reference. Alternatively, detectable label based protocols, including protocols that employ a signal producing system, may be employed. The particular protocol employed varies, depending on the nature of the label that is employed. Where fluorescent labels are employed, any convenient fluorescence scanner device, i.e., fluorimeter, may be employed, where numerous such devices and methods for their use are known to those of skill in the art.

Following detection of the surface bound binding complexes, the presence of any surface bound binding complexes is then related to the presence of the one or more analytes in the sample. In many embodiments, the signal intensity value obtained for any binding complex is quantitatively related to the presence of the corresponding analyte in the sample, so as to provide a quantitative determination of the analyte amount in the sample. This relating step is readily accomplished in that the position on the array at which a particular surface bound complex is located indicates the identity of the analyte or protein, since the binding agent for the protein is attached to a known specific location on the array. Thus, this relating step merely comprises determining the location on the array on which a binding complex is present, comparing that location to a reference that provides information regarding the correlation of each location to a particular analyte and thereby deriving the identity of the analyte in the sample. In sum, the location of the surface bound binding complexes is used to determine the identity of the one or more analytes of interest in the sample.

By way of further illustration, the following representative protein assay is summarized. Where one is interested in assaying a sample for the presence of 100 different proteins, an array displaying a collection of 100 different antibody binding agents is prepared, where each different antibody binding agents in the collection specifically binds to a different protein member of the 100 different proteins being assayed. The array is then contacted with the sample being assayed under conditions sufficient for binding complexes to be produced between the probe binding agent spots and their corresponding target proteins in the sample. Any resultant binding complexes on the surface of the array are then detected and the location of the detected binding complexes is used to determine which of the 100 proteins of interest is present in the sample.

In certain embodiments, two or more physiological sources, e.g., cell extracts (e.g., MEC cell extracts, variant MEC cell extracts, etc.), are assayed according to the above protocols in order to generate analyte profiles for the two or more sources that may be compared. In such embodiments, analyte containing sample may be separately contacted to identical arrays or together to the same array under binding conditions, depending on whether a means for distinguishing the patterns generated by the different populations of analytes is employed, e.g. distinguishable labels, such as two or more different emission wavelength fluorescent dyes, such as Cy3 and Cy5, two or more isotopes with different energy of emission, such as $^{32}$P and $^{33}$P, gold or silver particles with different scattering spectra, labels which generate signals under different treatment conditions, like temperature, pH, treatment by additional chemical agents, etc., or generate signals at different time points after treatment. Biological Assays In some embodiments, a subject detection method is a biological assay, to detect one or more of a morphological, physiological, or functional characteristic of an MEC. Biological assays include, e.g., an assay involving contacting a reporter epithelial cell with a test fibroblast obtained from a patient; and determining the effect, if any, of the test fibroblast on the reporter epithelial cell.

A biological assay includes an assay that detects one or more of: 1) the presence and/or level of markers present in a reporter epithelial cell; 2) the presence and/or level of a nucleic acid (e.g., an mRNA, a cDNA copy of an mRNA, etc.) in a reporter epithelial cell; 3) mobility of a reporter epithelial cell (e.g., ability to cross a membrane); 4) epigenetic modification of a reporter epithelial cell (e.g., histone modification; DNA hypermethylation; etc.); 5) secretion or release of molecules from a test fibroblast; 6) secretion or release of molecules from a reporter epithelial cell; and 7) phenotypic changes.

The present invention provides a method of detecting an effect of a component of stroma on tumor progression in a variant human mammary epithelial cell (vMEC). The method generally involves: a) contacting a test stomal component with a vMEC in vitro; and b) determining the effect, if any, of the test stromal component on a cell characteristic of the vMEC, wherein a test stromal component that induces a cell characteristic change in the vMEC that is indicative of tumor progression indicates that the test stromal component has carcinogenic potential.

In some embodiments, a variant (pre-cancerous) HMEC is immortalized by genetically modifying the cell in vitro with a construct encoding a constitutively active oncogene, e.g., constitutively active Ha-Ras V12, to generate an immortalized variant HMEC. The variant HMEC is contacted in vitro with a test fibroblast or other component of the stroma. The effect, if any, of the fibroblast on a cell characteristic of the immortalized vHMEC is determined. Where the immortalized vMEC exhibits an altered cell characteristic in the presence of the test fibroblast, the test fibroblast is considered to be pre-cancerous or cancerous, or to have carcinogenic potential. Cell characteristics include, but are not limited to, increased motility; acquisition of mesenchymal features; increased telomerase activity; phenotypic changes associated with de novo methylation, e.g., methylation of a promoter region; anchorage independent growth; genomic instability; and capacity for in vivo survival.

In some embodiments, the cell characteristic is acquisition of mesenchymal features, e.g., the reporter epithelial cell undergoes an epithelial-to-mesenchymal transition (EMT). Features that are characteristic of EMT include down-regulation of genes such as those encoding cellular adhesion molecules, and up-regulation of mesenchymal markers. Gene products that are down-regulated (e.g., are present, if at all, at reduced levels) include, but are not limited to, E-cadherin, β1-integrin, and cytokeratin. Gene products that are up-regulated include, but are not limited to, N-cadherin, fibronectin, and twist. Changes in the level of a gene product can be detected as described above, e.g., using an above-described method for detecting a change in protein level and/or using an above-described method for detecting a change in an mRNA level.

In other embodiments, the cell characteristic is a morphological change. For example, the reporter epithelial cell can acquire a spindle-shaped morphology. In other embodiments, the cell characteristic is increased motility of the reporter epithelial cell. Motility can be assessed using any known assay, e.g., an assay as described in Valster et al. (2005) *Methods* 37:208. For example, a transwell migration assay can be used. The transwell migration assay has been amply described in the art; see, e.g., McKinnon et al. (2001) *J. Clin. Endocrinol. Metab.* 86:3665; Redmond et al. (1999) *Thromb. Haemost.* 81:293; and Seton-Rogers et al. (2004) *Proc. Natl. Acad. Sci. USA* 101:1257.

Suitable reporter epithelial cells include primary epithelial cells and immortalized epithelial cells (e.g., immortalized epithelial cell lines). In some embodiments, a reporter epithelial cell is a primary mammary epithelial cell, e.g., a primary human mammary epithelial cell. Primary human mammary epithelial cells can be obtained from a suitable source such as reduction mammoplasty. Reporter epithelial cells can be cultured as described in, e.g., Band and Sager (1989) *Proc. Natl. Acad. Sci. USA* 86:1249-1253; Hammond et al. (1984) *Proc. Natl. Acad. Sci. USA* 81:5435; and Romanov et al. (2001) *Nature* 409:633. In some embodiments, the reporter epithelial cell is a subject immortalized vHMEC, as described above.

In some embodiments, a reporter epithelial cell is genetically modified with a nucleic acid comprising a nucleotide sequence encoding a polypeptide that provides a detectable signal. Polypeptides that provide a detectable signal include fluorescent proteins, chromogenic proteins, enzymes that catalyze the production of a product that is luminescent, fluorescent, or colored, etc. Suitable fluorescent proteins include, but are not limited to, a green fluorescent protein (GFP; Chalfie, et al., Science 263(5148):802-805 (Feb. 11, 1994); an enhanced GFP (EGFP), Clontech—Genbank Accession Number U55762); a blue fluorescent protein (BFP; 1. Quantum Biotechnologies, Inc. 1801 de Maisonneuve Blvd. West, 8th Floor, Montreal (Quebec) Canada H3H1J9; 2. Stauber, R. H. Biotechniques 24(3):462-471 (1998); 3. Heim, R. and Tsien, R. Y. Curr. Biol. 6:178-182 (1996)); an enhanced yellow fluorescent protein (EYFP; Clontech Laboratories, Inc., 1020 East Meadow Circle, Palo Alto, CA 94303); a fluorescent protein as described in, e.g., WO 92/15673, WO 95/07463, WO 98/14605, WO 98/26277, WO 99/49019, U.S. Pat. Nos. 5,292,658, 5,418, 155, 5,683,888, 5,741,668, 5,777,079, 5,804,387, 5,874,304, 5,876,995, and 5,925,558; a GFP from species such as *Renilla reniformis, Renilla mulleri,* or *Ptilosarcus guernyi,* as described in, e.g., WO 99/49019 and Peelle et al. (2001) *J. Protein Chem.* 20:507-519; "humanized" recombinant GFP (hrGFP) (Stratagene); any of a variety of fluorescent and colored proteins from Anthozoan species, as described in, e.g., Matz et al. (1999) *Nature Biotechnol.* 17:969-973, U.S. Patent Publication No. 2002/0197676, or U.S. Patent Publication No. 2005/0032085; and the like. Enzymes that catalyze production of a product that provides a detectable signal include, but are not limited to, luciferase, β-galactosidase, horse radish peroxidase, and alkaline phosphatase.

Detecting Altered Metabolism

In some embodiments, a subject method of detecting a pre-cancerous MEC involves use of a method that detects a cell with altered metabolism (e.g., altered glucose metabolism; altered protein synthesis, e.g., incorporation of amino acids into proteins; altered nucleic acid synthesis, e.g., altered incorporation of nucleotides into nucleic acids; etc.). It has been found that a pre-cancerous MEC (e.g., a vHMEC) exhibits altered metabolism, e.g., an altered metabolism characteristic of a cancer cell. For example, a pre-cancerous MEC exhibits increased glucose metabolism, compared to a normal, non-cancerous MEC. In some embodiments, the methods involve administering to in individual being tested an agent that is selectively taken up by a pre-cancerous MEC, compared to a normal, non-cancerous MEC. For example, the agent is taken up by a pre-cancerous MEC, and is substantially not taken up by a normal, non-cancerous MEC. The agent can be imaged using, e.g., Positron Emission Tomography (PET), computer-assisted tomography (CT), magnetic resonance imaging (MRI), and the like.

In some embodiments, a subject method involves imaging an individual for the presence of an agent that selectively labels cells with altered (e.g., increased) glucose metabolism, where a pre-cancerous MEC selectively takes up the agent. An example of such an agent is the positron-emitting $^{18}F$-labeled fluorodeoxyglucose (FDG), or a glucose derivative as described in U.S. Pat. No. 5,904,915, e.g., a halogenated glucose derivative, where the halogen is a radioisotope of a halogen atom.

In other embodiments, a subject method involves imaging an individual for the presence of an agent that selectively labels cells with altered (e.g., increased) protein synthesis, where a pre-cancerous MEC selectively takes up the agent. An example of such an agent is $^{11}C$-methionine.

In other embodiments, a subject method involves imaging an individual for the presence of an agent that selectively labels cells with altered (e.g., increased) DNA synthesis, where a pre-cancerous MEC selectively takes up the agent. An example of such an agent is $^{18}F$ thymidine.

Imaging Methods

As noted above, a subject detection method is useful in an imaging method. For example, detection (e.g., detection of an MEC signature) can be carried out in the context of risk assessment, where the analysis can be carried out on a woman who is considered to be at low risk of developing breast cancer, or on a woman who is considered at greater risk of developing breast cancer.

In some embodiments, a biological sample from a patient is subjected to an above-described detection method. Detection of an MEC signature that is indicative of a pre cancerous MEC provides an indication of an increased risk of breast cancer. For example, in some embodiments, detection of an MEC signature that is indicative of a pre-cancerous MEC provides an indication that the individual from whom the biological sample was obtained has an at least about 25%, at least about 50%, at least about 75%, at least about 2-fold, at least about 5-fold, or at least about 10-fold, or higher, increased risk of developing breast cancer within the next year, within the next 5 years, or within the next 10 years, compared to the risk of developing breast cancer in an individual not having the MEC signature.

In some embodiments, a biological sample is a sample that comprises cells, which can include living cells, dead cells, cells that have been treated for histochemical analysis, etc. In other embodiments, a biological sample is a liquid sample that may or may not include living cells, where liquid samples include bodily fluids such as nipple aspirate fluid, urine, blood, serum, plasma, and the like. In other embodiments, a biological sample is a liquid sample that may or may not include living cells, where the liquid sample is a lavage sample, e.g., a ductal lavage sample. In some embodiments, a biological sample has been treated prior to use in a subject detection method, e.g., by enrichment for one or more components (e.g., proteins, nucleic acids, etc.); removal of cells or cell debris; processing for histochemical analysis; and the like.

In some embodiments, where an MEC signature indicative of a pre-cancerous MEC is detected, monitoring of the individual on a regular basis will be recommended. For example, where an MEC signature indicative of a pre-cancerous MEC is detected, the individual will be monitored yearly, twice yearly, three times per year, or four times per year, where the monitoring will include one or more of carrying out a subject detection method, MRI, and the like.

Diagnostic Methods

As noted above, a subject detection method is useful in a diagnostic method. For example, detection (e.g., detection of an MEC signature) can be carried out following, or in conjunction with, another diagnostic assay, such mammography, magnetic resonance imaging (MRI) of breast tissue and/or axillary lymph node tissue, etc.

In some embodiments, a subject detection method is carried out on a woman who is considered to be at high risk of developing breast cancer. In other embodiments, a subject detection method is carried out on a woman who has undergone mammography or MRI, where the mammogram indicates the presence, or the possible presence, of cancerous breast tissue.

Prognostic Methods

As noted above, a subject detection method is useful in a prognostic method. In some embodiments, a subject prognostic method is carried out on an individual who has undergone a benign breast biopsy. In some embodiments, a subject prognostic method is carried out on an individual who has been diagnosed with ductal carcinoma in situ. The methods generally involve carrying out a subject detection method on such individuals. In these embodiments, a subject detection method can provide for a determination of the likelihood that an individual will go on to develop a malignant breast cancer. If such a determination is made, then treatment for cancer may be recommended, or further monitoring may be recommended.

In some embodiments, subject method provides for determination of the likelihood that an individual diagnosed with ductal carcinoma in situ (DCIS) will develop a malignant breast cancer. In some embodiments, the methods involve detecting an MEC signature, e.g., detecting a gene product produced by an MEC, e.g., detecting one or more of the gene products listed in FIG. 14, e.g., detecting one or more of CD73, CD138, notch receptor-3, CD90, BMI-1, COX-2, ER, PR, ERBB2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2 gene products, as described in detail above. In some embodiments, the methods involve detecting an MEC signature, e.g., detecting one or more of the following proteins: CD73, CD138, notch receptor-3, CD90, BMI-1, COX-2, ER, PR, ERBB2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin and MEK1/2. In some embodiments, the methods involve detecting one or more of CD73, CD138, notch receptor-3, CD90, BMI-1, and COX-2 polypeptides. In some embodiments, the methods involve detecting one or more of COX-2, Ki67, and p16 polypeptides. In some embodiments, the methods involve detecting one or more of ER, PR, ERBB2, COX-2, Ki67, and p16 polypeptides. In some embodiments, the methods involve detecting each of ER, ERBB2, COX-2, Ki67, and p16. In some embodiments, the methods involve detecting each of PR, ERBB2, COX-2, Ki67, and p16. In some embodiments, the methods involve detecting each of ER, PR, ERBB2, COX-2, Ki67, and p16. In some embodiments, the methods involve detecting at least one of the following combinations of biomarkers: 1) ER, ERBB2, Ki67, COX-2, and p16; 2) ER, ERBB2, Ki67; and 3) Ki67, COX-2, and p16. In some embodiments, the methods involve detecting at least one of the following combinations of biomarkers: 1) PR, ERBB2, Ki67, COX-2, and p16; 2) PR, ERBB2, Ki67; and 3) Ki67, COX-2, and p16. In some embodiments, the methods involve detecting at least one of the following combinations of biomarkers: 1) ER, PR, ERBB2, Ki67, COX-2, and p16; 2) ER, PR, ERBB2, Ki67; and 3) Ki67, COX-2, and p16.

Categorizing Risk of a Subsequent DCIS Event

Some embodiments of the method provide for determination of the likelihood that an individual with a benign breast biopsy (BBB) will develop a malignant breast cancer. In some embodiments, the methods involve detecting an MEC signature, e.g., detecting a gene product produced by an MEC, e.g., detecting one or more of CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2 gene products, as described in detail above. In some embodiments, the methods involve detecting an MEC signature, e.g., detecting one or more of the following proteins: CD73, CD138, notch receptor-3, CD90, BMI-1, COX-2, Ki67, p16, IGF2, YKL-40, EGR-R, c-jun, PCNA, jnk, cyclin B1, c-kit, STAT3, cyclin D1, PI3K, MAPK, MAPKK, DDR2, TRF2, activin, and MEK1/2. In some embodiments, the methods involve detecting one or more of CD73, CD138, notch receptor-3, CD90, BMI-1, and COX-2 polypeptides. In some embodiments, the methods involve detecting the presence or absence of one or more of COX-2, Ki67, and p16 polypeptides.

Monitoring Method

As noted above, a subject detection method is useful in a monitoring method, e.g., monitoring efficacy of a breast cancer treatment; monitoring patient response to a breast cancer treatment; etc. In some embodiments, a subject monitoring method involves carrying out a subject detection method on an individual who has undergone, or is undergoing, one or more treatments for breast cancer, where the treatments include, e.g., cancer chemotherapy, radiation therapy, a biological therapy (e.g., antibody treatments, etc.), and surgery (e.g., mastectomy, lumpectomy, etc.). A subject monitoring method can be carried out before the beginning of any such treatment and/or during the course of a treatment regimen, and/or following a treatment regimen. For example, a subject monitoring method can be carried out at the end of a treatment regimen, and at various time intervals thereafter, to monitor patient response to the treatment, and/or to monitor the efficacy of the treatment.

Carcinomas

The methods are useful for detecting, and/or staging, and/or grading a wide variety of cancers, including carcinomas. Carcinomas that can be detected using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Computer-Based Systems and Methods

The invention also provides a variety of computer-related embodiments. Specifically, the automated means for performing the methods described above may be controlled using computer-readable instructions, i.e., programming. Accordingly, in some embodiments the invention provides computer programming for analyzing and comparing a pattern of gene product expression present in a biological sample obtained from a subject to a library of gene product expression patterns known to be indicative of the presence or absence of a pre-cancerous epithelial cell, wherein the comparing indicates the presence or absence of a pre cancerous epithelial cell.

In another embodiment, the invention provides computer programming for analyzing and comparing a first and a second pattern of expression of gene products from biological samples taken from a subject in at least two different time points, wherein the first pattern is indicative of a pre-cancerous epithelial cell, and/or progression from a pre-cancerous epithelial cell to a cancerous epithelial cell. In such embodiments, the comparing provides for monitoring of the progression of the pre-cancerous epithelial cell or for monitoring progression of a carcinoma from the first time point to the second time point.

In some embodiments, the invention provides computer programming for determining for a subject with DCIS, the subject's risk of a subsequent DCIS and/or invasive cancer, by comparing biomarker expression patterns with a database of risk factors. In such embodiments, the system also can include clinical and/or histopathological characteristic data including tumor margins and palpable DCIS. In such embodiments, the system also can include clinical and/or histopathological characteristic data including Van Nuys Prognostic Index and palpable DCIS. In such embodiments, the system also can include clinical and/or histopathological characteristic data including age, tumor margins and palpable DCIS. The system can generate a report (either printed or electronic) that can be delivered to a physician or a subject, and including the risk assessment and any treatment recommendations. In some embodiments, the programming includes software for determining whether or not a sample is positive or negative for one or more biomarkers in the following collections: ER, ERBB2, and Ki67; COX-2, Ki67, and p16; and ER, ERBB2, Ki67, COX-2, and p16. In some embodiments, the programming includes software for determining whether or not a sample is positive, negative, and/or a specific percent of a population (e.g., 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100%, including ranges defined between any of the two preceding values or greater than any of the preceding values) for one or more biomarkers in the following collections: PR, ERBB2, and Ki67; COX-2, Ki67, and p16; and PR, ERBB2, Ki67, COX-2, and p16. In some embodiments, the programming includes software for determining whether or not a sample is positive, negative, and/or a specific percent of a population (e.g., 1, 2, 3, 4, 5, 6, 7, 8, 9, 10, 15, 20, 25, 30, 35, 40, 45, 50, 55, 60, 65, 70, 75, 80, 85, 90, 95, 96, 97, 98, 99, or 100%, including ranges defined between any of the two preceding values or greater than any of the preceding values) for one or more biomarkers in the following collections: ER, PR, ERBB2, and Ki67; COX-2, Ki67, and p16; and ER, PR, ERBB2, Ki67, COX-2, and p16. In some embodiments, the programming can also compare these scores with a data table, (e.g., with conditions set forth in Table 12), to provide a risk category for the sample and subject. In some embodiments, the programming can also prepare a sample for assaying a protein and/or place a sample or part thereof onto an array for detection of the biomarkers.

In yet another embodiment, the invention provides computer programming for analyzing and comparing a pattern of gene product expression from a biological sample to a library of gene product expression patterns known to be indicative of the presence or absence of a carcinoma, wherein the comparing providing a differential diagnosis between a benign carcinoma, and an aggressive carcinoma, e.g., the gene product expression pattern provides for staging and/or grading of a carcinoma.

The methods and systems described herein can be implemented in numerous ways. In one embodiment of particular interest, the methods involve use of a communications infrastructure, for example the internet. Several embodiments of the invention are discussed below. It is also to be understood that the present invention may be implemented in various forms of hardware, software, firmware, processors, or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of gene product expression for a sample), as well as any processed data, including assessment of a subject's risk of subsequent DCIS or invasive cancer. Test result data also can include clinical recommendations related to the risk category of a subject. This information received can be stored at least temporarily in a database, and data analyzed in comparison to a library of gene product expression patterns known to be indicative of the presence or absence of a pre-cancerous epithelial cell, or known to be indicative of a stage and/or grade of a carcinoma.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In an embodiment of particular interest, all or a portion of the input data and/or all or a portion of the output data (e.g., usually at least the library of gene product expression patterns known to be indicative of the presence or absence of a pre-cancerous epithelial cell, or the risk of subsequent DCIS or invasive cancer, as well as any clinical and/or histopathological characteristic data, as well as the risk category a subject is placed in) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where gene product expression data for a biological sample obtained from a subject is to be input by a user (e.g., a technician or someone performing the activity assays)) and transmitted to a remote site to a second computer processor for analysis (e.g., where the pattern of gene expression is compared to a library of gene product expression patterns known to be indicative of the presence or absence of a pre-cancerous epithelial cell), where the first and second computer processors are connected by a network, e.g., via an intranet or internet). The system can also include a user component(s) for input; and a reviewer component(s) for review of data, and generation of reports, including detection of a pre cancerous epithelial cell, staging and/or grading of a carcinoma, or monitoring the progression of a pre-cancerous epithelial cell or a carcinoma. Additional components of the system can include a server component(s); and a database(s) for storing data (e.g., as in a database of report elements, e.g., a library of gene product expression patterns known to be indicative of the presence or absence of a pre-cancerous cell and/or known to be indicative of a grade and/or a stage of a carcinoma, or the risk factor of subsequent invasive cancer or DCIS determined from gene expression pattern, alone or in combination with clinical and/or histopathological characteristic data, including for example, information on the margins of a tumor removed by lumpectomy or the Van Nuys Prognostic index, or a relational database (RDB) which can include data input by the user and data output. The computer processors can be processors that are typically found in personal desktop computers (e.g., IBM, Dell, Macintosh), portable computers, mainframes, minicomputers, or other computing devices.

The networked client/server architecture can be selected as desired, and can be, for example, a classic two or three tier client server model. A relational database management system (RDMS), either as part of an application server component or as a separate component (RDB machine) provides the interface to the database.

In one embodiment, the architecture is provided as a database-centric user/server architecture, in which the user application generally requests services from the application server which makes requests to the database (or the database server) to populate the activity assay report with the various report elements as required, especially the assay results for each activity assay. The server(s) (e.g., either as part of the application server machine or a separate RDB/relational database machine) responds to the user's requests.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe and offers data management, information sharing between clients, network administration and security. The application and any databases used can be on the same or different servers.

Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

Computer-Readable Storage Media

The invention also contemplates a computer-readable storage medium (e.g. CD-ROM, memory key, flash memory card, diskette, etc.) having stored thereon a program which, when executed in a computing environment, provides for implementation of algorithms to carry out all or a portion of the methods described herein, including detection of a pre-cancerous epithelial cell, staging and/or grading of a carcinoma, or monitoring the progression of a pre cancerous epithelial cell or a carcinoma. Where the computer-readable medium contains a complete program for carrying out the methods described herein, the program includes program instructions for collecting, analyzing and comparing a pattern of gene product expression patterns from a biological sample (e.g., a biopsy sample) obtained from a subject to a library of gene product expression patterns known to be indicative of the presence or absence of a pre cancerous epithelial cell, or for determining the risk of subsequent DCIS and/or invasive cancer, and generally includes computer readable code devices for interacting with a user as described herein, processing that data in conjunction with analytical information, and generating unique printed or electronic media for that user.

Where the storage medium provides a program which provides for implementation of a portion of the methods described herein (e.g., the user-side aspect of the methods (e.g., data input, report receipt capabilities, etc.)), the program provides for transmission of data input by the user (e.g., via the internet, via an intranet, etc.) to a computing environment at a remote site. Processing or completion of processing of the data may be carried out at the remote site to provide for detection of a pre-cancerous epithelial cell, staging and/or grading of a carcinoma, determining the risk of subsequent DCIS and/or invasive cancer, or monitoring the progression of a pre-cancerous epithelial cell or a carcinoma. The computer-readable storage medium can also be provided in combination with one or more reagents for carrying out one or more of the activity assays (e.g., control compounds, cells, probes, arrays, or other activity assay test kit components).

Kits and Systems

Also provided by the subject invention are kits for practicing the subject methods, as described above, including detection of a cancerous or pre-cancerous epithelial cell, differential diagnosis malignant versus benign cancer, determining the risk of subsequent DCIS and/or invasive cancer, or monitoring the progression of a cancer. The subject kits include at least one or more of: a probe or primer for detection of a marker polynucleotide, a marker polypeptide, or an anti-marker polypeptide antibody. Other optional components of the kit include: restriction enzymes, control primers and plasmids; nucleic acid or polypeptide standards; buffers; reaction mixtures (e.g., for carrying out the assay); enzymes (e.g., DNA polymerase, reverse transcriptase, and the like); cells; and the like. The various components of the kit may be present in separate containers or certain compatible components may be precombined into a single container, as desired.

In some embodiments, the kit includes anti-biomarker antibodies for at least two, three, four or all of ER, ERBB2, COX-2, Ki67 and p16. In another embodiment, the kit includes an array of antibodies against each of ER, ERBB2, COX-2, Ki67 and p16. In some embodiments, the kit includes anti-biomarker antibodies for at least two, three, four or all of PR, ERBB2, COX-2, Ki67 and p16. In another embodiment, the kit includes an array of antibodies against each of PR, ERBB2, COX-2, Ki67 and p16. In some embodiments, the kit includes anti-biomarker antibodies for at least two, three, four or all of ER, PR, ERBB2, COX-2, Ki67 and p16. In another embodiment, the kit includes an array of antibodies against each of ER, PR, ERBB2, COX-2, Ki67 and p16.

Kits for Detecting a Target Nucleic Acid

A subject kit comprises a pair of nucleic acids (primer pairs), one or more nucleic acid probes, or both, where the primer pairs and probes are suitable for use in a subject method, as described above. The nucleic acids will in some embodiments be present in a suitable storage medium, e.g., buffered solution, typically in a suitable container. The kit includes the primers and/or probes, and may further include a buffer; reagents (e.g., for polymerase chain reaction (e.g., deoxynucleotide triphosphates (dATP, dTTP, dCTP, and dGTP), a thermostable DNA polymerase, a buffer suitable for polymerase chain reaction, a solution containing $Mg^{2+}$ ions (e.g., $MgCl_2$), and other components well known to those skilled in the art for carrying out a polymerase chain reaction)). The kit may further include instructions for use of the kit, which instructions may be provided in a variety of forms, e.g., as printed information, on a compact disc, and the like. The kit may further include reagents necessary for extraction of DNA (or mRNA) from a biological sample (e.g., breast biopsy, axillary lymph node biopsy, etc.) from an individual. The kit may further include reagents necessary for reverse transcription of an mRNA, to make a cDNA copy of the mRNA.

The kit may further include positive and negative controls. An example of a positive control is a target nucleic acid that includes a region that will be amplified by primer pairs included in the kit. An example of a negative control is a nucleic acid (e.g., an albumin encoding nucleic acid) that will not be amplified by nucleic acid primers included in the kit. The kits are useful in diagnostic applications, as described in detail above. A subject kit is useful to determine whether a target mRNA is present at higher or lower than normal levels in an epithelial cell.

A kit will in some embodiments provide a standard for normalization of a level of a target polynucleotide to a standard, e.g., a level of a glucose-6-phosphate dehydrogenase polynucleotide (e.g, a G6PDH mRNA or cDNA copy of a G6PDH mRNA).

Exemplary kits include at least one primer, at least two primers (a 5' and a 3' primer), or at least two primers and a probe, as described above. Also included in the subject kits may be buffers, dNTPs, and controls, (e.g., positive and negative control nucleic acids) for performing the subject methods. Primers in the subject kits may be detectably labeled or unlabeled).

Kits for Detecting a Target Polypeptide

A subject kit for detecting a target polypeptide comprises one or more anti-target polypeptide antibody reagents. For example, a subject kit will include antibody reagent(s) specific for a polypeptide that is included in an MEC signature (e.g., a variant MEC signature). In some embodiments, the antibody will comprise a detectable label. In some embodiments, the antibody will be bound to an insoluble support, e.g., a bead (e.g., a polystyrene bead, a magnetic bead, etc.); a plastic surface (e.g., the well of an ELISA plate); a membrane (e.g., a test strip; a polyvinylpyrrolidone membrane; a nitrocellulose membrane; etc.); and the like.

A subject kit can further include, if desired, one or more of various conventional components, such as, for example, containers with one or more buffers (e.g., wash buffers), detection reagents or antibodies. Printed instructions, either as inserts or as labels, indicating quantities of the components to be used and guidelines for their use, can also be included in the kit. In the present disclosure it should be understood that the specified materials and conditions are important in practicing the invention but that unspecified materials and conditions are not excluded so long as they do not prevent the benefits of the invention from being realized.

A kit will in some embodiments provide a standard for normalization of a level of a target polypeptide to a standard, e.g., a level of an actin polypeptide, a level of a GAPDH polypeptide, etc. A kit will in some embodiments further include negative controls, e.g., antibodies specific for a non-target polypeptide; and the like.

Kits may also include components for conducting western blots (e.g., pre made gels, membranes, transfer systems, etc.); components for carrying out ELISAs (e.g., 96-well plates; plates containing wells in multiples of 96); components for conducting immunohistochemical analysis of a tissue sample; and the like.

Additional Components

In addition to above-mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Methods for Isolating vMEC

The present invention provides methods for isolating vMEC, e.g., a human vMEC (vHMEC), from a sample that comprises, in addition to vMEC, one or more other cell types, e.g., one or more of MEC, fibroblasts, and the like. The methods generally involve contacting the sample comprising a mixed cell population comprising a vMEC with a specific binding reagent that binds specifically to CD73, where the specific binding reagent binds CD73 present on the cell surface of a vMEC present in the sample, forming a complex between the specific binding reagent and the vMEC; and separating the complex from the sample. In some embodiments, the specific binding reagent is immobilized on an insoluble support.

In some embodiments, the specific binding reagent is an antibody specific for CD73. In these embodiments, the method generally involves contacting a sample comprising a mixed cell population comprising a vMEC with an antibody specific for CD73, where the anti-CD73 antibody binds CD73 present on the cell surface of a vMEC present in the sample, forming a complex between the specific binding reagent and the vMEC; and separating the complex from the sample. In some embodiments, the anti-CD73 antibody is immobilized on an insoluble support.

Suitable insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (MA), and the like); sheets, e.g., nylon, nitrocellulose, and the like; and chips, e.g., $SiO_2$ chips such as those used in microarrays.

The separation step is carried out in any of a varied of ways, depending in part on the nature of the insoluble support to which the anti-CD73 antibody is bound. In some embodiments, an anti-CD73 antibody is immobilized on the surface of a magnetic bead, and the separation step comprises applying a magnetic field to the sample comprising a complex formed between the anti-CD73 antibody and a vMEC. In other embodiments, an anti-CD73 antibody is immobilized on the surface of a plastic bead, and the separation step comprises low-speed centrifugation.

A subject method of isolating a vMEC from a mixed cell population comprising a vMEC can include one or more washing steps. For example, a washing step can be included after the formation of a complex between an anti-CD73 antibody and a vMEC, and before and/or after the separation step.

A subject method of isolating a vMEC from a mixed cell population yields a substantially pure vMEC cell population, e.g, a cell population comprising at least about 75%, at least about 80%, at least about 85%, at least about 90%, at least about 95%, at least about 98%, or at least about 99% vMEC. The vMEC are CD73$^+$, and are morphologically normal (e.g., do not exhibit a cancerous morphology).

The present invention further provides inter alia a CD73 binding reagent, e.g., a reagent that specifically binds CD73, immobilized on the surface of an insoluble support. A subject immobilized CD73 binding reagent is useful for isolating a vMEC from a mixed population of cells comprising a vMEC. In some embodiments, the CD73 binding reagent is an antibody that binds specifically to CD73.

Suitable insoluble supports include, but are not limited to, beads (e.g., polystyrene beads, magnetic beads, and the like); plastic surfaces (e.g., polystyrene or polycarbonate multi-well plates typically used in an enzyme-linked immunosorbent assay (ELISA) or radioimmunoassay (MA), and the like); sheets, e.g., nylon, nitrocellulose, and the like; and chips, e.g., $SiO_2$ chips such as those used in microarrays.

Methods of Categorizing Risk of Subsequent Events and Characterizing a Sample

In some embodiments, the invention provides a method of categorizing a risk that a subject that has Ductal Carcinoma in situ (DCIS) will have a subsequent DCIS event. While there are various embodiments for this, in some embodiments, a cell signature of a DCIS lesion is analyzed for a group of biomarkers, including at least one of: Ki67, ERBB2, and ER and at least one of the following: COX-2 and p16. In some embodiments, a cell signature of a DCIS lesion is analyzed for a group of biomarkers, including at least one of: Ki67, ERBB2, and PR and at least one of the following: COX-2 and p16. In some embodiments, a cell signature of a DCIS lesion is analyzed for a group of biomarkers, including at least one of: Ki67, ERBB2, ER and PR and at least one of the following: COX-2 and p16. Based on the cell signature determined, the subject is placed into a specific risk category for a subsequent DCIS event (or a risk estimate is provided). The specific risk category can be a qualitative, quantitative or descriptive level of risk. For example, a risk category could be "low risk" or "high risk". In another example, risk categories could be "under 10% risk" and "10% or higher risk" (and thus also be categorized as a risk estimate). The category also can be a level of risk, for example, "about 10% risk."

Various embodiments of this aspect are depicted in FIG. 25. In some embodiments, one starts the process by identifying a subject that may or does have DCIS 100. In some embodiments, this person can be identified by core biopsy or excisional biopsy of breast tissue and examination of the tissue by a clinical pathologist. In some embodiments, this process can be omitted.

Once the subject has been confirmed as having DCIS, one can obtain or provide a biological sample from the DCIS lesion 110. The sample can be obtained from the initial diagnostic tissue paraffin embedded tissue block from the diagnosing hospital. In some embodiments, this process can be omitted.

One can prepare the biological sample for an assay to test for the presence, absence or amount of various biomarkers 120. As will be appreciated, the sample preparation will vary depending on what the target for detection is. Thus, protein detection and mRNA detection can differ in their methods; however, such approaches are well known in the art. In some embodiments, clinical diagnostic paraffin embedded blocks can be used and one can cut standard 5 micron slides from these blocks and stain them for the 5 markers. In some embodiments, this process can be omitted.

One can assay the biological sample for the presence or absence of Ki67, ERBB2, and ER 130. In some embodiments, this process can be omitted. Alternatively, one can assay the biological sample for the presence or absence of Ki67, ERBB2, and PR 130. In some embodiments, this process can be omitted.

One can assay the biological sample for the presence or absence of COX-2 and p16 140. In some embodiments, this process can be omitted.

For the assay processes, one or more of each of the markers can be assayed for whether sample is positive or negative for such marker. In some embodiments, each marker is assayed separately. In some embodiments, one or more of the markers are assayed simultaneously. In some embodiments, the determination of whether or not a sample is positive or negative for a marker is determined as outlined herein. In some embodiments, at least one of the DCIS or invasive cancer sets of markers are reviewed between processes 130 and 140 (as outlined in Table 12).

In some embodiments, one can further look at additional factors prior to or following process 120, 130, and 140. In some embodiments, this includes clinical and/or histopathological characteristics relating to margin (e.g., well defined and size of 1 mm or more) and/or Van Nuys Prognostic Index, and if the DCIS was detected by palpation or mammography. In some embodiments, the process explicitly excludes factoring in various clinical and/or histopathological characteristics such as necrosis type, extent of necrosis, nuclear grade, and tumor size.

One can then place the subject into a risk category or provide a risk estimate for the subject for whether or not they will have a subsequent event, and whether or not the event will be DCIS or an invasive cancer event 150. In some embodiments, for example, when data on the above biomarkers is already available for a specific DCIS tumor, then this process can be performed practically without having the same individual perform any of the other processes. Thus, in some embodiments, this process is sufficient. In some embodiments, the placement of a subject into one or more categories or estimating a risk for the subject can be in regard to subsequent DCIS occurrence and/or subsequent invasive cancer occurrence. In some embodiments, the specific combination of markers examined include at least the 3 outlined in Table 12 for DCIS and/or the 3 outlined in Table 12 for invasive cancer. In some embodiments, the placement not only includes reviewing 3 or more biomarkers from Table 12, but the positive and negative results indicated in Table 12 and the corresponding risk category or risk estimate. In some embodiments, the positive and negative scoring system used for the biomarkers is that outlined in Example 5B below.

As will be appreciated by those of skill in the art, the above processes can be performed by various individuals or groups, and thus, need not be performed by a single individual. In some embodiments, the method is just a subset of the depicted steps; some of the shortened methods are depicted by the alternative arrow routes. In some embodiments, the method stops at an earlier processes (such as 130 or 140). In some embodiments, the method omits one or more of the processes (such as 100, 110, 120, 130, 140, and/or 150). Thus, in some embodiments, the method comprises 130 and/or 140 without the other steps or can simply comprise 150 without the other noted processes, for example. In some embodiments, additional processes are included between or after any process. In some embodiments, the processes overlap in time, and therefore do not need to occur sequentially. In some embodiments, a method can allow for one or more of the processes to occur simultaneously and optionally, without the need for a separate analysis. For example, an assay system that not only detects the presence/absence of the two or more markers, but also emits or provides a specific signature that is uniquely correlated with the risk estimation or risk category can effectively combine processes 130, 140, and 150 into a single event (as the assay results can translate directly into a risk category or estimate). In some embodiments, the various embodiments in FIG. 25 describe a method consisting of those steps. In some embodiments, the various embodiments in FIG. 25 describe a method consisting essentially of those steps. In some embodiments, while other processes can occur in the embodiments in FIG. 25, no other clinical and/or histopathological characteristics are factored in the process for estimating the risk that a subject will have a subsequent invasive cancer event.

FIG. 26 depicts additional embodiments of methods for estimating a risk or placing a subject into a risk category for a subsequent invasive cancer. In some embodiments, one obtains a sample from a subject 200. One can then score the expression levels of one or more biomarkers in the sample 205. One can then estimate a risk that the subject will have a subsequent invasive cancer event based on the scoring of the biomarkers 210. This can involve factoring in numerous variables, and in some embodiments, excluding various variables from consideration. In some embodiments, one can factor in nuclear grade when estimating a risk 220. In other embodiments, one does not factor in nuclear grade. In some embodiments, one can factor in margins when estimating a risk 230. In some embodiments, one can factor in if the DCIS lesion was detected mammographically when estimating a risk 240. In some embodiments, one can factor in (for example, "consider") if the DCIS lesion was detected by palpation when estimating a risk 250. As shown in FIG. 26, any one or combination of these can be employed and combined with the biomarker results to estimate a risk. In some embodiments, the biomarker results can be interpreted according to the data and arrangement in Table 12 and thus include the following: Ki67, cyclooxygenase-2 (COX-2) and p16 negative-triple negative (Ki67$^-$COX-2$^-$p16$^-$) 260A (very low risk for invasive cancer); Ki67-negative and either COX-2-positive (Ki67$^-$COX-2$^+$) or p16-positive (Ki67$^-$p16$^+$) or both positive (Ki67$^-$COX-2$^+$p16$^+$ 260B (low risk for invasive cancer); Ki67-positive and either COX-2-positive (Ki67$^+$COX-2$^+$) or p16-positive (Ki67$^+$p16$^+$) or COX-2-negative/p16-negative (Ki67$^+$COX-2$^-$p16$^-$) 260C (medium risk for invasive cancer); and p16, Ki67, and COX-2-triple positive (p16$^+$Ki67$^+$COX-2$^+$) 260D (high risk for invasive cancer). The risk groups in 260A, 260B, 260C, and 260D are presented as a logic system for the sake of brevity. Thus, in some embodiments, to determine if a set of biomarker results falls into a particular grouping, one compares the biomarker results with the set of biomarkers in 260D, and if the results do not fall into 260D, one then compares the biomarker results with the set in 260C, and if the results do not fall into 260C, one then compares the biomarker results with the set in 260B and if the results do not fall into 260B, one then compares the biomarker results with the set in group 260A. This is simply presented in this manner for brevity and all possible logical combinations described by this system are contemplated for use. Of course, one need not systematically analyze results in this manner. For example, in some embodiments, one can simply provide the full list of combinations for a particular risk group and see if the biomarker results from a subject fall within that particular set of options for the risk group.

In some embodiments, the biomarkers for 260A (lowest risk) include one or more of the following: Ki67, cyclooxygenase-2 (COX-2) and p16 negative-triple negative (Ki67$^-$COX-2$^-$p16$^-$). In some embodiments, the method of detection is not performed or analyzed. In some embodiments, the DCIS is also mammographically detected.

In some embodiments, the biomarkers for 260B (low risk) include one or more of the following: Ki67-negative and either COX-2-positive/p16-negative (Ki67$^-$COX-2$^+$p16$^-$)

or p16-positive/COX-2-negative (Ki67⁻p16⁺COX-2⁻) or both positive (Ki67⁻COX-2⁺p16⁺). In some embodiments, the method of detection is not performed or analyzed. In some embodiments, the DCIS is also mammographically detected.

In some embodiments, the biomarkers for 260C (intermediate risk) include one or more of the following: Ki67-positive and either COX-2-positive/p16-negative (Ki67⁺ COX-2⁺p16⁻) or p16-positive/COX-2-negative (Ki67⁺p16⁺ COX-2⁻) or COX-2-negative/p16-negative (Ki67⁺COX-2⁻ p16⁻). In some embodiments, the method of detection is not performed or analyzed. In some embodiments, the DCIS is also mammographically detected.

In some embodiments, the biomarkers for 260D (high risk) include one or more of the following: p16, Ki67, and COX-2-triple positive (p16⁺Ki67⁺COX-2⁺. In some embodiments, the method of detection is not performed or analyzed. In some embodiments, the DCIS is also detected via palpation.

While the examples discussed herein may include how the DCIS was detected, this is simply for convenience and does not imply that the form of detection (e.g., mammographically or palpation) is a "biomarker".

As will be appreciated by those of skill in the art, the above processes can be performed by various individuals or groups, and thus, need not be performed by a single individual. In some embodiments, the method is just a subset of the depicted steps, some of the shortened methods are depicted by the alternative arrow routes. In some embodiments, the method omits one or more of the processes (such as 220, 200, 205, 230, 250, and 240. Thus, in some embodiments, the method comprises 210 and one of the 260s, but omits the other noted processes. In some embodiments, additional steps are included between or after any process. In some embodiments, the processes overlap in time, and therefore do not need to occur sequentially. In some embodiments, a method can allow for one or more of the processes to occur simultaneously and optionally, without the need for a separate analysis. For example, an assay system that not only detects the presence/absence of the two or more markers, but also emits or provides a specific signature that is uniquely correlated with the risk estimation or risk category can effectively combine processes into a single event (as scoring can be made integral to estimation of risk or placement into risk category in some embodiments. In some embodiments, the various embodiments in FIG. 26 describe a method consisting of those steps. In some embodiments, the various embodiments in FIG. 26 describe a method consisting essentially of those steps. In some embodiments, while other processes can occur in the embodiments in FIG. 26, no other clinical and/or histopathological characteristics are included in the process for estimating the risk that a subject will have a subsequent invasive cancer event.

FIGS. 27A-27C depict additional embodiments for estimating a risk that a subject with DCIS will have a subsequent event (DCIS and/or invasive cancer) or no subsequent DCIS and/or invasive cancer event.

FIG. 27A outlines some embodiments generally, with FIG. 27B outlining process 400 for invasive cancer categorization/risk estimation and FIG. 27C outlining process 400 for DCIS categorization/risk estimation.

In some embodiments, one can, identify a subject that has DCIS 300. In some embodiments, one can, obtain a biological sample of a DCIS lesion from the subject 310. In some embodiments, one can, prepare a biological sample for an assay of one or more proteins in cells of the sample 320. In some embodiments, one can, use antibodies to determine a protein based cell signature for cells in a sample 330. In some embodiments, one can, place the subject and/or sample into one or more risk categories and/or providing an estimate of the risk of a subsequent DCIS event and/or invasive cancer event, according to the arrangements in 27B and/or 27C 400. In some embodiments, one can notify the subject of the estimate of their risk or their risk category 340. In some embodiments, one can recommend and/or provide a treatment based in part upon the estimate of risk of risk category 350.

In some embodiments, process 400 is based on the results of various biomarker assays for particular biomarkers, which are then used to predict a risk or place a subject in a risk category for a subsequent invasive cancer. Some embodiments of this are outlined in FIG. 27B. In some embodiments, one can provide assay results for one or more of Ki67, COX-2, and p16 410. In some embodiments, one can factor in nuclear grade when estimating a risk 420. In some embodiments, one can, factor in margins when estimating a risk 425. In some embodiments, one can factor in if the DCIS lesion was detected mammographically when estimating a risk 430. In some embodiments, one can factor in if the DCIS lesion was detected by palpation when estimating a risk 435. In some embodiments, a biomarker assay result of: Ki67, cyclooxygenase-2 (COX-2) and p16 negative-triple negative (Ki67⁻COX-2⁻p16⁻) 440A, places the subject into the lowest risk category (or a lowest estimation of risk) for a subsequent invasive cancer. In some embodiments, a biomarker assay result of: Ki67-negative and either COX-2-positive (Ki67⁻COX-2⁺) or p16-positive (Ki67⁻p16⁺) or both positive (Ki67⁻COX-2⁺p16⁺, as shown in 440B, places the subject into the low risk category (or a low estimation of risk) for subsequent invasive cancer. In some embodiments, a biomarker assay result of: Ki67-positive and either COX-2-positive (Ki67⁺COX-2⁺) or p16-positive (Ki67⁺p16⁺) or COX-2-negative/p16-negative (Ki67⁺COX-2⁻p16⁻) 440C, places the subject into the medium risk category (or a medium risk estimation) for subsequent invasive cancer. In some embodiments, a biomarker assay result of: p16, Ki67, and COX-2-triple positive (p16⁺Ki67⁺COX-2⁺) 440D, places the subject into the high risk category (or high risk estimation) for subsequent invasive cancer.

The risk groups in 440A, 440B, 440C, and 440D are presented as a logic system for the sake of brevity. Thus, in some embodiments, to determine if a set of biomarker results falls into a particular grouping, one compares the biomarker results with the set of biomarkers in 440D, and if the results do not fall into 440D, one then compares the biomarker results with the set in 440C, and if the results do not fall into 440C, one then compares the biomarker results with the set in 440B and if the results do not fall into 440B, one then compares the biomarker results with the set in group 440A. This is simply presented in this manner for brevity and all possible logical combinations described by this system are contemplated for use. Of course, one need not systematically analyze results in this manner. For example, in some embodiments, one can simply provide the full list of combinations for a particular risk group and see if the biomarker results from a subject fall within that particular set of options for the risk group.

In some embodiments, the biomarkers for 440A (lowest risk) include one or more of the following: Ki67, cyclooxygenase-2 (COX-2) and p16 negative-triple negative (Ki67⁻ *cox*-2⁻p16⁻). In some embodiments, the method of detection is not performed or analyzed. In some embodiments, the DCIS is also mammographically detected.

In some embodiments, the biomarkers for 440B (low risk) include one or more of the following: Ki67-negative and either COX-2-positive/p16-negative (Ki67⁻COX-2⁺p16⁻) or p16-positive/COX-2-negative (Ki67⁻p16⁺COX-2⁻) or both positive (Ki67⁻COX-2⁺p16⁺). In some embodiments, the method of detection is not performed or analyzed. In some embodiments, the DCIS is also mammographically detected.

In some embodiments, the biomarkers for 440C (intermediate risk) include one or more of the following: Ki67-positive and either COX-2-positive/p16-negative (Ki67⁺COX-2⁺p16⁻) or p16-positive/COX-2-negative (Ki67⁺p16⁺COX-2⁻) or COX-2-negative/p16-negative (Ki67⁺COX-2⁻p16⁻). In some embodiments, the method of detection is not performed or analyzed. In some embodiments, the DCIS is also mammographically detected.

In some embodiments, the biomarkers for 440D (high risk) include one or more of the following: p16, Ki67, and COX-2-triple positive (p16⁺Ki67⁺COX-2⁺). In some embodiments, the method of detection is not performed or analyzed. In some embodiments, the DCIS is instead detected via palpation and thus placed as a high risk for subsequent invasive cancer.

In some embodiments, process 400 is based on the results of various biomarker assays for particular biomarkers, which are then used to predict a risk or place a subject in a risk category for a subsequent DCIS event, as outlined in FIG. 27C. In some embodiments, one can factor in nuclear grade when estimating a risk 460. In some embodiments, one can factor in margins when estimating a risk 465. In some embodiments, one can factor in if the DCIS lesion was detected mammographically when estimating a risk 470. In some embodiments, one can factor in if the DCIS lesion was detected by palpation when estimating a risk 475.

In some embodiments, a biomarker assay result of: estrogen receptor (ER) positive and HER2/neu-oncoprotein (ERBB2) negative and Ki67-negative (ER⁺ERBB2⁻Ki67⁻) places the subject into the lowest risk category (or a lowest estimation of risk) for a subsequent DCIS event 480A. In some embodiments, a biomarker assay result of: estrogen receptor (ER) positive and HER2/neu-oncoprotein (ERBB2) negative and Ki67-negative (ER+ERBB2-Ki67-); estrogen receptor (ER) positive and HER2/neu-oncoprotein (ERBB2) negative and Ki67-positive (ER+ERBB2-Ki67+); or estrogen receptor (ER) positive and HER2/neu-oncoprotein (ERBB2) positive and Ki67-negative (ER+ERBB2+Ki67-) places the subject into the lowest risk category (or a lowest estimation of risk) for a subsequent DCIS event 480A. In some embodiments, a biomarker assay result of: either ER-negative, ERBB2 negative (ER⁻ERBB2⁻) or p16 and Ki67-positive (p16⁺Ki67⁺) or COX-2-negative, Ki67-positive (COX-2⁻Ki67⁺) or COX-2-positive, Ki67-positive (COX-2⁺Ki67⁺) or ERBB2-positive, Ki67-positive (ERBB2⁺Ki67⁺) places the subject into the low risk category (or a low estimation of risk) for a subsequent DCIS event 480B. In some embodiments, a biomarker assay result of: ER-negative, Ki67-positive (ER⁻Ki67⁺) or ER negative, ERBB2-positive (ER⁻ERBB2⁺) places the subject into the intermediate risk category (or a medium estimation of risk) for a subsequent DCIS event 480C. In some embodiments, a biomarker assay result of: ER-negative/ERBB2-positive/Ki67-positive (ER⁻ERBB2⁺Ki67⁺) or p16/Ki67-positive and COX-2-negative (p16⁺COX-2⁻Ki67⁺) places the subject into the high risk category (or a high estimation of risk) for a subsequent DCIS event 480D.

In some embodiments, a biomarker assay result of: progesterone receptor (PR) positive and HER2/neu-oncoprotein (ERBB2) negative and Ki67-negative (PR⁺ERBB2⁻Ki67⁻) places the subject into the lowest risk category (or a lowest estimation of risk) for a subsequent DCIS event 480A. In some embodiments, a biomarker assay result of: either PR-negative, ERBB2 negative (PR⁻ERBB2⁻) or p16 and Ki67-positive (p16⁺Ki67⁺) or COX-2-negative, Ki67-positive (COX-2⁻Ki67⁺) or COX-2-positive, Ki67-positive (COX-2⁺Ki67⁺) or ERBB2-positive, Ki67-positive (ERBB2⁺Ki67⁺) places the subject into the low risk category (or a low estimation of risk) for a subsequent DCIS event 480B. In some embodiments, a biomarker assay result of: PR-negative, Ki67-positive (ER⁻Ki67⁺) or PR-negative, ERBB2-positive (PR⁻ERBB2⁺) places the subject into the intermediate risk category (or a medium estimation of risk) for a subsequent DCIS event 480C. In some embodiments, a biomarker assay result of: PR-negative/ERBB2-positive/Ki67-positive (PR⁻ERBB2⁺Ki67⁺) or p16/Ki67-positive and COX-2-negative (p16⁺COX-2⁻Ki67⁺) places the subject into the high risk category (or a high estimation of risk) for a subsequent DCIS event 480D.

The risk groups in 480A, 480B, 480C, and 480D are presented as a logic system for the sake of brevity. Thus, in some embodiments, to determine if a set of biomarker results falls into a particular grouping, one compares the biomarker results with the set of biomarkers in 480D, and if the results do not fall into 480D, one then compares the biomarker results with the set in 480C, and if the results do not fall into 480C, one then compares the biomarker results with the set in 480B and if the results do not fall into 480B, one then compares the biomarker results with the set in group 480A. This is simply presented in this manner for brevity and all possible logical combinations described by this system are contemplated for use. Of course, one need not systematically analyze results in this manner. For example, in some embodiments, one can simply provide the full list of combinations for a particular risk group and see if the biomarker results from a subject fall within that particular set of options for the risk group. As will be clear to one of skill in the art, the method of characterizing or analyzing a sample need not include the "logic" system described herein for the sake of brevity. Thus, comparisons of specific test results to a simple table where a direct comparison is possible are provided herein as well (for all embodiments described herein).

In some embodiments, the biomarkers for 480A (lowest risk) include one or more of the following: DCIS with margins of 1 millimeter or greater disease-free plus estrogen receptor (ER) positive and HER2/neu-oncoprotein (ERBB2) negative and Ki67-negative (ER⁺ERBB2⁻Ki67⁻) or estrogen receptor (ER) positive and HER2/neu-oncoprotein (ERBB2) negative and Ki67-positive (ER⁺ERBB2⁻Ki67⁺) or estrogen receptor (ER) positive and HER2/neu-oncoprotein (ERBB2) positive and Ki67-negative (ER⁺ERBB2⁺Ki67⁻). In some embodiments, the biomarkers are examined without the margins being examined or factored in.

In some embodiments, the biomarkers for 480B (low risk) include one or more of the following: DCIS with margins of 1 millimeter or greater disease-free plus either ER-negative, ERBB2 negative, Ki67-negative (ER⁻ERBB2⁻Ki6T) or p16, Ki67-positive, and COX-2-positive (p16⁺Ki67⁺COX-2⁺) or p16-negative, COX-2-negative, Ki67-positive (p16⁻cox-2⁻Ki67⁺) or p16-negative, COX-2-positive, Ki67-positive (p16⁻COX-2⁺Ki67⁺) or ER-positive, ERBB2-positive, Ki67-positive (ER⁺ERBB2⁺Ki67⁺). In some embodiments, the biomarkers are examined without the margins being examined or factored in.

In some embodiments, the biomarkers for 480C (intermediate risk) include one or more of the following: positive or uncertain margins or ER-negative, ERBB2-negative, Ki67-positive (ER⁻ERBB2⁻Ki67⁺) or ER-negative, ERBB2-positive, Ki67-negative (ER⁻ERBB2⁺Ki6T). In some embodiments, the biomarkers are examined without the margins being examined or factored in.

In some embodiments, the biomarkers for 480D (high risk) include one or more of the following: DCIS with margins of 1 millimeter or greater disease-free plus ER-negative/ERBB2-positive/Ki67-positive (ER⁻ERBB2⁺ Ki67⁺) or p16/Ki67-positive and COX-2-negative (p16⁺ COX-2⁻Ki67⁺). In some embodiments, the biomarkers are examined without the margins being examined or factored in. In some embodiments, a subject having ER, ERBB2⁻, p16⁺, ki67⁺, and Cox2⁻ would be identified as high risk because the subject was p16⁺/ki67⁺/Cox2⁻ (and thus would fall into this grouping first in the analysis process).

In some embodiments, the lowest risk group for subsequent DCIS has a biomarker set as follows: a DCIS with margins of 1 millimeter or greater disease-free plus estrogen receptor (ER) positive and HER2/neu-oncoprotein (ERBB2) negative and Ki67-negative (ER+ERBB2–Ki67–) or estrogen receptor (ER) positive and HER2/neu-oncoprotein (ERBB2) negative and Ki67-positive (ER+ERBB2–Ki67+) or estrogen receptor (ER) positive and HER2/neu-oncoprotein (ERBB2) positive and Ki67-negative (ER+ERBB2+Ki67–). In some embodiments, the biomarkers are examined without the margins being examined or factored in.

In some embodiments, the low risk group for subsequent DCIS has a biomarker set as follows: DCIS with margins of 1 millimeter or greater disease-free plus either ER-negative, ERBB2 negative, Ki67-negative (ER⁻ERBB2⁻Ki6T) or p16, Ki67-positive, and COX-2-positive (p16⁺Ki67⁺COX-2⁺) or p16-negative, COX-2-negative, Ki67-positive (p16⁻ COX-2⁻Ki67⁺) or p16-negativeCOX-2-positive, Ki67-positive (p16⁻COX-2⁺Ki67⁺) or ER-positive, ERBB2-positive, Ki67-positive (ER⁺ERBB2⁺Ki67⁺). In some embodiments, the biomarkers are examined without the margins being examined or factored in.

In some embodiments, the intermediate risk group for subsequent DCIS has a biomarker set as follows: positive or uncertain margins or ER-negative/ERBB2-negative/Ki67-positive ER ERBB2⁻Ki67⁺) or ER-negative, ERBB2-positive/Ki67-negative (ER⁻ERBB2⁺Ki6T). In some embodiments, the biomarkers are examined without the margins being examined or factored in.

In some embodiments, the high risk group for subsequent DCIS has a biomarker set as follows: DCIS with margins of 1 millimeter or greater disease-free plus ER-negative/ERBB2-positive/Ki67-positive (ER⁻ERBB2⁺Ki67⁺) or p16/ Ki67-positive and COX-2-negative (p16⁺COX-2⁻Ki67⁺). In some embodiments, the biomarkers are examined without the margins being examined or factored in.

As will be appreciated by those of skill in the art, the above processes (outlined 27A-27C) can be performed by various individuals or groups, and thus, need not be performed by a single individual. In some embodiments, the method comprises, consists, or consists essentially of a subset of the depicted steps, some of the shortened methods are depicted by the alternative arrow routes. In some embodiments, the method omits one or more of the processes (such as 300, 310, 320, 330, 340, 350, 420, 425, 430, 435, 460, 465, 470, and/or 475). Thus, in some embodiments, the method comprises 400 but omits the other processes depicted in the figures. In some embodiments, additional steps are included between or after any process. In some embodiments, the processes overlap in time. In some embodiments, the processes do not occur sequentially. In some embodiments, a method can allow for one or more of the processes to occur simultaneously and optionally, without the need for a separate analysis. For example, an assay system that not only detects the presence/absence of the two or more markers, but also emits or provides a specific signature that is uniquely correlated with the risk estimation or risk category can effectively combine processes into a single event (as scoring can be made integral to estimation of risk or placement into risk category in some embodiments. In some embodiments, the various embodiments in FIGS. 27A-27B describe a method consisting of those steps (or simply those in 27B or 27C). In some embodiments, the various embodiments in FIGS. 27A-27C describe a method consisting essentially of those steps. In some embodiments, while other processes can occur in the embodiments in FIG. 27A-27C, no other clinical and/or histopathological characteristics are factored in for estimating the risk that a subject will have a subsequent invasive cancer event.

FIG. 28 depicts some embodiments for characterizing a sample for various biomarkers. In some embodiments, one can start by identifying a subject that may have or has been confirmed to have DCIS 500. In some embodiments, one can obtain a biological sample from the subject of a DCIS lesion 510. In some embodiments, one can prepare the biological sample for an assay to test for the various biomarkers 520. In some embodiments, one can then assay for the presence or absence of Ki67 (protein, mRNA, etc.) 530. In some embodiments, one can then assay for the presence or absence of any of the following a) COX-2 and p16, b) ERBB2 and ER, or c) COX-2, p16, ERBB2, and ER 540. In some embodiments, one assays for various combinations of the above biomarkers. In some embodiments, one assays for COX-2, ERBB2, and ER. In some embodiments, one assays for p16, ERBB2, and ER. In some embodiments, one assays for COX-2, p16, and ERBB2. In some embodiments, one assays for COX-2, p16, and ER. In some embodiments, one can then assay for the presence or absence of any of the following a) COX-2 and p16, b) ERBB2 and PR, or c) COX-2, p16, ERBB2, and PR. In some embodiments, one assays for various combinations of the above biomarkers. In some embodiments, one assays for COX-2, ERBB2, and PR. In some embodiments, one assays for p16, ERBB2, and PR. In some embodiments, one assays for COX-2, p16, and ERBB2. In some embodiments, one assays for COX-2, p16, and PR. In some embodiments, one assays for COX-2, ERBB2, ER, and PR. In some embodiments, one assays for p16, ERBB2, ER, and PR. In some embodiments, one assays for COX-2, p16, and ERBB2. In some embodiments, one assays for COX-2, p16, ER, and PR. In some embodiments, any and/or all of the embodiments described herein that include "ER" can have "ER" replaced with (or substituted by) "PR". Similarly, in some embodiments, and/or all of the embodiments described herein that include "PR" can have "PR" replaced with (or substituted by) "ER".

In some embodiments, the method described in FIG. 28 comprises processes 530 and 540. In some embodiments, the method described in FIG. 28 further comprises process 520 and/or process 510, and/or process 500.

In some embodiments, the method comprises any of the embodiments described in regard to FIG. 28. In some embodiments the method consists of any of the above embodiments described in regard to FIG. 28. In some embodiments the method consists essentially of any of the above embodiments described in regard to FIG. 28.

In some embodiments, the methods in FIG. 28 exclude the consideration of any clinical and/or histopathological characteristics if the results from the analysis are subsequently used to determine a risk that a subject will have a subsequent DCIS or invasive cancer event. In some embodiments, the methods in FIG. 28 exclude the use of grade in determining a risk that a subject will have a DCIS recurrence or invasive cancer event, if the method is subsequently used to determine a risk that a subject will have a subsequent DCIS or invasive cancer event. In some embodiments, the only clinical and/or histopathological characteristic that is used in determining a risk that a subject will have a DCIS recurrence or invasive cancer event, is margin, if the methods are subsequently used to determine a risk that a subject will have a subsequent DCIS or invasive cancer event.

In some embodiments, following the analysis of Ki67 530 and one or more of the other noted biomarkers 540 in FIG. 28, one can provide the results to a doctor or directly to a subject. In some embodiments, one determines the risk of a subsequent event (or places a sample or subject into a risk category) by using the above results and the results presented in Table 12. Thus, margin can be examined to further provide an estimation of risk in some embodiments. Furthermore, in some embodiments, the subject is placed into one of four categories for risk of a subsequent DCIS, subsequent invasive cancer or both. In some embodiments, no other clinical and/or histopathological characteristics are used (apart from margin) in estimating risk.

In some embodiments, the methods provided in any of Tables 25-28, when used to estimate a risk or place a subject into a risk category can be described in a variety of ways, including, but not limited to, those embodiments depicted in Table 12. Thus, in some embodiments, a risk estimation or categorization is provided by placing a subject into one of a number of categories (e.g., columns 1 or 5 of Table 12). As noted above, the number of categories and titles for the categories can vary. In some embodiments, a risk estimation or categorization is provided by identifying the prevalence of the particular biomarker combination in a population (e.g., Table 12, columns 2 and 6). In some embodiments, a risk estimation or categorization is provided by providing a likelihood of subsequent event as a percentage (e.g., columns 3, 4, 7, or 8 of Table 12), optionally with a confidence interval, such as 90%, 95%, 98%, or 99%. In some embodiments, this can be for a specified period of time, e.g., 4, 5, 6, 7, 8, 9, 10 or more years.

In some embodiments, while the methods depicted in FIGS. 25-28 can include the measurement of margins of the DCIS lesion, the risk analysis will not factor in or weigh in other clinical and/or histopathological characteristic or surgical factors. Thus, in some embodiments, any of the embodiments depicted in FIGS. 25-28 can exclude tumor size, nuclear grade, necrosis type and quantity of necrosis, while still providing beneficial if not superior estimation of risk for a subsequent DCIS or an invasive cancer. In some embodiments, any of the embodiments depicted in FIGS. 25-28 can exclude factoring in PR and/or p53 in determining a risk assessment for a subsequent DCIS and/or an invasive cancer. In some embodiments, any one or more of the histopathological factors or molecular markers in Tables 8 or 9 that are shown to not be effective in predicting risk of a subsequent DCIS event or invasive cancer event can be excluded from the methods depicted in FIGS. 25-28 for the analysis or assaying process and provide as good, and even surprisingly superior risk estimation capabilities.

In some embodiments, any one or more of the clinical and/or histopathological characteristics provided in Table 4 that is not linked to invasive cancer can be excluded from a risk estimation analysis and provide as good, if not a surprisingly superior, risk assessment. In some embodiments, any one or more of the clinical and/or histopathological characteristics provided in Table 4 that is not linked to a DCIS event can be excluded from a risk estimation analysis and provide as good, if not a surprisingly superior, risk assessment. Thus, in some embodiments, age and nuclear grade are excluded from DCIS risk estimations. In some embodiments, age and nuclear grade are excluded from invasive cancer estimations.

In some embodiments, one or more of the clinical and/or histopathological factors in Tables 2 and 4 are inadequate to replace the predictive ability of the combinations of biomarkers discussed in regard to Example 5B, Table 12, and FIGS. 25-28. Thus, in some embodiments, tumor size, nuclear grade, age, necrosis type, even when combined with margins, are insufficient to provide the level of risk estimation that is achievable with the combination of biomarkers disclosed in FIGS. 25-28 and Table 12.

In some embodiments, the specific risk categories can be linked to the percentage risk of a DCIS recurrence within a specific time period, within a confidence interval (CI). In some embodiments, the first, or lowest risk category has a five year risk of DCIS recurrence of less than about 6%, less than about 5%, less than about 4%, less than about 3%, or even less than about 2.7%. In some embodiments, the lowest risk category is defined by having five year risk of DCIS of 2.7% (with a 95% CI of 2.4-3.2). In some embodiments, a subject in the lowest risk category would have an 8 year risk of DCIS recurrence of less than about 8%, less than about 7%, less than about 6%, less than about 5% and less than about 4%. In some embodiments, the first or lowest risk category is defined as having an eight year risk of DCIS of 3.9% (with a 95% CI of 3.3-4.8).

In some embodiments, the second risk category is subdivided into a first and second subgroup, with the first subgroup having a lower risk. In some embodiments, a subject placed in the first subgroup having a lower risk would have a five year risk of DCIS recurrence of less than, greater than, or between about 11%, about 10%, about 9%, and about 8%. In some embodiments, the five year risk of DCIS recurrence for the first subgroup of the second risk category is 7.8% (with a 95% CI of 6.8-8.7). In some embodiments, a subject placed in the first subgroup (lower risk) would have an eight year risk of DCIS recurrence of less than, greater than, or between about 13%, about 12%, about 11%, and about 10%. In some embodiments, the eight year risk of DCIS recurrence for the first subgroup of the second risk category is 10.2% (with a 95% CI of 8.1-12.7).

In some embodiments, the second risk category is subdivided into a first and second subgroup, with the second subgroup having an intermediate risk. In some embodiments, a subject placed in the first subgroup having a lower risk would have a five year risk of DCIS recurrence of less than, greater than, or between about 17%, about 16%, about 15%, about 14%, about 13% and about 12%. In some embodiments, the five year risk of DCIS recurrence for the second subgroup of the second risk category is 12% (with a 95% CL of 11.4-12.6). In some embodiments, a subject placed in the second subgroup (intermediate risk) would have an eight year risk of DCIS recurrence of less than, greater than, or between about 16%, about 15%, about 14%, about 13%, and about 12%. In some embodiments, the eight year risk of DCIS recurrence for the second subgroup of the second risk category is 14.4% (with a 95% Cl of 13.6-15.2).

In some embodiments, a subject placed in the third risk category (highest risk) would have a five year risk of DCIS recurrence of greater than about 15%, about 16%, about 17%, about 18%, about 19% and about 20%. In some embodiments, the five year risk of DCIS recurrence for the third (highest) risk category is 19.2% (with a 95% CL of 15.3-23.9). In some embodiments, a subject placed in the third risk category (highest risk) would have an eight year risk of DCIS recurrence of greater than about 17%, about 18%, about 19%, about 20%, about 21%, abut 22%, about 23%, and about 24%. In some embodiments, the eight year risk of DCIS recurrence for the third risk category is 23.6% (with a 95% Cl of 18.1-34).

Biomarkers

As described above, in some embodiments, the cell signature is determined for a DCIS lesion for the method of assessing risk of DCIS recurrence, using at least one of: Ki67, ERBB2, and ER and at least one of the following: COX-2 and p16. Any combination of those biomarkers can be analyzed, including for example: Ki67 and COX-2; Ki67 and p16; ERBB2 and COX-2; ERBB2 and p16; ER and COX-2; ER and p16; Ki67, ERBB2 and COX-2; Ki67, ERBB2 and p16; Ki67, ER and COX-2; Ki67, ER and p16; Ki67, ERBB2, ER and COX-2; Ki67, ERBB2, ER and p16; ERBB2, ER and COX-2; ERBB2, ER and p16; Ki67, COX-2 and p16; ERBB2, COX-2 and p16; ER, COX-2 and p16; Ki67, ERBB2, COX-2 and p16; Ki67, ER, COX-2 and p16; ERBB2, ER, COX-2 and p16; and Ki67, ERBB2, ER, COX-2 and p16. According to such methods, a cell signature can include the biomarkers disclosed above, but also can include any additional markers known to one of skill in the art.

As described above, in some embodiments, the cell signature is determined for a DCIS lesion for the method of assessing risk of DCIS recurrence, using at least one of: Ki67, ERBB2, and PR and at least one of the following: COX-2 and p16. Any combination of those biomarkers can be analyzed, including for example: Ki67 and COX-2; Ki67 and p16; ERBB2 and COX-2; ERBB2 and p16; PR and COX-2; PR and p16; Ki67, ERBB2 and COX-2; Ki67, ERBB2 and p16; Ki67, PR and COX-2; Ki67, PR and p16; Ki67, ERBB2, PR and COX-2; Ki67, ERBB2, PR and p16; ERBB2, PR and COX-2; ERBB2, PR and p16; Ki67, COX-2 and p16; ERBB2, COX-2 and p16; PR, COX-2 and p16; Ki67, ERBB2, COX-2 and p16; Ki67, PR, COX-2 and p16; ERBB2, PR, COX-2 and p16; and Ki67, ERBB2, PR, COX-2 and p16. According to such methods, a cell signature can include the biomarkers disclosed above, but also can include any additional markers known to one of skill in the art.

In some embodiments, the biomarkers included are those that are indicative of whether or not a DCIS event can be detected via palpation. Thus, in some embodiments, rather than factoring in whether or not the DCIS lesion was or is actually detectable via palpation, biomarkers are used that indicate whether or not a DCIS lesion is detectable via palpation.

In some embodiments, whether a DCIS lesion was palpable is a risk factor for an invasive breast cancer recurrence. The "palpable" characteristic of the DCIS lesion may alternatively be defined by biomarkers that are differentially expressed in the "palpable" lesions. In order for a tumor to be palpable its mechanical properties must be increased with respect to the surrounding tissue. This increase in the factors such as stiffness can be accomplished by an increase in the content of structural ECM proteins as well as by an increase in the degree of the crosslinking of the structural ECM proteins.

Tumors are characterized by extracellular matrix (ECM) remodeling and stiffening. Ductal carcinoma in situ arises overwhelmingly in dense regions of the breast (Ursin et al., 2005). Importantly, areas of increased breast density are associated with significantly increased fibrillar collagen deposition (Guo Y P, Martin L J, Hanna W, Banerjee D, Miller N, Fishell E et al. (2001). Growth factors and stromal matrix proteins associated with mammographic densities. Cancer Epidemiol Biomarkers Prey 10: 243-248; Alowami S, Troup S, Al-Haddad S, Kirkpatrick I, Watson P H. (2003). Mammographic density is related to stroma and stromal proteoglycan expression. [Breast Cancer Res 5: R129-R135; Li T, Sun L, Miller N, Nicklee T, Woo J, Hulse-Smith L et al. (2005)]. The association of measured breast tissue characteristics with mammographic density and other risk factors for breast cancer. [Cancer Epidemiol Biomarkers Prey 14: 343-349.]. High tissue density is associated with a greater risk for invasive breast carcinoma [Habel et al., 2004; Gill et al., 2006]. This is consistent with the identified increased risk for palpable DCIS masses to have a recurrence of (and/or be associated with subsequent) invasive cancer.

Breast tumorigenesis is accompanied by collagen crosslinking, ECM stiffening, and increased focal adhesions. Elevated deposition of fibrillar collagen, the most abundant ECM protein in the stroma, has been particularly associated with an altered stroma during breast tumorigenesis, correlating with increased mammographic density and greater breast cancer risk [Provenzano et al., 2006]. It has been demonstrated that induction of collagen crosslinking stiffened the ECM. Unconfined compression and rheological testing in the MMTV-Neu model mouse model showed an incremental stiffening of the mammary gland as it transitioned from normal to premalignant to invasive cancer and demonstrated that the stromal tissue adjacent to the invading epithelium was also substantially stiffer than normal. Total levels and amount of fibrillar collagen increased markedly as it transitioned from normal to premalignant to invasive cancer. [Kandice R. Levental, Matrix Crosslinking Forces Tumor Progression by Enhancing Integrin Signaling, Cell, Volume 139, Issue 5, 25 Nov. 2009, Pages 891-906] Thus, increased collagen-matrix density increases matrix stiffness to promote an invasive phenotype.

Collagen crosslinking could account for the dramatic ECM remodeling and stiffening, as was demonstrated by an increase in the levels of the major reducible bifunctional collagen crosslinks, dehydrodihydroxylysinonorleucine (DHLNL), and hydroxylysinonorleucine (HLNL) in the breast tumors, reflecting elevated crosslinked collagen. [Kandice R. Levental, Matrix Crosslinking Forces Tumor Progression by Enhancing Integrin Signaling, Cell, Volume 139, Issue 5, 25 Nov. 2009, Pages 891-906]. Therefore the phenotype of a palpable DCIS lesion can be characterized by one or more of the following factors, increased collagen content, increased fibrillar collagen levels, increased collagen crosslinking levels as measured by increased levels of major reducible bifunctional collagen crosslinks, dehydrodihydroxylysinonorleucine (DHLNL), and hydroxylysinonorleucine (HLNL). [Kandice R. Levental, Matrix Crosslinking Forces Tumor Progression by Enhancing Integrin Signaling, Cell, Volume 139, Issue 5, 25 Nov. 2009, Pages 891-906]

An alternative to characterizing the mechanical changes characterizing a palpable DCIS lesion is to identify factors which are associated with or induce the mechanical changes. LOX is an amine oxidase crosslinking enzyme is an extracellular copper dependent enzyme catalyzing lysine-derived cross-links in extracellular matrix proteins. Increased levels of LOX have been detected in the stromal cells during premalignant tumorgenesis. LOX protein expression is elevated in many types of tumors, is associated with poor prognosis, and is shown to be involved in recruiting inflammatory stromal cells that contribute to tumor progression (Erler et al., 2009 J. T. Erler, K. L. Bennewith, T. R. Cox, G. Lang, D. Bird, A. Koong, Q. Le and A. J. Giaccia, Cancer Cell 15 (2009), pp. 35-44). Therefore a palpable DCIS lesion or its inferred risk may alternatively be characterized by an increased level of LOX.

In some embodiments, these additional biomarkers include biomarkers for at least one of the following: collagen, inflammatory markers, fibronectin, IGF-1, IGFBP-3, Tenascin, PM-1, MMP-2, major reducible bifunctional collagen crosslinks, dehydrodihydroxylysinonorleucine (DHLNL), and hydroxylysinonorleucine (HLNL), and LOX. In some embodiments, this includes the genus of structural proteins, such as those listed above.

Assessing Biomarker Expression

A variety of techniques can be used to assay the expression of a biomarker to denote if it is positive or negative, including those identified herein.

In some embodiments, expression is measured by assessing levels of mRNA (or cDNAs derived therefrom). In other embodiments, expression is measured by assessing protein levels. In some embodiment, expression levels are determined using antibodies.

In some embodiments, for any given biomarker, a sample or tissue is said to be "positive" or "negative" for the marker, based on its relative expression to a control sample. In some embodiments, the expression level of a biomarker is scored by evaluation of a tissue sample labeled with a capture agent. In some embodiments, the capture agent comprises an antibody protein. In such embodiment, an antibody protein is used to label the tissue sample. The antibody protein can be detected by any method known to one of skill in the art, including those set forth herein. In some embodiments, the antibodies are detected using labeled secondary antibodies. In some embodiments, the method includes use of mouse antibodies. A secondary anti-mouse antibody can be used to detect mouse antibodies that have bound. The anti-mouse antibody can be labeled directly or indirectly. In some methods, a variety of known antibody proteins can be used, including commercially available antibody proteins.

For example, the presence of the following proteins was assessed using the indicated mouse monoclonal antibodies: for estrogen receptor (ER) using antibody 1D5 (DAKO, Carpentria, California), for progesterone receptor (PR) using antibody 1A6 (Novocastra, Bannockburn, Illinois), for Ki67 antigen [MKI67 (FHA domain) interacting nucleolar phosphoprotein] using a 1:100 dilution of antibody MIB-1 (DAKO), for p53 (TP53) using a 1:200 dilution of antibody PAb 1801 (Neomarkers, Fremont, California), for human epidermal growth factor receptor-2 (ERBB2) using a 1:200 dilution of antibody TAB250 (Invitrogen, Grand Island, New York), for cyclo-oxygenase-2 (COX-2) using a 1:200 dilution of antibody M3617 (DAKO), and for p16 (cyclin-dependent kinase inhibitor 2A) using a 1:200 dilution of antibody MS218 (Neomarkers) (21, 22). Staining with primary antibodies can be followed by staining with biotinylated labeled secondary antibodies and detection with an avidin biotin complex-HRP system. Specimens can be counterstained with hematoxylin.

For any biomarker, expression levels can be compared in a sample from a subject with a control sample. A control sample can be a cell, tissue, or protein sample. For example, positive and negative control tissues were used for assessment of each marker as follows: ER, breast tumor case and cell line MCF-7; PR, breast tumor case and cell line T47D; Ki67, breast tumor case; p53, colon tumor case and cell line T47D; ERBB2, breast tumor case and cell line SKBR3; COX-2, a DCIS case; and p16, normal breast tissue and colon tumor.

In some embodiments, a sample is deemed "positive" for a biomarker expression when its expression is present in a higher level than a negative control sample or at a level similar to a positive control sample.

In some embodiments, a sample can be scored as "positive" if a certain percentage of cells within the sample are stained with a capture agent, or a certain percentage of cells are stained with a certain intensity with a capture agent. Conversely, in some embodiments, a sample is deemed "negative" when it is present at a comparable level to a negative control sample or less than a positive control sample. In some embodiments, a sample is deemed "negative" if the number of cells staining or staining above a certain intensity level is less than a defined threshold of intensity. Staining intensities can be assessed by one of skill in the art. A positive control sample is a tissue or other sample that is known to express the biomarker. A negative control sample is a tissue or other sample that is known to express the biomarker at a reduced level or not at all. "Positive" can indicate either the presence of a biomarker or overexpression of a biomarker relative to a defined level. Similarly, "negative" with respect to a biomarker can indicate either the absence of the biomarker or a reduced level compared to a defined level. The defined levels can be absolute amounts (e.g., the percentage of cells staining with a particular antibody protein) or can be relative amounts (e.g., higher expression than a control sample). In some embodiments, the defined level is the median level of staining for a set of tumor cells.

When using antibodies as capture agents to detect protein biomarkers, the staining of the antibodies can be assessed in different ways known to one of skill in the art. Assessments can be made by an individual or individuals, in some cases a pathologist, or by an automated image detection and processing system, or by a human-aided image processing system. In some embodiments, the staining is assessed by observing the percentage of cells (or a subset thereof) stained or stained above a certain threshold in a sample with an antibody against a biomarker. An increase of more than, less than, or between, about 5%, about 10%, about 15%, about 20%, or about 25% can be used to indicate that a tissue is "positive" for the biomarker. In one some embodiments, the percentage of cells within a sample (or a subset thereof) that are stained with an antibody or stained above a certain intensity level must by at least 10% for the lesion considered "positive" for that marker. In some embodiments, the percentage of cells stained must be at least about 25% to be considered "positive" for that marker. The threshold for determining a "positive" expression level will vary based on the biomarker being studied. Conversely, in one embodiment, a "negative" expression level is determined when the percentage of cells stained with antibody or stained below a certain threshold is about 5%, about 10%, about 15%, about 20%, or about 25% (including ranges between any two of the preceding values and below any preceding value.

For example, in some embodiments, for p53, ERBB2, ER, and PR, the percentage of tumor cells that show staining of any intensity can be estimated and recorded. The marker p53 can be considered to be overexpressed, and ER and PR can be considered to be present or "positive" when greater than 5%, greater than 10%, greater than 15% or greater than 20% of the cells in a sample showed staining. In some embodiments, ER and PR can be considered "positive" when 10% or more of the cells in a sample stain with a biomarker specific antibody. In some embodiments, scoring of p16 can be evaluated on a scale of 0, 1, 2, or 3 based on the percentage of positively staining tumor cells, irrespective of staining intensity (0=no staining, 1=<25% of cells stained, 2=25% to 75%, 3=>75%) (22). In some embodiments, a sample is considered positive for p16 if at least 10% of the cells are stained, for example at least 10%, 20%, 25%, or 30% (including any range above any of the preceding values and any range defined between any two of the preceding values) of the cells in the sample were stained with an anti-p16 antibody. In some embodiments, tissues with a stained percentage of greater than or equal to about 25% can be considered to overexpress or be "positive" for p16.

In some embodiments, a sample is categorized as ERBB2 positive if greater than about 10% or more the cells in a lesion are moderately or strongly stained with an ERBB2 specific antibody. For example, if 10, 20, 30, 40, 50, 60 percent or more of the cells are stained for ERBB2, the sample can be considered positive. In some embodiments, a sample is categorized as ERBB2 negative if less than about 10% or more the cells in a sample are moderately or strongly stained with an ERBB2 specific antibody. For example, if 1, 2, 3, 4, 5, 6, 7, 8, or 9 percent or less (of any of the preceding values) of the cells are stained for ERBB2, the sample can be considered negative.

In some embodiments, expression is scored by first assessing the intensity of staining with an antibody protein. The percentage of cells staining above a certain threshold of intensity can be used to set a threshold for a "positive" versus a negative expression score. The percentage can be compared to positive and/or negative controls.

In some embodiments, COX-2 staining can be evaluated on a scale of 0, 1, 2, or 3, with each value corresponding to a combination of two Allred classes (0=Allred class 0; 1=Allred classes 2, 3 and 4; 2=Allred classes 5 and 6; 3=Allred classes 7 and 8. Cells can be considered positive that have an Allred class of 2 or greater, 3 or greater, 4 or greater, 5 or greater, 6 or greater, 7 or greater or 8. Allred score is a 0-8 scale based upon the sum of a proportion score and intensity score. Allred proportion score is defined as 0=no staining, 1=<1% staining, 2=1-10% staining, 3=11-33% staining, 4=34-66% staining, 5=>66% staining. Allred intensity score is derived from average staining throughout the lesion and is defined as 0=no staining, 1=low intensity staining, 2=medium intensity staining, 3=high intensity staining. In some embodiments, tissues with a score of greater than or equal to 2 (Allred classes 5 and 6 or higher) can be considered to overexpress COX-2. In such an embodiment, the quantity and intensity of staining is assessed qualitatively. In some embodiments, when COX-2 is assessed as a dichotomous variable, negative COX-2 is defined as a score of 0 or 1 and positive COX-2 is defined as a score of 2 or 3.

In some embodiments, tissues can be considered to have high or "positive" Ki67 expression if more than 10% of tumor cells are stained, which can be more than the median value for all tumors evaluated.

Use or Exclusion of Clinical and/or Histopathological Characteristic Data in Estimating Risk In some embodiments, one can use or exclude various clinical and/or histopathological characteristics in estimating a risk that a subsequent event (DCIS and/or invasive tumor) will occur. In some embodiments, the clinical and/or histopathological characteristics are selected from the group of: nuclear grade of the DCIS, family history, age at diagnosis, menopausal status, race/ethnicity, oral contraceptives, postmenopausal hormone therapy, body mass index, tumor size, necrosis type, quantity of necrosis, cell polarity, Architectural growth pattern, calcification, and any combination thereof.

In some embodiments, the methods of risk assessment are particularly useful for the assessment of risk of a subsequent DCIS event after surgery to remove a DCIS from the subject. Unlike some risk assessment methods, in some embodiments, the method of risk assessment can be performed without grading the tumor according to pathology grading schemes. In some embodiments, clinical and/or histopathological data can be (or not be) analyzed in addition to the biomarkers to assess the risk category of a subject. For example, if a subject has had surgery to remove a DCIS lesion, the disease free margins of the tumor can be used with the cell signature to assess the risk of DCIS recurrence.

In some embodiments, the method by which the DCIS was detected (e.g., palpation vs. mammography) is used in estimating the risk that a subject will develop a subsequent invasive cancer event (see, e.g., Table 10). However, in some embodiments, tumor size is not greater in DCIS lesions detected by palpation and those detected by mammography among women who have a subsequent invasive or DCIS event (7.5 mm vs. 9 mm for invasive cases; 7.6 mm vs. 10.8 mm for DCIS cases, and 9.6 mm vs. 8.1 mm for controls, respectively). In some embodiments, tumor size is not an independent predictor of subsequent invasive cancer or DCIS (Kerlikowske, et al, JNCI, 2003). In some embodiments, nuclear grade is not an independent risk factor associated with subsequent invasive cancer or DCIS when molecular markers are in the model, Table 10. Comedo type can be more prevalent among mammographically detected lesions (44%) than lesions detected by palpation (24%) (P=0.002).

In some embodiments, those factors indicated as significant (being above the referent) in Tables 8, 9, and/or 10 can be included in estimating a risk for each of (or both) the subsequent events (DCIS and/or invasive). The factors that are indicated as significant can be included together or individually, or any combination thereof between the 3 tables. In some embodiments, those factors (in Tables 8, 9, and/or 10) that are indicated as not being significant (not being above referent) are not included in a method (and can be specifically excluded from any of the methods described herein). In some embodiments, one or more of the following: tumor size, margins, nuclear grade, and/or quantity of necrosis can be examined or considered for estimating a risk of a subsequent DCIS event.

Surprisingly, in some embodiments, the methods can be used without any clinical and/or histopathological characteristic information. In some embodiments, the placement of the subject into a risk category does not include the use of analysis of the grade of the DCIS lesion. In some embodiments, the placement of the subject into a risk category depends only on a single clinical and/or histopathological characteristic. In some embodiments, the single clinical and/or histopathological characteristic is the disease free tumor margin. Tumor free margins can be determined by one of skill in the art. For example, DCIS slides that are hematoxylin-eosin-stained slides can be assessed to determine margin width of a DCIS lesion. Margins can be measured as a distance in millimeters of disease-free tissue surrounding a tumor that has been removed surgically, for example, in a lumpectomy.

In some embodiments, Margins can be categorized into different distance categories to allow for risk analysis. For example, margins measured in millimeters can be grouped into categories of: uncertain, having malignant or diseased tissue within one millimeter, having greater than about 1 mm of disease free tissue, having between about 1 mm and about 10 mm of disease free tissue, and having greater than about 10 mm of disease free tissue. As described herein, the smaller the margin, generally, the higher the subject's risk of DCIS recurrence. Patients having a disease free margin of greater than or equal to 10 mm, can be placed in a low risk category (with 2.8% five year risk of recurrence (and/or subsequent DCIS) and about 4.4% eight year risk of DCIS recurrence (and/or subsequent DCIS)) without inclusion of any cell signature information related to biomarkers. Inclusion of the margin information also can be used in conjunction with the biomarkers to determine which risk category to place a subject. Additional risk estimates are described in Table 12.

In some embodiments, the placement of the subject into a risk category does not include one or more of the following: the use of analysis of the grade of the DCIS, family history, age at diagnosis, menopausal status, tumor size, tumor necrosis, multifocality, and any combination thereof. In some embodiments, the estimation of a risk of a subsequent DCIS or invasive cancer event does not include one or more of the factors outlined in Table 8 or 10 for the specified DCIS or invasive cancer event. In some embodiments, those histopathological factors indicated in Table 8 as being significant are included in a risk estimate, while those that are not significant (tumor size for DCIS and invasive cancer, nuclear grade for invasive, necrosis type for DCIS and invasive cancer, and quantity of necrosis for invasive cancer) are excluded for the process. The same applies to age of subject at diagnosis (Table 10), and nuclear grade which can be excluded from both invasive and DCIS risk evaluations in some embodiments (Table 10).

Multiple Risk Categories

In some embodiments, the subject is placed into one of at least three risk categories, wherein the at least three risk categories comprise a first risk category of DCIS recurrence, a second risk category of DCIS recurrence, and a third risk category of DCIS recurrence, wherein the risk of DCIS recurrence for the first category is lower than the risk of DCIS recurrence for the second category, and wherein the risk of DCIS recurrence for the second category is lower than the risk of DCIS recurrence for the third category. According to such methods, the first risk category can indicate a lowest risk of recurrence, the third risk category indicates a highest risk of recurrence, and the second risk category can indicate an intermediate level of risk relative to the first and second risk categories. In some embodiments, the second risk category is divided into at least two subgroups, a first subgroup having a low risk of recurrence and a second subgroup having an intermediate risk of recurrence that is intermediate to the low risk of recurrence and the highest risk of recurrence. In each case, the category definitions will depend on the biomarkers used for the cell signature, and the results of the cell signature.

Certain cell signatures for the DCIS lesion can be used to place a subject into a risk category. In some embodiments, if the tumor is ER positive, ERBB2 negative, and Ki67 negative, the subject falls within the first or low risk category. As discussed above, the cell signature also can include clinical and/or histopathological characteristic data such as the margin of a tumor. If the DCIS lesion is ER positive, ERBB2 negative, and Ki67 negative, and the DCIS lesion has a margin of 1 mm or greater that is disease free, the subject falls within the first or low risk category. If the tumor is a) ER negative, ERBB2 positive, and Ki67 positive, or b) p16 positive, Ki67 positive, and COX-2 negative, the subject falls within the third (or highest) risk category. A subject with a DCIS lesion having a cell signature for those biomarkers will be placed in the third or highest risk category, and if the tumor has a margin of 1 mm or greater that is disease free, the subject also falls within the third risk category.

In some embodiments, if the subject's tumor is either a) ER negative and ERBB2 negative, b) p16 positive and Ki67 positive, c) COX-2 negative and Ki67 positive, d) COX-2 positive or Ki67 positive, or e) ERBB2 positive and ER positive the subject falls within the first subgroup (low risk) of the second risk category. If the subject's tumor has one of these cell signatures, the subject will remain in the first subgroup of the second risk category (the lower risk category), if the tumor has a margin of 1 mm or greater that is disease free. However, in some embodiments, if the tumor is a) ER negative and Ki67 positive or b) ER negative and ERBB2 positive, the subject falls within the second subgroup (intermediate risk) of the second risk category. If the tumor has such a cell signature, and has positive or uncertain margins, the subject falls within the second subgroup of the second risk category.

Treatment Options and Treatments

In some embodiments, the invention includes the step of recommending and/or performing an appropriate treatment for a subject based on the risk category of the subject with respect to either a subsequent DCIS event or risk of subsequent invasive cancer. For example, for patients in a high risk group, mastectomy can be recommended. Other treatments including chemotherapies, immunotherapies, and x-ray treatments can be recommended depending on the risk category of the subject. As discussed, herein, a subject also can be recommended for monitoring or no additional treatment. In some embodiments, the methods also include treating the subject based on such recommendation.

In some embodiments, the risk categorization methods are applied to subjects who have not undergone any treatment for the DCIS lesion. In such embodiments, the methods of the invention can be applied to a biopsy from the DCIS lesion. When such a patient is categorized as a high risk patient, the methods can include recommending a lumpectomy procedure to remove the DCIS lesion. In one embodiment, the methods include performing a lumpectomy on the subject. When the risk categorization places a subject in a high risk group for the development of subsequent invasive cancers, the methods can include recommending mastectomy. In one embodiment, the methods include performing a mastectomy on the subject.

Methods of Categorizing Risk of Subsequent Invasive Cancers

In some embodiments of the invention, a method for categorizing a risk that a subject that has Ductal Carcinoma in situ (DCIS) will have a subsequent tumor event is provided. In some embodiments, a cell signature from a subject (e.g., a DCIS sample from a subject) for at least one of a group of biomarkers is obtained or provided. The biomarkers are selected from at least the following: COX-2, Ki67, and p16, or some combination thereof. In some embodiments, the biomarkers include p16. In some embodiments, the biomarkers include each of COX-2, Ki67 and p16. In some embodiments, the biomarkers consist essentially of COX-2, Ki67 and p16. The subject then can be placed into a into a risk category for a subsequent tumor event based upon the analysis of the cell signature for the group of biomarkers. The subsequent tumor event can include an invasive cancer. The subject then can be placed into a specific risk category for an invasive cancer.

According to some embodiments, the subject is placed into one of at least two risk categories for risk of subsequent invasive cancer. In some embodiments, the subject is placed into one of at least three categories of risk of subsequent tumor. In some embodiments, the subject is placed into one of four categories of invasive cancer.

In some such embodiments, the subject is placed into a category based on particular cell signatures from the tissue being analyzed. In some embodiments, four risk categories are established, a first risk category (lowest risk), a second risk category (low risk), a third risk category (intermediate risk) and a fourth risk category (high risk). In some embodiments, certain cell signatures can be used to place the subject within a risk category. For example, a subject can be placed in the first category with respect to the risk of invasive cancer, where the DCIS sample is Ki67 negative, COX-2 negative, and p16 negative. In such an embodiment, a subject whose DCIS sample is Ki67 negative and b) any of: COX-2 positive, p16 positive, or COX-2 and p16 positive, is placed within the second category. Also in such an embodiment, a subject whose DCIS sample is Ki67 positive and either a) COX-2 positive, b) p16 positive, or c) COX-2 negative and p16 negative, is placed within the third category. Also in such an embodiment, a subject whose DCIS sample is p16 positive, Ki67 positive, and COX-2 positive, is placed within the fourth category.

Methods of Categorizing Risk of Subsequent Invasive Cancers and DCIS Recurrence

In some embodiments, a method for categorizing a risk that a subject that has Ductal Carcinoma in situ (DCIS) will have a subsequent tumor event is provided. In some embodiments, the methods of the invention can be used to categorize a patient's risk both of a subsequent DCIS event and a risk of invasive cancer. In some embodiments, a cell signature from a subject for at least one of a group of biomarkers is obtained, wherein the biomarkers comprise at least the following: COX-2, Ki67, p16, erb-B2, and ER. In some embodiments, cell signature is determined for at least two, at least three, at least four, or each of COX-2, Ki67, p16, erb-B2, and ER. In some embodiments, the biomarkers consist essentially of COX-2, Ki67, p16, erb-B2, and ER. In some embodiments, the biomarkers are selected from the following: COX-2, Ki67, and p16, or some combination thereof. In one embodiment, the biomarkers include p16. In some embodiments, the biomarkers include each of COX-2, Ki67 and p16. In some embodiments, the biomarkers consist essentially of COX-2, Ki67 and p16.

The subject then can be placed into a into a risk category for a subsequent tumor event based upon the analysis of the cell signature for the group of biomarkers. The subsequent tumor event can be an invasive cancer or a subsequent DCIS event. The subject then can be placed into a specific risk category for an invasive cancer and/or for a subsequent DCIS event.

In some embodiments, the subject is placed into a category based on particular cell signatures from the tissue being analyzed. For example, in some embodiments, four risk categories are established, a first risk category (lowest risk), a second risk category (low risk), a third risk category (intermediate risk) and a fourth risk category (high risk). In such embodiments, certain cell signatures can be used to place the subject within a risk category. For example, a subject can be placed in the first category with respect to the risk of invasive cancer, where the subject's tissue is Ki67 negative, COX-2 negative, and p16 negative. In such an embodiment, a subject whose tissue is Ki67 negative and b) any of: COX-2 positive, p16 positive, or COX-2 and p16 positive, is placed within the second category. Also in such an embodiment, a subject whose tissue is Ki67 positive and either a) COX-2 positive, b) p16 positive, or c) COX-2 negative and p16 negative, is placed within the third category. Also in such an embodiment, a subject whose tissue is p16 positive, Ki67 positive, and COX-2 positive, is placed within the fourth category. In such an embodiment, the risk of invasive cancer for the first category is lower than the risk of invasive cancer for the second category, and the risk of invasive cancer for the second category is lower than the risk of invasive cancer for the third category, and the risk of invasive cancer of the third category is lower than the risk of invasive cancer in the fourth category. The various categories can be combined in any combination. For example, risk categories one and two could be combined to leave three remaining risk categories. Similarly, the first three risk categories can be combined to give a "not high risk" category, and the fourth category could remain as a "high risk" category. Further, additional categories can be added.

In some embodiments, the subject also can be placed into a risk category for DCIS recurrence. In such an embodiment, if the subject's tissue is ERBB2 negative and Ki67 negative, then the subject falls (or is placed) within the first category. If the subject's tissue is a) ER negative and ERBB2 negative, b) p16 and Ki67 positive, c) COX-2 negative and Ki67 positive, d) COX-2 positive and Ki67 positive, or e) ERBB2 positive and ER positive, then the subject falls within the second category. If the subject's tissue is a) ER negative and Ki67 positive or b) ER negative and ERBB2 positive, then the subject falls within the third category. If the subject is a) ER negative, ERBB2 positive, and Ki67 positive, or b) p16 positive, Ki67 positive and COX-2 negative, then the subject falls within the fourth category. In such embodiments, the risk of DCIS recurrence for the first category is lower than the risk of DCIS recurrence for the second category, wherein the risk of DCIS recurrence for the second category is lower than the risk of DCIS recurrence for the third category, and wherein the risk of DCIS recurrence of the third category is lower than the risk of DCIS recurrence in the fourth category. The various categories can be combined in any combination. For example, risk categories one and two could be combined to leave three remaining risk categories. Similarly, the first three risk categories can be combined to give a "not high risk" category, and the fourth category could remain as a "high risk" category. Further, additional categories can be added.

In one embodiment, the method includes recommending a removal step. For example, when the subject is in the fourth category of risk (high risk) for DCIS, the recommendation is appropriate for reducing the chance of DCIS recurrence. If the subject is in the fourth category of risk for invasive cancer, the recommendation is appropriate for reducing the chance of invasive cancer. In some embodiments, recommendations include, for example, lumpectomy and mastectomy. If a subject is in the fourth or high risk category for invasive cancer, a recommendation can include mastectomy. In some embodiments, if a subject is a high risk for subsequent DCIS, the recommendation may include lumpectomy. If the subject has previously undergone a lumpectomy of the tissue for which a cell signature is analyzed, a recommendation can include mastectomy in some embodiments or can include a lumpectomy in some embodiments.

In some embodiments, a subject placed in the first the first category of risk of invasive cancer would have a five year risk of invasive cancer of less than, greater than, or between about 4%, about 3%, about 2%, and about 1%. In some embodiments, the five year risk of invasive cancer for the first risk category is 2.1% (with a 95% CI of 1.9 to 2.6). In some embodiments, a subject placed in the first risk category would have an eight year risk of invasive cancer of less than, greater than, or between about 6%, about 5%, about 4% and about 3%. In some embodiments, the eight year risk of invasive cancer for the second subgroup of the second risk category is 4.1% (with a 95% CI of 3.4 to 5.0).

In some embodiments, a subject placed in the second category of risk of invasive cancer would have a five year risk of invasive cancer of less than, greater than, or between about 5%, about 4%, about 4%, and about 2%. In some embodiments, the five year risk of invasive cancer for the second risk category is 4.4% (with a 95% CI of 4.0 to 5.0). In some embodiments, a subject placed in the first risk category would have an eight year risk of invasive cancer of less than, greater than, or between about 7%, about 6%, about 5% and about 4%. In some embodiments, the eight year risk of DCIS recurrence for the second subgroup of the second risk category is 6.9% (with a 95% CI of 6.1 to 8.0).

In some embodiments, a subject placed in the third category of risk of invasive cancer would have a five year risk of invasive cancer of less than, greater than, or between about 8%, about 7%, about 6%, and about 5%. In one embodiment, the five year risk of invasive cancer for the third risk category is 7.7% (with a 95% CI of 7.0 to 8.5). In some embodiments, a subject placed in the third risk category would have an eight year risk of invasive cancer of less than, greater than, or between about 13%, about 12%, about 11%, about 10% and about 9%. In one embodiment, the eight year risk of DCIS recurrence for the second subgroup of the second risk category is 11.5% (with a 95% CI of 10.3 to 12.8).

In some embodiments, a subject placed in the fourth category of risk of invasive cancer would have a five year risk of invasive cancer of less than, greater than, or between about 16%, about 15%, about 14%, about 13%, and about 12%. In some embodiments, the five year risk of invasive cancer for the fourth risk category is 14.1% (with a 95% CI of 13.1 to 15.3). In some embodiments, a subject placed in the third risk category would have an eight year risk of invasive cancer of less than, greater than, or between about 22%, about 21%, about 20%, about 19% and about 18%. In some embodiments, the eight year risk of DCIS recurrence for the second subgroup of the second risk category is 19.6% (with a 95% CI of 18.0 to 21.3).

Assay Kits for Risk Assessment

In some embodiments, the invention provides assay kits for detecting a risk that a subject having DCIS will experience at least one of the following: a subsequent DCIS event, invasive breast cancer, no subsequent cancer event, or some combination thereof. In one embodiment, such a kit includes reagents for determining a mammary epithelial cell signature, wherein the signature comprises a collection of measurements of at least five characteristics of the mammary epithelial cell (and/or, in some embodiments, stroma markers) said at least five characteristics selected from one or more of the following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism, and wherein said reagents determine at least the following: COX-2, Ki67, p16, ERBB2, and ER. In one embodiment, the kit essentially consists of reagents to determine COX-2, Ki67, p16, ERBB2, and ER. In some embodiments, the kit consists essentially of reagents to determine COX-2, Ki67, p16, ERBB2, and PR. In one embodiment, the kit essential consists of reagents to determine COX-2, Ki67, p16, ERBB2, ER and PR.

In some embodiments, kits can utilize specific binding agents or capture agents as described herein. For example, antibodies can be used to detect at least the expression of COX-2, Ki67, p16, ERBB2 and ER. For example, antibodies can be used to detect at least the expression of COX-2, Ki67, p16, ERBB2 and PR. For example, antibodies can be used to detect at least the expression of COX-2, Ki67, p16, ERBB2 and PR. In some embodiments, the antibodies are provided in a multiplex format, including, for example, on a chip, plate or microfluidic system. In such embodiments, the expression level of protein can be detected for a variety of biomarkers at the same time or on the same chip, plate or system. Kits also can include probes or other reagents for determining the expression of mRNA or cDNA for at least COX-2, Ki67, p16, ERBB2 and ER. In some embodiments, kits also can include probes or other reagents for determining the expression of mRNA or cDNA for at least COX-2, Ki67, p16, ERBB2 and PR. Kits also can include probes or other reagents for determining the expression of mRNA or cDNA for at least COX-2, Ki67, p16, ERBB2 ER and PR. Kits also can include secondary antibody proteins and labels to visualize the staining of samples.

In some embodiments, kits can be for general use or can be specific for a particular type of tissue sample. For example, a kit may be developed for formalin fixed paraffin embedded histology samples. Such samples are often archived for patients. In another embodiment, the kit is designed to assay biopsy samples that have not been fixed.

In some embodiments, kits also can contain a control sample or control samples for analyzing the markers relative to expression in the control sample or samples. In some embodiments, different control samples are provided for two or more of the biomarkers.

Reports

In some embodiments, methods of making medical reports related to the risk of recurrence in a subject are provided. In some embodiments, a biological sample is provided from the subject. In some embodiments, the method also involves determining a mammary epithelial cell signature for the biological sample, wherein the signature comprises a collection of measurements of at least two characteristics of the mammary epithelial cell, said at least two characteristics selected from one or more of following: presence and/or level of a protein; and presence and/or level of a mRNA; presence and/or level of a posttranslationally modified polypeptide; presence of a chromatin modification; presence and/or level of a sequence of DNA; presence and/or level of a microRNA; integrity of a nucleic acid; methylation status of a nucleic acid; secretion and/or release of a factor; and alteration in a metabolism. In some embodiments, the cell signature is compared with a mammary epithelial cell signature of a control sample or control samples, and a risk of breast cancer is then determined.

In some embodiments, a report can be generated related to the risk of breast cancer. The report is typically a written report. It can be in electronic format or paper format. The report can include a percentage risk for a subject's risk of DCIS recurrence, invasive cancer, no subsequent cancer, or a combination of both. In some embodiments, the report can include a category of risk, such as "lowest risk", "low risk" "intermediate risk" or "high risk" or other combined categories. For example, a report could indicate only "high risk" or "not high risk" with respect to any or all of a patient's risk of DCIS recurrence, invasive cancer, no subsequent cancer, or a combination of both.

Reports also can include treatment recommendations based on the assessment of risk. In some embodiments, the report also will include background information to assist the recipient of the report in interpreting the risk data presented on the report. Such background information can include medical or other scientific publications.

In some embodiments, the reporting method is practiced by an analytical or pathology laboratory. The report can be sent to a physician, to a subject or to another health care provider, including, for example, a health maintenance organization, physician practice group, or insurance company.

In some embodiments, the clinical and/or histopathological characteristics that can be part of the analysis for risk estimation or categorization for FIGS. 25-28 can include alternative clinical and/or histopathological characteristics. In some embodiments, one or more of the Van Nuys Prognostic indicator ("VNPI") factors (i.e., one or more of age, necrosis, nuclear grade, and/or margin) is used in place of the "margin" option as indicated in FIGS. 25, and 27-28 in determining the risk of a subsequent DCIS event. Thus, in some embodiments, rather than including margin in determining risk of a subsequent DCIS event (as outlined in Example 5B and Table 12 for example), one or more of the following are used: age, necrosis, and/or margin. In some embodiments, instead of margins for DCIS, Van Nuys index could be used. In some embodiments, the embodiments depicted in FIGS. 25-28 allow one to predict the risk of invasive cancer separately from the risk of a subsequent DCIS event. As will be appreciated by one of skill in the art, this represents an improvement over previous VPI uses, which only addressed DCIS and did not predict invasive cancer. In some embodiments, the full VNPI index is not predictive of subsequent invasive cancer (HR 1.0; 95% CI 0.8 to 1.2) when substituted for age, while palpation and Ki67-positive/p16-positive/COX-2-positive lesions remains predictive (HR 2.7, 95% CI 1.3 to 5.5) of subsequent invasive cancer. In some embodiments, the full VNPI index is predictive for DCIS when substituted for age, margins and nuclear grade (HR 1.5, 95% CI 1.1 to 2.1) and Estrogen-negative/HER2-positive/Ki67-positive (HR=4.2 (95% CI 1.9 to 8.5) and Ki67-positive/p16-positive/COX-2-negative (HR 4.0, 95% CI 1.9 to 8.5) remain predictive of subsequent DCIS.

In some embodiments, progesterone receptor negative can be substituted for estrogen receptor negative/HER2-positive/Ki67-positive and be an independent predictor of a subsequent DCIS event [Progesterone-negative/HER2-positive/Ki67-positive has a HR=4.0 (95% CI 1.6-10.3)]. However, in some embodiments, the association is not as strong as with Estrogen-negative/HER2-positive/Ki67-positive (HR=5.8 (95% CI 2.4 to 14). Thus, in some embodiments, Estrogen-negative/HER2-positive/Ki67-positive, is a superior predictor of subsequent DCIS event.

In some embodiments, the population of subjects selected for screening is done by selecting those at risk of developing DCIS and/or breast cancer. In some embodiments, the subject that one or more of the described embodiments is performed upon is identified as a subject having DCIS. In some embodiments, this can be detected via palpation and/or mammography. In some embodiments, the subject is identified as a subject at risk of developing cancer based upon family history or another set of biomarkers. In some embodiments, the subject is excluded from treatment if there are indications that the subject will not benefit from it. For example, in some embodiments, if the subject has atypical hyperplasia (e.g., as described in "p16 Expression and Breast Cancer Risk in Women with Atypical Hyperplasia, M. Santistenban et al.) the subject is excluded from the screening process. In some embodiments, any one or more of the subject classes excluded from Example 5B can also be excluded from the method.

DCIS

Ductal carcinoma in situ (DCIS) has become a relatively common diagnosis (1, 2), yet the clinical and biologic significance of DCIS lesions is not fully understood. It appears that 5 to 10% of women diagnosed with DCIS who are treated by lumpectomy alone develop a subsequent invasive cancer within 5 years, and a similar proportion develops a subsequent DCIS lesion (3-7). Adjuvant radiation and tamoxifen have been shown to decrease the rate of subsequent tumors (3, 8, 9), but not to influence breast cancer mortality (4-6, 10-12).

Clinical trials and population-based studies have failed to consistently identify which women will be at high vs. low risk of subsequent invasive cancer among those diagnosed with DCIS (10, 13), thereby creating a dilemma for physicians in choosing the intensity of their treatment (14). Identification of biomarkers that can accurately predict subsequent invasive cancer and/or DCIS could aid in stratifying an individual's risk for subsequent tumors. A few studies have examined biomarkers including the estrogen receptor (ER), progesterone receptor (PR), human epidermal growth factor receptor-2 oncoprotein (HER2/neu, a.k.a. ERBB2), human epidermal growth factor receptor-4 oncoprotein (HER4/neu), Ki67, and cyclooxygenase (COX-2) as predictors of subsequent tumors in women diagnosed with DCIS, but the results have been inconsistent (15-20). These studies were based primarily on follow-up of non-population-based case series of women in whom DCIS had been managed with a variety of treatment modalities, making it difficult to know whether the results were a function of biomarkers, or treatment, or both. In addition, most of the studies were small, conducted at a single institution, had short length of follow-up, tested only individual markers, and did not stratify by type of subsequent tumor. These study design restrictions limit the ability of published results to be generalized.

One result of the study presented in Example 5B was to identify clinical, histopathological, and molecular characteristics of initial DCIS lesions that are associated with subsequent invasive cancer or DCIS. A large population-based cohort of women with DCIS who were treated by lumpectomy alone was studied to determine risk of subsequent disease as a function of these factors.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Markers Associated with Pre-Cancerous ("Variant") Mammary Epithelial Cells

Figure 1:
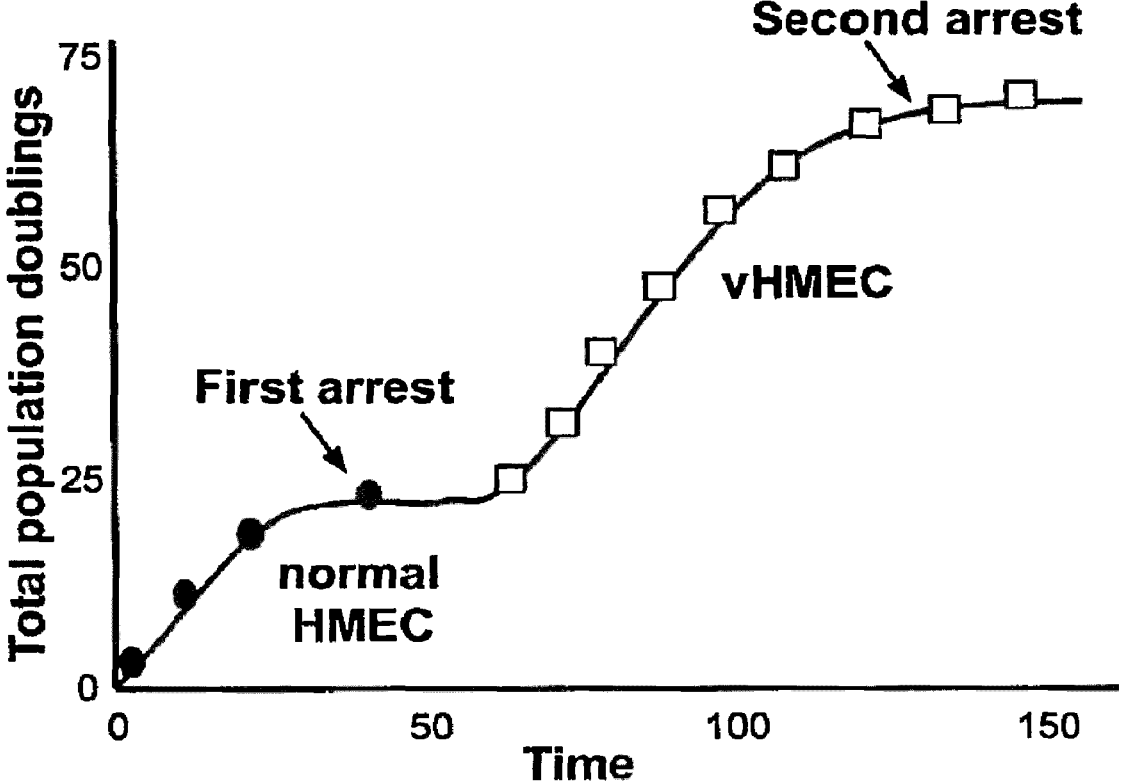
FIG. 1 is a growth curve of normal human mammary epithelial cells (HMEC) and variant human mammary epithelial cells (vHMEC).

Breast cancer affects one out of eight women in the U.S., and it is the second leading cause of cancer deaths in U.S. women. This work focused on understanding the early events of breast cancer development; specifically, events that can cause normal cells to transition to cancer cells. A model culture system of growing normal mammary epithelial cells (HMEC) was employed to identify molecular events leading to early transformation. When normal human mammary epithelial cells (HMEC) are grown in serum-free conditions in vitro, majority of the cells enter a growth arrest after 10 to 20 population doublings. However, a subpopulation of the cells, "variant" HMEC (vHMEC), continues to grow for an additional 30 to 50 population doublings when the bulk of the normal HMEC are arrested (FIG. 1). All vHMEC grown from women of various ages, parities, and genetic backgrounds share silencing of p16$^{INK4a}$ expression via promoter-hypermethylation. p16$^{INK4a}$ is a key cyclin-dependent kinase (CDK) inhibitor that inhibits CDK4/6-cyclinD activity, and which activity is needed to phosphorylate RB thereby allowing cells to pass through the G1/S phase of the cell cycle. Loss of p16$^{INK4a}$ activity has been found in 31 percent of all human breast cancers and loss of p16$^{INK4a}$ confers many characteristics associated with malignancy in vHMEC. p16$^{INK4a}$ loss in vHMEC is sufficient to induce centrosome dysfunction leading to genomic abnormalities and it also results in hypermethylation of HOXA9 transcriptional regulatory region and silencing of HOXA9 expression which may be preventing vHMEC from undergoing normal differentiation. Moreover, vHMEC contain a subpopulation of cells that express high levels of cyclooxygenase-2 (COX-2). The presence of COX-2 provides several "hallmarks" of cancers to vHMEC, such as resistance to apoptosis, increase chemo-attraction, motility, and invasion that may lead to initiation of angiogenesis. COX-2 overexpression has been shown to be sufficient to induce mammary tumors in mice. Cells with silenced p16INK4A via promoter hypermethylation exist in normal mammary tissue and that COX-2 overexpressing cells overlap in areas of tissues containing p16$^{INK4a}$-silenced cells.

It was hypothesized that vHMEC exist in normal mammary tissue and that these cells are likely candidates to be breast cancer precursors in vivo. To test this hypothesis, expression micro-array analysis comparing vHMEC vs. HMEC was performed. From the micro-array analysis, 26 potential cell surface markers were screened that may distinguish vHMEC from normal HMEC via fluorescent activated cell sorting (FACS). Markers were identified that facilitate the prospective isolation of a subpopulation of cells from normal mammary reduction tissues having extended growth characteristics which phenocopies cultured vHMEC.

Figure 2:
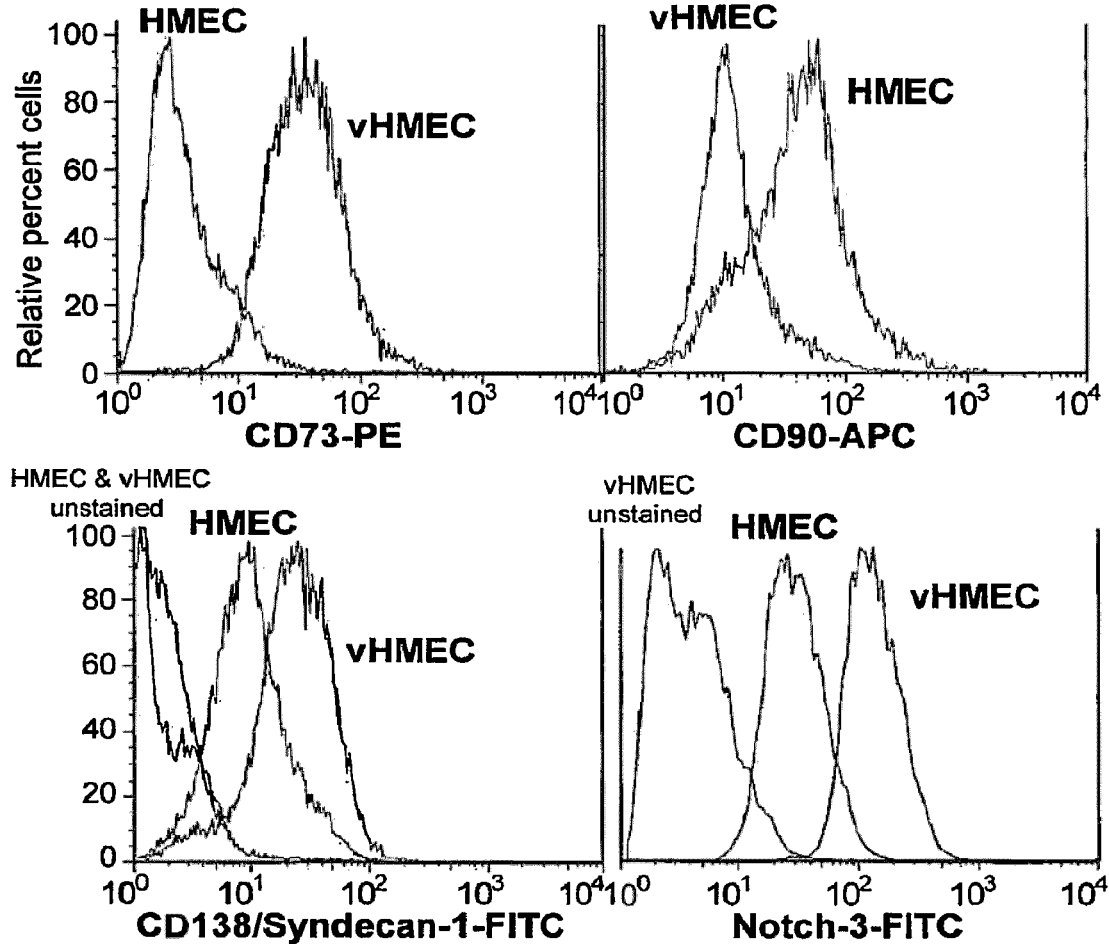
FIG. 2 depicts fluorescence activated cell sorting (FACS) analysis of CD73, CD90, CD138, and Notch receptor-3 expression on vHMEC and HMEC cells.

FIG. 2. Marker expression on vHMEC and HMEC A) FACS analysis profiles of CD73, CD90, CD138, and Notch receptor-3 expression on vHMEC (blue) and HMEC (green) is shown. Cultured vHMEC and HMEC from mammary reductions were trypsinized to single cells incubated with anti-CD73-PE, -CD90-APC, CD138-FITC, and -notch receptor-3-FITC antibodies and analyzed by FACS. Immunocytochemistry of vHMEC and HMEC with anti-CD73 and anti-CD90 antibodies. Cells were grown on coverslips, fixed and stained with anti-CD73 and -CD90 antibodies followed by anti-mouse-FITC secondary antibodies and fluorescent signal was visualized by confocal microscopy. Cell nuclei were stained with Hoechst dye (blue) and CD73 and CD90 expression shown in green. Cell distribution of vHMEC (blue) and HMEC (green) co-stained with anti-CD73 and -CD90 antibodies. Cultured vHMEC and HMEC from mammary reductions were trypsinized to single cells, incubated with anti-CD73-PE and -CD90-APC antibodies and analyzed by FACS.

Figure 3:
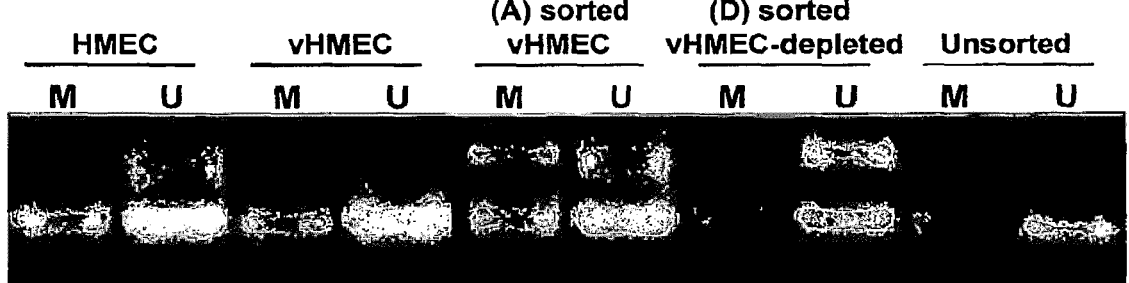
FIG. 3 depicts p16$^{INK4a}$ promoter methylation status in HMEC and vHMEC cells.

FIG. 3. p16$^{INK4a}$-promoter methylation specific PCR (p16 MSP) indicated that cells in the CD73$^+$CD90$^-$ (vHMEC) population exhibited p16$^{INK4a}$ promoter hypermethylation, whereas p16$^{INK4a}$ promoter methylation was not detected in the CD73$^-$CD90$^+$ (vHMEC-depleted) or unsorted population. Cells that were sorted as indicated previously were cultured for 10 to 22 days, trypsinized, and frozen as pellets. Genomic DNA was extracted from cells, bisulfate treated, and subjected to p16 MSP. M represents a PCR reaction using p16-promoter-methylation specific PCR primers, and U represents a PCR reaction using unmethylated promoter PCR primers.

Figure 4:
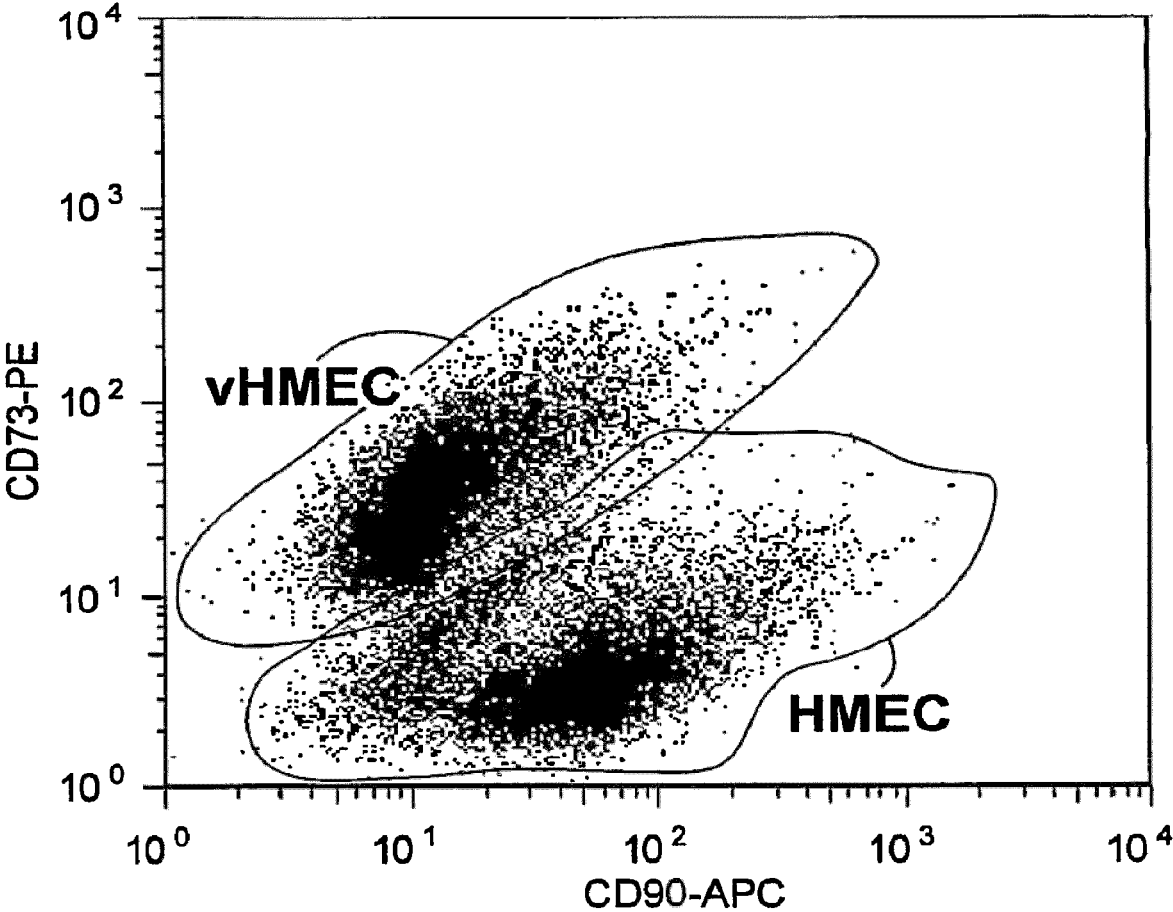
FIG. 4 depicts isolation of CD73$^+$CD90$^-$ vHMEC from disease-free mammary reduction tissue.

FIG. 4. Isolation of vHMEC from disease-free mammary reduction tissues: Mammary reduction tissues were digested to single cells and cells were incubated with anti-CD73-PE and -CD90-APC antibodies and subjected to FACS. Scatter plot representing total cell population and the gates used to isolate the designated subpopulations are shown. Cells were first gated for small cells based on forward and side scatter, and small cells were further separated by designated gates as shown. Percentage of cells sorted from each population is as indicated. Cells exhibited extended growth resided in CD73$^+$CD90$^-$ (vHMEC), whereas CD73$^-$CD90$^+$population (vHMEC-depleted) entered a proliferation plateau within a short period of time.

Figure 5:
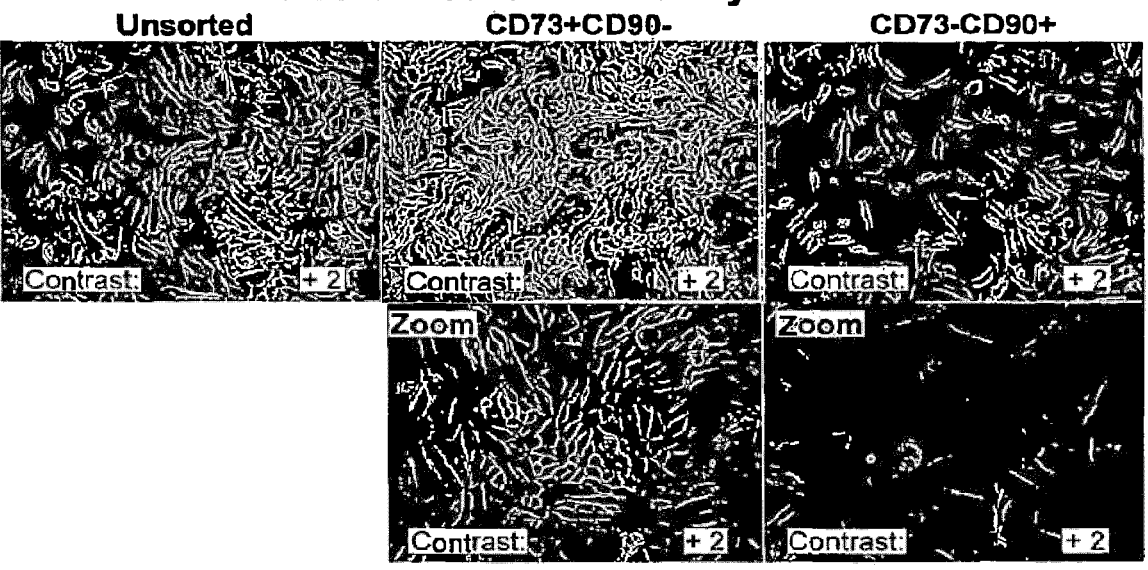
FIG. 5 depicts unsorted HMEC, CD73$^+$CD90$^-$ vHMEC, and CD73$^-$ CD90$^+$ HMEC from mammary reduction tissue, cultured in vitro.

FIG. 5. Cells that were sorted based on the gates as shown in FIG. 4 were grown in culture, and growth curves of the sorted cells are shown. Total population doublings were determined after every passage of the cells. Phase contrast pictures of sorted CD73$^+$CD90$^-$ and CD73$^-$CD90$^+$ cells are shown. After 16 days of culturing CD73$^+$CD90$^-$ cells remained small shiny and continued to grow, whereas CD73$^-$CD90$^+$ cells were large, flat, vacuolated, and appeared senescent.

Figure 6:
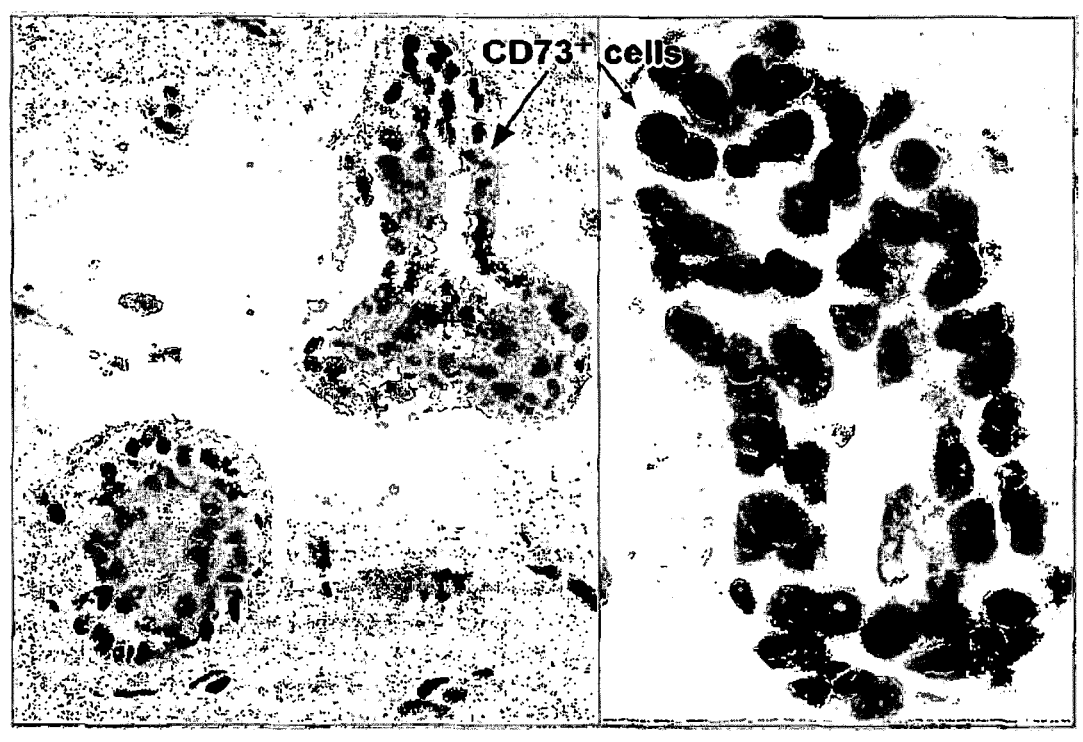
FIG. 6 depicts paraffin-embedded section of normal mammary tissue stained with anti-CD73 antibody.

FIG. 6. CD73 positive cells are predominantly located at the basal region. Paraffin-embedded sections of normal mammary tissue were stained with anti-CD73 antibody. Cells expressing CD73 are brown, whereas CD73 negative cells are light blue. Arrows indicate sample areas that contain CD73 positive cells. The right panel is a magnified area of the same tissue section as the left panel.

The data indicate that: 1) variant HMEC (vHMEC) can be distinguished by markers CD73$^{high}$ CD138$^{high}$ Notch Receptor-3$^{high}$ and CD90$^{low}$; 2) CD73$^+$CD90$^-$ cell population isolated from normal mammary reduction tissues have vHMEC growth characteristics, whereas CD73⁻CD90⁺ population is devoid of vHMEC; and 3) normal HMEC can acquire vHMEC growth characteristics by reducing p16 expression.

Example 2

Abrogated Stress Response Distinguishes Basal-Like Tumors and DCIS with Worse Prognosis

Material and Methods

Cells and cell culture. Human mammary epithelial cells (HMEC) and variant HMEC (vHMEC) were isolated from reduction mammoplasties (RM) of multiple individuals RM13, RM 15, RM16, RM18, RM21. Cells were propagated in modified MCBC 170 media (MEGM, BioWhittaker) as previously described ((Hammond, Ham et al. 1984; Romanov, Kozakiewicz et al. 2001)). All experiments were conducted with exponentially growing HMEC between population doublings 7 to 10, and exponentially growing mid-passage vHMEC between population doublings 20 to 34. Non-tumorigenic immortalized 184A1 breast cells were a kind gift from M. Stampfer (Lawrence Berkeley National Laboratories). Breast cancer cell lines T47D, SKBr3, BT549 and MDA-MB-231 were obtained from the ATCC.

DNA constructs. DNA constructs used in this study are as follows: pMSCV, pMSCV-shp16 (G. Hannon and S. Lowe, Cold Spring Harbor Laboratories); pLXSN, pLXSN-HPV16 E7 (D. Galloway, Fred Hutchinson Cancer Center); pMKO, pMKO-shRb (W. Hahn, Harvard Medical School and Dana-Farber Cancer Institute), pBabe; pBabe-cyclin D1 (O. Tetsu, UCSF Cancer Center), pBabe, pBabe-hTert (K. Collins, UC-Berkeley); LXSP and LXSP-COX-2 (D. Dixon, Vanderbilt University Medical Center). All constructs were packaged in Phoenix A cells for viral propagation. To generate stable cell lines we exposed HMEC, vHMEC or breast cell lines to viral supernatant containing 8 µg/ml Polybrene (Sigma). Cells containing stable DNA integration were selected in medium containing 4 µg/ml puromycin (pMSCV, pMKO, and LXSP constructs), 50 µg/ml G418 (LXSN constructs) or 20 µg/ml hygromycin (pBabe). Where indicated, cell lines were imaged using a standard phase contrast microscopy.

Western Blot. Total protein (15-20 µg) lysates were electrophoretically separated by SDS-PAGE and transferred onto polyvinylidene difluoride (PVDF) membranes according to standard procedures. Antisera against COX-2 (160107; Cayman Chemical, MI), Rb (554136, BD Pharmingen), p16 (16P07 Neomarkers), E2F1 (sc-251 Santa Cruz), cyclinD1 (2926, Cell Signaling), p53 (sc-126, Santa Cruz), p21 (SC-6246 Santa Cruz) were used according to manufacturers protocols.

Tumor samples. The primary gene expression analyses were performed on a cohort of 130 primary breast cancers from UC San Francisco and California Pacific Medical Center. Details of this cohort have been previously described. (Chin, DeVries et al. 2006) Raw microarray data and additional sample information is available (e.g., available on the Internet at http:// followed by cancer.lbl.gov/ breastcancer/data.php). Paraffin-embedded tumor samples corresponding to 61 of the 130 cases were obtained with Institutional Review Board approval and analyzed by immunohistochemistry.

Gene expression profiling analyses The 130 UCSF/ CPMC CEL files were background adjusted and normalized using RMA Express (available on the Internet at http:// followed by rmaexpress.bmbolstad.com/). Nearest centroid determination was performed using BRB Arraytools (available on the Internet at http:// followed by linus.nci.nih.gov/ BRB-ArrayTools.html). Hierarchical clustering analyses were performed using Cluster 3.0 (available on the Internet at http:// followed by bonsai.ims.u-tokyo.ac.jp/~mdehoon/ software/cluster/software.htm) on median-centered log expression values using Pearson correlation and centroid linkage. Clustered data was visualized using Java Treeview (on the Internet at http:// followed by jtreereview.sourceforge.net/).

Derivation of molecular subtypes The recently defined 1300-gene "Intrinsic/UNC" gene set, derived from Agilent Human oligonucleotide platform data was cross-referenced to Affymetrix U133A to derive an intrinsic set for these studies. A subset of 1090 genes from the intrinsic/UNC genes represented on the U133A platform were additionally filtered for top 20% of variability within the 130 tumor set. This analysis resulted in 589 unique genes that are intrinsically variable and available for this analysis.

Molecular subtype classification was also determined through a nearest centroid based classifier. Hu et. al. derived a subset of 306 intrinsic genes that are conserved across microarray platforms. 297 of these genes are represented on the U133A platform. Based upon the 297-subset of training data available on the Internet (at http:// followed by genome.unc.edu/pubsup/breasttumor) a nearest centroid class prediction analysis was performed on the 130 tumor samples with leave-one-out cross validation and probability calculated using the Bayesian Analog of Compound Covariate Predictor.

Pre-malignant samples. We analyzed a series of archival paraffin-embedded normal breast tissue specimens from reduction mammoplasties (n=47), tissue containing atypical ductal hyperplasia (n=33) and ductal carcinoma in situ (n=70). The DCIS samples comprise a subset of a large population-based cohort study among women in the San Francisco Bay Area diagnosed with DCIS and treated by lumpectomy alone between 1983 and 1996. This patient population was followed for an average of 12.4 years. All tissue was acquired with Institutional Review Board approval from the surgical pathology laboratory of the University of California, San Francisco and California Pacific Medical Center. Patients were identified through anonymous reference numbers in accordance with federal guidelines.

Tissue Preparation and Immunohistochemistry. Five-micron sections cut from formalin-fixed paraffin embedded tissue blocks were deparaffinized and rehydrated following standard protocol. After incubation with hydrogen peroxide, slides were microwaved in 1 mM EDTA, pH8, for antigen retrieval. Nonspecific protein binding was blocked with horse serum (Vectstain Elite ABC kit, Vector Labs). Sections were incubated with antisera against COX-2 (Dako M3617, 1/200), p16 (Neomarkers MS218, 1/150), Ki67 (Dako M7250, 1/80) overnight at 4° C. Antigen-antibody complexes were labelled using the Vectastain Elite ABC and following standard protocol (Vector Laboratories, CA) and visualised using 2.5% 3-amino-9-ethyl-carbazole in 50 mM acetate buffer pH5, with 0.05% hydrogen peroxide. Sections were counterstained in Mayers hematoxylin mounted in Crystal Mount (BMM02, American Mastertech). Once dry the sections were permanently mounted with a glass coverslip using clearmount (MMCLE1, American Mastertech).

Evaluation of immunohistochemistry staining. All staining was evaluated by light microscopy after examination of the entire slide and without knowledge of the patients' clinical information. Estimation of COX-2 protein expression was determined by COX-2 staining intensity on a 0, 1, 2, 3 scale (0— no staining, 1—weak; 2—moderate; 3—strong staining). p16 immunostaining was also scored on a 0, 1, 2, 3 scale based on the extent of immunopositive cells (0— no staining; 1—<25% nuclear and/or cytoplasmic staining; 2—26-80% nuclear and/or cytoplasmic staining; 3—>80% nuclear and/or cytoplasmic staining). Where indicated for both COX-2 and p16, high immunostaining reflects specimens that have a score of ≥2. Ki67 immunostaining was determined by manually counting immunopositive nuclei among a minimum of 1000 total nuclei in an average of three fields of view. Where indicated high Ki67 immunopositivity reflects specimens that contain a minimum of 10% of nuclei positive for Ki67.

Statistical analysis. Chi-square tests were used to test for associations between p16, COX-2, Ki67, nuclear grade and combinations therein with subsequent tumor development among women with DCIS. IMP-In statistical package (SAS Institute) was used for all analyses.

A Cox Proportional Hazards Model stratified by year of diagnosis was used to study the ability of four markers (grade and expression of Cox2, p16 and Ki67) to predict recurrence during follow-up. Controls were matched to cases by year of diagnosis. There were too few cases and controls for several of the years of diagnosis, so years were grouped as shown in Table 1 for the stratified analyses. First we analyzed that biomarkers separately and then in combinations of two factors. There were too few cases to warrant finer breakdowns of combinations of factors. Results are expressed as Hazard Ratios, which take time to recurrence, for cases, and follow-up time for controls into account.

TABLE 1

| Years of recurrent diagnosis were grouped to stratify analysis | | | |
|---|---|---|---|
| year of dx | non-recur | recur | group |
| 1983 | | 1 | 1 |
| 1984 | 3 | 1 | 1 |
| 1985 | 6 | 1 | 1 |
| 1986 | 3 | 2 | 2 |
| 1987 | 5 | 4 | 2 |
| 1988 | 3 | 5 | 3 |
| 1989 | 4 | 3 | 3 |
| 1990 | 10 | 5 | 4 |
| 1991 | 3 | 8 | 5 |
| 1992 | 2 | 1 | 6 |
| 1993 | 1 | 3 | 6 |
| 1994 | 1 | 1 | 6 |
| 1995 | 1 | | 6 |
| 1996 | 3 | 2 | 6 |

Results
Determination of Risk for Subsequent Tumor Events in Women Diagnosed with DCIS and Treated with Lumpectomy Alone.

One goal was to evaluate potential predictive characteristics and their association with outcome in a population-based cohort of women in the San Francisco Bay Area diagnosed with DCIS between 1983 and 1996 and treated by lumpectomy alone. Similar to rates reported by others (Fisher et al SemOnco12001; Cornfield et al. 2004 Cancer; Bijker et al 2006JC0), ~25% of these women exhibited a subsequent tumor event within 10 years after surgical lumpectomy without additional therapy. In this study, a subsequent tumor event (also termed disease recurrence) was defined as a subsequent DCIS lesion or invasive cancer lesion diagnosed in the ipsilateral breast at least 6 months following the initial diagnosis of DCIS. In a previous study, 3 characteristics of DCIS lesions were found that were each associated with a higher risk for subsequent tumor development (Kerlikowske et al, 2003). These DCIS lesions were (1) detected in younger women (<50 years of age) (2) detected by palpation or (3) exhibited positive surgical margins. None of these characteristics provided a positive predictive value of more than 60%.

In the present study a subset of this population-based cohort (38 controls and 32 cases) was used, followed for an average 12.4 years, to evaluate novel pathways that identify women that have an increased risk of developing subsequent tumor events (both DCIS and invasive cancer). These samples are a representative subset of the larger DCIS cohort previously described (Kerlikowske et al, 2003). The biological features that characterize DCIS lesions that portend a better or worse prognosis and improve the predictive power of defined biomarkers was examined.

Histologic markers, such as nuclear grade, were the first to be examined in this cohort. Similar to previous findings (Silverstein et al. 1995 Lancet; Barnes et al, 2000JP; Bijker et al, 2001 BrjC; Kerlikowske et al. 2003; Millis et al BJC2004), DCIS of high nuclear grade significantly increases the risk of developing a subsequent tumor event and inversely correlates with recurrence-free survival (HR 5.6, 95% CI 1.2 to 25.5, P=0.025 for high grade DCIS. However, although nuclear grade statistically stratifies a subpopulation of women with increased risk for a subsequent tumor event, a substantial fraction of women with high nuclear grade DCIS (36%, 9/25) do not develop subsequent disease. Likewise, 25% of women with low grade DCIS (3/12) experience subsequent disease. In other words, high nuclear grade has a positive predictive value of 64% and low nuclear grade has a negative predictive value of 75%.

Figure 7:
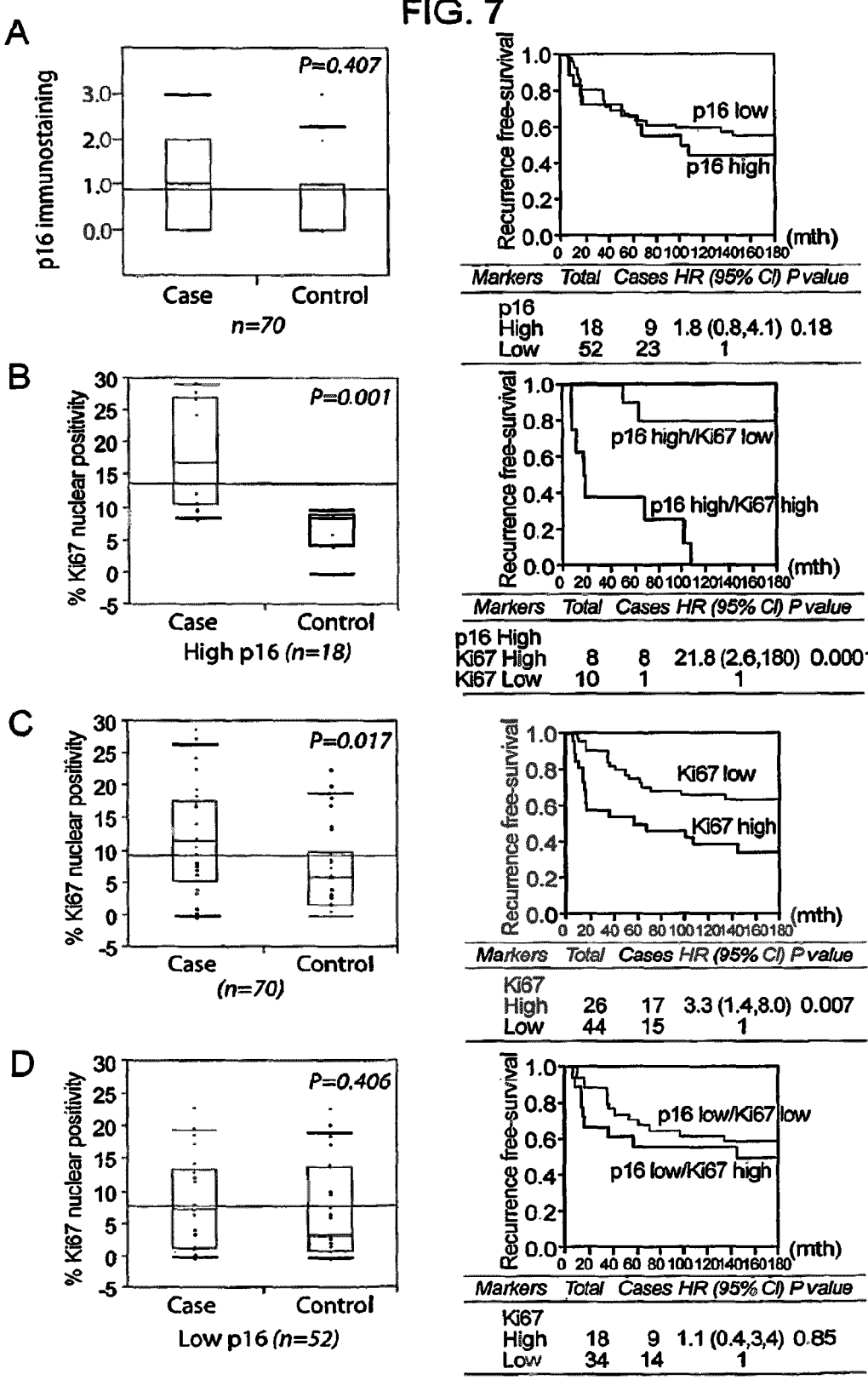
FIGS. 7A-D depict correlation of p16 overexpression, coupled with proliferation, with increased risk of subsequent tumor events among women with ductal carcinoma in situ (DCIS).

To date, few molecular markers have been found that adequately predict which of the women initially diagnosed with DCIS have an increased risk of developing a subsequent tumor event. One of the first molecular markers that were considered in this study for risk stratification is a marker for proliferative index, Ki67. The level of Ki67 immunostaining was determined by manually counting immunopositive nuclei in a minimum of 1000 nuclei in an average of three fields of view. High Ki67 immunopositivity reflects specimens that contain a minimum of 10% of nuclei positive for Ki67. Similar to previous findings (Ringberg et al 2001; Barnes et al 2005; ClinCancerRes; Wilson et al 2006 BrJCancer;) examining the role of Ki67 measured as a single variable in modifying risk, it was found that high Ki67 significantly stratifies women that develop a subsequent tumor (DCIS and invasive combined; P=0.011; Table 2) and predicts a reduced recurrence-free survival (HR 3.3, 95% CI 1.4 to 8.0, P=007; FIG. 7C) as compared to those that do not. However, a high proliferative index has a positive predictive value of 65% and a low proliferative index (Ki67 in less than 10% of nuclei) has a negative predictive value of 65%.

TABLE 2

| Marker | n | Control | Case | P-value |
|---|---|---|---|---|
| p16 | 70 | | | |
| High | | 50% (9/18) | 50% (9/18) | 0.672 |
| Low | | 56% (29/52) | 46% (23/52) | |
| p16 High | 18 | | | |
| Ki67 High | | 0% (0/8) | 100% (8/8) | <0.001 |
| K67 Low | | 90% (9/10) | 10% (1/10) | |
| p16 Low | 52 | | | |

TABLE 2-continued

| Marker | n | Control | Case | P-value |
|---|---|---|---|---|
| Ki67 High | | 50% (9/18) | 50% (9/18) | 0.542 |
| Ki67 Low | | 59% (20/34) | 41% (14/34) | |
| Ki67 | 70 | | | |
| High | | 35% (9/26) | 65% (17/26) | 0.011 |
| Low | | 66% (29/44) | 34% (15/44) | | p16 staining intensity with a score >2 is considered positive,
Ki67 positive cases exhbited >10% nuclei immunopositivity.
P-values were determined using Pearson Chi-quare test.

Deregulation of p16/Rb Increases the Risk of Subsequent Tumor Events Among Women Diagnosed with DCIS.

A well-recognized barrier to carcinogenesis is the induction of a senescent cellular response. Activated p16 signalling is a hallmark of the senescent cellular response pathway that induces a growth arrest in response to various cellular stressors such as genotoxic, oxidative, oncogenic or metabolic stress (see Mooi & Peeper, 2006; Schmitt, 2003; Collado & Serrano, 2005; Campisi, 2005). This response is believed to be a crucial mechanism for controlling unchecked proliferation by limiting the propagation of damaged cells. One would predict that DCIS lesions expressing markers that are activated during a senescent cellular response, such as increased p16 expression, would be associated with fewer subsequent tumor events.

To determine if expression of this tumor suppressor pathway in DCIS lesions provides mechanistic insight about subsequent tumor events, 70 samples of DCIS were stained for p16 expression by immunohistochemistry, Immunostaining was scored on a 0, 1, 2, 3 scale where a score of 0 or 1 was considered low staining and a score of 2 or 3 was considered high. It was found that 26% (18/70) of DCIS lesions show high p16 staining (FIG. 7A, Table 3). This p16 immunopositivity is not associated with any clinicopathological variables such as nuclear grade or hormone receptor status (Table 3). Cases positive for p16 staining displayed moderate to intense p16 staining in the epithelium with varying degrees of lobular heterogeneity. At one extreme, a minority of cases, 28% (5/18) exhibited intense p16 staining in virtually all epithelial cells. The remaining p16 positive cases (13/18) exhibited heterogeneous immunopositivity in 26% to 80% of epithelial cells. The surrounding stromal compartment in a fraction of cases (10%) also exhibited p16 staining, primarily confined to fibroblasts surrounding cystic ducts. One would predict that high p16 expression induces a cellular growth arrest, and thus DCIS lesions overexpressing p16 would represent lesions that do not develop a subsequent recurrent disease. This prediction was not substantiated. It was found that high p16 expression did not significantly stratify women at increased risk for developing a subsequent tumor event (DCIS and invasive cancer combined; FIG. 7A, Table 3). Furthermore, high p16 expression demonstrated no correlation with nuclear grade (Table 3).

Paradoxically, overexpression of p16 can represent two different biological processes; a response to cellular stress (Mooi & Peeper, 2006; Schmitt, 2003; Collado & Serrano, 2005; Campisi, 2005)) or abrogation of functional Rb signalling (Serrano et al 1993; Nature; Bates S et al 1994 Oncogene; Parry et al 1995 EMBO;). Interestingly, inactivation of key Rb members leads to the upregulation of p16 due to unobstructed negative feedback regulation. The presence of proliferation can distinguish between these two situations. A cell that has maintained functional p16/Rb signalling will experience stress-induced overexpression of p16 that will cause a proliferative arrest characteristic of cellular senescence. On the other hand, a cell that has compromised the pRb pathway will experience a regulatory-induced over expression of p16 and can disregard the many stress signals that induce senescence and cellular arrest thereby allowing unimpeded proliferation and bypass of senescence.

Since high p16 expression can reflect two opposing phenotypes that can be distinguished by proliferation, serial sections were stained for Ki67. 37% (26/70) and 63% (44/70) of the lesions within this cohort express high and low Ki67, respectively. Almost half (8/18) of DCIS lesions exhibiting high p16 levels also show high Ki67 index labelling (Table 2). It was determined if this phenotype, representing deregulated p16/Rb signaling, identifies DCIS with worse prognosis. The analysis demonstrated that all women with DCIS that show high p16 and high Ki67 develop a subsequent tumor (Table 2) and thus Ki67 significantly stratifies high p16 expressing lesions in women who develop a subsequent breast cancer (Wilcox on rank test; P=0.001, FIG. 7B) as compared to those that do not. Consequently, it was calculated that women with DCIS that exhibit high p16 and high Ki67 have a substantially increased risk of developing a subsequent tumor (HR=21.8, 95% CI, 2.6 to 180; P=0.0001; FIG. 7B) as compared to women with lesions that show high p16 and low Ki67 labelling. In fact, DCIS lesions that show high p16 and low Ki67 index labelling identify benign lesions (90%, 9/10 are non-recurrent samples; Table 2). Therefore, proliferation is an obligate qualifier of p16 because the presence or absence of high Ki67 in lesions that show high p16 expression dictates their risk for developing subsequent disease (Wilcoxon rank test; P=0.426; FIG. 7D, Table 2). Moreover, women with DCIS that exhibit low p16 irrespective of Ki67 do not have a differential risk of developing recurrent disease (HR=1.1, 95% CI, 0.4 to 3.4; P=0.85). The high Ki67/high p16 phenotype is weighed toward higher grade lesions, such that 75% (6/8) are high grade DCIS and the remaining 25% (2/8) are intermediate grade (Table 3). Strikingly, lesions expressing high Ki67/high p16 phenotype exhibit a positive predictive value of 100% and lesions expressing a low Ki67/high p16 phenotype have a negative predictive value of 90%.

TABLE 3

| | n | p16+ | COX-2+ | Ki67+ | p16+/Ki67+ | COX-2+/Ki67+ | p16+/COX-2+/Ki67+ |
|---|---|---|---|---|---|---|---|
| ALL DCIS | | 26% (18/70) | 56% (39/70) | 37% (26/70) | 11% (8/70) | 26% (18/70) | 9% (6/70) |
| Nuclear Grade | | | | | | | |
| Low | 12 | 25% (3/12) | 67% (8/12) | 0% (0/12) | 0% (0/12) | 0% (0/12) | 0% (0/12) |
| Intermediate | 32 | 22% (7/32) | 34% (11/32) | 25% (8/32) | 6% (2/32) | 13% (4/32) | 6% (2/32) |
| High | 26 | 31% (8/26) | 77% (20/26) | 69% (18/26) | 23% (6/26) | 54% (14/26) | 15% (4/26) |
| P-value | | 0.742 | 0.004 | <0.001 | 0.046 | 0.003 | 0.013 | p16 and COX-2 staining intensity with a score >2 is considered positive, Ki67 positive cases exhibited >10% nuclei immunopositivity.
P-values were determined using Pearson Chi-quare test.

FIGS. 7A-D. p16 overexpression coupled with proliferation increases the risk of subsequent tumor events among women with DCIS. High p16 staining (immunopositivity score of ≥2) fails to stratify women with DCIS that develop subsequent disease (case versus control). Kaplan-Meier estimates of recurrence-free survival demonstrate that women with DCIS staining high or low for p16 immunopositivity develop subsequent disease at the same rate. Box plots and corresponding P-values were determined using Wilcoxon/Kruskal-Wallis rank of sums test (shown in FIG. 7A). DCIS lesions high for p16 immunostaining and elevated Ki67 significantly stratify women that develop subsequent breast cancer from those that do not develop recurrent disease. Recurrence-free survival among women with DCIS that exhibit high p16 and high Ki67 (>10% of nuclei positive for Ki67) is significantly reduced compared to lesions that are high p16/low Ki67 (shown in FIG. 7B). Active proliferation measured by elevated Ki67 index labeling significantly stratifies women with DCIS that develop recurrent disease. DCIS with elevated Ki67 identifies women with decreased recurrence-free survival and increased risk for developing a subsequent tumor. Ki67 positivity was determined by counting a minimum of 1000 nuclei, with a score of >10% Ki67 nuclear staining considered positive (shown in FIG. 7C). DCIS lesions with low p16 immunostaining irrespective of Ki67 labelling do not have a differential risk of developing subsequent disease (shown in FIG. 7D). FIG. 7E depicts the immunohistochemistry staining for p16. Staining was scored on a 0, 1, 2, 3 scale with a score of ≥2 considered positive.

These data demonstrate that high p16 expression stratifies DCIS into two clinically significant populations. One population shows high p16 expression in presence of active proliferation, indicating deregulated p16/Rb signalling, and identifies DCIS lesions with worse prognosis. The second population shows high p16 in the absence of proliferation, indicating functional p16/Rb signaling, and identifies DCIS lesion with good prognosis. Interestingly, the tumor events that develop subsequent to DCIS with high p16 and high Ki67 are more often diagnosed as invasive breast cancer (62%). These data predict that the association of high p16 levels with a high Ki67 index will be well-represented in invasive cancers and that the association of high p16 levels with a low Ki67 index will be underrepresented in invasive cancers (since this phenotype is postulated to be a barrier to carcinogenesis). To test this prediction, invasive cancers were examined for the distribution of p16 overexpression and high Ki67 as a coupled phenotype.

High p16 mRNA Levels Defines the Basal-Like Subtype of Invasive Cancers

Previous reports have demonstrated that ipsilateral tumors that develop subsequent to DCIS share many histological and genetic alternations with the primary lesion (Millis et al. 2004 BrJCancer; Bijker et al 2001 BrJCancer;). For example, primary high grade DCIS is associated with the development of recurrent high grade DCIS or high grade invasive carcinoma. High concordance of genetic alterations demonstrated by loss of heterozygosity or comparative genomic hybridization between primary DCIS and subsequent recurrences also suggest a clonal relationship ((Lininger, Park et al. 1998; Waldman, DeVries et al. 2000). Given our finding that all DCIS lesions expressing high p16 and a high Ki67 index are followed by subsequent tumor formation and that these lesions are weighed toward invasive disease, one might predict that this phenotype would be reflected in invasive carcinomas.

To explore the subtype distribution of p16 overexpression, gene expression profiles of 130 primary invasive breast tumors were examined using Affymetrix U133A derived oligonucleotide microarray data generated at our institution (Chin et al, 2006). Recent studies have defined distinct molecular subtypes that display an intrinsic heterogeneity with prognostic significance for invasive cancers. Molecular subtypes were derived based upon a nearest centroid approach using molecular subtype training data as previously defined (see Materials and Methods) (Hu, Fan et al. 2006). Unsupervised clustering of these 130 samples with a set of intrinsically variable genes identifies luminal A, luminal B, normal-like, ERBB2 positive and basal-like clusters.

It was found that increased p16 mRNA preferentially characterizes the highly proliferative basal-like tumor subtype. The expression of the p16 gene is increased in the majority of basal-like tumors with 81% of basal-like samples showing p16 mRNA levels greater than 1.5-fold above the median. In addition, it was found that high p16 expression falls within a gene cluster comprised of many well-established basal-like genes, such as keratin 5, 17, SFRP5, and MMP-7. In keeping with the expected biology, the basal-like sample cluster that expresses high p16 mRNA is enriched for tumors with relatively low levels of Rb and cyclin D1 mRNA. Increased cyclin D1 levels were found to be most consistently elevated in the luminal B subtype.

To confirm the reproducibility of the observed differential subtype specificity of p16/Rb/Cyclin D1, gene expression levels in four publicly available datasets from three different platforms were analyzed. In each case, tumors with overexpression of p16 were consistently found to be classified as basal-like tumors. The low transcript levels of both Rb and cyclin D1 were also enriched in the basal-like tumor subtype.

These data demonstrate that transcriptional upregulation of p16 is a characteristic feature of highly proliferative basal-like tumors. Taken together with the observation that Rb transcript levels are among the lowest in this subgroup this suggests that loss of functional p16/Rb signalling may play a defining role in the biology of basal-like tumors. Overexpression of p16 does not simply reflect proliferating tumor cells since highly proliferating Luminal B tumors do not exhibit p16 levels above the median. Instead, the Luminal B subgroup of tumors commonly overexpresses cyclin D1. Deregulation of p16/Rb signalling, exemplified by overexpression of p16 in actively proliferating cells was demonstrated to define basal-like tumors and identify DCIS lesions with worse prognosis.

High COX-2 mRNA Levels are Enriched in Basal-Like Tumors

To further analyze p16 and explore gene expression interactions, hierarchical clustering was performed on top variable genes in 130 tumors. To select for genes with variable expression, those with >1.5 fold change from the median in at least 10% of samples and with a log intensity variation p<0.001 was filtered, resulting in 6000 unique genes. To classify the 6000-gene clustering into molecular subtypes, tumors were grouped according to the sample clustering using the 589 intrinsic gene set. Members of the p16/Rb/cyclin D1 pathway did show variable expression, as well as many members of the E2F family. This analysis also demonstrated that among the variable genes, overexpression of COX-2 falls within the basal gene cluster along with the overexpression of p16. The finding that COX-2 mRNA expression is enriched in basal-like tumors was of particular interest because it has been previously shown that COX-2 is overexpressed in mammary epithelial cells with deregulated p16/Rb signalling (Crawford et al, Gauthier et al).

COX-2 mRNA levels were >1.5 fold above the median in 18% of the tumors analyzed with COX-2 overexpression distributed in two major subtype classes of tumors, basal-like and normal-like. It was found that 50% (16/32) of basal-like and 33% (4/12) of normal-like tumors overexpress the COX-2 transcript. The basal and normal-like subtypes are known to share high levels of basal genes. Consistent with the subtype distribution of increased COX-2 mRNA, unsupervised hierarchical clustering demonstrated that COX-2 clusters with basal-like genes. In contrast, luminal tumors and ERBB2 positive tumors tended to express COX-2 mRNA levels below the median.

To determine if the prevalence of COX-2 overexpression in basal and normal-like tumors is unique to this tumor set, four independent published microarray data sets were analyzed across 3 different platforms. In each independent series, the highest levels of COX-2 mRNA were found within the basal-like tumors. Similar to the distribution in our original set of invasive cancers, the independent datasets also exhibited increased COX-2 in normal-like samples and lower levels of COX-2 gene expression in the majority of luminal and ERBB2 subtypes.

Concordance Between p16 or COX-2 mRNA and Protein Expression in Tumors

The low levels of COX-2 mRNA expression in ERBB2 positive tumors was intriguing because previous studies had demonstrated that, when assessed with immunohistochemistry, COX-2 protein levels were enriched in ERBB2 amplified tumors (Ristimaki et al, 2002 CancerRes 62:632; cho et al. 2005. Breast; Boland et al. 2004, BrJCancer 90:423;). Notably, microarray analyses of human tumor samples are typically average measurements of numerous cell types that often represent arbitrary units relative to a median value and fail to address post-transcriptional and post-translational regulation. Any one these reasons could underlie the discordance between mRNA levels and protein expression as determined by immunohistochemistry. To interpret the biological significance of microarray based measurements of mRNA expression in vivo, one should relate thresholds of detection of mRNA by microarray to levels of protein expression as measured by immunohistochemistry. Further, it is useful to determine the contributions of distinct cell types to overall levels of gene expression and the relative locations within different cellular compartments. To address these issues and to better understand p16 and COX-2 regulation in vivo, p16 and COX-2 immunohistochemistry was performed on paraffin-embedded tumor blocks representing 54 of the 130 tumors analyzed by microarray (FIGS. 8A-D). These samples were chosen to represent all 5 molecular subtypes and span a continuum from the lowest to the highest levels of p16 and COX-2 microarray gene expression.

In samples of invasive cancers that showed elevated p16 via microarray analysis, immunopositivity was predominantly found in carcinoma cells. To a lesser extent, heterogeneous foci exhibiting p16 staining were detectable in the morphologically normal epithelial cells within or adjacent to the invasive cancer. Occasional p16 positivity was also observed in fibroblasts, predominantly those within desmoplastic appearing stroma. Cases with elevated COX-2 showed abundant staining within the carcinoma cells as well as in the morphologically normal epithelial. In rare cases, intense COX-2 staining in macrophages infiltrating and surrounding the invasive cancers was found. COX-2 staining was not observed in mesenchymal cells.

Figure 8:
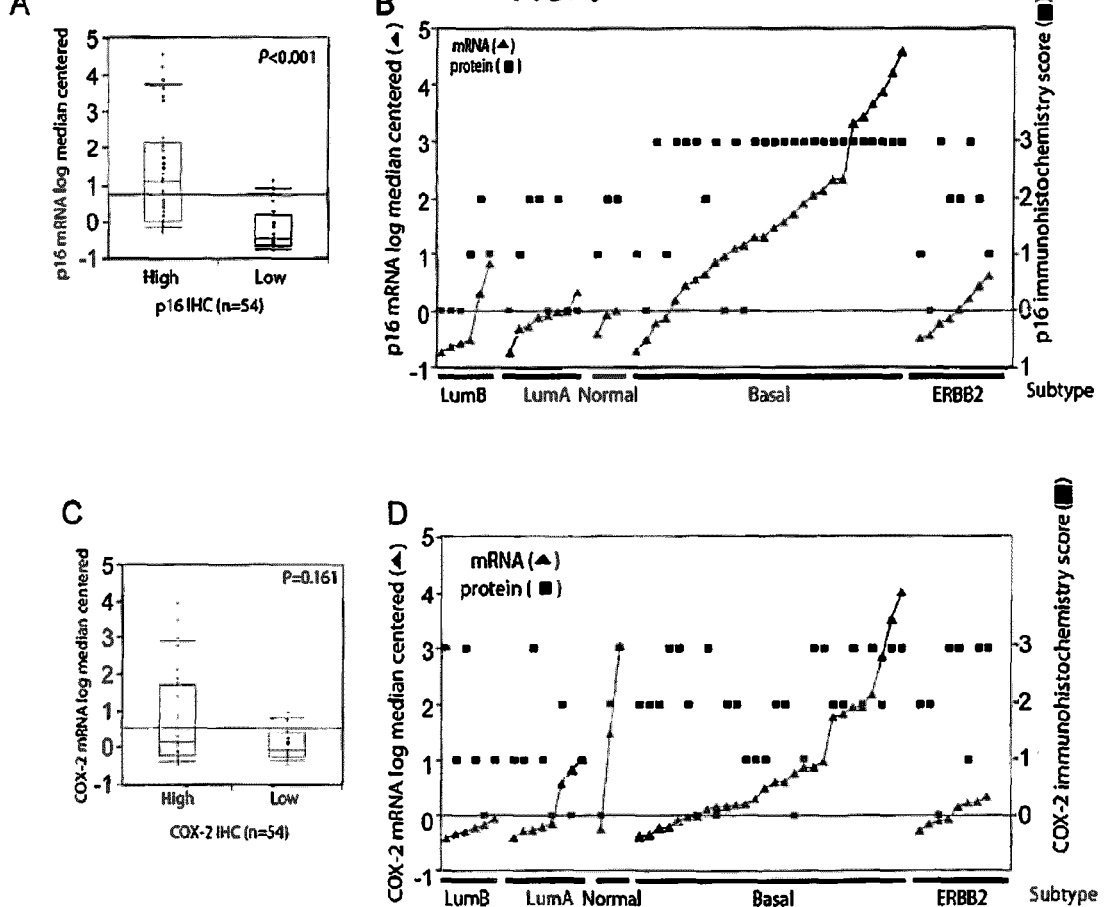

For p16, a significant correlation was observed (Wilcoxon rank of sums, P<0.0001) between mRNA levels by microarray and protein expression by IHC among all tumors analyzed (FIG. 8A). Basal tumors that express the highest levels of p16 mRNA showed intense p16 protein staining by immunohistochemistry (score 3+, FIG. 8B). A small fraction of ERBB2 positive tumors (2/8) were observed that showed intense p16 staining despite having low levels of mRNA expression. This overall concordance between mRNA and protein suggests that p16 protein levels are primarily regulated at the transcriptional level and that p16 protein levels reflect the subtype specificity.

In contrast, evaluation of COX-2 demonstrated poor correlation (Wilcoxon rank of sums, P=0.161) between mRNA levels determined by microarray and protein levels determined by IHC among the tumors analyzed (FIG. 8C). In examining those cases with the highest levels of COX-2 mRNA, as defined by a greater than 2-fold increase over the median value, there is complete concordance as all showed high COX-2 immunoreactivity (FIG. 8D). Ten of the 54 invasive cancers show COX-2 mRNA levels greater than 2-fold above the median, eight of these cases are basal and the remaining two are classified as normal-like. In remaining cases (44/54), 10 of them exhibited relatively low mRNA detected by microarray analysis and were discordant with the elevated protein expression as measured by IHC (FIG. 8D). It was found that 80% of the discordant samples were in the ErBB2 sub-type.

The observation of high COX-2 protein expression by IHC in the absence of high COX-2 mRNA by microarray has a number of possible explanations including technical (i.e. inconsistent sampling of tumor tissue in microarray samples) and biological (i.e. post-transcriptional or post-translational regulation of COX-2). Inconsistent sampling of tumor tissue in microarray samples appears an unlikely explanation as all of the samples exhibiting low COX-2 mRNA still showed robust basal-like tumor microarray signatures (FIGS. 8B,C). Furthermore, a number of the samples discordant for COX-2 showed concordant IHC and microarray elevations in p16. A biological explanation for the discrepant protein/IHC and mRNA/microarray levels for COX-2 is most likely given the particularly striking discordance in the ERBB2 positive tumors. The majority of ERRB2 tumors (75%, 6/8) showed high COX-2 immunoreactivity, yet none of these tumors showed elevated COX-2 mRNA (FIG. 8D). Many in vitro studies have demonstrated that COX-2 in addition to being regulated through de novo transcription is also often regulated by mRNA stabilization (Dixon, Kaplan et al. 2000; Ramsay, Ciznadija et al. 2003). While both these methods of regulation would be reflected in the gene expression analysis, post-translational regulation of COX-2 would not. These results suggest that ERBB2 positive invasive cancers target protein stabilization of COX-2 as a distinct and important mechanism of achieving COX-2 protein overexpression.

FIG. 8A-D. Concordance between p16 or COX-2 mRNA and protein expression in tumors. There was good concordance between p16 mRNA expression determined by gene expression profiling and protein levels determined by immunohistochemistry. The correlation between the mRNA levels (expressed as log median centered) and high or low p16 immunostaining was determined using Wilcoxon rank of sums analysis (shown in FIG. 8A). The level of concordance among invasive cancer subtypes was determined. The log median centered mRNA level of p16 for each sample analyzed was plotted as a continuous variable (red triangles) distributed by breast cancer subtype. The corresponding protein levels of p16 were plotted as immunohistochemistry scores 0, 1, 2, or 3 (black squares) (shown in FIG. 8B). There is poor concordance between COX-2 mRNA and protein levels. The correlation between the mRNA levels (expressed as log median centered) and high or low COX-2 immunostaining was determined using Wilcoxon rank of sums analysis (shown in FIG. 8C). The discordance of mRNA (red triangles) and protein (black squares) levels of COX-2 in invasive cancers within different molecular subtypes determined by hierarchical clustering was analyzed. The log median centered mRNA level of COX-2 for each sample analyzed was plotted as a continuous variable (red triangles) distributed by breast cancer subtype. The corresponding protein levels of COX-2 were plotted as immunohistochemistry scores 0, 1, 2, or 3 (black squares) (shown in FIG. 8D). COX-2 Overexpression Coupled with Proliferation Increases the Risk of Subsequent Tumor Events Among Women with DCIS.

After the findings that COX-2 mRNA levels were enriched in basal-like tumors and that COX-2 protein levels were elevated in both basal and ERBB2 positive tumors, it was next determined if elevated COX-2 protein expression in DCIS also portends a worse prognosis. In the 70 cases previously analyzed for p16 and Ki67, serial sections were stained for COX-2 for evaluation by immunohistochemistry. The level of COX-2 staining on a 0, 1, 2, 3 scale of immunopositivity was determined. Representative COX-2 staining was illustrated in FIG. 9C). A score of 0 or 1 was considered to represent low staining and a score of 2 or 3 to be high immunostaining. It was found find that 56% (39/70) of DCIS lesions show high COX-2 protein levels (Table 3). To determine if expression of COX-2 in DCIS is clinically significant, it was determined if cases with high COX-2 staining stratifies risk for developing subsequent disease. It was found that high COX-2 immunopositivity by itself did not stratify risk for subsequent tumor formation and, similar to p16 overexpression by itself, is equally distributed among women that developed subsequent DCIS or invasive cancer (case) and those that did not (control; HR=1.0, 95% CI, 0.5 to 2.2, P=0.99; Table 4; FIG. 9A).

TABLE 4

| Marker | n | Control | Case | P-value |
|---|---|---|---|---|
| COX-2 | 70 | | | |
| High | | 56% (22/39) | 44% (17/39) | 0.689 |
| Low | | 52% (16/31) | 48% (15/31) | |
| COX-2 High | 39 | | | |
| Ki67 High | | 27% (5/18) | 72% (13/18) | <0.001 |
| K67 Low | | 81% (17/21) | 19% (4/21) | |
| COX-2 Low | 31 | | | |
| Ki67 High | | 50% (4/8) | 50% (4/8) | 0.916 |
| Ki67 Low | | 52% (12/23) | 48% (11/23) | |
| Ki67 | 70 | | | |
| High | | 35% (9/26) | 65% (17/26) | 0.011 |
| Low | | 66% (29/44) | 34% (15/44) | |

COX-2 staining intensity with a score >2 is considered positive,
Ki67 positive cases exhibited >10% nuclei immunopositivity.
P-values were determined using Pearson Chi-quare test.

Since COX-2 expression in invasive cancers was found in actively proliferating cells, the fraction of DCIS expressing high COX-2 and high Ki67 was determined. Almost half (18/39) of DCIS lesions showing high COX-2 also exhibited high Ki67 and was weighed toward higher grade lesions (Table 3). It was determined if this phenotype (high COX-2 coupled with high Ki67) identified DCIS lesions with worse prognosis. Indeed, stratifying high and low COX-2 DCIS lesions by proliferation identified women with differential risk for recurrent disease. FIG. 6B shows that a significantly higher fraction of women (13 of 18) with DCIS showing high COX-2 and high Ki67 developed a subsequent tumor (Wilcoxon rank test; P=0.0002). A significant increased risk of developing a subsequent breast cancer and decreased recurrence-free survival was calculated when the primary DCIS lesion exhibited high COX-2 and high Ki67 labelling as compared to lesions that show high COX-2 and low Ki67 (HR=4.72, 95% CI, 1.0 to 22.1, P=0.0004; FIG. 9B, Table 4). Similar to the findings for p16, proliferation is an obligate qualifier of COX-2 because high Ki67 did not stratify low COX-2 expressing lesions (Wilcoxon rank test; P=0.925). Correspondingly, a differential risk for recurrent disease in women that exhibited low COX-2 expressing DCIS irrespective of Ki67 (HR=0.86, 95% CI, 0.2 to 3.3, P=0.79) was not observed. In examining the lesions that develop subsequent to DCIS that are immunopositive for both COX-2 and Ki67, it was found that 8 of the 13 cases recur as invasive breast cancer. These data suggested that COX-2 and Ki67 immunopositive cells identify an aggressive cellular phenotype.

FIG. 9A-C. COX-2 overexpression coupled with proliferation increased the risk of subsequent tumor events among women with DCIS. FIG. 9A shows that COX-2 staining intensity (score 0, 1, 2, or 3) failed to stratify women with DCIS that have a differential risk of developing recurrent disease. Recurrence-free survival was not different in women with DCIS that exhibits high or low for COX-2 immunopositivity (score of >2 was considered high). Box plots and corresponding P-values were determined using Wilcoxon/Kruskal-Wallis rank of sums test. FIG. 9B shows that DCIS lesions high for COX-2 immunostaining and elevated Ki67 significantly stratified women that develop subsequent breast cancer from those that did not develop subsequent disease. Recurrence-free survival among women with DCIS that exhibited high COX-2/high Ki67 was significantly reduced compared to lesions that are high COX-2/Low Ki67. FIG. 9C shows that DCIS lesions with low COX-2 immunostaining irrespective of Ki67 labelling did not have a differential risk of developing recurrent disease. FIG. 9D shows the immunohistochemistry staining for COX-2. Staining was scored on a 0, 1, 2, 3 scale with a score of >2 considered positive.

Predicting Invasive Cancer Formation Using Molecular Markers

The findings with COX-2 and Ki67 paralleled the observations in examining the expression of p16 and Ki67. Given that 12% (8/65) of the DCIS lesions we examined from the UCSF cohort show high p16/high Ki67 and 25% (16/65) show high COX-2/high Ki67 (Table 3), it was determined if one phenotype is enriched for the other. It was found that 75% (6/8) of high 16/high Ki67 DCIS exhibits overexpression of COX-2, and 38% (6/16) of high COX-2/high Ki67 lesions show high p16 expression (FIG. 10). Strikingly, expression of all three markers, high p16, high COX-2, high Ki67, provided the first signature that was strong in predicting a subsequent invasive event over a non-invasive (DCIS) event. Since invasive lesions have the potential to invade and seed metastatic foci, this distinction is clinically relevant. Of the 6 DCIS lesion that overexpress all three markers, all develop a subsequent tumor event, 5 develop invasive breast cancer.

FIG. 10 is a diagram representing DCIS lesions expressing combinations of p16, COX-2 and Ki67. High COX-2 and/or high p16 classifies two clinically different populations of cells in DCIS that can be stratified by proliferation. One population overexpresses COX-2 and/or p16 in the presence of proliferation and identifies women that developed subsequent DCIS (black circles) or invasive breast cancer (red circles). The second population overexpresses COX-2 and/or p16 in the absence of proliferation and identifies women that did not develop subsequent disease (open circles).

Similar to the observations that elevated p16 in the absence of proliferation identified more benign lesions (Table 2), 81% (17/21) of women with high COX-2 and low Ki67 expressing lesions did not develop a subsequent tumor event (Table 4). Therefore, elevated levels of either p16 or COX-2 in the absence of proliferation suggest stress activation and identify a phenotype with more favourable prognosis. Equally intriguing, expression of high p16, high COX and low Ki67 marks a low risk of developing subsequent disease. 7 DCIS lesions exhibiting high COX-2/high p16 and low Ki67, of which 6 do not develop a subsequent tumor event were observed. The one sample that developed subsequent disease recurred as DCIS. These observations suggest high COX-2 and high p16 classified two clinically different populations of cells in DCIS that can be stratified by proliferation. One population overexpressed COX-2 and/ or p16 in the presence of proliferation and identified lesions with poor prognosis. The second population overexpressed COX-2 and/or p16 absence of proliferation and identified DCIS lesions with good prognosis (FIG. 10).

COX-2 Overexpression Causes Cell Cycle Arrest in Cells that Maintain Functional p16/Rb Signaling.

It is well appreciated that in vitro, cell cycle checkpoints are essential to preserve genomic stability. Overexpression of p16 in normal cells, induced by exogenous stressors or genetic manipulation, causes an irreversible cell cycle arrest and morphological changes characteristic of cellular senescence. It has been speculated that inactivation of this critical checkpoint in vivo would allow cells to propagate under unfavourable conditions that promote genomic instability and accelerate tumorigenesis. The observations that abrogation of this checkpoint, reflected by high p16/high Ki67 expressing lesions in DCIS, portends a worse prognosis support this hypothesis.

These observations parallel the findings with COX-2 expression and elevated Ki67. It was observed that high COX-2 expressing DCIS lesions identified two distinct populations of cells, one that is quiescent and the other that is actively proliferating, that have different prognoses. The cellular context that governs COX-2 was then determined and if it is associated with quiescence or proliferation. The S-phase fraction was investigated in a continuum of cell populations from normal to malignant engineered to constitutively overexpress COX-2 compared to vector control populations. S-phase fraction was determined following a 4 h pulse of BrdU incorporation and flow cytometric analysis.

It was found that in normal cells, COX-2 inhibits cell proliferation while, in pre-malignant and malignant cells, overexpression of COX-2 subsists in the presence of ongoing proliferation. COX-2 expression was increased in normal human mammary epithelial cells (HMEC) generated from reduction mammoplasty tissue from 3 different individuals via expression of an exogenous COX-2 construct; it was found that sustained COX-2 overexpression significantly reduces the number of cycling cells (FIG. 11A). The diminished S-phase fraction of HMEC-COX-2 cells limits the proliferative capacity and reduces the lifespan of these cells in culture. These data parallel the finding when p16 was overexpressed in HMEC. In contrast, in non-tumorigenic cells that exhibit pre-malignant characteristics, both mortal (variant HMEC, vHMEC) and immortal (vHMEC-hTert and 184A1) as well as tumorigenic breast cancer cell lines (T47D, SKBr3, BT549 and MDA-MB-231), COX-2 overexpression neither induced nor diminished proliferation (FIG. 11A). Functional p16/Rb signaling is one of the distinguishing features of normal cells compared to all other cells we examined. Therefore, it was hypothesized that COX-2 overexpression resulting in a cell cycle arrest is only observed in normal breast epithelial cells that retain functional p16/Rb signalling. All other cells that were examined have compromised p16/Rb signalling through diverse mechanisms including p16 hypermethylation (vHMEC, vHMEC-hTert, T47D), p16 deletion (MDA-MB-231), or Rb deletion (BT549). These analyses suggested cells with compromised p16/Rb signalling supported COX-2 expression and its ensuing phenotypes in actively proliferating cells.

To extend this analysis, the differential response to COX-2 overexpression in HMEC versus a subpopulation of HMEC that have lost p16 expression through promoter hypermethylation (variant HMEC) was further explored. Constitutive expression of COX-2 in HMEC produced enlarged flattened cells that are growth arrested compared to vector control cells (FIG. 11B). In contrast, overexpression of COX-2 in cells lacking p16 (vHMEC) continued to proliferate without morphologic change (FIG. 11B). To characterize the molecular changes underlying the differential phenotypic response to COX-2 overexpression, cell lysates were probed for cell cycle regulatory proteins by immunoblotting. HMEC overexpressing COX-2 exhibited elevated protein levels of p16, p53 and p21 (FIG. 11C). This is in contrast to vHMEC where overexpression COX-2 did not alter the level of p53 or p21. Thus, COX-2 induced a cell-cycle arrest in p16 expressing cells while p16-silenced cells were refractive to COX-2-induced growth inhibition. This phenotype is also observed in cells that have abrogated all Rb family members. Targeted degradation of Rb, p107 and p130 (all three Rb family members) by HPV16-E7 in HMEC results in ongoing proliferation in the presence of COX-2 overexpression (FIG. 11B). Thus, COX-2 overexpression in cells with functional p16/Rb signalling induces a p16-dependent growth arrest, while cells with disrupted p16/Rb signalling continue to proliferate in the presence of COX-2 overexpression.

FIG. 11A-C. Overexpression of COX-2 in the absence or presence of proliferation is dependent on p16/Rb dysfunction. FIG. 11A shows that cell populations with varying malignancy were retrovirally infected with a constitutive COX-2 expressing construct (COX-2) or an empty vector control (LXSP). Cells were pulsed for 4 h with BrdU and analyzed by flow cytometry following propidium iodide staining. The S-phase fraction of COX-2 expressing cells were compared to vector control cells and represented as fold increase of controls. FIG. 11B shows phase contrast micrographs of primary human mammary epithelial cells (HMEC), variant HMEC (vHMEC) lacking p16 expression and HMEC expressing HPV16-E7 retrovirally infected with a constitutive COX-2 expressing construct (COX-2) or an empty vector control (LXSP). The molecular changes underlying the differential phenotypic response to COX-2 was determined by probing cell lysates from COX-2 overexpressing and vector control HMEC and vHMEC for COX-2, p16, p53 and p21 (results in FIG. 11C).

Deregulation of p16/Rb Signalling Causes COX-2 Overexpression.

Figure 12:
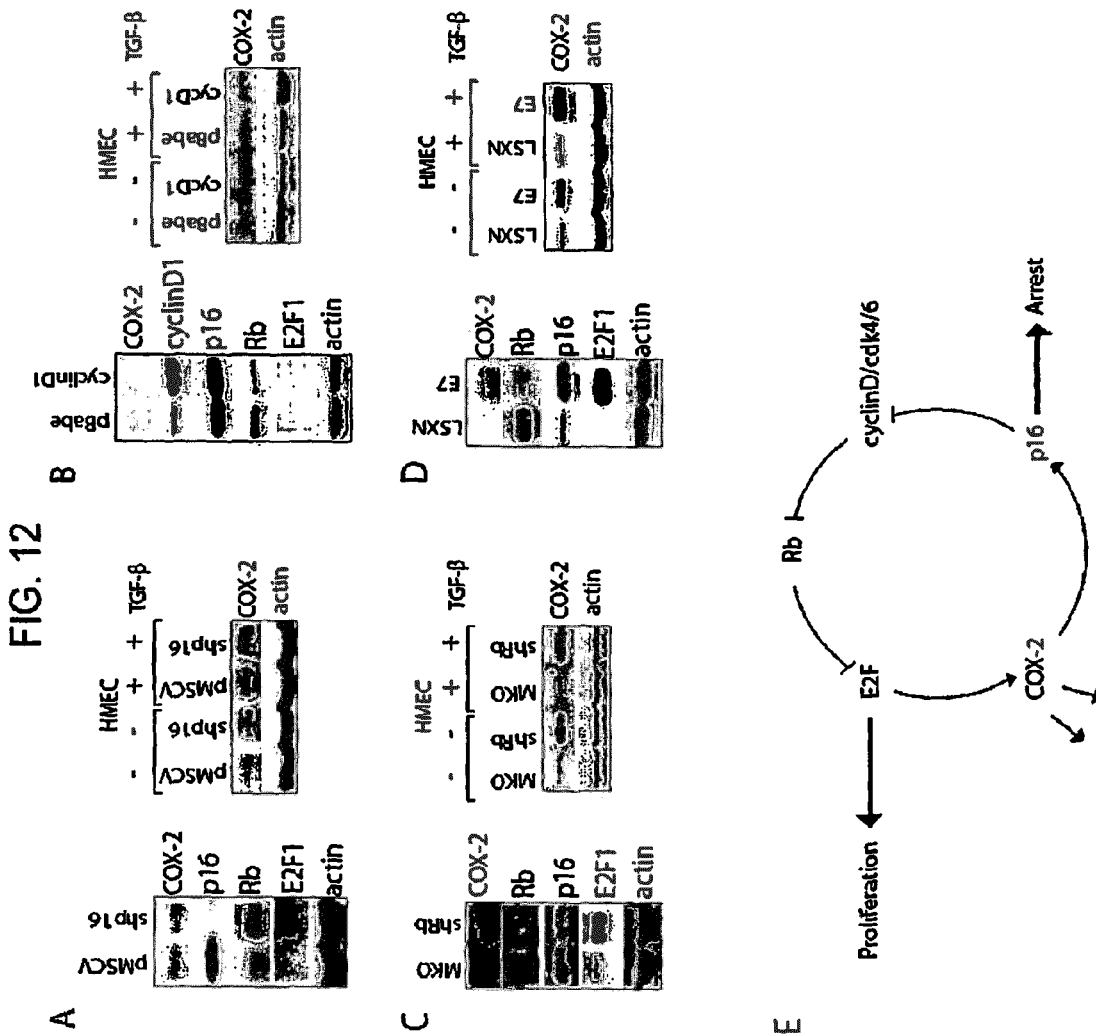

The finding that the majority of high p16/high Ki67 DCIS lesions overexpress COX-2 suggested that deregulation of p16/Rb may drive COX-2 expression. To test this hypothesis, specific members of the p16/Rb pathway were genetically modulated, and the levels of COX-2 protein expression compared to HMEC that maintain p16 expression were determined. First, basal and induced COX-2 protein levels in HMEC lacking p16 activity were compared. Sequence specific silencing of p16 by retroviral infection of HMEC with a short hairpin RNA (shp16) downregulated p16 protein levels leading to the upregulation of both Rb and E2F1 compared to control HMEC infected with an empty pMSCV vector (FIG. 12A and Zhang et al. 2006). Basal levels of COX-2 expression did not change with the removal of p16 activity. However, exogenous induction of COX-2 by exposure to inducing stimuli (for example TGF-β) resulted in COX-2 upregulation in p16 silenced cells while vector control cells remain unresponsive. These results were observed in two independent reduction mammoplasties and three independent determinations after exposure to TGF-13. These findings demonstrate that while the basal levels of COX-2 protein remained unchanged with the removal of p16 activity, the genetic silencing of p16 sensitizes cells to exogenous COX-2 induction and demonstrates that a secondary event is necessary for COX-2 overexpression.

To extend this analysis, it was determined how other alterations within this pathway, mutations common in cancer, affect COX-2 expression. The p16/Rb pathway was modulated by three additional methods, cyclin D1 overexpression, pRb downregulation, and expression of a viral oncoprotein, HPV16-E7 and determined the effect on basal and exogenously-induced COX-2 protein levels. To determine if cyclin D1 induces and/or sensitizes cells to COX-2 induction, COX-2 protein levels in HMEC engineered to stably express cyclin D1 under the regulation of an independent, constitutively active promoter were measured. Cyclin D1 was introduced into cells generated from three different reduction mammoplasties and resulted in cyclin D1 protein overproduction similar in level to that measured in tumor cells. Overexpression of cyclin D1 alone did not cause hyperphosphorylation of Rb, and instead lead to a slight reduction in overall Rb protein levels (FIG. 12B). These results are consistent with previous findings (Lundberg et al, 1998) that overexpression of cyclin D1 is not sufficient for Rb inactivation. The absence of E2F1 upregulation following cyclin D1 overexpression supports the finding that Rb remains active. It was demonstrated that overexpression of cyclin D1 did not induce basal COX-2 expression and failed to render cells sensitive to exogenous induction by TGF-β (FIG. 12B). These data indicate that cyclin D1 overexpression does not modulate Rb activity, does not alter basal levels of COX-2 expression or render cells sensitive to exogenous COX-2 induction. To determine if inactivation of Rb is sufficient for the upregulation of COX-2, HMEC were infected with a retrovirus containing a short hairpin RNA against Rb (shRb) and COX-2 protein levels were determined in cells from two independent experiments. As anticipated, sequence specific silencing of Rb downregulated Rb protein levels and caused the upregulation of E2F1 compared to control HMEC infected with an empty pMKO vector (FIG. 12C). Viral transduction with shRb was integrated In these cells, both basal levels and exogenously induced levels of COX-2 protein were increased (FIG. 12C) supporting a central role for the loss of Rb in driving COX-2 overexpression. Similar to results obtained with Rb genetic silencing, expression of the human papilloma virus 16-E7 (HPV16-E7) elevated both basal and induced levels of COX-2 protein (FIG. 12D). Stable expression of HPV16-E7 was performed in cells generated from three independent reduction mammoplasties. Mammary epithelial cells expressing HPV16-E7 show downregulation of Rb and thus inactivation of Rb and consequently upregulation of E2F1 (FIG. 12D). HPV16-E7 is well characterized for its role as a transforming oncoprotein through targeted degradation of all three members of Rb family (Rb, p107 and p130) and driving E2F-dependent transactivation.

FIG. 12A-E. Deregulation of distinct members of the p16/cyclin D1/Rb pathway differentially regulate COX-2. To determine if p16 is necessary for the upregulation of COX-2, HMEC were retrovirally infected with a construct encoding a short hair-pin RNA against p16 (shp16) or an empty vector control construct (pMSCV). Cell lysates were probed by western blot for COX-2, p16, Rb and E2F1 (the results are shown in FIG. 12A). To determine if genetic downregulation of p16 in HMEC are sensitive to the upregulation of COX-2 in response to exogenous induction, cell lysates were probed for COX-2 by immunoblotting following 24 h exposure to 1 ng/ml TGF-β (the results are shown in FIG. 12A). To determine if cyclin D1 is necessary for COX-2 upregulation, HMEC were retrovirally infected with a constitutely expressing cyclin D1 construct (cycD1) or an empty vector control construct (pBabe) (the results are shown in FIG. 12B). Cell lysates were probed by western blot for COX-2, cyclin D1, p16, Rb and E2F1. To determine if genetic upregulation of cyclin D1 in HMEC are sensitive to the upregulate COX-2 in response to exogenous induction, cell lysates were probed for COX-2 by immunoblotting following 24 h exposure to 1 ng/ml TGF-β (the results are shown in FIG. 12B). To determine if Rb is necessary for COX-2 upregulation, HMEC were retrovirally infected with a construct encoding a short hair-pin RNA against Rb (shRb) or an empty vector control construct (pMKO). Cell lysates were probed by western blot for COX-2, Rb, p16 and E2F1. To determine if genetic downregulation of Rb in HMEC are sensitive to the upregulate COX-2 in response to exogenous induction, cell lysates were probed for COX-2 by immunoblotting following 24 h exposure to 1 ng/ml TGF-β (the results are shown in FIG. 12C). To determine if Rb family members (Rb, p107 and p130) are necessary for the upregulation of COX-2, HMEC were retrovirally infected with HPV16-E7 or an empty vector control construct (pLSXN). Cell lysates were probed by western blot for COX-2, Rb. p16 and E2F1. To determine if genetic downregulation of all Rb family members in HMEC are sensitive to the upregulate COX-2 in response to exogenous induction, cell lysates were probed for COX-2 by immunoblotting following 24 h exposure to 1 ng/ml TGF-β (the results are shown in 12D). FIG. 12E is a diagram representing the connection between p16/Rb pathway and COX-2.

These data demonstrate that abrogation of p16/Rb signalling through genetic silencing of p16, Rb and Rb family members sensitizes cells to COX-2 upregulation. Thus, the propensity of COX-2 overexpression in DCIS lesions that exhibit high p16/high Ki67 may be a consequence of deregulation of the p16/Rb pathway.

p16 and COX-2 Overexpression can be Found in a Subset of Epithelial Cells in Normal Breast Tissue and Atypical Ductal Hyperplasias.

Two cellular phenotypes that define a subset of invasive cancers and DCIS with worse prognosis have been described. The prevalence of these phenotypes in normal breast tissue and in tissue biopsies diagnosed with atypical ductal hyperplasia (no DCIS present) was determined. p16 and COX-2 expression and proliferation index in normal breast biopsies (n=40) and atypical ductal hyperplasias (ADH; n=20) was characterized. Representative p16 immunostaining in normal and ADH biopsies is shown in FIG. 13). The majority of disease-free breast tissues exhibited low levels or were devoid of p16 expression while 7.5% of the cases displayed heterogeneous 16 staining in 25%-85% of the morphologically normal epithelium (Table 5). In examining a series of ADH lesions, 27% of cases showed heterogeneous p16 immunostaining, an increase as compared to disease-free tissue that did not reach statistical significance (Table 5; Pearson chi-square test P=0.394). Similar to the findings in DCIS, the surrounding stromal compartment in a fraction of cases (10%), both in normal tissue and tissue containing ADH also exhibited p16 staining in fibroblasts surrounding cystic ducts. For COX-2, it has been demonstrated, and herein illustrated, that approximately 20%-30% of tissue from disease-free women exhibit foci of cells with heterogeneous COX-2 staining in normal epithelium (FIG. 13; Crawford et al, 2004; Gauthier et al. 2005) and others have confirmed this observation (Boland et al. 2005).

FIGS. 13A and 13B. p16 and COX-2 overexpression identified a subset of epithelial cells in normal breast tissue and atypical ductal hyperplasias that may provide risk stratification. Representative of p16, COX-2 and Ki67 immunostaining in normal disease-free breast tissue, atypical ductal hyperplasia (ADH) and DCIS are illustrated in FIG. 13A. The bar graph demonstrates the percent positive cases for each biomarker. p16 and COX-2 staining intensity with a score ≥2 is considered positive. Ki67 immunostaining is considered positive in cases exhibiting more that 10% nuclei immunopositivity. To determine if p16 and/or COX-2 is correlated with proliferation, p16 and COX-2 immunopositive staining (score of ≥2 was considered high) with the percent Ki67 nuclear positivity expressed as a continuous variable in normal, ADH and DCIS was evaluated (FIG. 13B). Box plots and corresponding P-values were determined using Wilcoxon/Kruskal-Wallis rank of sums test.

In ADH lesions, it was found that 65% of lesions (13/20) stained positive for COX-2 (Table 5) a significant increase as compared to disease-free breast tissue, p=0.01). In examining the relationship between p16 and COX-2, concomitant overexpression was observed in 2.5% (1/40) of normal tissue devoid of disease (Table 6). In ADH and DCIS, ~10% (2/20) and 19% (13/70) lesions overexpressed both p16 and COX-2, respectively (Table 6).

In the analysis of DCIS, it was demonstrated that proliferation was an obligate qualifier for p16 and COX-2 in determining which lesions have worse prognosis. In ADH, only 1 case of 20 that exhibits coupled high Ki67 and high p16 staining (Table 5). There were no examples of high Ki67/high COX-2 staining in ADH lesions. However, it remains to be determined if elevated levels of coincident overexpression of p16 and COX-2 (2.5% in isolated normal lobules and 10% of ADH cases) may facilitate genomic instability and provide a selection pressure for clonal outgrowth. If these cells manifest the same tumorigenic proclivity as those that overexpress COX-2 and p16 in DCIS, it would be predicted that women from which these types of biopsies are obtained would exhibit subsequent disease.

As discussed above, the recently defined 1300-gene "Intrinsic/UNC" gene set, derived from Agilent Human oligonucleotide platform data was cross-referenced to Affymetrix U133A to derive a intrinsic set for these studies. A subset of 1090 genes from the intrinsic/UNC genes represented on the U133A platform were additionally filtered for top 20% of variability within the 130 tumor set. This analysis resulted in 589 unique genes that are intrinsically variable and available for this analysis. Hierarchical clustering utilizing this set of 589 genes is shown in FIG. 14. The genes listed in FIG. 14 are differentially expressed in vHMECs, and allow one to distinguish HMEC (e.g., normal, or non-pre-cancerous HMEC) from vHMEC.

Example 3

Extracellular Signaling and Intracellular Ras Activation Cooperate to Modulate Endothelial-to-Mesenchymal Transition (EMT) and De Novo Methylation in Human Mammary Epithelial Cells Over fifty percent of human breast carcinomas express elevated levels of normal Ha-Ras 3, and expression of oncogenic Ras is one of the components required for transformation of HMEC 2. As described in Example 1, a subpopulation of HMEC that display tumorigenic pheno-

TABLE 5

| Epithelium | p16+ | COX-2+ | Ki67+ | p16+/Ki67+ | COX-2+/Ki67+ | p16+/COX-2+/Ki67+ |
|---|---|---|---|---|---|---|
| Normal | 7.5% 93/40) | 30% (12/40) | 0% (0/40) | 0% (0/40) | 0% (0/40) | 0% (0/40) |
| ADH | 20% (4/20) | 65% (13/20) | 5% (1/20) | 5% (1/20) | 0% (0/20) | 0% (0/20) |
| DCIS | 26% (18/70) | 56% (39/70) | 37% (26/70) | 11% (8/70) | 26% (18/70) | 9% (6/70) | p16 and COX-2 staining intensity with a score >2 is considered positive, Ki67 positive cases exhibited >10% nuclei immunopositivity.
P-values were determined using Pearson Chi-quare test.

TABLE 6

| Epithelium | p16 High | p16 Low | P-value |
|---|---|---|---|
| Normal | | | |
| COX-2 high | 2.5% (1/40) | 27.5% (11/40) | 0.605 |
| COX-2 low | 5% (2/40) | 65% (26/40) | |
| ADH | | | |
| COX-2 high | 10% (2/20) | 55% (11/20) | 0.481 |
| COX-2 low | 10% (2/20) | 25% (5/20) | |
| DCIS | | | |
| COX-2 high | 19% (13/70) | 37% (26/70) | 0.101 |
| COX-2 low | 7% (5/70) | 37% (26/70) | | p16 and COX-2 staining intensity with a score >2 is considered positive.
P-values were determined using Pearson Chi-quare test.

types was isolated from disease-free women; these "variant HMEC" appear to have engaged the process of malignant transformation. Stable expression of constitutively active Ha-Ras V12 into these cells led to their immortalization. These immortalized variant HMEC (vHMEC) are a valuable model of pre-malignant mammary epithelia to study the effects of stromal components on mammary tumor progression.

In order to examine the effect of oncogenic stress on the behavior of vHMECs, vHMECs were transduced with a retroviral construct encoding constitutively active Ha-Ras V12. Unlike normal cells, vHMEC expressing oncogenic ras failed to undergo a proliferative arrest. Since the microenvironment can modulate characteristics of epithelial cells, the possibility that extracellular signaling might cooperate with intracellular Ras activation in altering the phenotypes of vHMEC was tested. To mimic secretory aspects of the extracellular environment, both vHMEC carrying control vector and vHMEC expressing Ha-Ras V12 were exposed at agonesence to media containing 0.5% serum. It was found that extracellular stimulation resulting from the presence of 0.5% serum was sufficient to cause immortalization of vHMEC expressing Ha-Ras but not control vHMEC.

It was observed that HMEC-Ras cells undergo a morphological change, and acquire mesenchymal features, when co-cultured with carcinoma-associated fibroblasts, as well as with certain BRCA1 mutant fibroblasts. In contrast, this morphological change was not observed when HMEC-Ras are co-cultured with normal fibroblasts. Since HMEC-Ras cells respond differentially to normal and cancer stroma, they can be used as a reporter cell line for the sensing of stromal signals.

vHMEC are Resistant to Ha-Ras-Induced Proliferative Arrest and Display Chromosomal Abnormalities.

To test the effect of oncogenic stress on primary HMEC and vHMEC exhibiting p16 promoter hypermethylation, cells were retrovirally transduced with constitutively active Ha-rasV12. Expression of Ha-rasV12 was confirmed by immunoblot analysis (FIG. 15A). Despite oncogenic ras expression, vHMEC failed to undergo a proliferative arrest as seen normal HMEC (FIG. 15B), and previously shown in normal fibroblasts. Instead, they continued to grow, and did so until entering agonescence, a period of heightened growth and apoptosis.

In order to determine whether the resistance to ras-induced proliferative arrest was associated with alterations in genomic integrity, a chromosomal analysis of vHMEC expressing Ha-rasV12 or the control vector was performed. The results indicate that upon continued propagation, vHMEC-ras cells became increasingly genomically unstable as evidenced by the accumulation of a number of chromosomal abnormalities, including structural abnormalities, telomeric associations and alterations in ploidy (FIG. 15C). These chromosomal abnormalities do not appear to be due to centrosome dysfunction as no differences in centrosome number were detected between the cell populations.

FIGS. 15A-C. vHMEC are resistant to Ha-ras-induced proliferative arrest and display chromosomal abnormalities. FIG. 15A is a depiction of an immunoblot analysis demonstrating Ha-rasV12 expression in HMEC and vHMEC following retroviral transduction with pLXSP3-Ha-rasV12 (r) or the control pLXSP3 vector (v). Constructs were expressed in HMEC and vHMEC derived from five different individuals. A representative blot is shown along with actin as a loading control. Cell cycle analysis and corresponding growth curves of HMEC and vHMEC expressing Ha-rasV12 or control vector demonstrating that the number of cells in S-phase dropped from 33.8% to 8.8% following Ha-rasV12 expression in HMEC, but remained the same in vHMEC. HMEC underwent a proliferative arrest in response to oncogenic ras, while vHMEC continued to proliferate (shown in FIG. 15B). FIG. 15C shows the results of a chromosomal analysis of vHMEC-vector and vHMEC-ras cells. Control vHMEC (vector) and vHMEC expressing oncogenic Ha-RasV12 (ras) were harvested at different passages, as indicated, and processed for metaphase analysis. Standard G-banding karyotypic analysis was performed on at least fifty metaphase spreads for each cell population. The number of abnormalities observed are presented as percentages. "Total" refers to all structural abnormalities and telomeric associations, not including numerical abnormalities. "Structural" refers to all deletions, duplications, rings, marker chromosomes, chromatid exchanges and translocations. "TAS" refers to telomeric associations. "Aneuploidy" refers to additions or deletions of whole chromosomes.

Combined Serum-Induced Extracellular Signaling and Intracellular Ras Activation Leads to Immortalization of vHMEC and Upregulation of Telomerase Activity.

Since the microenvironment can modulate the characteristics of epithelial cells, the possibility that extracellular signaling might cooperate with intracellular ras activation in altering the behavior of vHMEC was tested. Studies have shown that the gene expression pattern of cultured primary fibroblasts in response to serum exposure resembles that of a wounding response, and that this wound-response signature is strongly predictive of metastasis and progression for a variety of carcinomas. Chang et al. (2004) *PLoS Biol.* 2:E7. Studies were initiated by exposing both vHMEC carrying control vector (vHMEC-vector) and vHMEC expressing Ha-rasV12 (vHMEC-ras) at agonesence to media containing 0.5% or 10% serum. It was found that extracellular stimulation resulting from the presence of either 0.5% serum (vHMEC-ras0.5) or 10% serum (vHMEC-ras10) was sufficient to cause immortalization of vHMEC-ras but not control vHMEC (FIG. 16A, left graph).

To address whether constitutive extracellular stimulation resulting from the exposure to serum is required for the continued proliferation of vHMEC-ras0.5 and vHMEC-ras10, serum stimulation was withdrawn by placing these cells into mammary epithelial growth media (MEGM) without serum. It was found that both cell populations were capable of continued proliferation under these conditions, indicating that once immortalization is initiated by extracellular serum stimulation, the proliferation is independent of continued serum stimulation (FIG. 16A, middle and right graphs). Consistent with this, once immortalized, vHMEC expressing Ha-rasV12 displayed an increase in telomerase activity (FIG. 16B).

FIGS. 16A and 16B. Serum-induced extracellular signaling and intracellular ras activation leads to immortalization of vHMEC and increased telomerase activity. FIG. 16A are growth curves of vHMEC expressing Ha-rasV12 or control vector in the absence or presence of 0.5% or 10% serum. Arrow indicates time at which serum was added (day 150). vHMEC cultured in the presence of both 0.5% (vHMEC-ras0.5) and 10% (vHMEC-ras10) serum resumed proliferation and began being passaged again after 93 and 129 days, respectively (left graph). Both vHMEC-ras0.5 and vHMEC-ras10 continued to proliferate in the absence of serum (vHMEC-ras0.5→0; middle graph) and vHMEC-ras10→0; right graph) once they were immortalized FIG. 16B depicts the Results from the telomerase activity assay. Telomerase activity was measured using the Quantitative Telomerase Detection Kit from Allied Biotech and is represented as the amount of telomerase activity in 1 μg of lysate compared to the TDA standard provided in the kit. Each sample was analyzed in triplicate. A no template control, heat inactivated sample, and cell lysates from telomerase positive (MDA MB231) and telomerase negative (U2OS) cells were included with each experiment.

Extracellular Signaling and Intracellular Ras Activation Cooperate to Induce EMT.

Although vHMEC expressing oncogenic ras upregulated telomerase activity and became immortalized in the presence of both 0.5% and 10% serum, the cells grown in 10% serum underwent a distinguishing change in morphology that was not observed in the presence of 0.5% serum (FIG. 17A, first panel). In the presence of 10% serum, the cells assumed a mesenchymal appearance suggestive of an epithelial to mesenchymal transition (EMT). This mesenchymal phenotype did not require constitutive extracellular serum stimulation, as it was maintained upon serum withdrawal (FIG. 17A, second panel). The epithelial phenotype of ras-expressing vHMEC grown in 0.5% serum (vHMEC-ras0.5), and the mesenchymal phenotype of the same cells grown in 10% serum (vHMEC-ras10), were manifested both on plastic (2D) and in matrigel (3D). The epithelial vHMEC-ras0.5 formed mammospheres, while the mesenchymal vHMEC-ras10 retained their spindle morphology when cultured alone in matrigel (FIG. 17A, third panel). In addition, when the epithelial vHMEC-ras0.5 were co-cultured in 3D with normal human mammary fibroblasts derived from reduction mammoplasties, they were capable of forming ductal structures reminiscent of breast ducts in vivo. In contrast, the mesenchymal vHMEC-ras10 retained their spindle morphology under the same co-culture conditions (FIG. 17A, fourth panel).

EMT Occurs De Novo and is Accompanied by Molecular Alterations and Epigenetic Modifications at the E-Cadherin Locus.

EMT is characterized by a downregulation of cellular adhesion molecules, and an upregulation of mesenchymal markers. Since E-cadherin is a critical mediator of cell-cell contacts, loss of its expression is a characteristic feature of EMT. In addition, studies have shown that cell lines in which E-cadherin is irreversibly suppressed as a result of promoter methylation appear mesenchymal. Lombaerts et al. (2006) *Br. J. Cancer* 94:661. Since the mesenchymal appearance of vHMEC-ras10 appears to be irreversible (as it is maintained in the absence of extracellular serum stimulation), the hypothesis that epigenetic alterations may be involved in downregulating the expression of epithelial markers in these cells was tested.

Epigenetic modifications in the promoter region of E-cadherin were tested using both direct sequencing and methylation-specific PCR. MCF7 and MDA-MB-231 cells were used as negative and positive controls for methylation of E-cadherin, respectively. Consistent with the morphological appearance of the cells, methylation of the E-cadherin promoter was observed in the mesenchymal vHMEC-ras10, but not in the epithelial vHMEC-ras0.5 cells (FIG. 17B, lanes 1-4). This methylation pattern was also maintained after the cells were switched to no (0.5→0) or low (10→0.5) serum growth conditions (FIG. 17B, lanes 5-8), consistent with the maintenance of their morphology under those conditions. Interestingly, the E-cadherin promoter was unmethylated in early passage vHMEC-ras10 despite the fact that these cells appeared mesenchymal (FIG. 17B, lanes 11-14). This suggests that the emergence of vHMEC-ras exhibiting mesenchymal characteristics is unlikely due to the selection of a rare pre-existing population of vHMEC. Rather, the acquisition of mesenchymal features is likely to be the consequence of an active molecular process within vHMEC-ras10.

The protein 14-3-3σ is another mammary epithelial-specific marker that is often downregulated in breast cancer and methylated in fibroblasts, but unmethylated and expressed and in epithelial cells. Moreira et al. (2005) *Mol. Cell. Proteomics* 4:555; and Sato et al. (2006) *Cancer Lett.* 236:105. Consistent with the fact that all the cells are of epithelial origin, the promoter region of this gene remained unmethylated as detected by methylation-specific PCR (FIG. 17B). In addition, since E-cadherin is not methylated in human mammary fibroblasts (FIG. 17D), vHMEC-ras10 cells that have acquired a mesenchymal phenotype can be distinguished from fibroblasts on the basis of their E-cadherin methylation. Thus, together the data suggest that the mesenchymal appearing vHMEC-ras10 originated from mammary epithelial cells, not contaminating mammary fibroblasts.

To directly test the hypothesis that EMT is the result of an active process within vHMEC-ras10, two independent clones of vHMEC-ras0.5 (clone1 and clone2) were isolated, and the clones were exposed to media containing 10% serum. Both clones initially appeared epithelial in morphology (FIG. 17C) and expressed E-cadherin (FIG. 17D), as did all the vHMEC exhibiting an epithelial morphology, namely the parental vHMEC, vHMEC-vector, vHEMC-ras and vHMEC-ras0.5 from which the clones were isolated (FIG. 17D). However, after continued exposure to media containing 10% serum, both clones gradually acquired a mesenchymal morphology, their E-cadherin promoter became methylated (FIG. 17C), and E-cadherin expression was lost (FIG. 17D). Coincident with the loss of E-cadherin expression, the acquisition of mesenchymal morphology was associated with upregulation of the mesenchymal marker, N-cadherin as well as upregulation of fibronectin, demonstrating a functional consequence of the acquisition of a mesenchymal phenotype (FIG. 17D). In contrast, all vHMEC exhibiting an epithelial morphology expressed E-cadherin, but only very low levels of N-cadherin and fibronectin (FIG. 17D). This demonstrates that the changes in cellular morphology and methylation observed in vHMEC-ras exposed to 10% serum are the result of an EMT and occur de novo.

FIGS. 17A-D. Extracellular signaling and intracellular ras activation cooperate to modulate cellular morphology and methylation. FIG. 17A are photomicrographs of vHMEC-ras grown in 0.5% serum (ras0.5), top panel, or 10% serum (ras10), bottom panel, both in 2D and 3D. Photos of 2D cultures represent the cells grown in their original concentration of serum (0.5% and 10%), as well as after they were switched to no serum (0.5→0 and 10→0). Photos of 3D cultures represent the cells grown alone or in combination with normal fibroblasts derived from a reduction mammoplasty (+RMF). Photos were taken at 10× magnification after 7 days in culture. Methylation-specific PCR (MSP) analysis of E-cadherin and 14-3-3σ on PCR products from bisulfite-modified DNA isolated from vHMEC-ras cells grown in 0.5%, 10%, 0.5→0%, or 10→0.5% serum as well as early passage vHMEC-ras0.5 (E0.5) and two early passage vHMEC-ras10 cells (E10). Bisulfite-modified DNA from MCF7 and MDA-MB-231 cells was used as unmethylated and methylated control templates, respectively for E-cadherin, while bisulfite-modified DNA from MDA-MB-231 and MDA-MB-435 served as unmethylated and methylated controls for 14-3-3σ. Also included is a water control (no template). Product sizes from methylated or unmethylated sequences of E-cadherin were 116 bp and 97 bp, respectively, while product sizes for the methylated and unmethylated sequences of 14-3-3s were 107 bp. Molecular weight markers are indicated on the left in base pairs (results in FIG. 17B). FIG. 17C is a MSP analysis of E-cadherin and 14-3-3σ on two early (C1-E and C2-E) and late (C1-L and C2-L) passage clones isolated from vHMEC-ras0.5. Human mammary fibroblasts (HMF) were used as a positive control for methylation of 14-3-3σ. Photomicrographs of the early and late passage (P) clones analyzed for methylation are shown below the gel and depict the early epithelial and late mesenchymal morphology of the cells. Cells were photographed at 10× magnification. FIG. 17D depicts the immunoblot analysis of molecular markers associated with EMT, including fibronectin (Fn), N-cadherin (N-cad), and E-cadherin (E-cad) was performed on cell lysates prepared from parental vHMEC (par), vHMEC-vector (vec), vHMEC-ras (ras), vHMEC-ras0.5 (0.5), early and late passage vHMEC-ras10 (10E and 10L), early and late passage clone 1 (C1-E and C1-L), and early and late passage clone 2 (C2-E and C2-L). Actin is shown as a loading control.

TGFβ Cooperates with Oncogenic Ras to Induce EMT in Immortalized vHMEC.

Having observed that extracellular signaling induced by 10% serum can cooperate with intracellular ras activation to induce EMT in vHMEC, it was then asked whether appropriate growth factor stimulation could induce EMT in the immortalized vHMEC-ras0.5 cells which had maintained their epithelial morphology. TGFβ has been shown to play a critical role in the induction of EMT. Thiery et al. (2003) *Curr. Opinion Cell. Biol.* 15:740; and Zavadil et al. (2005) *Oncogene* 24:5764. vHMEC-ras0.5 cells were treated with TGFβ and the expression of molecular markers associated with EMT was assessed by immunofluorescence, flow cytometry, and immunoblot analysis. Within 48 h of treatment, the cells began to undergo a morphological change, which became clearly manifested by 72 h. This morphological change was associated with a diminution in cytokeratin expression and disruption of both cell-cell and cell-matrix contacts, as evidenced by the loss of E-cadherin and β1-integrin expression, respectively (FIG. 18A). Coincident with the loss of epithelial marker expression was an upregulation in the expression of the mesenchymal markers, twist (FIG. 18B), N-cadherin, and fibronectin (FIG. 18C). Vimentin is another molecular marker often upregulated following EMT. Although immunofluorescence staining indicated that it is endogenously expressed in vHMEC, its expression pattern following TGFβ treatment clearly reflects the reorganization of the epithelial cell morphology into a mesenchymal one (FIG. 18A).

Unlike the EMT observed in cells exposed to 10% serum, TGFβ-induced EMT is reversible. Consistent with that, methylation of the E-cadherin promoter in these cells following TGFβ treatment was not observed; however, methylation of the E-cadherin promoter was observed in MDA-MB-231 cells, which were used as a positive control (FIG. 18D). The promoter of the epithelial marker 14-3-3σ remained unmethylated in all the epithelial cells, and methylated in the human mammary fibroblasts, which were used as a positive control (FIG. 18D).

FIGS. 18A-D. TGFβ induces EMT in vHMEC-ras0.5 cells without modulating methylation of E-cadherin. FIG. 18A depicts the immunofluorescence analysis. Cells were treated with 2 ng/ml TGFβ for 72 h, and immunostained for pancytokeratin, E-cadherin, β1-integrin, and vimentin. FIG. 18B depicts the flow cytometric analysis of twist expression before (green curve) and after (purple curve) treatment with 2 ng/ml TGFβ for 72 h. FIG. 18C depicts the immunoblot analysis of the mesenchymal markers fibronectin (Fn) and N-cadherin (N-cad) was performed on cell lysates prepared from vHMEC-ras0.5 that were either untreated (−) or treated (+) with 2 ng/ml TGFβ for 72 h. Cell lysates prepared from human mammary fibroblasts were used as a positive control (C) and actin is shown as a loading control. FIG. 18D depicts the MSP analysis of E-cadherin and 14-3-3σ was conducted on the PCR products of bisulfite-treated DNA isolated from vHMEC-ras0.5 untreated (−TGF) or treated (+TGF) with 2 ng/ml TGFβ for 96 h as described in FIGS. 3B and C. Bisulfite-modified DNA from MCF7 and MDA-MB-231 cells was used as unmethylated and methylated control templates, respectively for E-cadherin, while bisulfite-modified DNA from MDA-MB-231 and human mammary fibroblasts (HMF) served as unmethylated and methylated controls for 14-3-3s. Also included is a water control (no template).

TGFβ-Induced EMT is Associated with Enhanced Motility in vHMEC-Ras0.5 Cells.

To determine whether the morphological change in vHMEC-ras0.5 following TGFβ treatment was associated with increased motility, confluent cell monolayers were scratched with a pipette tip, and the ability of the cells to migrate into the denuded area was assessed using time-lapse microscopy. It was found that although vHMEC-ras0.5 cells were very motile, the mesenchymal phenotype induced by TGFβ treatment led to an increase in directed migration, which allowed these cells to fill in the denuded area faster than untreated cells.

A transwell invasion assay was used to examine the invasive behavior of vHMEC-control, non-immortalized vHMEC-ras, vHMEC-ras0.5, vHMEC-ras10 in response to serum. It was found that regardless of the stimulus, vHMEC-ras10 were significantly more invasive than all other vHMEC. These data suggest that extracellular stimulation provided by either serum can initiate EMT in immortalized vHMEC and that acquisition of this mesenchymal phenotype is associated with increased invasive ability.

Immortalized vHMEC Expressing Oncogenic Ras are Capable of Anchorage-Independent Growth and can Survive and Proliferate In Vivo.

Since the immortalized vHMEC expressing oncogenic ras exhibited phenotypic and functional changes associated with targeted DNA methylation that are typically observed during tumor progression, it was asked if these cells had any tumorigenic potential. Anchorage-independent growth is the best in vitro correlate of tumorigenicity, therefore, it was first examined whether vHMEC expressing oncogenic ras could grow in soft agar. As shown in FIG. 19, the parental, vector control, and non-immortalized vHMEC-ras cells failed to grow in soft agar. In contrast, the immortalized vHMEC-ras0.5 and vHMEC-ras10 as well as the two clones isolated from vHMEC-ras0.5 cells displayed some, albeit weak, capacity for anchorage-independent growth, suggesting that they may have some tumorigenic potential.

FIG. 19. vHMEC immortalized with Ha-ras are capable of anchorage independent growth. Soft agar colony assay. Parental vHMEC (par), vHMEC-vector (vec), vHMEC-ras (ras), vHMEC-ras0.5 (ras0.5), vHMEC-ras 10 (ras10), clone 1 (C1), and clone 2 (C2) were plated in 35 mm dishes at a concentration of 50 000 cells per dish, in triplicate. After 14 days, colonies were counted manually in eight different fields. The data are presented as the average of the sum of 8 different fields counted.

Example 4

Overexpression of TRF2 Results in Activin A-Dependent Induction of COX-2 In Vitro and In Vivo Materials and Methods Tissue Samples: High (n=7) and low (n=8) grade+one unknown non-recurrent ductal carcinoma in situ (DCIS) specimens were obtained with institutional review board approval from the surgical pathology laboratory at the University of California, San Francisco. Patients were identified through anonymous reference numbers in accordance with federal guidelines.

Telomere Content Determination: A 5 μm tissue section was stained with hematoxylin and eosin and cellular morphology was evaluated. This reference slide was used to guide microdissection of 6×25 μm sections. Microdissection was performed using a Leica AS-LMD microdissection microscope on slides stained with methyl-green following standard procedures. DNA was purified from populations enriched for DCIS using proteinase K and chloroform/phenol. DNA was quantitated using Picogreen dye following the manufacturer's protocol (Invitrogen). Telomere content was determined as described previously (Fordyce et al, 2005). Briefly, DNA was denatured and fixed to positively charged membrane using a vacuum apparatus and then hybridized to a labeled telomere-specific probe (TTAGGG)$_4$ (IDT). The tagged probe was detected using an antibody conjugated to alkaline phosphatase and a chemiluminescent substrate, CDP-STAR (New England Biolabs). Blots were exposed to film, and the intensity of each spot was determined using Image Quant software (Molecular Dynamics). Samples were analyzed in triplicate. Data is expressed as a percentage of placental DNA.

Tissue Preparation and Immunohistochemistry (including evaluation): Five-micron sections were cut form paraffin-embedded tissue blocks adjacent to sections used for telomere content determination. Tissue sections were deparaffinized and rehydrated using standard protocols. Microwave antigen retrieval was accomplished using 0.001M EDTA, pH=8 for COX-2, 0.01 M citrate for γH2AX and Antigen Unmasking Solution (Vector Laboratories) for TRF2. Antiserum against COX-2 (1:200, Dako), γH2AX (1:150, Upstate) and TRF2 (1:20, Imgenex) was incubated on tissue sections for ~16 hrs at 4° C. Antigen-antibody complexes were labeled using the Vectastain Elite ABC following standard protocols (Vector Laboratories, CA) and visualized using 2.5% 3-amino-9-ethyl-carbazole in 50 mM acetate buffer pH5, with 0.05% hydrogen peroxide. Sections were counterstained in Mayers hematoxylin mounted in Crystal Mount (BMMO2, American Mastertech). Once dry, the sections were permanently mounted with a glass coverslip using clearmount (MMCLE1 American Mastertech). A blocking step (0.01% Triton X 1000 for 1 hr) was added to this protocol prior to addition of the primary antibody for the TRF2 staining.

The degree of γH2AX, COX-2 or TRF2 staining intensity was evaluated in a blinded fashion. For COX-2, staining intensity was examined by light microscopy and was scored as low to absent (1), moderate (2) or strong (3) in the majority of either DCIS or adjacent normal tissue. For the purpose of the study, COX-2 expression scored as 2 or 3 was considered high. TRF2 and γH2AX expression was evaluated by counting the number of positive nuclei in a minimum of 500 cells. The mean level of positive cells for either TRF2 (29%) or γH2AX (27%) was used to stratify the tissues into high and low groups.

Cell Culture: Human mammary epithelial cells (vHMEC) were isolated from reduction mammoplasty (RM) of four individuals RM9, RM15, RM16 and RM18. HMEC undergo a spontaneous proliferation barrier between 8 and 12 population doublings. Variant human mammary epithelial cells (vHMEC) escape this growth barrier and have silenced p16 through promoter methylation. Cells were propagated in 2D cultures in modified MCBD 170 media (MEGM, Lonza) as previously described (Romanov et al, 2001; Hammond et al 1984). All experiments were performed on exponentially growing early passage vHMEC (between 13 to 20 population doublings); RM9, 15, 16 and 18 cease to expand in cell number at population doublings 45, 60, 50 and 53, respectively. Activin A (Sigma) and the p38 inhibitor, SB203580, (Sigma) were added to culture media for 48 and 24 hours (respectively) prior to harvest at the doses shown in FIGS. 3 and 4. The same amount of solvent for each molecule was added to the culture media for controls.

Wound Closure Assay: Wound closure assays were performed as previously described (Dumont et al, 2003 JBC). Cells were plated in duplicate wells of a 6-well plate at 2×10$^5$ each and allowed to proliferate until confluent. Confluent cell monolayers were wounded by manually scrapping the cells with a pipette tip and an ocular ruler was used to verify the widths of the resulting wounds. Media was replaced and wound closure was monitored by microscopy.

Expression of TRF2: The TRF2 gene was excised from the pLPC construct using Hind III and EcoRI and inserted into the pWP1 lenti viral expression vector. The TRF2-pWP construct was packaged in 293T cells for viral propagation. Lenti-viral supernatant was diluted 1:1 with MEGM media containing polybrene (8 μm/ml; Sigma) and added to vHMEC for 4 to 6 hrs. Infection efficiency was monitored using GFP expression, which was driven from the same promoter via an IRES sequence.

Quantitative PCR: Total RNA was isolated from cells and cDNA synthesized using standard methods. cDNA was subsequently used for quantitative real-time PCR using the standard curve method. Primer-probe sets for COX-2 (Hs00153133), TRF2 (Hs00194619) and activin A (Hs00170103) were obtained from ABI (location). The expression of GUSB (IDT), an external control, was used to normalize for variances in input cDNA.

Western Blotting, ELISA and Immunofluorescence: Cell pellets were lysed in T-PER buffer (Pierce). Cell lysates were fractioned in gradient polyacrylamide gels (4-20%) and transferred to Hybond-P (Amersham Biosciences) membranes using standard procedures. Antibodies against COX-2 (1:200, Cayman), phospho-p38, (1:200, Cell Signaling) were used according to manufacturers' protocols. Activin A protein levels were measured using the Duo-Set Activin ELISA kit (R&D Systems) following the manufacturer's directions. Parental vHMEC or cells over expressing vector or TRF2 were plated in 6-well dishes at 1×10$^5$ in duplicate. Media was replaced the following day and allowed to condition for 72 hours prior to analysis. Levels of activin A were determined in cells from all four donors. For immunocytochemistry, 5×10$^4$ cells were seeded directly onto glass cover slips and fixed in 4% paraformaldehyde (PFA) for 15 minutes at room temperature and stored in 0.01% PFA at 4° C. Cover slips were treated with anti-TRF2 antibody (1:100, Imgenex) or anti-γH2AX (1:1000, Upstate) following the manufacturer's protocols. Nuclei were counterstained using Dapi (Molecular probes, location) and visualized using a LSM450 Zeiss confocal microscope. The mean fluorescent intensity of γH2AX signal (voxels) in each nucleus was determined with the Volocity 4.0.0 software package (Improvision) on Z-stacks.

Statistical Methods: ANOVA was used to test the relationship between gene expression or activin protein levels in the vHMEC treatment groups (parent, vector and TRF2 over-expressing cells). The relationship between telomere content and COX-2, γH2AX and TRF2 staining intensity was examined using a T-test. Chi-Square test was used to evaluate the relationship between staining intensity for TRF2 and COX-2 and γH2AX. The Jmp statistical package (SAS Institute) was used for all analyses.

Results

Telomere Content is Inversely Associated with γH2AX, TRF2 and COX-2 Expression in DCIS. Fifteen high and low grade non-recurrent DCIS lesions ductal carcinoma in situ (DCIS) lesions were microdissected and used for DNA purification. Telomere content, a proxy for telomere length, was measured in the nine lesions from which sufficient DNA was obtained. Telomere content ranged from 39 to 417% of the placental standard. Telomere content was not associated with patient age at surgery, ethnicity, menopausal status, DCIS grade or tumor size. To determine if the reduced telomere content measured in this cohort was associated with a DNA damage response, we evaluated the levels of γH2AX, a DNA damage marker, with immunohistochemistry on serial sections of the DCIS lesions. As shown in FIG. 20, telomere content was inversely associated with the proportion of γH2AX positive nuclei in the DCIS lesion (T-test, p=0.001).

Exogenous expression of the telomere binding protein, TRF2, results in progressive telomere shortening. De Lange (2002) Oncogene 21:532; de Lange (2005) Genes Dev. 19:2100; Smogorzewska et al. (2000) Mol. Cell. Biol. 20:1659; and Oh et al. (2005) Am. J. Pathol. 166:73. It was determined if there was an association between telomere content and TRF2 in our DCIS cohort. The proportion of TRF2 positive nuclei in DCIS lesions was evaluated in 14 of 15 cases. Telomere content was measured in 8 of these cases. As shown in FIG. 20, TRF2 expression was higher in the in DCIS lesions with low telomere content than in lesions with high telomere content (T-test, p=0.001). TRF2 expression was associated with the proportion of cells in the DCIS lesion expressing γH2AX (X2, p=0.005).

The observation that increases in COX-2 expression coincides with telomere loss and genomic instability in primary variant human mammary epithelial cells (vHMEC) in vitro, suggested that there might be a relationship between loss of telomere homeostasis and COX-2. It was postulated that the increase in γH2AX positive nuclei in DCIS lesions with reduced telomeres is indicative of loss of telomere homeostasis. The levels of COX-2 expression were evaluated, using immunohistochemistry in the DCIS cohort. Strikingly, there was a significant relationship between telomere content and the degree of COX-2 staining in the DCIS lesion (T-test, p=0.004). The degree of COX-2 and γH2AX expression were directly associated with each other (X2, p<0.0001). Likewise, there was a statistically significant relationship between TRF2 expression and COX-2 (X2, p=0.005). None of COX-2, γH2AX, and TRF2 were associated with any of the other parameters evaluated in this study. These data show that the reduced telomere content observed in the DCIS lesions is inversely associated with the induction of a DNA damage response, and the expression of TRF2 and COX-2.

FIG. 20: Telomere Content is Associated with COX-2 Expression. COX-2 and γH2AX levels were evaluated using immunohistochemistry. For COX-2, lesions were scored as low to absent (1), moderate (2) or strong (3) in the majority of either DCIS or adjacent normal tissue. For the purpose of the study, COX-2 expression scored as 2 or 3 was considered high. The number of γH2AX positive nuclei were manually counted and expressed as a percentage of the total number of nuclei within a region of DCIS. The mean percentage of γH2AX positive nuclei (27%) was used to stratify lesions. Telomere content, a proxy for telomere length was measured in DCIS following microdissection and is expressed as percentage of placental control. Box plots show the relationship between telomere content and either γH2AX (right) or COX-2 (left) when DCIS lesions are stratified into two groups (high or low staining intensity).

Exogenous Expression of TRF2 in vHMEC. To more directly access if changes in telomere length or structure can induce COX-2, an in vitro model system was used. The observation that TRF2 expression is associated with telomere content in this DCIS cohort is consistent with previous reports showing that exogenous expression of TRF2 results in telomere loss (de Lange supra; Smogorzewska et al. supra; Oh et al, 2005, supra). TRF2 is also an integral component of multiple protein complexes localized to the telomere and is important for the formation of the unique DNA loop at the extreme ends of the telomere (de Lange, supra). Exponentially growing early-passage (PD<15) variant human mammary epithelial cells (vHMEC) purified from four donors were mock infected or infected with lenti virus containing vector alone (pWP) or vector plus the TRF2 gene. Infection efficiency was monitored using GFP expression driven by an IRES sequence. TRF2 mRNA (ANOVA, p=0.0002) and protein levels were significantly up regulated in vHMEC infected with TRF2 containing lenti virus when compared to parent and vector controls. Over expression of proteins can result in altered localization. It was verified that TRF2 was confined to the nucleus using immunofluorescence. The rates of proliferation and number of population doublings for parent, vector and TRF2 over expressing cells from all four donors were evaluated using growth curve analysis. Consistent with previous reports, cells expressing TRF2 underwent slightly fewer population doublings than vector and parental controls, but had similar rates of cell replication, particularly at early passages. Flow cytometry for BrDu and propidium iodide was used to evaluate the proportion of cells in each phase of the cell cycle in cells over expressing TRF2 and parent and vector controls. There was no change in the proportion of cells in any phase of the cell cycle in parental vHMEC compared to cells infected with vector alone or over expressing TRF2.

Previous reports have shown that over expression of TRF2 leads to a preferential enrichment of single strand breaks at the telomeres and increased telomere loss. It was postulated that over expression of TRF2 would result in accumulation of the DNA damage marker γH2AX in vitro. vHMEC over expressing either TRF2 wt or vector and parental controls were grown on glass cover slips, fixed and treated with antiserum against γH2AX. The mean fluorescent intensity of γH2AX in vHMEC with or without TRF2 wt was determined. As shown in FIG. 21, there was a statistically significant increase in the mean number of γH2AX voxels in cells over expressing TRF2 (ANOVA, p<0.0001). Thus, exogenous expression of TRF2 up-regulates γH2AX in vHMEC and recapitulates the increase in γH2AX observed in DCIS with reduced telomeres.

FIG. 21: γH2AX is Up Regulated in vHMEC Expressing TRF2. Levels of γH2AX were determined using immunofluorescence with an anti-γH2AX antibody (Upstate). Levels of γH2AX expression were determined using Z-stacks obtained on a confocal microscope. The mean intensity of γH2AX voxels/nucleus were determined using Volocity software (company) in vHMEC from two donors.

COX-2 is Up Regulated in vHMEC expressing TRF2 in a Phospho-p38 Dependent Manner. Since COX-2 levels were associated with both telomere content and the levels of γH2AX expression in the DCIS cohort, the level of COX-2 in vHMEC over expressing TRF2 was evaluated. COX-2 mRNA and protein levels were evaluated using Q-PCR and immunoblotting, respectively. COX-2 mRNA levels were increased approximately two fold in vHMEC over expressing TRF2 (ANOVA, p=0.002, FIG. 22a). Likewise, COX-2 protein levels were increased in vHMEC over expressing TRF2 when compared to parental and vector controls. Next, it was determined if the increase in COX-2 observed in TRF2 over expressing vHMEC was able to induce a phenotype associated with COX-2 expression. Previous reports have shown that COX-2 expression enhances cell motility. A cell wounding assay was used to evaluate the motility of vHMEC over expressing TRF2 compared to vector and parental controls from two donors. Confluent monolayers in duplicate wells were manually wounded with a sterile pipette tip. After ensuring that the width of the wounds was similar, cells were monitored with microscopy for 12 hours. Cells over expressing TRF2 were able to fill the wound in 8 hours, while parent and vector controls required approximately 12 hours (FIG. 22c), demonstrating a modest, but consistent increase in cell motility.

It has previously been shown that the increase of COX-2 observed in late-passage vHMEC is dependent on the MAPK, p38. Here it is shown that the activated phospho-p38 is up-regulated in early passage vHMEC cells over expressing TRF2 (FIG. 22b). To determine if phospho-p38 is necessary for the induction of COX-2 in response to TRF2, early passage parent, vector, and TRF2 over expressing vHMEC were treated with the phospho-p38 inhibitor SB203580. As shown in FIGS. 22A and 22B, inhibition of phospho-p38 lead to a marked decrease in COX-2 mRNA (ANOVA, p=0.002) and protein levels in cells expressing TRF2. This finding demonstrates that expression of TRF2 is able to induce COX-2 in a phospho-p38 dependent manner in vHMEC.

FIGS. 22A-C: COX-2 is Induced in vHMEC Over Expressing TRF2 and is Dependent on p38. FIG. 22A is a box plot showing the levels of COX-2 mRNA as measured with Q-PCR in untreated parental vHMEC or vHMEC over expressing either vector (pWP) or TRF2, or treated with the phospho-p38 inhibitor SB203580 for 24 hrs at the indicated doses. Inset is p-value comparing either parent, vector and TRF2 cells or cells treated with SB203580 to untreated controls. FIG. 22B is a representative immunoblot showing COX-2, phospho-p38 and actin (loading control) for the conditions described in A. FIG. 22C is a representative example of wounding assay showing parent vHMEC and vHMEC over expressing vector or TRF2 at 0, 4 and 8 hrs following wounding.

Figure 23A:
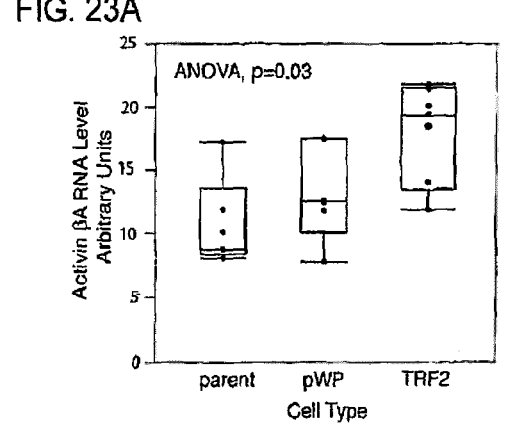

Activin A Induces COX-2 Up-regulation in vHMEC. A variety of signal transduction pathways can lead to the activation (and phosphorylation) of p38. To further elucidate the mechanisms by which TRF2 induces COX-2 in vHMEC, microarrays were used to screen for modulators of p38 activity. Activin A, a member of the TGF-β superfamily, was up regulated in vHMEC over expressing TRF2 when compared to parent and vector controls. Previous reports have demonstrated that binding of activin A to its receptor can lead to the phosphorylation and activation of p38. Activin A is a homodimer of the activin βA subunits. The activin βA monomer can also form a heterodimer with inhibin α, to produce the activin A antagonist, inhibin A. Microarray analysis demonstrated that inhibin a was not differentially expressed in vHMEC over expressing TRF2 when compared to controls. The results of the microarray analysis were validated using Q-PCR. As shown in FIG. 23A, activin βA was significantly up regulated in cells over expressing TRF2 (ANOVA, p=0.03).

Figure 23B:
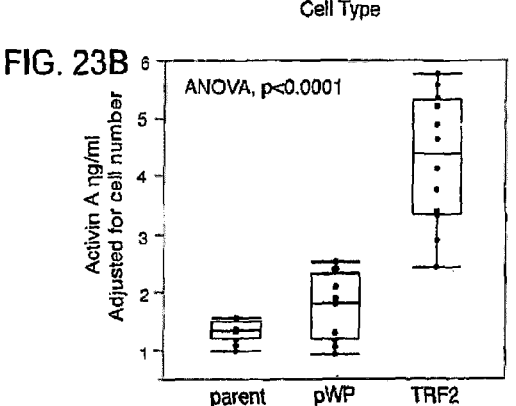

Activin A protein levels were measured using ELISA (FIG. 23B). Mean levels of activin A protein in condition media from parental vHMEC or vector controls was 1.3 ng/ml and 1.7 ng/ml, respectively. In contrast, the mean level of activin A in conditioned media from vHMEC expressing TRF2 was 4.4 ng/ml, an approximately 5-fold increase (p<0.0001, ANOVA). These data demonstrate that activin A is up regulated in vHMEC over expressing TRF2.

Figure 23C:
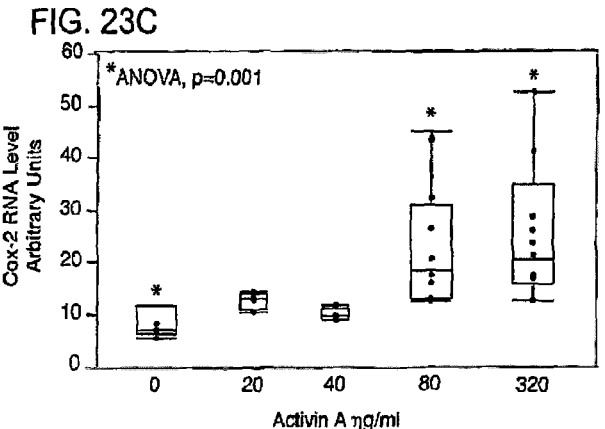
Figure 23D:
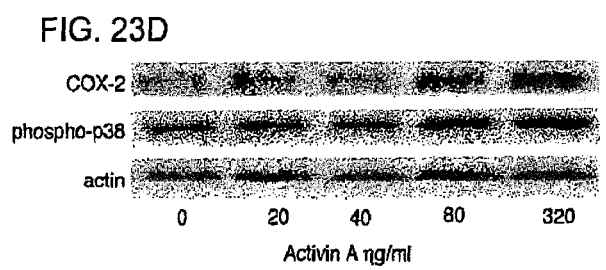

To determine if activin A was sufficient to induce COX-2 expression vHMEC from two donors in duplicate experiments were treated with exogenous activin A. As shown in FIG. 23C, exogenous activin A induced an approximately two-fold increase in COX-2 mRNA (ANOVA, p=0.001) and protein. Treatment with exogenous activin A also caused an increase in the levels of phospho-p38 (FIG. 23d). Since activin A is a secreted protein, it was reasoned that conditioned media from cells over expressing TRF2 should be able to induce COX-2 expression in vHMEC. Conditioned media from parent, vector and vHMEC over expressing TRF2 was collected from two donors and used to treat uninfected vHMEC obtained from three donors. COX-2 mRNA and protein were increased approximately two fold when vHMEC were treated with conditioned media from cells over expressing TRF2. Likewise, phospho-p38 levels were increased in vHMEC treated with conditioned media from cells over expressing TRF2. Taken together these data suggest that the induction of COX-2 expression observed in early-passage vHMEC over expressing TRF2 is driven by activin A.

FIGS. 23A-D: Activin A is Up Regulated in vHMEC and Induces COX-2. FIG. 23A is a box plot showing the levels of activin A mRNA measured using Q-PCR in parental vHMEC, or vHMEC over expressing vector (pWP) or TRF2 from 4 donors. p-value was calculated using ANOVA and is shown in the inset. FIG. 23B is a box plot showing the levels of activin A protein measured using ELISA in parental vHMEC or vHMEC over expressing vector (pWP) or TRF2 from 4 donors. Inset shows p-value calculated using ANOVA. vHMEC from 2 donors were treated with exogenous activin A for 48 hrs at the indicated doses. Box plot shows the levels of COX-2 mRNA as measured by Q-PCR (results in FIG. 23C). Inset shows p-values for untreated cells compared to the two highest doses of activin A. The experiment was performed in quadruplicate. FIG. 23D are representative immunoblots showing the levels of COX-2, phospho-p38 and actin (loading control) for cells and treatments described in C.

Example 5a

Cell Surface Markers that Identify Cancer Cell Precursors

Method & Materials

Screening of Markers

HMEC were trypsinized, washed, spun down, and counted. Cells were incubated in MEGM+2% FBS for 2 hours to regenerate cell surface markers. Cells were spun down, and incubated with anti-CD73-phycoerythrin (anti-CD73-PE; PE-conjugated antibody to CD73) (12 μL per 1×10⁶ cells) for 30 min. Then cells were spun down and incubated with anti-CD90-allophycocyanin (anti-CD90-APC; APC-conjugated antibody to CD90) (1 μL per 1×10⁶ cells). Following staining, cells were washed 3× with PBS and subjected by flow cytometry. Flow cytometry profiles were analyzed by Flowjo software.

Flow Sorting of Cells and Culturing of Cells

Human mammary tissue were digested as described (Romanov et al. (2001) Nature 409:633-7), and further digested to single cells as described (Liu et al. (2004) Proc Natl Acad Sci USA 101:4158-63). Cells were counted and incubated in MEGM+2% FBS for 2 hours. Cells were spun down, and incubated with CD73-PE (12 μL per 1×10⁶ cells) for 30 min. Then cells were spun down and incubated with CD90-APC (1 μL per 1×10⁶ cells) and anti-epithelial-specific antigen-fluorescein isothiocyanate (anti-ESA-FITC; FITC-conjugated antibody to ESA) (2 μL per 1×10⁶ cells). Following staining, cells were washed 3× with PBS and subjected to flow cytometry. Cells were sorted by BD FAC Aria. Once cells were isolated, they were plated in a 12-well plate with 1 mL of MEGM. Cells were passaged once reached ~70% confluency, counted and population doublings (PD) was determined.

Methylation-Specific PCR (MSP)

Cells were sorted and mixed with 0.5×10⁵ HeLa carrier cells. Genomic DNA was prepared, bisulfate treated, and subjected to methylation specific PCR.

Immunoblot

Cells were lysed by 1% SDS and 1% b-mecaptoethanol, and cell lysate was subjected to immunoblot analysis as described (Liu et al. (2003) *Oncogene* 22:9243-53). Anti-Bmi-1 antibody was purchased from Upstate Cell Technology.

Results

Based on microarray experiments, potential candidate markers were identified that are important for distinguishing cancer precursor cells from bulk epithelial cells. 19 cell surface markers were screened via flow cytometry. It was found that the markers CD73, CD138, CD90, CD133, and Notch receptor-3 clearly distinguished cultured vHMEC from HMEC. Expression of CD73, CD138, and Notch Receptor-3 in the vHMEC was increased by ~12-fold, ~5-fold, and ~6-fold respectively, as compared to HMEC (median vHMEC vs. HMEC; FIG. 24A), whereas expression of CD90 and CD133 in the vHMEC was decreased by ~7-fold, and ~3-fold respective relative to HMEC.

Immunocytochemical analysis of vHMEC and HMEC with anti-CD73 and anti-CD90 antibodies also showed results consistent with FACs analysis (FIG. 24B). Detectable levels of CD73 were seen in vHMEC but not in HMEC, and the localization of CD73 was predominantly on the cell surface. Likewise, only cell surface expression of CD90 was detected in HMEC, and not in vHMEC (FIG. 24B). When anti-CD73 and anti-CD90 antibodies were combined, the vHMEC population was easily distinguishable from the HMEC population; vHMEC were CD73⁺ (FIG. 24C).

FIGS. 24A-C: FIG. 24A is a histogram of flow cytometric analysis of CD73, CD90, CD138, Notch receptor-3, and p16 expression on vHMEC and HMEC is shown. Cultured vHMEC and HMEC from matched mammary reduction individual were trypsinized to single cells, incubated with anti-CD73, -CD90-APC, -CD138-FITC, Notch receptor-3-FITC, or -p16-PE antibodies, and analyzed by flow cytometry. FIG. 24B depicts immunocytochemistry of vHMEC and HMEC with anti-CD73 and anti-CD90 antibodies. Cells were grown on coverslips, fixed, and stained with anti-CD73 and -CD90 antibodies followed by anti-mouse-FITC secondary antibodies, and fluorescent signal was visualized by confocal microscopy. Cell nuclei were stained with Hoechst dye; and CD73 and CD90 expression was detected using antibodies. Cell distribution of vHMEC and HMEC costained with anti-CD73 and -CD90 antibodies. Cultured vHMEC and HMEC from matched mammary reduction individual were trypsinized to single cells, incubated with anti-CD73-PE and -CD90-APC antibodies, and analyzed by flow cytometry (results in FIG. 24C).

Since the markers CD73 and CD90 distinguish the variant population in cultured cells, the markers were applied to mammary tissues that have not subjected to culturing conditions. Mammary tissue from five individuals were processed and further digested to single cells. Cells were incubated with antibodies to ESA (to identify epithelial cells), CD73, and CD90; and sorted by flow cytometry. Cells were gated as indicated and isolated.

To determine whether the isolated cells contained the distinguishing characteristic of vHMEC, methylation of the p16 promoter, methylation-specific PCR was performed on the various gated cells. 10,000 cells were isolated from each CD73CD90 fraction and diluted the cells into 5×10⁵ carrier cells, HeLa cells. Genomic DNA was prepared, bisulfate converted, and subjected to methylation specific PCR. Methylation of the p16 promoter was detected in cell fractions with CD73+ epithelial cells, but not in bulk epithelial cell populations.

Example 5B

Biomarker Expression and Risk of Subsequent Tumors after Initial Ductal Carcinoma In Situ Diagnosis Study Sample and Methods The study sample and methods outlined in this example have been previously described (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702). In brief, data from the Surveillance, Epidemiology, and End Results (SEER) program of Northern California was used to identify women who were aged 40 years or older when diagnosed with DCIS and who were treated by lumpectomy alone in one of nine San Francisco Bay Area counties from Jan. 1, 1983 to Dec. 31, 1994. From an initial pool of 1568 women, 142 women who had DCIS treated by mastectomy or by lumpectomy plus radiation within 6 months of the initial diagnosis, 19 women who had a prior diagnosis of breast cancer, 18 women who died within 6 months of the initial diagnosis, 37 women whose initial DCIS lesion was found to have invasive cancer on standardized pathology review and 20 women whose DCIS diagnosis could not be confirmed were excluded. Of the 1,332 eligible participants, 29 women could not be located, 18 women did not speak fluent English, Cantonese, Spanish, or Russian (the languages we used to conduct the telephone interviews), 118 women refused to participate, and five women had a doctor's request not to be contacted. The study cohort included 1,162 women with an overall participation rate of 87%. This study was reviewed and approved by the University of California, San Francisco Committee on Human Research.

Telephone Interviews and Vital Status

Demographic information and a breast health history was obtained from each woman during a telephone interview on average 7.5 years after initial diagnosis, as previously described (5). In brief, the interview included questions about breast procedures a woman had undergone, family history of breast cancer, detection method at diagnosis, and menopausal status. To obtain information for 206 women who were either deceased or not able to participate in an interview because of illness, a proxy was interviewed and/or a medical record review was conducted. Data regarding vital status and underlying cause of death including breast cancer as of Dec. 31, 2005 from the California Department of Vital Statistics and/or death certificates was obtained.

Standardized Pathology Review for Nested Case-Control Study

Paraffin-embedded tissue samples and/or hematoxylin-eosin-stained slides of initial DCIS tissue from women who had subsequent tumors (case subjects) and women with DCIS who did not have subsequent tumors (control subjects) were retrieved from pathology laboratories. Control subjects were randomly selected and frequency matched to case subjects by year of diagnosis prior to retrieval of their DCIS tissue. Paraffin-embedded tissue blocks could not be obtained from some hospitals that had discarded the tissues, had insufficient staff to collect the tissues, and/or refused to provide tissue for research (80 case subjects, 93 control subjects). Subsequent tumors were defined as DCIS or invasive breast cancer that was diagnosed in the ipsilateral breast (that had contained the initial DCIS lesion) or at a regional or distant site (bone, brain, liver, lung, skin) more than 6 months after the initial diagnosis and treatment of DCIS. Women who had both DCIS and invasive cancer in subsequent tissue samples were categorized as having a subsequent invasive cancer. In order to classify a woman as having had a subsequent tumor event as defined above, the nature of all breast procedures reported by women during a telephone interview were investigated by obtaining and reviewing pathology reports for breast biopsies performed after the initial diagnosis and linking to the Northern California SEER program in 2002 and 2008. Pathology reports were available on 94% of breast biopsies performed after the initial diagnosis. Women who developed only contralateral breast cancer during the study period were included in the study as control subjects.

As previously described (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702), study pathologists blinded to the clinical outcome reviewed hematoxylin-eosin-stained slides (N=502) of the original DCIS lesions from 114 women who had a subsequent invasive cancer event, 109 women who had a subsequent DCIS event, and 279 control subjects who did not have a subsequent tumor event to verify initial diagnoses of DCIS; to verify diagnoses of subsequent disease; and to determine nuclear grade, type, and quantity of necrosis, tumor size, and margin width of the initial DCIS diagnosis. The pathologists established at least 80% agreement on identification of histopathological characteristics in a training set of women with DCIS prior to reviewing study case and control subjects. Disagreements were resolved by consensus. Nuclear grade, type and quantity of necrosis, cell polarity, architectural growth pattern, and type of calcification were classified according to consensus definitions (Consensus Conference Committee. Consensus conference on the classification of ductal carcinoma in situ. Cancer 1997; 80:1798-802). Lesion size was estimated by directly measuring the largest dimension on the slide showing the most extensive disease. In addition, if DCIS was present on more than one slide, the number of slides containing DCIS out of the total number of slides available was taken into account in order to estimate lesion size. When DCIS was present on more than one slide, it was assumed that each section was 0.3 cm in thickness and multiplied the number of slides that contain DCIS by 0.3 cm. The larger of these two measurements was used to estimate lesion size. In some cases, not all of the original slides for a specimen were available for review and the sequence of the slides relative to the gross specimen was not always known. Thus, the lesion sizes reported are best estimates given the available pathology material and information. Tumor margin width was determined by direct measurement of the smallest single distance between the edge of the tumor and the inked tumor margin or cautery artifact. Margins were considered positive if there was ink on the tumor. Tumor margins were classified as 'uncertain' if margin status was unknown or could not be assessed. Tumor margins in women who underwent reexcision and in whom no additional DCIS was found were reported as being at least 10 mm in width.

Measurement of Biomarkers for Nested Case-Control Study

Immunohistochemical (IHC) staining was used to identify DCIS phenotypes using slides from formalin-fixed paraffin-embedded tumor blocks (N=329) from 72 women who had a subsequent invasive cancer event, 71 women who had a subsequent DCIS event, and 186 control subjects who did not have a subsequent tumor event. The index lesion was scored for the presence of the following proteins using the indicated mouse monoclonal antibodies: for estrogen receptor (ER) using a 1:400 dilution of antibody 1D5 (DAKO, Carpentria, California), for progesterone receptor (PR) using a 1:25 dilution of antibody 1A6 (Novocastra, Bannockburn, Illinois), for Ki67 antigen [MKI67 (FHA domain) interacting nucleolar phosphoprotein] using a 1:100 dilution of antibody MIB-1 (DAKO), for p53 (TP53) using a 1:200 dilution of antibody PAb 1801 (Neomarkers, Fremont, California), for human epidermal growth factor receptor-2 (ERBB2) using a 1:200 dilution of antibody TAB250 (Invitrogen, Grand Island, New York), for cyclo-oxygenase-2 (COX-2) using a 1:200 dilution of antibody M3617 (DAKO), and for p16 (cyclin-dependent kinase inhibitor 2A) using a 1:200 dilution of antibody MS218 (Neomarkers) (21, 22). Staining with primary antibodies was followed by staining with biotinylated labeled secondary antibodies and detection with an avidin biotin complex-HRP system. Specimens were counterstained with hematoxylin. Positive and negative control tissues were used for assessment of each marker as follows: ER, breast tumor case and cell line MCF-7; PR, breast tumor case and cell line T47D; Ki67, breast tumor case; p53, colon tumor case and cell line T47D; ERBB2, breast tumor case and cell line SKBR3; COX-2, a DCIS case; and p16, normal breast tissue and colon tumor. It is noted that two additional years of data was subsequently added to the present analysis, increasing the above numbering as follows: an N of 392 (from 329), 92 women had a subsequent invasive cancer event (from 72), 85 women who had a subsequent DCIS event (from 71) and 186 control subjects who did not have a subsequent tumor event. The results were the same for all outcomes.

One investigator scored ER, PR, ERBB2, and p53 stains, and two investigators scored p16, COX-2, and Ki67 stains; all were blinded to clinical outcomes. For p53, ERBB2, ER, and PR, the percentage of tumor cells that showed staining of any intensity was estimated and recorded. The marker p53 was considered to be overexpressed, and ER and PR were considered to be present when 10% or more tumor cells showed staining. Similarly, ERBB2 was considered to be overexpressed when 10% or more tumor cells showed moderate or strong membrane staining (+2 or higher); these were criteria previously used for scoring DCIS lesions for ERBB2 (23).

Using a condensed Allred score (24), COX-2 staining was evaluated on a scale of 0, 1, 2, or 3, with each value corresponding to a combination of two Allred classes (0=Allred classes 0 and 1; 1=2 and 3; 2=5 and 6; 3=7 and 8). Scoring of p16 was evaluated on a scale of 0, 1, 2, or 3 based on the percentage of positively staining tumor cells, irrespective of staining intensity (0=no staining, 1=<25% of cells stained, 2=25% to 75%, 3=>75%) (22). Tissues with a score of ≥2 were considered to overexpress COX-2 or p16. For Ki67 scoring, a minimum of 1000 tumor cells were counted from at least three high powered (40×) fields in areas that showed the highest labeling. The labeling index was expressed as a percentage, and was calculated as the number of positive cells divided by the number of positive plus negative cells. Tissues were considered to have high Ki67 expression if more than 10% of tumor cells were stained, which was more than the median value for all tumors evaluated. In a random sample of 45 specimens, a comparison of two independent scorers of select IHC assays yielded a k statistic of 0.93 and concordance of 98% for p16, a k statistic of 0.73 and concordance of 87% for COX-2, and a k statistic of 0.82 and concordance of 91% for Ki67 (see Appendix for representative staining).

Statistical Analysis

Cox proportional-hazards models were used to determine univariate and multivariable hazard ratios (HR) for various clinical and histopathological characteristics and biomarkers among women in the cohort who had a subsequent tumor compared with women who did not. Combinations of biomarkers that were found as individual markers in univariate analyses to be statistically significantly associated with invasive cancer and/or DCIS, or were previously shown to have a biological basis for association with subsequent tumors after a DCIS diagnosis (Gauthier M L, Berman H K, Miller C, Kozakeiwicz K, Chew K, Moore D, et al. Abrogated stress response distinguishes basal-like tumors and DCIS lesions associated with subsequent tumor events. Cancer Cell 2007; 12(5):479-491), or were previously reported to be associated with breast cancer survival (Carey L A, Perou C M, Livasy C A, Dressler L G, Cowan D, Conway K, et al. Race, Breast cancer subtypes, and survival in the Carolina breast cancer study. JAMA 2006; 295(21): 2492-2502) were examined. For inclusion in the multivariable models, individual and combinations of factors were considered that were statistically significantly associated with invasive cancer and/or DCIS in univariate analyses. For multivariable models, margin width was considered as an ordinal variable (ordered as >10 mm, 2 to <10 mm, 1-1.9 mm, uncertain, and positive). The validity of the proportional hazards assumption was verified by log-cumulative hazard plots and, where appropriate, inclusion of a time-dependent variable. Subsequent invasive cancer, DCIS, and death from causes other than breast cancer were competing events. To calculate the appropriate hazard ratio (HR), the competing risk package cmprsk in R (http: followed by //cran.r-project.org/doc/packages/cmprsk.pdf) was used to estimate coefficients in the 'proportional subdistribution hazards' regression model described by Fine and Gray (Fine J P, Gray R J. A proportional hazards model for the subdistribution of a competing risk. JASA 1999; 94(446):496-509). This model can be used to directly assess the effect of covariates on the subdistribution of a particular type of outcome, in this case invasive cancer or DCIS, in a competing risk setting. In a sensitivity analysis, women who developed contralateral breast cancer were excluded and results were very similar to the results from the final models.

To estimate the risk of subsequent tumor events (invasive cancer or DCIS), a standard Kaplan-Meier survival curve was generated. To estimate the 5- and 8-year probability of subsequent tumor events for the population-based cohort by histopathological characteristics and biomarkers that were collected only for cases and controls, the results of the case-control study were converted to survival curves. To do so, histopathological characteristics and biomarker measurements were imputed for those women in the cohort who were not included in the nested case-control study. The imputed values were based on the observed prevalence of the individual histopathologic and biomarkers in the nested study stratified by case and control status as well as by the type of subsequent tumor event as previously described (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702). To estimate risk of subsequent invasive cancer with a DCIS event and death from causes other than breast cancer (N=125) as competing risks, and to estimate risk of subsequent DCIS with an invasive cancer event and death from causes other than breast cancer as competing risks, the code from Pepe and Mori (Pepe M S, Mori M. Kaplan-Meier, marginal or conditional probability curves in summarizing competing risks failure time data? Statistics in Medicine 1993; 12(8):737-751) was employed to estimate the marginal distribution, i.e., the cumulative incidence function (CIF). This process was repeated 2500 times, each time generating a new imputed value for each woman for whom there was missing data for a marker of interest. For each time point t, the 2500 Kaplan-Meier or CIF survival estimates were averaged and the 95% confidence interval (CI) was reported as the 0.025 and 0.975 quantiles of those survival estimates.

Four risk groups (e.g., lowest, low, intermediate, and high risk) were defined separately for subsequent invasive cancer and DCIS based on statistically significant univariate and multivariable associations as well as level of risk associated with clinical and histopathological characteristics, and molecular markers and subsequent invasive cancer or DCIS. Groups were defined by combining clinical and histopathological characteristics, and molecular markers that have similar strength associations and level of risk for subsequent tumor events. All statistical tests were two-sided. P values less than 0.05 were considered statistically significant.

Results

From Jan. 1, 1983 to May 1, 2008, 324 of the 1,162 women in the study cohort (27.9% overall or 3% per year) developed a subsequent breast tumor [median follow-up=98.0 months, or 8.2 years (range=6.3 to 299.1 months, or 0.5 to 25 years)]. Of the 1,162 women, 154 (13.3%) had subsequent local DCIS lesions, 170 had subsequent invasive cancer [of these, 120 (10.3%) had local disease, 33 (2.8%) regional disease, eight (0.7%) distant disease, and nine (0.7%) disease of unknown location] and 125 (10.8%) died of a cause other than breast cancer. Among the women who had subsequent invasive cancer, 34 (2.9%) died of breast cancer. The 8-year risk of subsequent invasive cancer was similar to the 8-year risk of subsequent DCIS (11.1% vs 11.6%, respectively).

Univariate Results of Factors Associated with Subsequent Invasive Cancer Versus DCIS The risk of subsequent invasive cancer was increased among women whose initial DCIS was detected by palpation compared with that for women whose DCIS was detected by mammography (HR=2.0, 95% CI=1.3 to 2.9). The proportional incidence of DCIS by mode of detection did not vary by year of diagnosis (data not shown). The risk of subsequent DCIS varied by age: there was increased risk for women aged 40-49 years compared with women aged 70 years and older (HR=2.2, 95% CI=1.4 to 3.4). Race and/or ethnicity, family history of breast cancer, and menopausal status were not associated with incidence of subsequent tumors (Table 7) and neither were oral contraceptive or postmenopausal hormone therapy use or body mass index (data not shown).

TABLE 7

PREVALENCE OF RISK FACTORS AMONG WOMEN INITIALLY
TREATED FOR DUCTAL CARCINOMA IN SITU (DCIS) BY
LUMPECTOMY ALONE ACCORDING TO TYPE OF SUBSEQUENT
TUMOR EVENT (INVASIVE CANCER OR DCIS)*

| Variable‡ | No Subsequent tumor event† (N = 838) % (No.) | Invasive event (N = 170) % (No.) | DCIS event (N = 154) % (No.) |
|---|---|---|---|
| Age at diagnosis, y | | | |
| 40-49 | 18 (154) | 26 (44) | 34 (53) |
| 50-59 | 23 (194) | 22 (38) | 23 (35) |
| 60-69 | 24 (198) | 22 (38) | 21 (33) |
| ≥70 | 35 (292) | 29 (50) | 21 (33) |
| P-value§ | Referent | .6 | <.001 |
| Race and/or ethnicity | | | |
| White | 77 (643) | 77 (131) | 82 (125) |
| African American | 7 (58) | 9 (15) | 5 (8) |
| Hispanic | 8 (65) | 8 (14) | 6 (9) |
| Asian | 8 (64) | 6 (10) | 7 (10) |
| P-value§ | Referent | .6 | .4 |
| Family history of breast cancer‖ | | | |
| Negative | 74 (459) | 70 (97) | 73 (95) |
| Positive | 26 (164) | 30 (42) | 27 (36) |
| P-value§ | Referent | .4 | .9 |
| Menopausal status ¶ | | | |
| Postmenopausal | 96 (791) | 93 (150) | 93 (143) |
| Premenopausal | 4 (32) | 7 (12) | 7 (11) |
| P-value§ | Referent | .13 | .8 |
| Detection method | | | |
| Mammography | 81 (519) | 73 (97) | 88 (112) |
| Palpation** | 19 (120) | 27 (37) | 12 (16) |
| P-value§ | Referent | <.001 | .06 |

*Excludes women with a history of breast cancer and women who had radiation therapy or mastectomy.
†Control subjects were a random sample of women with ductal carcinoma in situ who did not have a subsequent tumor event and were frequency matched by year of diagnosis to the case subjects who were women who had a subsequent tumor event.
‡There was no race and/or ethnicity data missing. However, 22.7% of subjects had missing data for family history, 2.0% for menopausal status, and 22.5% for detection method.
§Wald test calculated from the proportional subdistribution hazards regression coefficients; age- adjusted, two-sided test.
‖Defined as at least one first-degree relative (mother, sister, or daughter) with breast cancer.
¶ Women were considered to be postmenopausal if both ovaries had been removed, if they reported their periods had stopped permanently for reasons other than hysterectomy, if they were currently using postmenopausal hormone therapy, or if they were aged 55 or older.
**Palpable mass found by the woman or by her physician upon physical examination at the time of diagnosis.

Whereas histopathological characteristics were not associated with subsequent invasive cancer (Table 8), several such characteristics were associated with an increased risk of subsequent DCIS: initial DCIS lesions that were larger than 10 mm, had positive or uncertain margins, were of high nuclear grade, or had extensive necrosis (Table 8).

Whereas DCIS lesions with individual expression of the biomarkers ER, PR, p53, ERBB2, and COX-2 were not statistically significantly associated with subsequent invasive cancer, p16 and selected combinations of markers did provide stratification of risk (Table 9). Women whose initial DCIS lesions were p16-positive (p16$^+$), or p16 and Ki67-positive (p16$^+$Ki67$^+$) or p16, COX-2, and Ki67-positive (p16$^+$COX-2$^+$Ki67$^+$) had an increased risk of subsequent invasive cancer compared with women whose DCIS lesions did not express these combinations of markers (Table 9). Of note, Ki67 in combination with either ER, PR, p53 or ERBB2 was not associated with subsequent invasive cancer, nor was p16 in combination with ER, PR, p53 or ERBB2 (data not shown).

Markers associated with subsequent DCIS differed from those associated with subsequent invasive cancer. Women whose initial DCIS lesions were ER-negative (ER$^-$), ERBB2-positive (ERBB2$^+$), or Ki67-positive (Ki67$^+$) among individual markers; or were ER$^-$ERBB2$^+$ or ER$^-$Ki67$^+$ among marker combinations, had an increased risk of subsequent DCIS compared with women who had lesions that did not express these individual markers or combinations of markers. Subsequent DCIS also was associated with initial DCIS lesions that were p16$^+$Ki67$^+$ or p16$^+$COX-2$^-$Ki67$^+$.

Distributions by tumor size, margin status, and nuclear grade according to case-control status were similar for women for whom we could obtain tumor blocks and those we could not (data not shown).

Multivariable Results of Factors Associated with Subsequent Invasive Cancer Versus DCIS and Risk of Subsequent Tumors by these Factors In a multivariable competing risk model, we found both DCIS lesions that were detected by palpation and those that were p16$^+$COX-2$^+$Ki67$^+$ were statistically significantly associated with subsequent invasive cancer whereas nuclear grade was not (Table 10). When we examined the subgroup of women whose initial DCIS was detected by mammography, the independent association of p16$^+$COX-2$^+$Ki67$^+$ lesions with subsequent invasive cancer remained (HR=2.3, 95% CI=1.0 to 5.3). Among DCIS lesions associated with a subsequent invasive cancer, 25% were detected by palpation and 23% were p16$^+$COX-2$^+$Ki67$^+$; only two case subjects had both these traits. The 5- and 8-year risks of subsequent invasive cancer were high for women whose initial DCIS lesions were detected by palpation (13.2% and 17.8%, respectively, Table 11) and highest for women whose initial DCIS lesions were p16$^+$COX-2$^+$Ki67$^+$ (19.6% and 27.3%, respectively).

Factors that were independently associated with subsequent DCIS included positive or uncertain margins, DCIS lesions that were p16$^+$COX-2$^-$Ki67$^+$, and those that were ER ERBB2$^+$Ki67$^+$, whereas surprisingly nuclear grade was no longer statistically significant. The 5- and 8-year risks of subsequent DCIS were highest for women with defined molecular subtypes of DCIS (Tables 4 and 5). The 5- and 8-year risks of subsequent DCIS were lowest for women that had disease-free surgical margins of 10 mm or larger (Table 11).

Risk of Subsequent Invasive Cancer or DCIS by Risk Group

The 5- and 8-year risks of subsequent invasive cancer and DCIS were estimated for four risk groups based on the statistically significant univariate and multivariable factors reported in Tables 9 and 10, and 5- and 8-year risks reported in Table 11. Among women who were initially diagnosed with DCIS, 17.3% were in the lowest risk group, which had an 8-year risk of subsequent invasive cancer of 4.1%, and 26.8% were in the next to lowest risk group, which had an 8-year risk of 6.9% (Table 12). Over a quarter (27.6%) of the women were in the high-risk group, which had an 8-year risk of subsequent invasive cancer of 19.6%. The 8-year risk of subsequent invasive cancer was statistically significantly (P=0.018) higher for women with initial DCIS lesions that were detected by palpation or that were p16$^+$COX-2$^+$Ki67$^+$ (19.6%, 95% CI=18.0% to 21.3%) than for women with initial lesions that were detected by mammography and were p16$^-$COX-2$^-$Ki67$^-$ (4.1%, 95% CI=3.45 to 5.0%).

Women with DCIS could also be divided into groups according to risk for further DCIS. Here, 19.9% of the women initially diagnosed with DCIS were in the lowest risk group and had an 8-year risk of subsequent DCIS of 3.9%, and 21.2% were in the low risk group, with an 8-year risk of 10.2% (Table 12). In this case, only 5.1% of these women were in the high-risk group and had an 8-year risk of subsequent DCIS of 23.6%.

The present example examines the clinical and/or histopathological characteristics of women with DCIS who were treated by lumpectomy alone and determined the histopathological and molecular characteristics of their breast lesions to identify factors associated with the occurrence of subsequent tumors and to determine the risk of subsequent tumors as a function of these factors. It was found that initial DCIS lesions that were detected by palpation or had p16$^+$COX-2$^+$Ki67$^+$ expression were the two factors most strongly associated with risk of subsequent invasive cancer; however, these factors were not associated with risk of subsequent DCIS. A little over a quarter of these women (27.6%) were categorized as having a high-risk of subsequent invasive cancer (ie, 19.6% at 8 years). Many women (44.1%) who did not demonstrate one of these two factors were categorized as having a low risk of subsequent invasive cancer at 8 years (4.1% and 6.9% for the lowest- and low-risk groups, respectively). In addition, the ability was developed to distinguish factors associated with risk of subsequent invasive cancer versus risk of subsequent DCIS, an important clinical goal that could guide initial therapeutic decisions. Initial lesions that were ER$^-$ERBB2$^+$Ki67$^+$, lesions that were p16$^+$COX-2$^-$Ki67$^+$, and lesions that had positive or uncertain surgical margins were found to be strongly associated with risk of subsequent DCIS; however, these factors were not associated with risk of subsequent invasive cancer.

TABLE 8

UNIVARIATE RESULTS OF HISTOPATHOLOGICAL FACTORS ASSOCIATED WITH TYPE OF SUBSEQUENT TUMOR EVENT (INVASIVE CANCER OR DUCTAL CARCINOMA IN SITU [DCIS])*

| Factor‡ | No subsequent tumor event* (N = 279) % (No.) | Invasive event (N = 114) % (No.) | Risk of invasive event HR (95% CI) | DCIS event (N = 109) % (No.) | Risk of DCIS event HR† (95% CI) |
|---|---|---|---|---|---|
| Tumor size | | | | | |
| >10 mm | 30 (85) | 39 (44) | 1.2 (0.8 to 1.8) | 41 (45) | 1.4 (1.0 to 2.1) |
| ≤10 mm | 70 (194) | 61 (70) | 1.0 (referent) | 59 (64) | 1.0 (referent) |
| Margins | | | | | |
| Positive | 23 (62) | 36 (39) | 1.6 (0.9 to 2.7) | 37 (38) | 3.6 (1.8 to 7.2) |
| Uncertain§ | 22 (58) | 22 (24) | 1.1 (0.6 to 2.1) | 24 (25) | 2.7 (1.3 to 5.8) |
| 1 to 1.9 mm disease-free | 22 (57) | 15 (16) | 0.8 (0.4 to 1.6) | 20 (20) | 2.5 (1.1 to 5.4) |
| ≥2 to <10 mm disease-free | 10 (26) | 9 (10) | 1.1 (0.5 to 2.3) | 10 (10) | 2.3 (0.9 to 5.5) |
| ≥10 mm disease-free | 23 (62) | 18 (19) | 1.0 (referent) | 9 (9) | 1.0 (referent) |
| Nuclear grade ‖ | | | | | |
| High | 35 (92) | 44 (47) | 1.2 (0.8 to 2.1) | 60 (61) | 2.7 (1.5 to 4.8) |
| Intermediate | 33 (85) | 35 (38) | 1.3 (0.8 to 2.2) | 26 (26) | 1.4 (0.8 to 2.7) |
| Low | 32 (83) | 21 (22) | 1.0 (referent) | 14 (14) | 1.0 (referent) |
| Necrosis type | | | | | |
| Comedo | 39 (100) | 45 (48) | 1.1 (0.8 to 1.6) | 45 (46) | 1.1 (0.8 to 1.6) |
| Focal-punctate | 61 (159) | 55 (59) | 1.0 (referent) | 55 (56) | 1.0 (referent) |
| Quantity of necrosis | | | | | |
| Extensive | 18 (48) | 25 (26) | 1.2 (0.8 to 1.8) | 28 (29) | 1.5 (1.0 to 2.3) |
| Moderate/scant | 82 (212) | 75 (80) | 1.0 (referent) | 72 (73) | 1.0 (referent) |

*Control subjects were a random sample of women with ductal carcinoma in situ who did not have a subsequent tumor event and were frequency matched by year of diagnosis to the case subjects who were women who had a subsequent tumor event.
†Adjusted for diagnosis age
‡Here, 4.0% of specimens had missing data regarding margins, 6.8% for nuclear grade, type of necrosis, and extent of necrosis.
§Unknown or could not be assessed
‖ For lesions with more than one type of nuclear grade, an overall grade was assigned according to the highest grade present.

TABLE 9

UNIVARIATE RESULTS OF MOLECULAR MARKERS ASSOCIATED WITH TYPE OF SUBSEQUENT TUMOR EVENT (INVASIVE CANCER OR DUCTAL CARCINOMA IN SITU [DCIS])*

| Factor‡ | No subsequent tumor event* (N = 186) % (No.) | Invasive event (N = 72) % (No.) | Risk of invasive event HR†(95 CI) | DCIS event (N = 71) % (No.) | Risk of DCIS event HR†(95% CI) |
|---|---|---|---|---|---|
| Estrogen receptor (ER) | | | | | |
| Negative | 20 (35) | 20 (13) | 0.8 (0.4 to 1.5) | 31 (21) | 1.7 (1.0 to 2.9) |
| Positive | 80 (143) | 80 (53) | 1.0 (referent) | 69 (47) | 1.0 (referent) |

TABLE 9-continued

UNIVARIATE RESULTS OF MOLECULAR MARKERS ASSOCIATED WITH TYPE
OF SUBSEQUENT TUMOR EVENT (INVASIVE CANCER OR DUCTAL
CARCINOMA IN SITU [DCIS])*

| Factor‡ | No subsequent tumor event* (N = 186) % (No.) | Invasive event (N = 72) % (No.) | Risk of invasive event HR†(95 CI) | DCIS event (N = 71) % (No.) | Risk of DCIS event HR†(95% CI) |
|---|---|---|---|---|---|
| Progesterone receptor (PR) | | | | | |
| Negative | 21 (36) | 31 (20) | 1.3 (0.7 to 2.1) | 33 (21) | 1.5 (0.9 to 2.5) |
| Positive | 79 (138) | 69 (45) | 1.0 (referent) | 67 (42) | 1.0 (referent) |
| p53 | | | | | |
| Positive | 10 (17) | 10 (6) | 0.8 (0.4 to 1.9) | 17 (10) | 1.8 (0.9 to 3.5) |
| Negative | 90 (153) | 90 (57) | 1.0 (referent) | 83 (49) | 1.0 (referent) |
| ERBB2 oncoprotein | | | | | |
| Positive | 13 (25) | 19 (14) | 1.1 (0.6 to 1.9) | 30 (21) | 2.0 (1.2 to 3.2) |
| Negative | 87 (161) | 81 (58) | 1.0 (referent) | 70 (50) | 1.0 (referent) |
| Ki67 | | | | | |
| Positive§ | 36 (62) | 59 (38) | 1.7 (1.0 to 2.7) | 67 (40) | 2.3 (1.3 to 4.1) |
| Negative | 64 (109) | 41 (26) | 1.0 (referent) | 33 (20) | 1.0 (referent) |
| p16 | | | | | |
| Positive | 30 (43) | 57 (37) | 2.3 (1.4 to 3.8) | 41 (26) | 1.1 (0.7 to 1.8) |
| Negative | 70 (98) | 43 (28) | 1.0 (referent) | 59 (38) | 1.0 (referent) |
| Cyclooxygenase-2 (COX-2) | | | | | |
| Positive | 46 (68) | 50 (34) | 1.3 (0.8 to 2.0) | 34 (22) | 0.6 (0.4 to 1.1) |
| Negative | 54 (79) | 50 (34) | 1.0 (referent) | 66 (42) | 1.0 (referent) |
| p16/Ki67 | | | | | |
| Positive/positive | 11 (14) | 34 (18) | 2.1 (1.2 to 3.8) | 33 (18) | 2.0 (1.1 to 3.6) |
| All other groupings | 89 (111) | 66 (35) | 1.0 (referent) | 67 (36) | 1.0 (referent) |
| COX-2/Ki67 | | | | | |
| Positive/positive | 18 (24) | 33 (18) | 1.8 (1.0 to 3.2) | 25 (14) | 1.1 (0.6 to 2.1) |
| All other groupings | 82 (106) | 67 (37) | 1.0 (referent) | 75 (41) | 1.0 (referent) |
| p16/COX-2/Ki67 | | | | | |
| Positive/positive/positive | 8.5 (10) | 23 (12) | 2.2 (1.2 to 4.2) | 15 (8) | 1.2 (0.5 to 2.5) |
| All other groupings | 91.5 (107) | 77 (40) | 1.0 (referent) | 85 (44) | 1.0 (referent) |
| p16/COX-2/Ki67 | | | | | |
| Positive/negative/positive | 2.6 (3) | 12 (6) | 1.5 (0.6 to 3.6) | 19 (10) | 3.2 (1.5 to 6.9) |
| All other groupings | 97.4 (114) | 88 (46) | 1.0 (referent) | 81 (42) | 1.0 (referent) |
| ER/PR/ERBB2 | | | | | |
| Negative/negative/negative | 5 (9) | 6 (4) | 1.1 (0.4 to 3.3) | 6 (4) | 1.1 (0.4 to 3.0) |
| All other groupings | 95 (172) | 94 (64) | 1.0 (referent) | 94 (65) | 1.0 (referent) |
| ER/ERBB2 | | | | | |
| Negative/positive | 6.4 (11) | 5 (3) | 0.5 (0.2 to 1.5) | 19 (12) | 3.0 (1.6 to 5.7) |
| All other groupings | 93.6 (161) | 95 (61) | 1.0 (referent) | 81 (53) | 1.0 (referent) |
| ER/Ki67 | | | | | |
| Negative/positive | 9 (14) | 13 (7) | 0.8 (0.4 to 1.8) | 28 (15) | 2.8 (1.5 to 5.2) |
| All other groupings | 91 (136) | 87 (48) | 1.0 (referent) | 72 (39) | 1.0 (referent) |
| ERBB2/Ki67 | | | | | |
| Positive/positive | 7 (11) | 18 (10) | 1.6 (0.8 to 3.2) | 21 (12) | 1.9 (1.0 to 3.5) |
| All other groupings | 93 (146) | 82 (46) | 1.0 (referent) | 79 (46) | 1.0 (referent) |

TABLE 9-continued

UNIVARIATE RESULTS OF MOLECULAR MARKERS ASSOCIATED WITH TYPE
OF SUBSEQUENT TUMOR EVENT (INVASIVE CANCER OR DUCTAL
CARCINOMA IN SITU [DCIS])*

| Factor‡ | No subsequent tumor event* (N = 186) % (No.) | Invasive event (N = 72) % (No.) | Risk of invasive event HR†(95 CI) | DCIS event (N = 71) % (No.) | Risk of DCIS event HR†(95% CI) |
|---|---|---|---|---|---|
| ER/ERBB2/Ki67 | | | | | |
| Negative/positive/positive | 2.7 (4) | 6 (3) | 0.9 (0.3 to 2.7) | 15 (8) | 3.6 (1.7 to 7.8) |
| All other groupings | 97.3 (143) | 94 (50) | 1.0 (referent) | 85 (45) | 1.0 (referent) |

*Control subjects were a random sample of women with ductal carcinoma in situ who did not have a subsequent tumor event and were frequency matched by year of diagnosis to the case subjects, who were women who had a subsequent tumor event.
†Adjusted for diagnosis age
‡Missing data: 5.2% for ER status, 7.9% for PR status, 10.6% for p53 status, 0% for ERBB2, 10.3% for Ki67, 17.6% for p16, 15.2% for COX-2.
§More than 10% positive cells

TABLE 10

HAZARD RATIOS (HRS) AND 95% CONFIDENCE INTERVALS (CIS) FROM FINAL MULTIVARIABLE MODELS OF CLINICAL AND HISTOPATHOLOGICAL CHARACTERISTICS AND MOLECULAR MARKERS INDEPENDENTLY ASSOCIATED WITH SUBSEQUENT TUMOR EVENTS*

| Variable | Invasive cancer HR (95% CI) | Variable† | DCIS‡ HR (95% CI) |
|---|---|---|---|
| Age at diagnosis (years) | 1.0 (0.8 to 1.3) | Age at diagnosis (years) | 0.9 (0.7 to 1.1) |
| Detection by palpation (vs. mammography)‡ | 2.7 (1.4 to 5.5) | Margins ordinal (per category increase) | 1.3 (1.1 to 1.7) |
| Nuclear grade | | Nuclear grade | |
| High vs. low | 1.0 (0.4 to 2.3) | High vs. low | 1.7 (0.6 to 4.8) |
| Intermediate vs. low | 1.9 (0.8 to 4.3) | Intermediate vs. low | 1.3 (0.4 to 4.1) |

TABLE 10-continued

HAZARD RATIOS (HRS) AND 95% CONFIDENCE INTERVALS (CIS) FROM FINAL MULTIVARIABLE MODELS OF CLINICAL AND HISTOPATHOLOGICAL CHARACTERISTICS AND MOLECULAR MARKERS INDEPENDENTLY ASSOCIATED WITH SUBSEQUENT TUMOR EVENTS*

| Variable | Invasive cancer HR (95% CI) | Variable† | DCIS‡ HR (95% CI) |
|---|---|---|---|
| p16/COX-2/Ki67 | | p16/COX-2/Ki67 | |
| Positive/positive/positive | 2.2 (1.1 to 4.5) | Positive/negative/positive | 3.7 (1.7 to 7.9) |
| All other groupings | 1.0 (referent) | All other groupings | 1.0 (referent) |
| | | ER/ERBB2/Ki67 | |
| | | Negative/positive/positive | 5.8 (2.4 to 14) |
| | | All other groupings | 1.0 (referent) |

*DCIS = ductal carcinoma in situ.
†Margins ordinal defined as margin ≥10 mm disease free = 0, margin ≥2 to <10 mm disease free = 1, margin 1-1.9 mm disease free = 2, margin uncertain = 3, margin positive = 4
‡Palpable mass found by the woman or by her physician upon physical examination.

TABLE 11

ESTIMATE OF 5-YEAR AND 8-YEAR RISKS OF INVASIVE CANCER VS DUCTAL CARCINOMA IN SITU (DCIS) FOR CHARACTERISTICS AMONG WOMEN DIAGNOSED DCIS INDEPENDENTLY ASSOCIATED WITH SUBSEQUENT INVASIVE CANCER OR DCIS EVENTS*

| Variable | 5-year risk of invasive cancer % (95% CI) | 8-year risk of invasive cancer % (95% CI) | Variable | 5-year risk of DCIS % (95% CI) | 8-year risk of DCIS % (95% CI) |
|---|---|---|---|---|---|
| Overall | 7.8 (6.2 to 9.4) | 11.1 (9.2 to 13.0) | Overall | 9.7 (7.9 to 11.4) | 11.6 (9.7 to 13.5) |
| Detection Method | | | Margins | | |
| Palpation† | 13.2 (12.3 to 14.3) | 17.8 (16.2 to 19.4) | Positive or Uncertain | 12.4 (11.7 to 13.0) | 14.6 (13.8 to 15.4) |
| Mammography | 6.5 (6.3 to 6.6) | 9.3 (9.2 to 9.6) | 1 to <10 mm disease-free | 10.2 (9.4 to 10.9) | 11.7 (10.4 to 12.3) |
| | | | ≥10 mm disease-free | 2.8 (2.5 to 3.3) | 4.4 (3.9 to 5.2) |
| p16/COX-2/Ki67 | | | p16/COX-2/Ki67 | | |
| Positive/positive/positive | 19.6 (16.6 to 23.4) | 27.3 (22.9 to 33.9) | Positive/negative/positive | 20.8 (17.3 to 25.3) | 24.9 (20.3 to 33.4) |
| All other groupings | 6.8 (6.6 to 7.0) | 9.5 (9.2 to 9.8) | All other groupings | 8.6 (8.4 to 8.8) | 10.4 (10.1 to 10.7) |

TABLE 11-continued

ESTIMATE OF 5-YEAR AND 8-YEAR RISKS OF INVASIVE CANCER VS DUCTAL CARCINOMA IN SITU (DCIS) FOR
CHARACTERISTICS AMONG WOMEN DIAGNOSED DCIS INDEPENDENTLY ASSOCIATED WITH SUBSEQUENT
INVASIVE CANCER OR DCIS EVENTS*

| Variable | 5-year risk of invasive cancer % (95% CI) | 8-year risk of invasive cancer % (95% CI) | Variable | 5-year risk of DCIS % (95% CI) | 8-year risk of DCIS % (95% CI) |
|---|---|---|---|---|---|
| | | | ER/ERBB2/Ki67 | | |
| | | | Negative/positive/positive | 37.2 (29.3 to 49.0) | 40.5 (31.7 to 54.3) |
| | | | All other groupings | 8.8 (8.7 to 9.0) | 10.6 (10.4 to 10.8) |

*CI = confidence interval; COX-2 = cyclooxygenase-2; ER = estrogen receptor; ERBB2 = human epidermal growth factor receptor 2 (HER2/neu-oncoprotein).
†Palpable mass found by the woman or by her physician upon physical examination.

TABLE 12

STRATIFICATION OF WOMEN INTO LOW, INTERMEDIATE, AND HIGH 5-YEAR
AND
8-YEAR RISK BY TYPE OF SUBSEQUENT TUMOR EVENT

| Risk Category* | Prevalence in cohort %† | 5-year risk of invasive cancer % (95% CI) | 8-year risk of invasive cancer % (95% CI) | Risk Category* | Prevalence in cohort %† | 5-year risk of DCIS % (95% CI) | 8-year risk of DCIS % (95% CI) |
|---|---|---|---|---|---|---|---|
| Lowest‡ | 17.3 | 2.1 (1.9 to 2.6) | 4.1 (3.4 to 5.0) | Lowest** | 19.9 | 2.7 (2.4 to 3.2) | 3.9 (3.3 to 4.8) |
| Low§ | 26.8 | 4.4 (4.0 to 5.0) | 6.9 (6.1 to 8.0) | Low†† | 21.2 | 7.8 (6.8 to 8.7) | 10.2 (8.1 to 12.7) |
| Intermediate‖ | 28.3 | 7.7 (7.0 to 8.5) | 11.5 (10.3 to 12.8) | Intermediate‡‡ | 53.8 | 12.0 (11.4 to 12.6) | 14.4 (13.6 to 15.2) |
| High¶ | 27.6 | 14.1 (13.1 to 15.3) | 19.6 (18.0 to 21.3) | High§§ | 5.1 | 19.2 (15.3 to 23.9) | 23.6 (18.1 to 34.0) |

*Risk groups were defined separately for subsequent invasive cancer and DCIS based on multivariable associations in Table 10 as well as level of risk associated with factors in Table 11.
†Average prevalence estimated among 2500 cohorts of 1162 women with missing measures imputed as described in the statistical section
‡Group 1: DCIS mammographically detected plus Ki67, cyclooxygenase-2 (COX-2) and p16 negative - triple negative (Ki67⁻COX-2⁻p16⁻)
§Group 2: DCIS mammographically detected plus Ki67-negative and either COX-2-positive (Ki67⁻COX-2⁺) or p16-positive (Ki67⁻p16⁺) or both positive (Ki67⁻COX-2⁺p16⁺)
‖Group 3: DCIS mammographically detected plus Ki67-positive and either COX-2-positive (Ki67⁺COX-2⁺) or p16-positive (Ki67⁺p16⁺) or COX-2-negative/p16-negative (Ki67⁺COX-2⁻p16⁻)
¶Group 4: Detected by palpation or p16, Ki67, and COX-2-triple positive (p16⁺Ki67⁺COX-2⁺)
**Group 1: DCIS with margins of 1 millimeter or greater disease-free plus estrogen receptor (ER) positive and HER2/neu-oncoprotein (ERBB2) negative and Ki67-negative (ER+ERBB2−Ki67−) or estrogen receptor (ER) positive and HER2/neu-oncoprotein (ERBB2) negative and Ki67-positive (ER+ERBB2−Ki67+) or estrogen receptor (ER) positive and HER2/neu-oncoprotein (ERBB2) positive and Ki67-negative (ER+ERBB2−Ki67−).
††Group 2: DCIS with margins of 1 millimeter or greater disease-free plus either ER-negative, ERBB2 negative (ER⁻ERBB2⁻) or p16 and Ki67-positive (p16⁺Ki67⁺) or COX-2-negative, Ki67-positive (COX-2⁻Ki67⁺) or COX-2-positive, Ki67-positive (COX-2⁺Ki67⁺) or ERBB2-positive, Ki67-positive (ERBB2⁺Ki67⁺).
‡‡Group 3: Positive or uncertain margins or ER-negative, Ki67-positive (ER⁻Ki67⁺) or ER-negative, ERBB2-positive (ER⁻ERBB2⁺).
§§Group 4: DCIS with margins of 1 millimeter or greater disease-free plus ER-negative/ERBB2-positive/Ki67-positive (ER⁻ERBB2⁺Ki67⁺) or p16/Ki67-positive and COX-2-negative (p16⁺COX-2⁻Ki67⁺).

The risk groups in Table 12 are presented as a logic system for the sake of brevity. Thus, to determine if a set of biomarker results falls into a particular grouping, one compares the biomarker results with the set of biomarkers in group 4, and if the results do not fall into group 4, one then compares the biomarker results with the set in group 3, and if the results do not fall into group 3, one then compares the biomarker results with the set in group 2 and if the results do not fall into group 2, one then compares the biomarker results with the set in group 1.

For example, a more complete listing of the sets is as follows:

For Invasive:

‡ Group 1: DCIS mammographically detected plus Ki67, cyclooxygenase-2 (COX-2) and p16 negative-triple negative (Ki67⁻COX-2⁻p16⁻).

§ Group 2: DCIS mammographically detected plus Ki67-negative and either COX-2-positive/p16-negative (Ki67⁻COX-2⁺p16⁻) or p16-positive/COX-2-negative (Ki67⁻p16⁺COX-2⁻) or both positive (Ki67⁻COX-2⁺p16⁺).

‖ Group 3: DCIS mammographically detected plus Ki67-positive and either COX-2-positive/p16-negative (Ki67⁺COX-2⁺p16⁻) or p16-positive/COX-2-negative (Ki67⁺p16⁺COX-2⁻) or COX-2-negative/p16-negative (Ki67⁺COX-2⁻p16⁻).

¶ Group 4: Detected by palpation or p16, Ki67, and COX-2-triple positive (p16⁺Ki67⁺COX-2⁺).

For DCIS subsequent event:

** Group 1: DCIS with margins of 1 millimeter or greater disease-free plus estrogen receptor (ER) positive and HER2/neu-oncoprotein (ERBB2) negative and Ki67-negative (ER+ERBB2−Ki67−) or estrogen receptor (ER) positive and HER2/neu-oncoprotein (ERBB2) negative and Ki67-positive (ER+ERBB2−Ki67+) or estrogen receptor (ER) positive and HER2/neu-oncoprotein (ERBB2) positive and Ki67-negative (ER+ERBB2+Ki67−).

†† Group 2: DCIS with margins of 1 millimeter or greater disease-free plus either ER-negative, ERBB2 negative, Ki67-negative (ER–ERBB2– Ki67–) or p16, Ki67-positive, and COX-2-positive (p16+Ki67+COX-2+) or p16-negative, COX-2-negative, Ki67-positive (p16–COX-2–Ki67+) or p16-negativeCOX-2-positive, Ki67-positive (p16–COX-2+ Ki67+) or ER-positive, ERBB2-positive, Ki67-positive (ER+ERBB2+Ki67+).

‡‡ Group 3: Positive or uncertain margins or ER-negative/ERBB2-negative/Ki67-positive (ER– ERBB2-Ki67+) or ER-negative, ERBB2-positive/Ki67-negative (ER– ERBB2+Ki67–) §§ DCIS with margins of 1 millimeter or greater disease-free plus ER-negative/ERBB2-positive/Ki67-positive (ER–ERBB2+Ki67+) or p16/Ki67-positive and COX-2-negative (p16+COX-2–Ki67+).

§§ Group 4: DCIS with margins of 1 millimeter or greater disease-free plus ER-negative/ERBB2-positive/Ki67-positive (ER⁻ERBB2⁺Ki67⁺) or p16/Ki67-positive and COX-2-negative (p16⁺COX-2⁻Ki67⁺).

A subject having p16+/ki67+/COX2– would be identified as high risk because she was p16+/ki67+/Cox2–.

Detailed Description Discussion of Example 5B

Recent molecular studies on DCIS lesions may provide insights about the biological contributions of p16, COX-2, and Ki67 expression in p16⁺COX-2⁺Ki67⁺ lesions. Molecular studies have identified markers that distinguish different subtypes of DCIS (Gauthier M L, Berman H K, Miller C, Kozakeiwicz K, Chew K, Moore D, et al. Abrogated stress response distinguishes basal-like tumors and DCIS lesions associated with subsequent tumor events. Cancer Cell 2007; 12(5):479-491; Allred D, Wu Y, Mao S, Nagtegaal I, Lee S, Perou C, et al. Ductal carcinoma in situ and the emergence of diversity during breast cancer evolution. Clin Cancer Res 2008; 14(2):370-8; Bryan B, Schnitt S, Collins L. Ductal carcinoma in situ with basal-like phenotype: a possible precursor to invasive basal-like breast cancer. Mod Pathol 2006; 19(5):617-21; Dabbs D, Chivukula M, Carter G, Bhargava R. Basal phenotype of ductal carcinoma in situ: recognition and immunohistologic profile. Mod Pathol 2006; 19(11):1506-11; Livasy C, Perou C, Karaca G, Cowan D, Maia D, Jackson S, et al. Identification of a basal-like subtype of breast ductal carcinoma in situ. Hum Pathol 2007; 38(2):197-204) that may relate, in an unknown fashion, to molecularly defined subtypes of invasive breast cancer. Previously, it was reported in a pilot study that DCIS lesions that express p16 and COX-2 and have a high proliferative capacity share characteristics with basal-like invasive cancers (Gauthier M L, Berman H K, Miller C, Kozakeiwicz K, Chew K, Moore D, et al. Abrogated stress response distinguishes basal-like tumors and DCIS lesions associated with subsequent tumor events. Cancer Cell 2007; 12(5):479-491). Overexpression of p16 has been validated as a basal-like marker in two recent studies (Subhawong A, Subhawong T, Nassar H, Kouprina N, Begum S, Vang R, et al. Most basal-like breast carcinomas demonstrate the same Rb–/p16+ immunophenotype as the hpv-related poorly differentiated squamous cell carcinomas which they resemble morphologically. Am J Surg Pathol 2008; 33(2):163-75; Herschkowitz J, He X, Fan C, Perou C. The functional loss of the retinoblastoma tumour suppressor is a common event in basal-like and luminal B breast carcinomas. Breast Cancer Res 2008; 10(5):R75). In Example 5B, it was surprisingly demonstrated that expression of these markers indicates a high risk of subsequent invasive cancer, but not DCIS. Furthermore, the established role of COX-2 in promoting invasive potential (Crawford Y G, Gauthier M L, Joubel A, Mantei K, Kozakiewicz K, Afshari C A, et al.

Histologically normal human mammary epithelia with silenced p16(INK4a) overexpress COX-2, promoting a premalignant program. Cancer Cell 2004; 5(3):263-73; Hu M, Peluffo G, Chen H, Gelman R, Schnitt S, Polyak K. Role of COX-2 in epithelial-stromal cell interactions and progression of ductal carcinoma in situ of the breast. PNAS 2009; 106(9):3372-7; Minn A J, Gupta G P, Siegel P M, Bos P D, Shu W, Giri D D, et al. Genes that mediate breast cancer metastasis to lung. Nature 2005; 436(7050):518-24) provides a biological rationale for why the p16⁺COX-2⁺Ki67⁺ lesions tend to recur as invasive carcinomas whereas p16⁺ COX-2⁻Ki67⁺ lesions tend to recur as DCIS. Moreover, the p16⁺COX-2⁻Ki67⁺phenotype was independent of risk conferred by DCIS lesions detected by palpation. Palpable DCIS lesions accounted for 15-20% of DCIS lesions in this study, consistent with recent studies of women undergoing screening mammography (Ernster V L, Ballard-Barbash R, Barlow W E, Zheng Y, Weaver D, Cutter G, et al. Detection of DCIS in Women Undergoing Screening Mammography. J Natl Cancer Inst 2002; 94(20):1546-54). That palpable DCIS lesions appear to be more aggressive than mammography-detected lesions is consistent with the observation that palpable invasive cancer lesions tend to be more aggressive than mammography-discovered invasive lesions (Silverstein M, Skinner K, T J. L. Predicting axillary nodal positivity in 2282 patients with breast carcinoma. World J Surg 2001; 25(6):767-72).

Attempts to predict risk of subsequent invasive cancer versus DCIS using a woman's age at diagnosis and nuclear grade of the DCIS lesion have met with limited success (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702; Vicini F A, Kestin L L, Goldstein N S, Chen P Y, Pettinga J E, Frazier R C, et al. Impact of young age on outcome in patients with ductal carcinoma-in-situ treated with breast-conserving therapy. J Clin Oncol 2000; 18(2):296-306), in part, because there is only moderate agreement in assessing histopathological characteristics such as nuclear grade (Wells W A, Carney P A, Eliassen M S, Grove M R, Tosteson A N A. Pathologists' agreement with experts and reproducibility of breast ductal carcinoma-in-situ classification schemes. Am J Surg Pathol 2000; 24(5):651-659; Douglas-Jones A G, Morgan J M, Appleton M A C, Attanoos R L, Caslin A, Champ C S, et al. Consistency in the observation of features used to classify duct carcinoma in situ (DCIS) of the breast. J Clin Pathol 2000; 53(8):596-602). The above example combined biomarker data with data pertaining to diagnosis age and nuclear grade to predict risk of invasive cancer. Only initial DCIS lesions that had been detected by palpation and those mammography-detected lesions that were p16⁺COX-2⁺Ki67⁺ retained a statistically significant association with invasive cancer in a multivariable analysis. It has been previously reported an association between high nuclear and subsequent invasive cancer at a median follow-up of about 6 years (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702). An association was not observed between nuclear grade and invasive cancer at a median follow-up of about 8 years, consistent with a study that reported 10-year subsequent tumor rate was not statistically significantly different between women with high nuclear grade and all other grades (Solin L J, Kurtz J, Fourquet A, Amairic R, Recht A, Bornstein B A, et al. Fifteen-year results of breast-conserving surgery and definitive breast irradiation for the treatment of ductal carcinoma in situ of the breast. J Clin Oncol 1996; 14:754-763). One explanation for this observation is that the nuclear grade of the initial DCIS lesion was associated with short-term epithelial proliferation, but not long-term proliferation. The contribution of Ki67 to risk of subsequent invasive cancer can capture, in part, the previously observed association of nuclear grade and subsequent invasive cancer (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702) and has the benefit of signifying short and long-term risk of subsequent tumor in this cohort.

As shown in the above example, factors associated with subsequent DCIS differed from those associated with subsequent invasive cancer. Disease-free surgical margins have been strongly associated with a lower risk of subsequent tumors, in particular DCIS (Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22):1692-1702; Solin L J, Fourquet A, Vicini F A, Haffty B, Taylor M, McCormick B, et al. Mammographically detected ductal carcinoma in situ of the breast treated with breast-conserving surgery and definitive irradiation: long-term outcome and prognostic significance of patient age and margin status. Int J. Radiation Oncology Biol Phys 2001; 50(4):991-1002.) In the above example, when biomarkers were combined with data pertaining to margin status and nuclear grade, positive margins remained a strong predictor of subsequent DCIS, suggesting persistence of neoplastic cells from the original DCIS lesion may contribute to subsequent DCIS. Margin status did not predict subsequent invasive cancer implying most subsequent invasive cancer is an independent process from any residual, non-surgically removed DCIS. In addition to margin status, it was found that certain combinations of molecular markers are present in a very small number (5.1%) of DCIS lesions that are statistically significantly associated with a high risk of subsequent DCIS. The high risk lesions include lesions that are $ER^-ERBB2^+Ki67^+$ or $p16^+COX-2^-Ki67^+$. The striking differences in lesion characteristics associated with subsequent invasive cancer compared to subsequent DCIS suggest biologic heterogeneity among DCIS lesions.

The study illustrated in the above Example has several strengths. First, it is a large population-based study of women with DCIS treated by lumpectomy alone that has measures of clinical, histopathological, and molecular characteristics by type of subsequent tumor with a median follow-up of about 8 years. The results are directly applicable to women with different standard histological types of DCIS because the study included sufficient numbers of women within each category. Second, DCIS cases were collected from 63 hospitals, thereby minimizing the chance of selection bias due to specific clinical practices at some hospitals. Third, the large sample size allowed one to assess the combinations of biomarkers that independently associated with subsequent invasive cancer versus DCIS by using a multivariable model.

In theory, the study also has possible limitations. Clinical factors were assessed retrospectively, raising the possibility of recall bias. However, factors that a woman might attribute as causes of subsequent tumors and thus remember more readily when questioned, such as presence of family history of breast cancer, were not associated with subsequent tumors, suggesting that recall bias did not greatly affect the results. Because women treated by lumpectomy only were studied, it could not be determined whether various biomarker profiles are more likely to respond to adjuvant therapies. Additionally, biomarkers were only able to be measured on a subset of women based on the availability of tumor blocks at participating hospitals. The imputation of missing biomarker data may have resulted in a small overestimation or underestimation of risk of subsequent tumors. Similar to challenges presented by assessment of ERBB2 expression, the IHC interpretation of COX-2 and p16 expression can be challenging due to heterogeneity within DCIS. A refinement of IHC methods and validation in additional cohorts and independent laboratories can be employed to further validate the results. Likewise, identification of additional markers can further refine risk groups and increase the robustness of risk assessment.

The above example identified combinations of biomarkers in DCIS lesions whose expression patterns improve estimation of a woman's risk for subsequent invasive cancer. The results suggest for initial DCIS lesions that have $p16^+$ $COX-2^+Ki67^+$ expression or are detected by palpation are the two most important factors that predict higher risk of subsequent invasive cancer. Conversely, mammographically-detected Ki67-negative DCIS lesions, in particular those that are also p16 and COX-2-negative, are associated with a lower risk of subsequent invasive cancer that is similar to the risk of contralateral invasive cancer in women after their first primary invasive breast cancer (Chen Y, Thompson W, Semenciw R, Mao Y. Epidemiology of contralateral breast cancer. Cancer Epidemiol Biomarkers Prey 1999; 8(10):855-861). Of note, women in the lowest risk group have an 8-year risk of invasive breast cancer comparable to an average-risk 60-year-old woman's 10-year risk of invasive breast cancer. Margin status was confirmed as a strong predictor of subsequent DCIS and the example identified expression of novel combinations of biomarkers predicting subsequent DCIS, which differ from those of that predict subsequent invasive cancer. These markers, compared with nuclear grade, provide a superior estimation of risk for subsequent DCIS.

Many women who have been diagnosed with DCIS have an inaccurate perception of their risk of subsequent invasive cancer (Partridge A, Adloff K, Blood E, al. e. Risk perceptions and psychosocial outcomes of women with ductal carcinoma in situ: longitudinal results from a cohort study. J Natl Cancer Inst 2008; 100(4):243-251.) In the above example, it was shows that the mode of detection and the biomarkers p16, COX-2, and Ki67 can be used to help stratify a woman's risk of subsequent invasive cancer and to help her decide whether she should undergo adjuvant therapies.

Example 6

Determining Risk of Invasive Cancer Using Biomarkers and Palpation

The present example outlines how one can predict a risk that a subject will develop an invasive cancer.

First, a subject is identified that is at risk of developing DCIS. The subject is examined, and if DCIS is detected via palpation, a sample of the DCIS lesion is then examined for one or more of the biomarkers in Table 12. If the subject is positive for COX-2, p16, and Ki67, then the subject is placed into a high risk category.

In the alternative, if the subject simply has a DCIS that is detectable via palpation, or if the subject tests positive for COX-2, p16, and Ki67, then the subject is placed into a high risk category.

Example 7

Determining Risk of Invasive Cancer Using Biomarkers Including Markers that are Linked to Diagnosis by Palpation As noted above, the results in Example 5B indicate that several of the variables examined in Table 12 are independent from one another. Thus, a high risk of subsequent invasive cancer can be indicated by palpation or by if the subject tests positive for COX-2, p16, and Ki67. The present Example outlines additional embodiments employing this information.

A set of biomarkers that indicates the presence of a DCIS lesion that can be detected by palpation is used to screen various subjects at risk of developing DCIS. If the results from the biomarkers indicate that a subject is likely to develop DCIS that is detectable via palpation, then that subject will also be categorized as having a higher risk (e.g., which can include the categorization of "high risk") of developing invasive cancer.

In the alternative, the method in Example 7, employing the palpation biomarker set, can be combined with the invasive cancer biomarker set from Example 5B (Table 12), so that the subject's risk of developing an invasive cancer can be examined through both of these sets of biomarkers, without having to perform a palpation screen of the subjects.

Example 8

Method of Characterizing a Sample

The present example outlines one embodiment for characterizing a sample for various biomarkers. One can obtain a tissue sample from a DCIS lesion from a subject. The tissue sample can be tested for Ki67 and at least one of the following: COX-2, p16, ER, and ERBB2. In an alternative embodiment, the tissue sample is tested for at least Ki67 and a) COX-2 and p16 or b) ER and ERBB2. A positive or negative score is determined for each of the tests performed.

The sample is then characterized as one of the following: Ki67 (positive or negative) and at least one of the following: COX-2 (positive or negative), p16 (positive or negative), ER (positive or negative), and ERBB2 (positive or negative).

In an alternative embodiment, the tissue sample is then characterized as one of the following: a) Ki67 (positive or negative) and COX-2 (positive or negative) and p16 (positive or negative) or b) Ki67 (positive or negative) and ER (positive or negative) and ERBB2 (positive or negative).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

LITERATURE

Crawford et al. (2004) *Cancer Cell* 5:263; McDermott et al. (2006) *PLoS Biol.* 4:e51; Berman et al. (2005) *Cold Spring Harbor Symp. Quant. Biol.* 70:317; Gauthier et al.

(2005) *Cancer Res.* 65:1792; Shim et al. (2003) *Cancer Res.* 63:2347; Holst et al. (2003) *Cancer Res.* 63:1596; Tlsty et al. (2004) *J. Mammary Gland Biol. Neoplasia* 9:263; Krüger et al. (1991) *Br. J. Cancer* 63:114-118.

1. Ernster V L, Ballard-Barbash R, Barlow W E, Zheng Y, Weaver D, Cutter G, et al. Detection of DCIS in Women Undergoing Screening Mammography. J Natl Cancer Inst 2002; 94(20): 1546-54.
2. Smigal C, Jemal A, Ward E, Cokkinides V, Smith R, Howe H, et al. Trends in breast cancer by race and ethnicity: update 2006. CA Cancer J Clin 2006; 56(3): 168-83.
3. Fisher B, Costantino J, Redmond C, Fisher E, Margolese R, Dimitrov N, et al. Lumpectomy compared with lumpectomy and radiation therapy for the treatment of intraductal breast cancer. N Engl J Med 1993; 328(22): 1581-6.
4. Fisher B, Land S, Mamounas E, Dignam J, Fisher E, Wolmark N. Prevention of invasive breast cancer in women with ductal carcinoma in situ: an update of the national surgical adjuvant breast and bowel project experience. Semin Oncol 2001; 28(4):400-418.
5. Kerlikowske K, Molinaro A, Cha I, Ljung B, Ernster V, Stewart K, et al. Characteristics associated with recurrence among women with ductal carcinoma in situ treated by lumpectomy. J Natl Cancer Inst 2003; 95(22): 1692-1702.
6. Julien J P, Bijker N, Fentiman I S, Peterse J L, Delledonne V, Rouanet P, et al. Radiotherapy in breast-conserving treatment for ductal carcinoma in situ: first results of the EORTC randomised phase III trial 10853. The Lancet 2000; 355(9203):528-33.

Fisher B, Dignam J, Wolmark N, Costantino J P, Poller W, Fisher E, et al. Lumpectomy and radiation therapy for the treatment of intraductal breast cancer: findings from national surgical adjuvant breast and bowel project B-17. J Clin Oncol 1998; 16(2):441-452.
8. Warren J L, Weaver D L, Bocklage T, Key C R, Platz C E, Cronin K A, et al. The frequency of ipsilateral second tumors after breast-conserving surgery. Cancer 2005; 104 (9):1840-8.
9. Fisher B, Dignam J, Wolmark N, Wickerham D L, Fisher E, Mamounas E, et al. Tamoxifen in treatment of intraductal breast cancer National Surgical Adjuvant Breast and Bowel Project B-24 randomised controlled trial. The Lancet 1999; 353(9169):1993-2000.
10. Schwartz G F, Solin L J, Olivotto I A, Ernster V L, Pressman P I, and the consensus Conference Committee. The consensus conference on the treatment of in situ ductal carcinoma of the breast. Cancer 2000; 88(4):946-954.
11. Ernster V L, Barclay J, Kerlikowske K, Wilkie H, Barbash R. Mortality among women with ductal carcinoma in situ of the breast in the population-based SEER Program. Arch Intern Med 2000; 160(7):953-958.
12. Solin L, Fourquet A, Vicini F, Taylor M, Olivotto I, Haffty B, et al. Long-term outcome after breast-conservation treatment with radiation for mammographically detected ductal carcinoma in situ of the breast. Cancer 2005; 103(6):1137-46.
13. Ringberg A, Nordgren H, Thorstensson S, Idvall I, Garmo H, Granstrand B, et al. Histopathological risk factors for ipsilateral breast events after breast conserving treatment for ductal carcinoma in situ of the breast—results from the Swedish randomised trial. Eur J Cancer 2007; 43(2):291-98.

14. Silverstein M J. Ductal carcinoma in situ of the breast: 11 reasons to consider treatment with excision alone. Womens Health 2008; 4(6):565-77.

15. Ringberg A, Anagnostaki L, Anderson H, Idvall I, Ferno M. Cell biological factors in ductal carcinoma in situ (DCIS) of the breast-relationship to ipsilateral local recurrence and histopathological characteristics. European J Cancer 2001; 37(12):1514-1522.

16. Provenzano E, Hopper J L, Giles G G, Marr G, Venter D J, Armes J E. Biological markers that predict clinical recurrence in ductal carcinoma in situ of the breast. Eur J Cancer 2003; 39(5):622-30.

17. Cornfield D B, Palazzo J P, Schwartz G F, Goonewardene S A, Kovatich A J, Chervoneva I, et al. The prognostic significance of multiple morphologic features and biologic markers in ductal carcinoma in situe of the breast. Cancer 2004; 100(11):2317-27.

18. Roka S, Rudas M, Taucher S, Dusky P, Bachleitner-Hofmann T, Kandioler D, et al. High nuclear grade and negative estrogen receptor are significant risk factors for recurrence in DCIS. EJSO 2004; 30(3):243-247.

19. Barnes N L P, Khavari S, G. P. B, Cramer A, Knox W F, Bundred N J. Absence of HER4 expression predicts recurrence of ductal carcinoma in situ of the breast. Clin Cancer Res 2005; 11(6):2163-2168.

20. Barnes N, Haywood P, Knox W F, Bundred N J. Survivin expression in in situ and invasive breast cancer relates to COX-2 expression and DCIS recurrence. Br J Cancer 2006; 94(2):253-258.

21. Gauthier M, Pickering C, Miller C, Fordyce C, Chew K, Berman H, et al. p38 regulates cyclooxygenase-2 in human mammary epithelial cells and is activated in premalignant tissue. Cancer Res 2005; 65(5):1792-9.

22. Gauthier M L, Berman H K, Miller C, Kozakeiwicz K, Chew K, Moore D, et al. Abrogated stress response distinguishes basal-like tumors and DCIS lesions associated with subsequent tumor events. Cancer Cell 2007; 12(5):479-491.

23. Tamimi R, Baer H, Marott J, Galan M, Galaburda L, Fu Y, et al. Comparison of molecular phenotypes of ductal carcinoma in situ and invasive breast cancer. Breast Cancer Res 2008; 10(4):R67.

24. Allred D C, Harvey J M, Berardo M, Clark G M. Prognostic and predictive factors in breast cancer by immunohistochemical analysis. Mod Pathol 1998; 11(2): 155-168.

25. Carey L A, Perou C M, Livasy C A, Dressler L G, Cowan D, Conway K, et al. Race, Breast cancer subtypes, and survival in the Carolina breast cancer study. JAMA 2006; 295(21):2492-2502.

26. Fine J P, Gray R J. A proportional hazards model for the subdistribution of a competing risk. JASA 1999; 94(446): 496-509.

27. Pepe M S, Mori M. Kaplan-Meier, marginal or conditional probability curves in summarizing competing risks failure time data? Statistics in Medicine 1993; 12(8):737-751

28. Allred D, Wu Y, Mao S, Nagtegaal I, Lee S, Perou C, et al. Ductal carcinoma in situ and the emergence of diversity during breast cancer evolution. Clin Cancer Res 2008; 14(2):370-8.

29. Bryan B, Schnitt S, Collins L. Ductal carcinoma in situ with basal-like phenotype: a possible precursor to invasive basal-like breast cancer. Mod Pathol 2006; 19(5): 617-21.

30. Dabbs D, Chivukula M, Carter G, Bhargava R. Basal phenotype of ductal carcinoma in situ: recognition and immunohistologic profile. Mod Pathol 2006; 19(11): 1506-11.

31. Livasy C, Perou C, Karaca G, Cowan D, Maia D, Jackson S, et al. Identification of a basal-like subtype of breast ductal carcinoma in situ. Hum Pathol 2007; 38(2): 197-204.

32. Subhawong A, Subhawong T, Nassar H, Kouprina N, Begum S, Vang R, et al. Most basal-like breast carcinomas demonstrate the same Rb–/p16+ immunophenotype as the hpv-related poorly differentiated squamous cell carcinomas which they resemble morphologically. Am J Surg Pathol 2008; 33(2):163-75.

33. Herschkowitz J, He X, Fan C, Perou C. The functional loss of the retinoblastoma tumour suppressor is a common event in basal-like and luminal B breast carcinomas. Breast Cancer Res 2008; 10(5):R75. [Epub ahead of print].

34. Crawford Y G, Gauthier M L, Joubel A, Mantei K, Kozakiewicz K, Afshari C A, et al. Histologically normal human mammary epithelia with silenced p16(INK4a) overexpress COX-2, promoting a premalignant program. Cancer Cell 2004; 5(3):263-73.

35. Hu M, Peluffo G, Chen H, Gelman R, Schnitt S, Polyak K. Role of COX-2 in epithelial-stromal cell interactions and progression of ductal carcinoma in situ of the breast. PNAS 2009; 106(9):3372-7.

36. Minn A J, Gupta G P, Siegel P M, Bos P D, Shu W, Giri D D, et al. Genes that mediate breast cancer metastasis to lung. Nature 2005; 436(7050):518-24.

37. Silverstein M, Skinner K, T J. L. Predicting axillary nodal positivity in 2282 patients with breast carcinoma. World J Surg 2001; 25(6):767-72.

38. Vicini F A, Kestin L L, Goldstein N S, Chen P Y, Pettinga J E, Frazier R C, et al. Impact of young age on outcome in patients with ductal carcinoma-in-situ treated with breast-conserving therapy. J Clin Oncol 2000; 18(2):296-306.

39. Wells W A, Carney P A, Eliassen M S, Grove M R, Tosteson A N A. Pathologists' agreement with experts and reproducibility of breast ductal carcinoma-in-situ classification schemes. Am J Surg Pathol 2000; 24(5):651-659.

40. Douglas-Jones A G, Morgan J M, Appleton M A C, Attanoos R L, Caslin A, Champ C S, et al. Consistency in the observation of features used to classify duct carcinoma in situ (DCIS) of the breast. J Clin Pathol 2000; 53(8):596-602.

41. Solin L J, Kurtz J, Fourquet A, Amairic R, Recht A, Bornstein B A, et al. Fifteen-year results of breast-conserving surgery and definitive breast irradiation for the treatment of ductal carcinoma in situ of the breast. J Clin Oncol 1996; 14:754-763.

42. Solin L J, Fourquet A, Vicini F A, Haffty B, Taylor M, McCormick B, et al. Mammographically detected ductal carcinoma in situ of the breast treated with breast-conserving surgery and definitive irradiation: long-term outcome and prognostic significance of patient age and margin status. Int J. Radiation Oncology Biol Phys 2001; 50(4):991-1002.

43. Chen Y, Thompson W, Semenciw R, Mao Y. Epidemiology of contralateral breast cancer. Cancer Epidemiol Biomarkers Prey 1999; 8(10):855-861.

44. Partridge A, Adloff K, Blood E, al. e. Risk perceptions and psychosocial outcomes of women with ductal carcinoma in situ: longitudinal results from a cohort study. J Natl Cancer Inst 2008; 100(4):243-251.

Throughout this application various publications have been referenced. The disclosures of these publications in their entireties are hereby incorporated by reference in this application in order to more fully describe the state of the art to which this invention pertains. The entirety of U.S. patent application Ser. No. 12/373,047 (U.S. Pub. No. 2010/

0003189, published Jan. 7, 2010), which is the U.S. National Phase of International Application PCT/US2007/015584, filed Jul. 3, 2007, which claims priority to U.S. provisional application No. 60/830,960 is also incorporated herein by reference

What is claimed is:

1. A method of treating breast cancer in a subject, comprising:

collecting a tissue sample from an initial DCIS lesion from a subject;

analyzing a cell signature of the tissue sample, comprising:

contacting the tissue sample with an antibody protein specific for Ki67, detecting staining of at least 10% of tumor cells in the tissue sample by the antibody protein specific for Ki67, and identifying the sample as positive for Ki67;

contacting the tissue sample with an antibody protein specific for PR, detecting staining of less than 10% of tumor cells in the tissue sample by the antibody protein specific for PR, and identifying the sample as negative for PR; and contacting the tissue sample with an antibody protein specific for ERBB2, detecting moderate or strong membrane staining of at least 10% of tumor cells in the tissue sample by the antibody protein specific for ERBB2, and identifying the sample as positive for ERBB2;

determining that the cell signature of the tissue sample is at least: positive for Ki67, negative for PR, and positive for ERBB2;

placing the subject in a high risk of recurrence category for subsequent ipsilateral breast cancer based on at least the analysis of the cell signature; and treating the subject for the initial DCIS lesion, wherein the treatment comprises: removing the DCIS lesion by performing a lumpectomy with an adjuvant therapy; or performing a mastectomy on the subject, to thereby reduce a risk of subsequent ipsilateral breast cancer in the subject.

2. The method of claim 1, wherein the subject is less than 50 years old.

3. The method of claim 1, wherein the subject is 40-49 years old.

4. The method of claim 2, wherein analyzing the cell signature of the tissue sample further comprises:

detecting whether said sample is positive for COX-2, comprising contacting the tissue sample with at least one of an antibody protein, nucleic acid probe, or nucleic acid primer specific for COX-2 and detecting binding or absence of binding of the antibody protein, nucleic acid probe, or nucleic acid primer specific for COX-2;

detecting whether said sample is positive for p16, comprising contacting the tissue sample with at least one of an antibody protein, nucleic acid probe, or nucleic acid primer specific for p16 and detecting binding or absence of binding of the antibody protein, nucleic acid probe, or nucleic acid primer specific for p16;

determining that the cell signature of the tissue sample is further: p16 positive and COX-2 negative.

5. The method of claim 4, wherein the sample is positive for p16 when at least 25% of tumor cells in the tissue sample is stained by the antibody protein specific for p16, and the sample is positive for COX-2 when the tissue sample has an Allred score of at least 5 when stained with the antibody protein specific for COX-2.

6. The method of claim 2, wherein the adjuvant therapy is radiation therapy.

7. The method of claim 2, wherein a tumor-free margin of the removed DCIS lesion is 2 mm or greater.

8. The method of claim 2, wherein placing the subject in the risk category for subsequent breast cancer is independent of the nuclear grade of the initial DCIS lesion.

9. The method of claim 2, wherein the initial DCIS lesion does not have high nuclear grade.

10. The method of claim 2, further comprising, before collecting the tissue sample:

detecting the DCIS lesion by one or more of palpation, mammography, and magnetic resonance imaging (MRI); and identifying the subject as in need of treating the DCIS lesion.

11. A method of treating breast cancer in a subject, comprising:

having a tissue sample collected from an initial DCIS lesion from a subject;

having an analysis of a cell signature carried out on the tissue sample, the analysis of the cell signature comprising:

contacting the tissue sample with an antibody protein specific for Ki67, detecting staining of at least 10% of tumor cells in the tissue sample by the antibody protein specific for Ki67, and identifying the sample as positive for Ki67;

contacting the tissue sample with an antibody protein specific for PR, detecting staining of less than 10% of tumor cells in the tissue sample by the antibody protein specific for PR, and identifying the sample as negative for PR; and contacting the tissue sample with an antibody protein specific for ERBB2, detecting moderate or strong membrane staining of at least 10% of tumor cells in the tissue sample by the antibody protein specific for ERBB2, and identifying the sample as positive for ERBB2;

receiving a report comprising a treatment recommendation based on at least the analysis that the cell signature of said sample that is at least positive for Ki67, negative for PR, and positive for ERBB2, wherein the subject is placed in a high risk category for subsequent ipsilateral breast cancer based on at least the analysis of the cell signature;

wherein the recommended treatment is commensurate with the subject's risk category for subsequent ipsilateral breast cancer; and receiving the recommended treatment for the initial DCIS lesion, wherein the recommended treatment comprises: a lumpectomy with an adjuvant therapy or a mastectomy, to thereby reduce a risk of subsequent ipsilateral breast cancer.

12. The method of claim 11, wherein the subject is less than 50 years old.

13. The method of claim 11, wherein the subject is 40-49 years old.

14. The method of claim 12, wherein said antibody protein specific for Ki67, said antibody protein specific for PR, and said antibody protein specific for ERBB2 are part of a reagent panel consisting of:

said antibody protein specific for Ki67;

said antibody protein specific for PR; and antibody protein specific for ERBB2.

15. The method of claim 12, wherein the analysis of the cell signature further comprises:

detecting whether said sample is positive for COX-2, comprising contacting the tissue sample with at least one of an antibody protein, nucleic acid probe, or nucleic acid primer specific for COX-2 and detecting binding or absence of binding of the antibody protein, nucleic acid probe, or nucleic acid primer specific for COX-2; and detecting whether said sample is positive for p16, comprising contacting the tissue sample with at least one of an antibody protein, nucleic acid probe, or nucleic acid primer specific for p16 and detecting binding or absence of binding of the antibody protein, nucleic acid probe, or nucleic acid primer specific for p16.

16. The method of claim 15, wherein the sample is positive for p16 when at least 25% of tumor cells in the tissue sample is stained by the antibody protein specific for p16, and the sample is positive for COX-2 when the tissue sample has an Allred score of at least 5 when stained with the antibody protein specific for COX-2.

17. The method of claim 12, wherein the adjuvant therapy is radiation therapy.

18. The method of claim 12, wherein a tumor-free margin of the removed DCIS lesion is 2 mm or greater.

* * * * *

```
                           SEQUENCE LISTING

<160> NUMBER OF SEQ ID NOS: 84

<210> SEQ ID NO 1
<211> LENGTH: 75
<212> TYPE: RNA
<213> ORGANISM: Homo sapiens

<400> SEQUENCE: 1
uggagugggg gggcaggagg ggcucaggga gaaagugcau acagccccug gcccucucug      60
cccuuccguc cccug                                                       75

<210> SEQ ID NO 2
<211> LENGTH: 22
<212> TYPE: RNA
<213> ORGANISM: Homo sapiens

<400> SEQUENCE: 2
cuggcccucu cugcccuucc gu                                                22

<210> SEQ ID NO 3
<211> LENGTH: 22
<212> TYPE: DNA
<213> ORGANISM: Homo sapiens

<400> SEQUENCE: 3
acggaagggc agagagggcc ag                                                22

<210> SEQ ID NO 4
<211> LENGTH: 84
<212> TYPE: RNA
<213> ORGANISM: Homo sapiens

<400> SEQUENCE: 4
acuggucggu gauuuaggua guuuccuguu guugggaucc accuuucucu cgacagcacg      60
acacugccuu cauuacuuca guug                                             84

<210> SEQ ID NO 5
<211> LENGTH: 21
<212> TYPE: RNA
<213> ORGANISM: Homo sapiens

<400> SEQUENCE: 5
uagguaguuu ccuguuguug g                                                 21

<210> SEQ ID NO 6
<211> LENGTH: 21
<212> TYPE: DNA
<213> ORGANISM: Homo sapiens

<400> SEQUENCE: 6
ccaacaacag gaaactacct a                                                 21

<210> SEQ ID NO 7
<211> LENGTH: 71
<212> TYPE: RNA
<213> ORGANISM: Homo sapiens
```

<400> SEQUENCE: 7
gcgacuguaa acauccucga cuggaagcug ugaagccaca gaugggcuuu cagucggaug          60
uuugcagcug c                                                              71

<210> SEQ ID NO 8
<211> LENGTH: 22
<212> TYPE: RNA
<213> ORGANISM: Homo sapiens

<400> SEQUENCE: 8
uguaaacauc cucgacugga ag                                                  22

<210> SEQ ID NO 9
<211> LENGTH: 22
<212> TYPE: DNA
<213> ORGANISM: Homo sapiens

<400> SEQUENCE: 9
cttccagtcg aggatgttta ca                                                  22

<210> SEQ ID NO 10
<211> LENGTH: 88
<212> TYPE: RNA
<213> ORGANISM: Homo sapiens

<400> SEQUENCE: 10
ugcgcuccuc ucagucccug agacccuaac uugugauguu uaccguuuaa auccacgggu          60
uaggcucuug ggagcugcga gucgugcu                                            88

<210> SEQ ID NO 11
<211> LENGTH: 22
<212> TYPE: RNA
<213> ORGANISM: Homo sapiens

<400> SEQUENCE: 11
ucccugagac ccuaacuugu ga                                                  22

<210> SEQ ID NO 12
<211> LENGTH: 22
<212> TYPE: DNA
<213> ORGANISM: Homo sapiens

<400> SEQUENCE: 12
tcacaagtta gggtctcagg gt                                                  22

<210> SEQ ID NO 13
<211> LENGTH: 92
<212> TYPE: RNA
<213> ORGANISM: Homo sapiens

<400> SEQUENCE: 13
gggcagucuu ugcuacugua aacauccuug acuggaagcu guaaggyguu cagaggagcu          60
uucagucgga uguuuacagc ggcaggcugc ca                                       92

<210> SEQ ID NO 14
<211> LENGTH: 22
<212> TYPE: RNA
<213> ORGANISM: Homo sapiens -continued

<400> SEQUENCE: 14
cuuucagucg gauguuuaca gc                                          22

<210> SEQ ID NO 15
<211> LENGTH: 22
<212> TYPE: DNA
<213> ORGANISM: Homo sapiens

<400> SEQUENCE: 15
gctgtaaaca tccgactgaa ag                                          22

<210> SEQ ID NO 16
<211> LENGTH: 82
<212> TYPE: RNA
<213> ORGANISM: Homo sapiens

<400> SEQUENCE: 16
ccugccgggg cuaaagugcu gacagugcag auaguggucc ucuccgugcu accgcacugu    60
ggguacuugc ugcuccagca gg                                          82

<210> SEQ ID NO 17
<211> LENGTH: 21
<212> TYPE: RNA
<213> ORGANISM: Homo sapiens

<400> SEQUENCE: 17
uaaagugcug acagugcaga u                                           21

<210> SEQ ID NO 18
<211> LENGTH: 21
<212> TYPE: DNA
<213> ORGANISM: Homo sapiens

<400> SEQUENCE: 18
atctgcactg tcagcacttt a                                           21

<210> SEQ ID NO 19
<211> LENGTH: 73
<212> TYPE: RNA
<213> ORGANISM: Homo sapiens

<400> SEQUENCE: 19
cagggugugu gacugguuga ccagaggggc augcacugug uucacccugu gggccaccua    60
gucaccaacc cuc                                                    73

<210> SEQ ID NO 20
<211> LENGTH: 21
<212> TYPE: RNA
<213> ORGANISM: Homo sapiens

<400> SEQUENCE: 20
ugugacuggu ugaccagagg g                                           21

<210> SEQ ID NO 21
<211> LENGTH: 21
<212> TYPE: DNA
<213> ORGANISM: Homo sapiens

<400> SEQUENCE: 21
ccctctggtc aaccagtcac a                                           21

-continued

```
<210> SEQ ID NO 22
<211> LENGTH: 94
<212> TYPE: RNA
<213> ORGANISM: Homo sapiens

<400> SEQUENCE: 22
agagcaucgu gcuugaccuu ccacgcucuc guguccacua gcaggcaggu uuucugacac     60
aggcugcgga auucaggaca gugcaucaug gaga                                 94

<210> SEQ ID NO 23
<211> LENGTH: 19
<212> TYPE: RNA
<213> ORGANISM: Homo sapiens

<400> SEQUENCE: 23
aggcugcgga auucaggac                                                  19

<210> SEQ ID NO 24
<211> LENGTH: 19
<212> TYPE: DNA
<213> ORGANISM: Homo sapiens

<400> SEQUENCE: 24
gtcctgaatt ccgcagcct                                                  19

<210> SEQ ID NO 25
<211> LENGTH: 84
<212> TYPE: RNA
<213> ORGANISM: Homo sapiens

<400> SEQUENCE: 25
ugugcagugg gaagggggc cgauacacug uacgagagug aguagcaggu cucacaguga      60
accggucucu uucccuacug uguc                                            84

<210> SEQ ID NO 26
<211> LENGTH: 22
<212> TYPE: RNA
<213> ORGANISM: Homo sapiens

<400> SEQUENCE: 26
ucacagugaa ccggucucuu uc                                              22

<210> SEQ ID NO 27
<211> LENGTH: 22
<212> TYPE: DNA
<213> ORGANISM: Homo sapiens

<400> SEQUENCE: 27
gaaagagacc ggttcactgt ga                                              22

<210> SEQ ID NO 28
<211> LENGTH: 82
<212> TYPE: RNA
<213> ORGANISM: Homo sapiens

<400> SEQUENCE: 28
ugagcuguug gauucggggc cguagcacug ucugagaggu uuacauuucu cacagugaac     60
cggucucuuu uucagcugcu uc                                              82

<210> SEQ ID NO 29
<211> LENGTH: 22
```

-continued

```
<212> TYPE: RNA
<213> ORGANISM: Homo sapiens

<400> SEQUENCE: 29
ucacagugaa ccggucucuu uu                                            22

<210> SEQ ID NO 30
<211> LENGTH: 22
<212> TYPE: DNA
<213> ORGANISM: Homo sapiens

<400> SEQUENCE: 30
aaaagagacc ggttcactgt ga                                            22

<210> SEQ ID NO 31
<211> LENGTH: 94
<212> TYPE: RNA
<213> ORGANISM: Homo sapiens

<400> SEQUENCE: 31
gaguuugguu uuguuugggu uuguucuagg uaugguccca gggaucccag aucaaaccag    60
gccccugggc cuauccuaga accaaccuaa gcuc                                94

<210> SEQ ID NO 32
<211> LENGTH: 21
<212> TYPE: RNA
<213> ORGANISM: Homo sapiens

<400> SEQUENCE: 32
gccccugggc cuauccuaga a                                             21

<210> SEQ ID NO 33
<211> LENGTH: 21
<212> TYPE: DNA
<213> ORGANISM: Homo sapiens

<400> SEQUENCE: 33
ttctaggata ggcccagggg c                                             21

<210> SEQ ID NO 34
<211> LENGTH: 87
<212> TYPE: RNA
<213> ORGANISM: Homo sapiens

<400> SEQUENCE: 34
ucucaggcug ugacccucua aagggaagcg cuuucugugg ucagaaagaa aagcaagugc    60
uuccuuuuag aggguuaccg uuuggga                                       87

<210> SEQ ID NO 35
<211> LENGTH: 22
<212> TYPE: RNA
<213> ORGANISM: Homo sapiens

<400> SEQUENCE: 35
aagugcuucc uuuuagaggg uu                                            22

<210> SEQ ID NO 36
<211> LENGTH: 22
<212> TYPE: DNA
<213> ORGANISM: Homo sapiens
```

-continued

```
<400> SEQUENCE: 36
aaccctctaa aaggaagcac tt                                        22

<210> SEQ ID NO 37
<211> LENGTH: 63
<212> TYPE: RNA
<213> ORGANISM: Homo sapiens

<400> SEQUENCE: 37
aagaaauggu uuaccguccc acauacauuu ugaauaugua uguggggaugg uaaaccgcuu    60 cuu                                                             63

<210> SEQ ID NO 38
<211> LENGTH: 22
<212> TYPE: RNA
<213> ORGANISM: Homo sapiens

<400> SEQUENCE: 38 uauguggggau gguaaaccgc uu                                        22

<210> SEQ ID NO 39
<211> LENGTH: 22
<212> TYPE: DNA
<213> ORGANISM: Homo sapiens

<400> SEQUENCE: 39
aagcggttta ccatcccaca ta                                        22

<210> SEQ ID NO 40
<211> LENGTH: 88
<212> TYPE: RNA
<213> ORGANISM: Homo sapiens

<400> SEQUENCE: 40
ucccaugcug ugacccucua gaggaagcac uuucuguuug uugucugaga aaaaacaaag    60
ugcuucccuu uagaguuacu guuuggga                                   88

<210> SEQ ID NO 41
<211> LENGTH: 22
<212> TYPE: RNA
<213> ORGANISM: Homo sapiens

<400> SEQUENCE: 41
acaaagugcu ucccuuuaga gu                                         22

<210> SEQ ID NO 42
<211> LENGTH: 22
<212> TYPE: DNA
<213> ORGANISM: Homo sapiens

<400> SEQUENCE: 42
actctaaagg gaagcacttt ga                                         22

<210> SEQ ID NO 43
<211> LENGTH: 74
<212> TYPE: RNA
<213> ORGANISM: Homo sapiens
```

-continued

```
<400> SEQUENCE: 43
gugguguccu acucaggaga guggcaauca cauguaauua ggugugauug aaaccucuaa     60
gaguggagua acac                                                      74

<210> SEQ ID NO 44
<211> LENGTH: 23
<212> TYPE: RNA
<213> ORGANISM: Homo sapiens

<400> SEQUENCE: 44
uacucaggag aguggcaauc aca                                            23

<210> SEQ ID NO 45
<211> LENGTH: 23
<212> TYPE: DNA
<213> ORGANISM: Homo sapiens

<400> SEQUENCE: 45
tgtgattgcc actctcctga gta                                            23

<210> SEQ ID NO 46
<211> LENGTH: 87
<212> TYPE: RNA
<213> ORGANISM: Homo sapiens

<400> SEQUENCE: 46
accgcaggga aaaugaggga cuuuuggggg cagauguguu uccauccac uaucauaaug      60 ccccuaaaaa uccuuauugc ucuugca                                        87

<210> SEQ ID NO 47
<211> LENGTH: 22
<212> TYPE: RNA
<213> ORGANISM: Homo sapiens

<400> SEQUENCE: 47
uaaugccccu aaaaauccuu au                                             22

<210> SEQ ID NO 48
<211> LENGTH: 22
<212> TYPE: DNA
<213> ORGANISM: Homo sapiens

<400> SEQUENCE: 48
ataaggattt ttaggggcat ta                                             22

<210> SEQ ID NO 49
<211> LENGTH: 90
<212> TYPE: RNA
<213> ORGANISM: Homo sapiens

<400> SEQUENCE: 49
ucccaugcug ugacccucua gaggaagcac uuucuguuug uugucugaga aaaaacaaag     60
ugcuucccuu uagaguguua ccguuuggga                                     90

<210> SEQ ID NO 50
<211> LENGTH: 24
<212> TYPE: RNA
<213> ORGANISM: Homo sapiens
```

-continued

```
<400> SEQUENCE: 50
acaaagugcu ucccuuuaga gugu                                      24

<210> SEQ ID NO 51
<211> LENGTH: 24
<212> TYPE: DNA
<213> ORGANISM: Homo sapiens

<400> SEQUENCE: 51
acactctaaa gggaagcact ttga                                      24

<210> SEQ ID NO 52
<211> LENGTH: 83
<212> TYPE: RNA
<213> ORGANISM: Homo sapiens

<400> SEQUENCE: 52
cugacuaugc cuccccgcau ccccuagggc auuggguguaa agcuggagac ccacugcccc    60
aggugcugcu ggggguugua guc                                       83

<210> SEQ ID NO 53
<211> LENGTH: 22
<212> TYPE: RNA
<213> ORGANISM: Homo sapiens

<400> SEQUENCE: 53
ccacugcccc aggugcugcu gg                                        22

<210> SEQ ID NO 54
<211> LENGTH: 22
<212> TYPE: DNA
<213> ORGANISM: Homo sapiens

<400> SEQUENCE: 54
ccagcagcac ctggggcagt gg                                        22

<210> SEQ ID NO 55
<211> LENGTH: 86
<212> TYPE: RNA
<213> ORGANISM: Homo sapiens

<400> SEQUENCE: 55
ugccagucuc uaggucccug agacccuuua accugugagg acauccaggg ucacagguga    60
gguucuuggg agccuggcgu cuggcc                                    86

<210> SEQ ID NO 56
<211> LENGTH: 23
<212> TYPE: RNA
<213> ORGANISM: Homo sapiens

<400> SEQUENCE: 56
ucccugagac ccuuuaaccu gug                                       23

<210> SEQ ID NO 57
<211> LENGTH: 23
<212> TYPE: DNA
<213> ORGANISM: Homo sapiens

<400> SEQUENCE: 57
cacaggttaa agggtctcag ggt                                       23
```

```
<210> SEQ ID NO 58
<211> LENGTH: 68
<212> TYPE: RNA
<213> ORGANISM: Homo sapiens

<400> SEQUENCE: 58
ccucuacuuu aacauggagg cacuugcugu gacaugacaa aaauaagugc uuccauguuu      60
gagugugg                                                              68

<210> SEQ ID NO 59
<211> LENGTH: 23
<212> TYPE: RNA
<213> ORGANISM: Homo sapiens

<400> SEQUENCE: 59
uaagugcuuc cauguuugag ugu                                             23

<210> SEQ ID NO 60
<211> LENGTH: 23
<212> TYPE: DNA
<213> ORGANISM: Homo sapiens

<400> SEQUENCE: 60
acactcaaac atggaagcac tta                                             23

<210> SEQ ID NO 61
<211> LENGTH: 87
<212> TYPE: RNA
<213> ORGANISM: Homo sapiens

<400> SEQUENCE: 61
ucucaagcug ugagucuaca aagggaagcc cuuucuguug ucuaaaagaa aagaaagugc      60
uucucuuugg uggguuacgg uuugaga                                          87

<210> SEQ ID NO 62
<211> LENGTH: 23
<212> TYPE: RNA
<213> ORGANISM: Homo sapiens

<400> SEQUENCE: 62
ucuacaaagg gaagcccuuu cug                                             23

<210> SEQ ID NO 63
<211> LENGTH: 23
<212> TYPE: DNA
<213> ORGANISM: Homo sapiens

<400> SEQUENCE: 63
cagaaagggc ttccctttgt aga                                             23

<210> SEQ ID NO 64
<211> LENGTH: 98
<212> TYPE: RNA
<213> ORGANISM: Homo sapiens

<400> SEQUENCE: 64
acgaauggcu augcacugca caacccuagg agagggugcc auucacauag acuauaauug      60
aauggcgcca cuaggguugu gcagugcaca accuacac                              98

<210> SEQ ID NO 65
<211> LENGTH: 23
```

-continued

```
<212> TYPE: RNA
<213> ORGANISM: Homo sapiens

<400> SEQUENCE: 65
aauggcgcca cuaggguugu gca                                        23

<210> SEQ ID NO 66
<211> LENGTH: 23
<212> TYPE: DNA
<213> ORGANISM: Homo sapiens

<400> SEQUENCE: 66
tgcacaaccc tagtggcgcc att                                        23

<210> SEQ ID NO 67
<211> LENGTH: 87
<212> TYPE: RNA
<213> ORGANISM: Homo sapiens

<400> SEQUENCE: 67
ucucaggcug ucguccucua gagggaagca cuuucuguug ucugaaagaa aagaaagugc   60
uuccuuuuag aggguuaccg uuugaga                                      87

<210> SEQ ID NO 68
<211> LENGTH: 23
<212> TYPE: RNA
<213> ORGANISM: Homo sapiens

<400> SEQUENCE: 68
aaagugcuuc cuuuuagagg guu                                        23

<210> SEQ ID NO 69
<211> LENGTH: 23
<212> TYPE: DNA
<213> ORGANISM: Homo sapiens

<400> SEQUENCE: 69
aaccctctaa aaggaagcac ttt                                        23

<210> SEQ ID NO 70
<211> LENGTH: 94
<212> TYPE: RNA
<213> ORGANISM: Homo sapiens

<400> SEQUENCE: 70
uggggugucu gugcuauggc agcccuagca cacagauacg cccagagaaa gccugaacgu   60
ugggcguauc uguaugcuag ggcugcugua acaa                              94

<210> SEQ ID NO 71
<211> LENGTH: 19
<212> TYPE: RNA
<213> ORGANISM: Homo sapiens

<400> SEQUENCE: 71
ugggcguauc uguaugcua                                             19

<210> SEQ ID NO 72
<211> LENGTH: 19
<212> TYPE: DNA
<213> ORGANISM: Homo sapiens
```

-continued

<400> SEQUENCE: 72
tagcatacag atacgccca                                                19

<210> SEQ ID NO 73
<211> LENGTH: 96
<212> TYPE: RNA
<213> ORGANISM: Homo sapiens

<400> SEQUENCE: 73
uagauugagg aaggggcuga gugguaggcg gugcugcugu gcucugauga agacccaugu    60
ggcuagcaac agcgcuuacc uuuugucucu gggucc                             96

<210> SEQ ID NO 74
<211> LENGTH: 21
<212> TYPE: RNA
<213> ORGANISM: Homo sapiens

<400> SEQUENCE: 74
ggcuagcaac agcgcuuacc u                                             21

<210> SEQ ID NO 75
<211> LENGTH: 21
<212> TYPE: DNA
<213> ORGANISM: Homo sapiens

<400> SEQUENCE: 75
aggtaagcgc tgttgctagc c                                             21

<210> SEQ ID NO 76
<211> LENGTH: 97
<212> TYPE: RNA
<213> ORGANISM: Homo sapiens

<400> SEQUENCE: 76
cagaucucag acaucucggg gaucaucaug ucacgagaua ccagugugca cuugugacag    60
auugauaacu gaaaggucug ggagccacuc aucuuca                            97

<210> SEQ ID NO 77
<211> LENGTH: 22
<212> TYPE: RNA
<213> ORGANISM: Homo sapiens

<400> SEQUENCE: 77
ucggggauca ucaugucacg ag                                            22

<210> SEQ ID NO 78
<211> LENGTH: 22
<212> TYPE: DNA
<213> ORGANISM: Homo sapiens

<400> SEQUENCE: 78
ctcgtgacat gatgatcccc ga                                            22

<210> SEQ ID NO 79
<211> LENGTH: 95
<212> TYPE: RNA
<213> ORGANISM: Homo sapiens -continued

```
<400> SEQUENCE: 79
uccccucugg cggcugcgca cgggccgugu gagcuauugc gguggcugg ggcagaugac          60 gcgugcgccg gccggccgcc gaggggcuac cguuc                                    95

<210> SEQ ID NO 80
<211> LENGTH: 20
<212> TYPE: RNA
<213> ORGANISM: Homo sapiens

<400> SEQUENCE: 80
gcgugcgccg gccggccgcc                                                     20

<210> SEQ ID NO 81
<211> LENGTH: 20
<212> TYPE: DNA
<213> ORGANISM: Homo sapiens

<400> SEQUENCE: 81
ggcggccggc cggcgcacgc                                                     20

<210> SEQ ID NO 82
<211> LENGTH: 85
<212> TYPE: RNA
<213> ORGANISM: Homo sapiens

<400> SEQUENCE: 82
cgcuggcgac gggacauuau uacuuuuggu acgcgcugug acacuucaaa cucguaccgu          60
gaguaauaau gcgccgucca cggca                                               85

<210> SEQ ID NO 83
<211> LENGTH: 21
<212> TYPE: RNA
<213> ORGANISM: Homo sapiens

<400> SEQUENCE: 83
cauuauuacu uuugguacgc g                                                   21

<210> SEQ ID NO 84
<211> LENGTH: 21
<212> TYPE: DNA
<213> ORGANISM: Homo sapiens

<400> SEQUENCE: 84
cgcgtaccaa aagtaataat g                                                   21
```